US008552205B2

(12) United States Patent
Barbosa, Jr. et al.

(10) Patent No.: US 8,552,205 B2
(45) Date of Patent: Oct. 8, 2013

(54) DERIVATIVES OF 6,7-DIHYDRO-5H-IMIDAZO[1,2-ALPHA] IMIDAZOLE-3-CARBOXYLIC ACID AMIDES

(75) Inventors: Antonio Jose del Moral Barbosa, Jr., Middlebury, NY (US); Joerg Martin Bentzien, White Plains, NY (US); Steven Richard Brunette, New Milford, CT (US); Zhidong Chen, New Milford, CT (US); Derek Cogan, Sandy Hook, CT (US); Donghong A. Gao, Hopewell Junction, NY (US); Alexander Heim-Riether, Newtown, CT (US); Joshua Courtney Horan, Danbury, CT (US); Jennifer A. Kowalski, New Milford, CT (US); Michael David Lawlor, Seymour, CT (US); Rene Marc Lemieux, Newtown, CT (US); Weimin Liu, Sandy Hook, CT (US); Bryan McKibben, New Milford, CT (US); Craig Andrew Miller, Norwalk, CT (US); Neil Moss, Ridgefield, CT (US); Matt Aaron Tschantz, Newtown, CT (US); Zhaoming Xiong, Brookfield, CT (US); Hui Yu, New Milford, CT (US); Yang Yu, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 36 days.

(21) Appl. No.: 12/745,439

(22) PCT Filed: Nov. 20, 2008

(86) PCT No.: PCT/US2008/084149
§ 371 (c)(1),
(2), (4) Date: Jun. 2, 2011

(87) PCT Pub. No.: WO2009/070485
PCT Pub. Date: Jun. 4, 2009

(65) Prior Publication Data
US 2011/0224188 A1   Sep. 15, 2011

Related U.S. Application Data

(60) Provisional application No. 61/047,957, filed on Apr. 25, 2008, provisional application No. 60/990,960, filed on Nov. 29, 2007.

(51) Int. Cl.
*A61K 31/4188* (2006.01)
*C07D 403/14* (2006.01)
*C07D 403/12* (2006.01)
*C07D 401/12* (2006.01)
*C07D 401/14* (2006.01)

(52) U.S. Cl.
USPC ........ 548/303.1; 544/138; 544/139; 544/238; 544/279; 544/333; 546/122; 546/194; 546/199; 546/273.1; 548/113; 548/136; 548/181; 548/132; 548/235; 548/250; 548/266.4

(58) Field of Classification Search
USPC ....................................... 548/303.1
See application file for complete search history.

(56) References Cited

U.S. PATENT DOCUMENTS

| | | | |
|---|---|---|---|
| 3,668,217 A | 6/1972 | Fujinami et al. |
| 3,741,981 A | 6/1973 | Fujinami et al. |
| 3,846,441 A | 11/1974 | Mine et al. |
| 4,911,748 A | 3/1990 | Prisbylla |
| 4,944,791 A | 7/1990 | Schroder et al. |
| 4,977,270 A | 12/1990 | Wee |
| 5,208,250 A | 5/1993 | Cetenko et al. |
| 5,306,822 A | 4/1994 | Cetenko et al. |
| 5,334,606 A | 8/1994 | MacLeod |
| 5,464,856 A | 11/1995 | Cetenko et al. |
| 5,750,553 A | 5/1998 | Claussner et al. |
| 6,063,628 A | 5/2000 | Loeb et al. |
| 6,350,763 B1 | 2/2002 | Kelly et al. |
| 6,353,013 B1 | 3/2002 | Kelly et al. |
| 6,355,664 B1 | 3/2002 | Kelly et al. |
| 6,365,615 B1 | 4/2002 | Kelly et al. |
| 6,414,153 B1 | 7/2002 | Kelly et al. |
| 6,492,408 B1 | 12/2002 | Wu et al. |
| 6,689,804 B2 | 2/2004 | Wu et al. |
| 6,844,360 B2 | 1/2005 | Kelly et al. |
| 6,852,748 B1 | 2/2005 | Kelly et al. |
| 7,304,067 B2 | 12/2007 | Kelly et al. |
| 7,345,074 B2 | 3/2008 | Kelly et al. |
| 7,462,637 B2 | 12/2008 | Kelly et al. |

(Continued)

FOREIGN PATENT DOCUMENTS

EP   0343643 A2   11/1989
EP   0545478 A1   6/1993

(Continued)

OTHER PUBLICATIONS

Golub et al., Science, vol. 286, Oct. 15, 1999, pp. 531-537.*
International Search Report, Form PCT/ISA/210, for corresponding PCT/EP2008/084149, Date of mailing Jan. 1, 2009.
Anderson et al., Leukocyte LFA-1, p150,95 Deficiency Syndrome: Functional and Biosynthetic Studies of Three Kinds 1,2, Fed. Proc. 1985, 44, pp. 2671-2677.
Anderson et al., Targeting ICAM-1/LFA-1 interaction for controlling autoimmune diseases: designing peptide and small molecule inhibitors, Peptides, 24, pp. 487-501,2003.
Anderson et al., The Severe and Moderate Phenotypes of Heritable Mac-1, LFA-1 Deficiency: Their Quantitative Definition and Relation to Leukocyte Dysfunction and Clinical Features, J. Infect. Dis. 1985, 152, pp. 668-689.

(Continued)

*Primary Examiner* — Laura L. Stockton
(74) *Attorney, Agent, or Firm* — Michael P. Morris; Philip I. Datlow

(57) ABSTRACT

Derivatives of 6,7-dihydro-5H-imidazo[1,2-α]imidazole-3-carboxylic acid amide exhibit good inhibitory effect upon the interaction of CAMs and Leukointegrins and are thus useful in the treatment of inflammatory disease.

49 Claims, No Drawings

(56) References Cited

U.S. PATENT DOCUMENTS

| | | | |
|---|---|---|---|
| 7,517,897 | B2 | 4/2009 | Eriksson et al. |
| 7,550,494 | B2 | 6/2009 | Wu et al. |
| 7,572,921 | B2 | 8/2009 | Kim et al. |
| 7,589,114 | B2 | 9/2009 | Brunette |
| 7,589,115 | B2 | 9/2009 | Kelly et al. |
| 2003/0008848 | A1 | 1/2003 | Fleck et al. |
| 2003/0232817 | A1 | 12/2003 | Fleck et al. |
| 2004/0006011 | A1 | 1/2004 | Gour et al. |
| 2006/0025447 | A1 | 2/2006 | Wang et al. |
| 2006/0229287 | A1 | 10/2006 | Brunette |
| 2012/0178734 | A1 | 7/2012 | Kowalski et al. |
| 2012/0252817 | A1 | 10/2012 | Lemieux et al. |

FOREIGN PATENT DOCUMENTS

| | | |
|---|---|---|
| JP | 63270665 | 11/1988 |
| JP | 63270667 A | 11/1988 |
| JP | 04273877 A | 9/1992 |
| JP | 5188631 A | 7/1993 |
| WO | 9518794 A1 | 7/1995 |
| WO | 9839303 A1 | 9/1998 |
| WO | 9911258 A1 | 3/1999 |
| WO | 9949856 A2 | 10/1999 |
| WO | 0107440 A1 | 2/2001 |
| WO | 0130781 A2 | 5/2001 |
| WO | 2004041273 A1 | 5/2004 |
| WO | 2004041827 A2 | 5/2004 |
| WO | 2008065393 A1 | 6/2008 |
| WO | 2009068194 A2 | 6/2009 |
| WO | 2009069095 A2 | 6/2009 |
| WO | 2009069100 A1 | 6/2009 |
| WO | 2009069792 A1 | 6/2009 |

OTHER PUBLICATIONS

Becker et al., Soluble Intercellular Adhesion Molecule-1 Inhibits MHC-Restricted Specific T Cell/Tumor Interation; The Journal of Immunol. Dec. 1993, 151, pp. 7224-7232.
Beers et al., Crohn's Disease; Ulcerative Colitis; Psoriasis; Adult respiratory distress syndrome, The Merck Manual of Diagnosis and Therapy, Seventeenth Edition (online), 1999.
Boschelli, D. H., et al; "3-Alkoxybenzo[b]thiophene-2-carboxamides as Inhibitors of Neutrophil-Endothelial Cell Adhesion"; J. Med. Chem, 1994., 37, 717.
Boschelli, D. H., et al; "Inhibition of E-Selectin-, ICAM-1-, and VCAM-1-Mediated Cell Adhesion by Benzo[b] thiophene-, Benzofuran-, Indole-, and Naphthalene-2-carboxamides: Identification of PD 144795 as an Antiinflammatory Agent"; J. Med. Chem., 1995, 38, 4597-4614.
Bremner et al.. Therapy of Crohn's Disease in childhood, Expert Opinion Pharmacother. 3(7). pp. 809-825.2002.
Cosimi et al., In Vivo Effects of Monoclonal Antibody to ICAM-1 (CD54) in Nonhuman Primates With Renal Allografts 1; Journal of Immunology; 1990; vol. 144; pp. 4604-4612.
Diamond, MS., The dynamic regulation of integrin adhesiveness; Current Biology; 1994; vol. 4; No. 6; pp. 506-517.
Elgert, Autoimmunity, Immunology: Understanding the Immune System, pp. 315-330, 1996.
English translation of JP 63270665, 1988.
Gorski et al., The role of cell adhesion molecules in immunopathology; Immunology Today; 1994; vol. 15; pp. 251-255.
Halim, et al; "342-(3,5-Dimethylpyrazoly1)} Succinic Anhydride: Synthone for the Synthesis of Some Heterocycles with Potential Pharmaceutical Activity"; Monatshefte fuer Chemie, 1994, 125 1437-1442.
Kavanaugh et al., UGH, et al; Treatment of Refractory Rheumatoid Arthritis with a Monoclonal Antibody to Intercellular Adhesion Molecule 1; Arthritis & Rheumatism; Jul. 1994; vol. 37; No. 7; pp. 992-1004.
Kishimoto et al; Integrins, ICAMs, and Selectins: Role and Regulation of Adhesion Molecules in Neutrophil Recruitment to Inflammatory Sites; Advances in Pharmacology; 1994; vol. 25; pp. 117-138.
LeMauff et al., Effect of Anti-LFA1 (CD11a) Monocional Antibodies in Acute Regection inHuman Kidney Transplantation, Transplantation, Aug. 1991, 52, pp. 291-295.
Makagiansar et al., Inhibition of LFA-1/ICAM-1 and VLA-4/VCAM-1 as a Therapeutic Approach to Inflammation and Autoimmune Diseases, Medicinal Research Reviews, vol. 22, No. 2, 146-167, 2002.
Musza, L. L., et al, "Potent New Cell Adhesion Inhibitory Compounds from the Root of Trichilia rubra" ; Tetrahedron, 1994, 50, 11369-11378.
Patent Abstract of Japan; Publication No. 4273877; Publication Date: Sep. 30, 1992; Applicant: Sumitomo Pharma.
Patent Abstract of Japan; Publication No. 5188631; Publication Date: Jul. 30, 1993; Applicant: Mita Industrial Co. Ltd.
Patent Abstract of Japan; Publication No. 63270665; Publication Date: Aug. 11, 1998; Applicant: Wakamoto Pharmacuet Co. Ltd.
Robinson et al., Medical Therapy of Inflammatory Bowel Disease for the 21st Century. Eur. J. Surg. Suppl 582: 90-98. 1998.
Roep et al., Soluble forms of intercellular adhesion molecule-I in insulin-dependent diabetes mellitus; The Lancet, 1994, 343, pp. 1590-1593.
Rothlein et al; Leukocyte Adhesion in Inflammation: From Discovery to the Clinic; Adhesion Molecules; Wegner, C. D., ed.; 1994; pp. 1-8.
Sanfilippo, P. J., et al; "Novel Thiazole Based Heterocycles as Inhibitors of LFA-1/ICAM-1 Mediated Cell Adhesion"; J. Med. Chem. 1995, 38, 1057-1059.
Singh et al., Immune Therapy in inflammatory bowel disease and models of colitis, British Journal of Surgery, 88, 1558-1569, 2001.
Springer, et al., Adhesion receptors of the immune system; Nature; 1990; vol. 346; pp. 425-434.
Takayama, et al; "Quantitative Structure-activity Relationships of Antifungal 1-(3,5- Dichlorophenyl)-2,5-pyrrolidinediones and 3-(3,5-Diochlorophenyl)-2,4-oxazolidinediones"; Agric. Biol. Chem. 1982, 46, 2755-8.
Tanaka et al., Potential Immunosuppressive and Antiinflammatory Activities of Malaysian Medicinal Plants Characterized by Reduced Cell Surface Expression of Cell Adhesion Molecules, Phytotherapy Research, 15, pp. 681-686 (2001).
Toyofuku et al., CA 111:7403, 1989.
Wachlin et al., IL-1beta, IFN-1gamma and TNF-alpha increase vulnerability of pancreatic beta cells to autoimmune destruction, Journal of Autoimmunity, 20, pp. 303-312, 2003.
Wu, et al; Second-Generation Lymphocyte Function-Associated Antigen-I Inhibitors: 1H-Imidazo[1,2-a] imidazol-2-one Derivatives; Journal of Medicinal Chemistry, American Chemical Society, Washington, US; vol. 47; Sep. 29, 2004; pp. 5356-5366.

* cited by examiner

DERIVATIVES OF 6,7-DIHYDRO-5H-IMIDAZO[1,2-ALPHA] IMIDAZOLE-3-CARBOXYLIC ACID AMIDES

This application claims the benefit of U.S. Provisional Application No. 60/990,960, filed Nov. 29, 2007, and also U.S. Provisional Application No. 61/047,957, filed Apr. 25, 2008.

BACKGROUND OF THE INVENTION

1. Technical Field

The present invention relates generally to a series of novel derivatives of 6,7-dihydro-5H-imidazo[1,2-a]imidazole-3-carboxylic acid amides, the synthesis of these compounds their use in the treatment of inflammatory disease and pharmaceutical compositions comprising these compounds.

2. Background Information

Research spanning the last decade has helped to elucidate the molecular events attending cell-cell interactions in the body, especially those events involved in the movement and activation of cells in the immune system (see generally, von Andrian U H, et al. *N Engl J Med* 2000; 343(14):1020-1034). Cell surface proteins, and especially the Intercellular Cellular Adhesion Molecules ("ICAMs") and "Leukointegrins", including LFA-1, MAC-1 and p150,95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently accepted that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2 or ICAM-3 which are expressed on blood vessel endothelial cell surfaces and on other leukocytes. The interaction of the ICAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117-138 and Diamond, M.; Springer, T. *Current Biology,* 1994, 4, 506-532.

A group of individuals has been identified which lack the appropriate expression of Leukointegrins, a condition termed "Leukocyte Adhesion Deficiency I" (Anderson, D. C.; et al., *Fed. Proc.* 1985, 44, 2671-2677 and Anderson, D. C.; et al., *J. Infect. Dis.* 1985, 152, 668-689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it was believed that antagonism of CD18/CD11/ICAM interactions will also inhibit an inflammatory response. The role of LFA-1 in immune cell trafficking and activation is well established and supported by studies with LFA-1 deficient mice and blocking anti-LFA-1 antibodies. In vitro, LFA-1 deficient lymphocytes are characterized by defects in aggregation and proliferation. In vivo parallel deficits in delayed type hypersensitivity (DTH) responses are observed. In animal models of organ transplantation, anti-LFA-1 antibodies have shown efficacy. Taken together these studies provide support for the role of LFA-1 in initiating and/or propagating inflammatory responses (Giblin, P. A. et al. *Curr. Pharm. Design,* 2006, 12: 2771-2795).

It has been demonstrated that the antagonism of the interaction between the ICAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to ICAMs or Leukointegrins include antigen or mitogen-induced lymphocyte proliferation, homotypic aggregation of lymphocytes, T-cell mediated cytolysis and antigen-specific induced tolerance. The relevance of the in vitro studies is supported by in vivo studies with antibodies directed against ICAM-1 or LFA-1. In numerous models of transplant, including cardiac, bowel, islet and cornea, prolongation of graft survival was observed following treatment with anti-LFA-1, alone or in combination anti-ICAM-1 (see for example Nakakura E K et al., *Transplantation* 1993; 55(2):412-417). Anti-LFA-1 antibodies have also shown benefit in animal models of multiple sclerosis, lupus and inflammatory arthritis (see for example Kobayashi Y et al., *Cell Immunol* 1995; 164(2):295-305). The first LFA-1-targeted therapeutics to be tested clinically were anti-LFA-1 antibodies. Odulimomab showed efficacy in clinical trials of bone marrow transplant (Stoppa A M et al., *Transpl Int* 1991; 4(1):3-7) and in kidney transplant clinical trials (Hourmant M et al. *Transplantation* 1994; 58(3):377-380). The humanized anti-LFA-1 antibody Raptiva® (anti-CD11a, hu1124, efalizumab), marketed for psoriasis has provided the clinical proof of concept for the role of LFA-1 (Leonardi C L et al., *J Am Acad Dermatol* 2005; 52(3 Pt 1):425-433).

Thus, the prior art has demonstrated that large protein molecules which antagonize the binding of the ICAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

It follows that small molecules having the similar ability as large protein molecules to directly and selectively antagonize the binding of the ICAMs to the Leukointegrins would make preferable therapeutic agents.

Several small molecules have been described in the literature that affect the interaction of ICAMs and Leukointegrins. For example, U.S. Pat. No. 6,355,664 (and the corresponding WO 98/39303), 6,710,664, 6,977,267, 7,199,125 and WO 2006065908 disclose a class of small molecules, having a hydantoin core, that are inhibitors of the interaction of LFA-1 and ICAM-1. U.S. Pat. No. 6,492,408 (and corresponding WO 01/07440 A1), U.S. Pat. No. 6,844,360, U.S. Pat. No. 6,852,748, WO 2006/107941 and WO 2007/027233 all discloses compounds having this same activity that instead have a 6,7-dihydro-5H-imidazo[1,2-a]imidazole core. In addition, U.S. Pat. Nos. 6,673,825 and 6,974,815 and US Patent Application Publication 20060052434 disclose small molecules having a urazole, hexahydrobenzimidazole and pyrrolizine core respectively that are inhibitors of the interaction of LFA-1 and ICAM-1.

BRIEF SUMMARY OF THE INVENTION

The invention comprises a novel class of derivatives of 6,7-dihydro-5H-imidazo[1,2-a]imidazole-3-carboxylic acid amides and methods for making the same. These compounds are useful for the treatment of inflammatory conditions in that they exhibit good inhibitory effect upon the interaction of ICAMs and Leukointegrins. Thus, the invention further comprises the use of these compounds for the treatment of inflammatory conditions and pharmaceutical compositions comprising the same as active ingredients.

DETAILED DESCRIPTION OF THE INVENTION

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl. All alkyl groups shall be understood as being branched or unbranched, where structurally possible and unless otherwise specified. Other more specific definitions are as follows:

The term "$C_{3-6}$cycloalkyl" means a cyclic saturated hydrocarbon monovalent radical containing 3-6 carbons in the cyclic ring, such as cyclopropyl, cyclobutyl, cyclopentyl and cyclohexyl.

The terms "heterocycle" or "heterocyclyl" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolidinonyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, 5-oxo-4,5-dihydroisoxazol-3-yl, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N,O and S. Unless otherwise stated, such heteroaryls include thienyl, furanyl, isoxazolyl, oxazolyl, thiazolyl, thiadiazolyl, oxadiazolyl, 3-hydroxy-1H-pyrazol-5-yl, 5-oxo-4,5-dihydro-1,2,4-oxadiazol-3-yl, 5-oxo-4,5-dihydro-1,2,4-thiadiazol-3-yl, 3-hydroxyisoxazol-5-yl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl. Any nitrogen heteroatom in the heteroaryl ring can be an oxidized nitrogen atom, e.g., forming a quaternized nitrogen atom.

The term "halogen" as used in the present specification shall be understood to mean bromine, chlorine, fluorine or iodine, preferably fluorine or chlorine.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

Specific compounds of the present invention may be identified in the present specification by chemical name and/or chemical structure. In the event of any conflict between the chemical name and chemical structure, the chemical structure will control.

In general, all tautomeric and isomeric forms and mixtures thereof, for example, the individual geometric isomers, stereoisomers, enantiomers, diastereomers, racemates, racemic or non-racemic mixtures of stereoisomers, mixtures of diastereomers, or mixtures of any of the foregoing, of a depicted chemical structure or compound is intended, unless the specific stereochemistry or isomeric form is specifically indicated in the compound name or structure. Any compound of this invention containing one or more asymmetric carbon atoms may occur as a racemate or racemic mixture, single enantiomer, diastereomeric mixture and individual diastereomer, or mixtures of any of the foregoing. All such isomeric forms of these compounds are expressly included in the present invention. Each stereogenic carbon may be in the R or S configuration, or a combination of configurations. Some of the compounds of formula (I) can exist in more than one tautomeric form. The invention includes methods using all such tautomers.

In further detail, the compounds of the invention and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures using methods well know in the art. For example, individual stereoisomers of compounds may be prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in *Chiral Separation Techniques: A Practical Approach* (2nd Ed.), G. Subramanian (ed.), Wiley-VCH, 2000; T. E. Beesley and R. P. W. Scott, *Chiral Chromatography*, John Wiley & Sons, 1999; and Satinder Ahuja, *Chiral Separations by Chromatography*, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

The compounds of the invention are meant to embrace compounds of Formula (I) as herein described, as well as the pharmaceutically acceptable salts thereof. The term "salt" means an ionic form of the parent compound or the product of the reaction between the parent compound with a suitable acid or base to make the acid salt or base salt of the parent compound. Salts of the compounds of the present invention can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically acceptable acid addition salts and pharmaceutically acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

Examples of suitable acids for preparing salts include hydrochloric, hydrobromic, carbonic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—($C_{1-4}$ alkyl)$_4^+$ salts.

In an embodiment, there are provided compounds of formula I

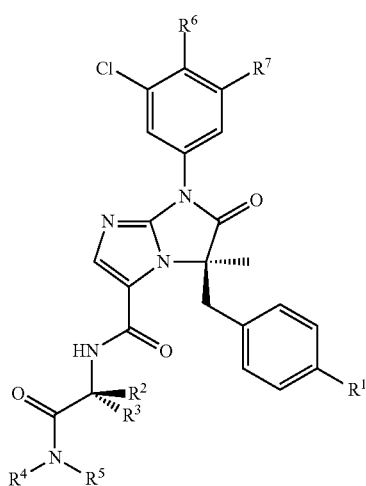

wherein:
$R^1$ is selected from —CN, —OCF$_3$, halogen, heteroaryl, optionally substituted with halogen or $C_{1-3}$alkyl optionally substituted with halogen and phenyl, optionally substituted with halogen;

$R^2$ is selected from:
(A) H,
(B) $C_{1-3}$alkyl optionally substituted with one or two groups selected from:
  a) $C_{3-6}$cycloalkyl,
  b) —OR$^9$,
  c) —NR$^9$R$^{10}$,
  d) —SOR$^9$,
  e) —SO$_2$R$^9$,
  f) —C(O)NH$_2$,
  g) heteroaryl optionally substituted with $C_{1-2}$alkyl,
  h) heterocyclyl,
  i) phenyl,
  j) —CO$_2$R$^9$.
  k) —OPO(OH)$_2$, and
  l) —OSO$_2$(OH);
(C) $C_{3-6}$cycloalkyl,
(D) heteroaryl, and
(E) phenyl, optionally substituted with halogen, —OR$^9$, —CN or —CF$_3$;

$R^3$ is H or $C_{1-3}$alkyl; or
$R^2$ and $R^3$, together with the carbon they are bonded to, form a saturated hydrocarbon ring of 3 to 7 carbon atoms and wherein one carbon atom in said hydrocarbon ring may be optionally replaced by —O—, —S—, —S(O)—, —SO$_2$—, —NC(O)R$^9$— or —NR$^9$—;

$R^4$ is selected from:
(A) $C_{1-5}$alkyl substituted with one or two groups selected from:
  a) —CF$_3$,
  b) —C(O)OR$^9$,
  c) —C(O)NR$^9$R$^{10}$,
  d) —C(S)NR$^9$R$^{10}$,
  e) —NR$^9$R$^{10}$
  f) —N(R$^9$)C(O)R$^{10}$
  g) —C(O)NH(CH$_2$)$_2$—O—(CH$_2$)$_2$OH,
  h) —OR$^9$,
  i) phenyl optionally substituted with halogen, —NR$^9$R$^{10}$, —OR$^9$, $C_{3-5}$cycloalkyl or $C_{1-5}$alkyl, wherein said $C_{1-5}$alkyl is optionally substituted with —F, —NR$^9$R$^{10}$ or —OR$^9$,
  j) heteroaryl optionally substituted with halogen, —NR$^9$R$^{10}$, —OR$^9$, $C_{3-5}$cycloalkyl or $C_{1-5}$alkyl, wherein said $C_{1-5}$alkyl is optionally substituted with —F, —NR$^9$R$^{10}$ or —OR$^9$,
  k) —SO$_2$NR$^9$R$^{10}$,
  l) —SO$_2$R$^9$, and
  m) —SO$_2$Het, wherein Het is selected from heterocyclyl and heteroaryl;
(B) $C_{3-6}$cycloalkyl substituted with one or two groups selected from:
  a) —C(O)OR$^9$,
  b) —C(O)NR$^9$R$^{10}$,
  c) —C(S)NR$^9$R$^{10}$,
  d) —OR$^9$,
  e) phenyl optionally substituted with halogen, —NR$^9$R$^{10}$, —OR$^9$, $C_{3-5}$cycloalkyl or $C_{1-5}$alkyl, wherein said $C_{1-5}$alkyl is optionally substituted with —F, —CF$_3$, —NR$^9$R$^{10}$ or —OR$^9$, and
  f) heteroaryl optionally substituted with:
    1) —NR$^9$R$^{10}$,
    2) —NHC(O)R$^9$,
    3) —NHSO$_2$R$^9$,
    4) —OR$^9$,
    5) —C$_{1-2}$alkylNR$^9$R$^{10}$,
    6) —C$_{1-2}$alkylNR$^{10}$(CO)NR$^9$R$^{10}$,
    7) —C$_{1-2}$alkylNR$^{10}$(CO)R$^9$, 8) —$C_{1-2}$alkylOR$^9$,
9) —$C_{1-2}$alkylNHSO$_2$R$^9$,
10) —CO$_2$R$^9$,
11) —COCH$_3$,
12) halogen,
13) —SO$_2$R$^9$,
14) —$C_{3-5}$cycloalkyl,
15) -cyano and
16) $C_{1-5}$alkyl, wherein said $C_{1-5}$alkyl is optionally substituted with halogen, —CF$_3$, —NR$^9$R$^{10}$ or —OR$^9$;

(C) heteroaryl optionally substituted with one to two groups selected from:
  a) —R$^9$ optionally substituted with halogen or —OH,
  b) —CF$_3$,
  c) —OR$^9$,
  d) —NR$^9$R$^{10}$,
  e) halogen,
  f) —C(O)NR$^9$R$^{10}$,
  g) —C(O)NH(CH$_2$)$_2$OH,
  h) —$C_{1-3}$alkylNR$^9$R$^{10}$;

(D) —$C_{0-5}$alkylheterocyclyl wherein the heterocycle is optionally substituted with —C(O)CH$_3$, oxo, or —$C_{1-3}$C(S)NH$_2$, R$^5$ is selected from H, $C_{1-3}$alkyl, —(CH$_2$)$_2$OH and —(CH$_2$)$_2$OCH$_3$; or R$^4$ and R$^5$ constitute a saturated hydrocarbon bridge of 3 to 6 carbon atoms which together with the N they are bonded to, form a heterocyclic ring, and wherein:
a) one or two carbon atoms in said heterocyclic ring are mono or disubstituted with R$^8$ and
b) one carbon atom in said heterocyclic ring is optionally replaced by —O—, —S—, —S(O)—, —SO$_2$— or —NC(O)CH$_3$—;

R$^6$ is H or halogen;
R$^7$ is halogen or —CF$_3$;
R$^8$ is selected from $C_{1-3}$alkyl, halogen, —OH, —CH$_2$OH, —C(O)R$^9$, —SO$_2$R$^9$, —C(O)CH$_2$CO$_2$R$^9$, —NR$^9$R$^{10}$, —C(O)NR$^9$R$^{10}$, —CN, —C(O)OR$^9$, —N(R$^9$)C(O)R$^{10}$, heterocyclyl and heteroaryl, wherein said heterocyclyl and heteroaryl are optionally substituted with $C_{1-4}$alkyl, —OH or —CF$_3$;

R$^9$ is H or $C_{1-5}$alkyl or $C_{3-4}$cycloalkyl, which $C_{1-5}$alkyl is optionally substituted with —OH;
R$^{10}$ is —H or —CH$_3$; or
R$^9$ and R$^{10}$ constitute a saturated hydrocarbon bridge of 3 to 6 carbon atoms which together with the N they are bonded to, form a heterocyclic ring, wherein one carbon atom in said heterocyclic ring may be optionally monosubstituted with —OH or wherein one carbon atom in said heterocyclic ring may be optionally replaced by —O—, —S—, —SO—, —SO$_2$—, —NH—, —NCH$_3$—, or —NC(O)CH$_3$—;

or a pharmaceutically acceptable salt thereof.

In another embodiment are compounds of the formula I wherein:

R$^1$ is selected from —CN, —OCF$_3$, —CF$_3$, —Cl, —Br and phenyl, pyrimidinyl and triazolyl, wherein said phenyl ring is optionally substituted with —F;

R$^2$ is selected from:
(A) H,
(B) $C_{1-2}$alkyl optionally substituted with one or two groups selected from:
  a) —OR$^9$,
  b) —S(O)R$^9$,
  c) —SO$_2$R$^9$,
  d) —C(O)NH$_2$,
  e) —CO$_2$R$^9$.
  f) —OPO(OH)$_2$,
  g) —OSO$_2$(OH),
  h) triazolyl,
  i) imidazolyl optionally substituted with $C_{1-2}$alkyl, and
  j) —NR$^9$R$^{10}$;

R$^3$ is H or —CH$_3$; or
R$^2$ and R$^3$, together with the carbon they are bonded to, form a saturated hydrocarbon ring of 3 to 6 carbon atoms and wherein one carbon atom in said hydrocarbon ring may be optionally replaced by —O—, —SO$_2$—, —NC(O)R$^9$— or —NR$^9$—;

R$^4$ is selected from:
(A) $C_{1-5}$alkyl substituted with one or two groups selected from:
  a) —CF$_3$,
  b) —C(O)OR$^9$,
  c) —C(O)NR$^9$R$^{10}$,
  d) —C(S)NH$_2$,
  e) —NR$^9$R$^{10}$,
  f) —N(R$^9$)C(O)R$^{10}$,
  g) —C(O)NH(CH$_2$)$_2$O(CH$_2$)$_2$OH,
  h) —OR$^9$,
  i) phenyl, and
  j) heteroaryl, optionally substituted with —OH;

(B) $C_{3-5}$cycloalkyl substituted with one group selected from:
  a) —C(O)OR$^9$,
  b) —C(O)NR$^9$R$^{10}$,
  c) —C(S)NR$^9$R$^{10}$, and
  d) heteroaryl optionally substituted with:
    1) —NR$^9$R$^{10}$,
    2) —NHC(O)R$^9$,
    3) —NHSO$_2$R$^9$,
    4) —OR$^9$,
    5) —$C_{1-2}$alkylNR$^9$R$^{10}$,
    6) —$C_{1-2}$alkylNR$^{10}$(CO)NR$^9$R$^{10}$,
    7) —$C_{1-2}$alkylNR$^{10}$(CO)R$^9$,
    8) —$C_{1-2}$alkylOR$^9$,
    9) —$C_{1-2}$alkylNHSO$_2$R$^9$,
    10) —CO$_2$R$^9$,
    11) —COCH$_3$,
    12) halogen,
    13) —SO$_2$R$^9$,
    14) —$C_{1-2}$alkyl optionally substituted with halogen,
    15) -cyano and
    16) —$C_{3-5}$cycloalkyl;

(C) heteroaryl optionally substituted with one to two groups selected from:
  a) —R$^9$ optionally substituted with halogen or —OH,
  b) —C(O)NR$^9$R$^{10}$,
  c) —C(O)NH(CH$_2$)$_2$OH,
  d) —NR$^9$R$^{10}$
  e) —$C_{1-3}$alkylNR$^9$R$^{10}$, and
  f) halogen;

(D) —$C_{0-5}$alkylheterocyclyl wherein the heterocycle is optionally substituted with —C(O)CH$_3$, oxo, or —$C_{1-3}$C(S)NH$_2$;

R$^5$ is selected from H, and $C_{1-3}$alkyl; or
R$^4$ and R$^5$ constitute a saturated hydrocarbon bridge of 3 to 5 carbon atoms which together with the N they are bonded to, form a heterocyclic ring, and wherein:
a) one or two carbon atoms in said heterocyclic ring are mono or disubstituted with R$^8$, and
b) one carbon atom in said heterocyclic ring may be optionally replaced by —NC(O)CH$_3$—;

R$^6$ is H, —F or —Cl;
R$^7$ is —Cl;
R$^8$ is selected from —CH$_3$, —F, —OH, —CH$_2$OH, —SO$_2$CH$_3$, —N(CH$_3$)$_2$, —C(O)NR$^9$R$^{10}$, —C(O)

$CH_2CO_2Et$, —CN, —C(O)OR$^9$, —N(R$^9$)C(O)R$^{10}$, heterocyclyl and heteroaryl, wherein said heteroaryl is optionally substituted with $C_{1-4}$alkyl or —OH;
R$^9$ is H, $C_{1-5}$alkyl or $C_{3-4}$cycloalkyl, which $C_{1-5}$alkyl is optionally substituted with —OH; and
R$^{10}$ is H or —CH$_3$; or
R$^9$ and R$^{10}$ constitute a saturated hydrocarbon bridge of 3 to 6 carbon atoms which together with the N they are bonded to, form a heterocyclic ring, wherein one carbon atom in said heterocyclic ring may be optionally monosubstituted with —OH or wherein one carbon atom in said heterocyclic ring may be optionally replaced by —O—, —NCH$_3$— or —NC(O)CH$_3$—;
or a pharmaceutically acceptable salt thereof.

In a further embodiment are compounds of the formula I wherein:
R$^1$ is selected from —CN, —OCF$_3$, —CF$_3$, —Cl, —Br, phenyl, pyrimidinyl and triazolyl wherein said phenyl ring is optionally substituted with —F;
R$^2$ is selected from:
(A) H,
(B) $C_{1-2}$alkyl optionally substituted with one or two groups selected from:
  a) —OH,
  b) —OCH$_3$,
  c) —S(O)R$^9$,
  d) —SO$_2$R$^9$,
  e) —C(O)NH$_2$,
  f) —CO$_2$R$^9$,
  g) —OPO(OH)$_2$,
  h) —OSO$_2$(OH)
  h) triazolyl,
  i) imidazolyl optionally substituted with $C_{1-2}$alkyl, and
  j) —NR$^9$R$^{10}$;
R$^3$ is H or —CH$_3$; or
R$^2$ and R$^3$, together with the carbon they are bonded to, form a saturated hydrocarbon ring of 3 to 6 carbon atoms and wherein one carbon atom in said hydrocarbon ring may be optionally replaced by —O—, —SO$_2$—, —NC(O)R$^9$— or —NR$^9$—;
R$^4$ is selected from:
(A) $C_{1-3}$alkyl substituted with one or two groups selected from:
  a) —CF$_3$,
  b) —C(O)OR$^9$,
  c) —C(O)NH$_2$,
  d) —C(S)NH$_2$,
  e) —NHC(O)CH$_3$,
  f) —OR$^9$,
  g) phenyl, and
  h) heteroaryl optionally substituted with —OH,
(B) $C_{3-5}$cycloalkyl substituted with one group selected from:
  a) —CO$_2$CH$_3$,
  b) —CONH$_2$,
  c) —CSNH$_2$, and
  d) heteroaryl optionally substituted with:
    1) —NR$^9$R$^{10}$,
    2) —NHC(O)R$^9$,
    3) —NHSO$_2$R$^9$,
    4) —OR$^9$,
    5) —$C_{1-2}$alkylNR$^9$R$^{10}$,
    6) —$C_{1-2}$alkylNR$^{10}$(CO)NR$^9$R$^{10}$,
    7) —$C_{1-2}$alkylNR$^{10}$(CO)R$^9$,
    8) —$C_{1-2}$alkylOR$^9$,
    9) —$C_{1-2}$alkylNHSO$_2$R$^9$,
    10) —CO$_2$R$^9$,
    11) —COCH$_3$,
    12) halogen,
    13) —SO$_2$R$^9$,
    14) —$C_{1-2}$alkyl optionally substituted with halogen,
    15) -cyano and
    16) —$C_{3-5}$cycloalkyl;
(C) heteroaryl optionally substituted with one to two groups selected from:
  a) —R$^9$ optionally substituted with —F or —OH,
  b) —C(O)NR$^9$R$^{10}$,
  c) —C(O)NH(CH$_2$)$_2$OH,
  d) —NR$^9$R$^{10}$,
  e) —$C_{1-3}$alkylNR$^9$R$^{10}$, and
  f) halogen;
(D) —$C_{0-3}$alkylheterocyclyl wherein the heterocycle is optionally substituted with —C(O)CH$_3$ or oxo;
R$^5$ is selected from H, and —CH$_3$; or
R$^4$ and R$^5$ constitute a saturated hydrocarbon bridge of 3 to 5 carbon atoms which together with the N they are bonded to, form a heterocyclic ring, and wherein:
  a) one or two carbon atoms in said heterocyclic ring are mono or disubstituted with R$^8$ and
  b) one carbon atom in said heterocyclic ring is optionally replaced by —NC(O)CH$_3$—;
R$^6$ is H—F or —Cl;
R$^7$ is —Cl;
R$^8$ is selected from —CH$_3$, —F, —OH, —CH$_2$OH, —SO$_2$CH$_3$, —N(CH$_3$)$_2$, —C(O)NH$_2$, —C(O)N(CH$_3$)$_2$, —CN, —C(O)OR$^9$, —N(R$^9$)C(O)CH$_3$, heterocyclyl and heteroaryl, wherein said heteroaryl is optionally substituted with $C_{1-4}$alkyl or —OH;
R$^9$ is H, $C_{1-4}$alkyl or $C_{3-4}$cycloalkyl, which $C_{1-4}$alkyl is optionally substituted with —OH; and
R$^{10}$ is H or —CH$_3$; or
R$^9$ and R$^{10}$ constitute a saturated hydrocarbon bridge of 3 to 6 carbon atoms which together with the N they are bonded to, form a heterocyclic ring, wherein one carbon atom in said heterocyclic ring may be optionally monosubstituted with —OH or wherein one carbon atom in said heterocyclic ring may be optionally replaced by —O— or —NCH$_3$—;
or a pharmaceutically acceptable salt thereof.

In yet another embodiment are compounds of the formula I wherein:
R$^1$ is selected from —CN, —OCF$_3$, —CF$_3$, —Cl, phenyl, pyrimidinyl and triazolyl;
R$^2$ is selected from:
(A) $C_{1-2}$alkyl optionally substituted with one or two groups selected from:
  a) —OH,
  b) —OCH$_3$,
  c) —S(O)R$^9$,
  d) —SO$_2$R$^9$,
  e) —C(O)NH$_2$,
  f) —CO$_2$R$^9$,
  g) —OPO(OH)$_2$,
  h) —OSO$_2$(OH),
  i) triazolyl,
  j) imidazolyl optionally substituted with $C_{1-2}$alkyl, and
  k) —NR$^9$R$^{10}$;
R$^3$ is H; or
R$^2$ and R$^3$, together with the carbon they are bonded to, form a saturated hydrocarbon ring of 3 to 6 carbon atoms and wherein one carbon atom in said hydrocarbon ring may be optionally replaced by —O—, —SO$_2$— or —NC(O)R$^9$—;
R$^4$ is selected from:
(A) $C_{2-3}$alkyl substituted with pyridinyl, thiazolyl, or pyrrolopyridinyl, and (B) $C_{3-5}$cycloalkyl substituted with one group selected from:
  a) —C(O)NH$_2$,
  b) pyridinyl optionally substituted with:
    1) —NR$^9$R$^{10}$,
    2) —NHC(O)R$^9$,
    3) —NHSO$_2$R$^9$,
    4) —OR$^9$,
    5) —C$_{1-2}$alkylNR$^9$R$^{10}$,
    6) —C$_{1-2}$alkylNR$^{10}$(CO)NR$^9$R$^{10}$,
    7) —C$_{1-2}$alkylNR$^{10}$(CO)R$^9$,
    8) —C$_{1-2}$alkylOR$^9$,
    9) —C$_{1-2}$alkylNHSO$_2$R$^9$,
    10) —CO$_2$R$^9$,
    11) —COCH$_3$,
    12) halogen,
    13) —SO$_2$R$^9$,
    14) —C$_{1-2}$alkyl optionally substituted with halogen, and
    15) -cyano;
  c) oxadiazolyl optionally substituted with, —NR$^9$R$^{10}$, or R$^9$ wherein R$^9$ is optionally substituted with —F or —OH,
  d) imidazolyl optionally substituted with R$^9$ or —CF$_3$,
  e) triazolyl optionally substituted with R$^9$,
  f) oxazolyl optionally substituted with R$^9$ or —CONH$_2$,
  g) thiazolyl optionally substituted with R$^9$,
  h) thiadiazolyl,
  i) pyrimidinyl optionally substituted with —NR$^9$R$^{10}$,
  j) pyridopyrimidinyl,
  k) pyrazinyl optionally substituted with C$_{1-2}$alkyl,
  l) pyridazinyl optionally substituted with C$_{1-3}$alkylNR$^9$R$^{10}$,
  m) naphthyridinyl,
  n) quinazolinyl optionally substituted with halogen,
  o) pyrrolopyridin-6-yl,
  p) quinolinyl,
  q) triazinyl mono- or disubstituted with —NH$_2$,
  r) oxazolopyridinyl,
  s) benzooxazolyl,
  t) tetrazolyl, and
  u) isoxazolyl;
R$^5$ is H; or
R$^4$ and R$^5$ constitute a saturated hydrocarbon bridge of 3 to 5 carbon atoms which together with the N they are bonded to, form a heterocyclic ring, and wherein one carbon atom in said heterocyclic ring is mono or disubstituted with R$^8$;
R$^6$ is H or —F;
R$^7$ is —Cl;
R$^8$ is selected from —F, —OH, —CH$_2$OH, —NHC(O)CH$_3$, —C(O)NH$_2$, —CN, —CO$_2$Et, —CO$_2$H, 3-hydroxy-1H-pyrazol-5-yl, 5-oxo-4,5-dihydro-1,2,4-oxadiazol-3-yl, 5-oxo-4,5-dihydro-1,2,4-thiadiazol-3-yl and tetrazolyl, wherein said tetrazolyl is optionally substituted with C$_{1-4}$alkyl;
R$^9$ is H, C$_{1-4}$alkyl or C$_{3-4}$cycloalkyl and
R$^{10}$ is H or —CH$_3$; or
R$^9$ and R$^{10}$ constitute a saturated hydrocarbon bridge of 3 to 6 carbon atoms which together with the N they are bonded to, form a heterocyclic ring, wherein one carbon atom in said heterocyclic ring is optionally monosubstituted with —OH or wherein one carbon atom in said heterocyclic ring may be optionally replaced by —O—;
or a pharmaceutically acceptable salt thereof.

In yet a further embodiment are compounds of the formula I wherein:
R$^1$ is selected from —CN and —OCF$_3$, —CF$_3$, pyrimidin-5-yl or triazolyl;

R$^2$ is selected from:
(A) C$_{1-2}$alkyl optionally substituted with one or two groups selected from:
  a) —OH,
  b) —OCH$_3$,
  c) —SO$_2$R$^9$,
  d) —C(O)NH$_2$,
  e) —CO$_2$R$^9$, and
  f) —OPO(OH)$_2$,
  g) —OSO$_2$(OH), and
  h) heteroaryl selected from triazol-2-yl or imidazol-4-yl which imidazol-4-yl is optionally substituted with C$_{1-2}$alkyl;
R$^3$ is H; or
R$^2$ and R$^3$, together with the carbon they are bonded to, form a saturated hydrocarbon ring of 3 to 6 carbon atoms and wherein one carbon atom in said hydrocarbon ring is optionally replaced by —O—, —SO$_2$—, or —NC(O)R$^9$—;
R$^4$ is selected from:
(A) C$_2$alkyl substituted with pyridin-2-yl, and
(B) Cyclopropyl substituted with one group selected from:
  a) —C(O)NH$_2$,
  b) pyridin-2-yl optionally substituted with:
    1) —NR$^9$R$^{10}$,
    2) —NHC(O)R$^9$,
    3) —OR$^9$,
    4) —C$_{1-2}$alkylNR$^9$R$^{10}$,
    5) —C$_{1-2}$alkylNR$^{10}$(CO)NR$^9$R$^{10}$,
    6) —C$_{1-2}$alkylNR$^{10}$(CO)R$^9$,
    7) —C$_{1-2}$alkylOR$^9$,
    8) —CO$_2$R$^9$,
    9) —COCH$_3$,
    10) halogen,
    11) —C$_{1-2}$alkylNHSO$_2$R$^9$,
    12) —SO$_2$R$^9$,
    13) —C$_{1-2}$alkyl;
  c) 1,2,4-oxadiazolyl substituted with R$^9$, —CHF$_2$, C$_{1-2}$alkylOH or —NR$^9$R$^{10}$
  d) imidazolyl optionally substituted with R$^9$ or —CF$_3$,
  e) 1,2,4-triazol-3-yl, optionally substituted with R$^9$,
  f) oxazolyl optionally substituted with R$^9$ or —CONH$_2$,
  g) thiazol-2-yl optionally substituted with R$^9$,
  h) thiazol-4-yl optionally substituted with —CH$_3$,
  i) 1,3,4-thiadiazol-2-yl,
  j) pyrimidinyl optionally substituted with —NH$_2$,
  k) pyrido[2,3-d]pyrimidin-2-yl,
  l) pyrazin-2-yl optionally substituted with C$_{1-2}$alkyl,
  m) pyridazin-3-yl,
  n) naphthyridin-2-yl,
  o) quinazolin-2-yl optionally substituted with halogen,
  p) 1H-pyrrolo[2,3-β]pyridin-6-yl,
  q) quinolin-2-yl,
  r) oxazolopyridin-2-yl, and
  s) benzooxazol-2-yl;
R$^5$ is H; or
R$^4$ and R$^5$ constitute a saturated hydrocarbon bridge of 3 to 5 carbon atoms which together with the N they are bonded to, form a heterocyclic ring, and wherein one carbon atom in said heterocyclic ring is mono or disubstituted with R$^8$;
R$^6$ is H or F;
R$^7$ is Cl;
R$^8$ is selected from —F, —OH, —NHC(O)CH$_3$, —C(O)NH$_2$, —CN, —CO$_2$H, 5-oxo-4,5-dihydro-1,2,4-oxadiazol-3-yl, and tetrazolyl, wherein tetrazolyl is optionally substituted with C$_{1-4}$alkyl;
R$^9$ is H, C$_{1-4}$alkyl or C$_{3-4}$cycloalkyl and
R$^{10}$ is H or —CH$_3$; or $R^9$ and $R^{10}$ constitute a saturated hydrocarbon bridge of 3 to 6 carbon atoms which together with the N they are bonded to, form a heterocyclic ring, wherein one carbon atom in said heterocyclic ring is optionally monosubstituted with —OH or wherein one carbon atom in said heterocyclic ring may be optionally replaced by —O—;
or a pharmaceutically acceptable salt thereof.

In an even further embodiment are compounds of the formula I wherein:
$R^1$ is selected from —CN and —OCF$_3$ or pyrimidin-5-yl;
$R^2$ is selected from:
(A) C$_{1-2}$alkyl optionally substituted with one group selected from:
  a) —OH,
  b) —CO$_2$H,
  c) —CONH$_2$,
  d) —OPO(OH)$_2$ and
  e) —OSO$_2$(OH);
$R^3$ is H; or
$R^2$ and $R^3$, together with the carbon they are bonded to, form a cyclopropyl or cyclohexyl ring wherein one carbon atom in said cyclohexyl ring is replaced with —NC(O)R$^9$— or —SO$_2$—;

$R^4$ is cyclopropyl substituted with one group selected from:
(A) pyridin-2-yl optionally substituted with:
  a) —NHC(O)R$^9$,
  b) —CH$_2$NH$_2$,
  b) —CH$_2$NHC(O)R$^9$,
  c) —CH$_2$NHSO$_2$R$^9$,
  d) —CO$_2$H,
  e) —NR$^5$R$^{10}$, or
  f) —OR$^9$;
(B) pyridazin-3-yl,
(C) pyrimidin-2-yl,
(D) naphthyridin-2-yl,
(E) quinazolin-2-yl optionally substituted with chlorine,
(F) 1H-pyrrolo[2,3-β]pyridin-6-yl,
(G) 2-isopropyl-oxazol-4-yl,
(H) 1-isopropyl-1H-imidazol-4-yl, or
(I) thiazol-2-yl;
$R^5$ is H;
$R^6$ is H or F;
$R^7$ is Cl;
$R^9$ is H, —CH$_3$ or cyclopropyl;
$R^{10}$ is H or —CH$_3$;
or a pharmaceutically acceptable salt thereof.

In another embodiment there is provided the compounds in the table below and the pharmaceutically acceptable salts thereof:

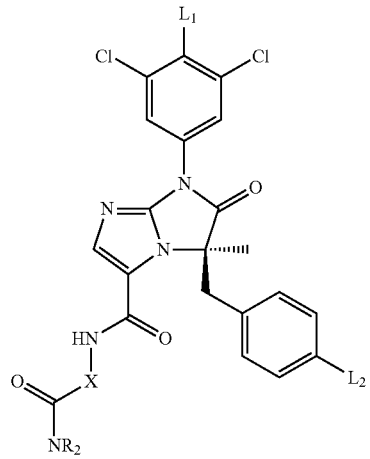

| Cpd # | NR$_2$ | X | L$_1$ | L$_2$ |
|---|---|---|---|---|
| 1 | piperidine-tetrazole | isopropyl | H | CN |
| 2 | (pyridin-2-yl)ethylamine | isopropyl | H | CN |

-continued
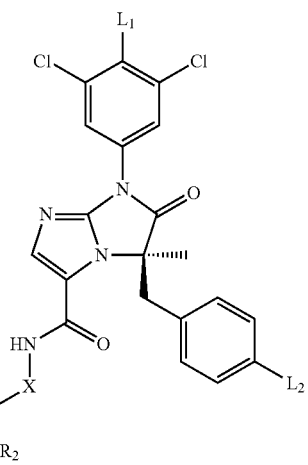
| Cpd # | NR2 | X | L1 | L2 |
|---|---|---|---|---|
| 3 | (S)-1-(pyridin-2-yl)ethylamino | cyclopropyl | H | CN |
| 4 | (R)-3-(5-oxo-4,5-dihydro-1,2,4-oxadiazol-3-yl)pyrrolidin-1-yl | cyclopropyl | H | OCF3 |
| 5 | (R)-3-(2H-tetrazol-5-yl)pyrrolidin-1-yl | cyclopropyl | H | OCF3 |
| 6 | 3,3-difluoroazetidin-1-yl | cyclopropyl | H | CN |
| 7 | (R)-3-(2H-tetrazol-5-yl)piperidin-1-yl | (R)-1-methylethyl | H | OCF3 |

-continued
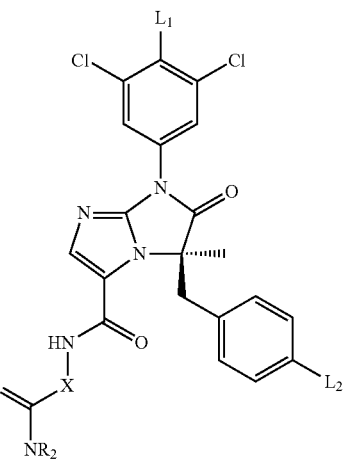
| Cpd # | NR₂ | X | L₁ | L₂ |
|---|---|---|---|---|
| 8 | N-methyl pyrrolidinyl tetrazole | cyclopropyl | H | CN |
| 9 | pyrrolidinyl oxadiazolone | cyclopropyl | H | CN |
| 10 | pyrrolidinyl acetamide | cyclopropyl | H | OCF3 |
| 11 | 3-hydroxypyrrolidinyl | cyclopropyl | H | OCF3 |
| 12 | pyrrolidinyl acetamide | cyclopropyl | H | CN |

-continued
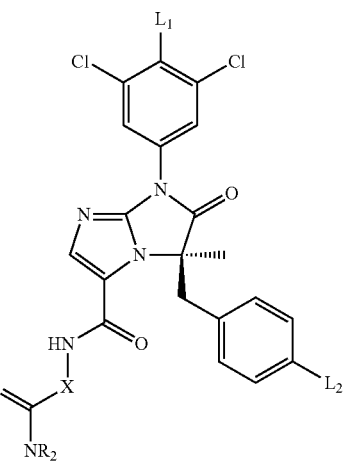
| Cpd # | NR₂ | X | L₁ | L₂ |
|---|---|---|---|---|
| 13 | (S)-piperidine-3-carboxamide (N-linked) | CH(CH₃) | H | CN |
| 14 | (S)-3-acetamidopyrrolidine (N-linked) | cyclopropyl | H | CN |
| 15 | (S)-3-(2-methyltetrazol-5-yl)pyrrolidine (N-linked) | cyclopropyl | H | OCF3 |
| 16 | (S)-3-acetamidopyrrolidine (N-linked) | cyclopropyl | H | OCF3 |
| 17 | 3,3-difluoropyrrolidine (N-linked) | cyclopropyl | H | CN |

-continued
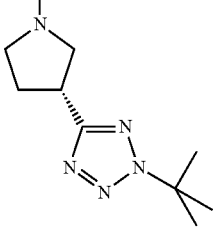
| Cpd # | NR₂ | X | L₁ | L₂ |
|---|---|---|---|---|
| 18 | 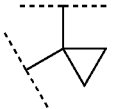 | 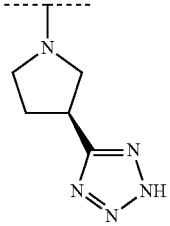 | H | OCF3 |
| 19 | 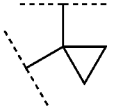 | 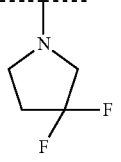 | H | OCF3 |
| 20 | 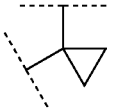 | 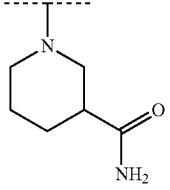 | H | OCF3 |
| 21 | 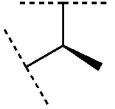 | 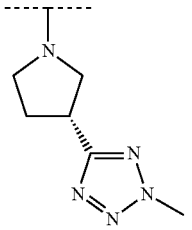 | H | CN |
| 22 | 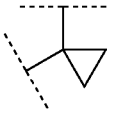 | 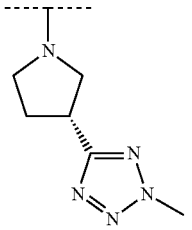 | H | CN |

-continued
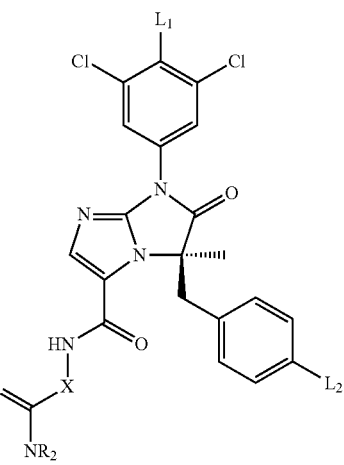
| Cpd # | NR₂ | X | L₁ | L₂ |
|---|---|---|---|---|
| 23 | (S)-3-cyanopyrrolidin-1-yl | 1,1-cyclopropyl | H | OCF3 |
| 24 | 1-(pyridin-2-yl)cyclopropylamino | CH(CH₂OH) | H | CN |
| 25 | 1-(pyridin-2-yl)cyclopropylamino | CH(CH(OH)CH₃) | H | CN |
| 26 | 1-(pyridin-2-yl)cyclopropylamino | 4,4-dioxo-tetrahydrothiopyran-4-yl | H | CN |
| 27 | 1-(pyridin-2-yl)cyclopropylamino | CH(CH₂CH₂C(O)NH₂) | H | CN |

-continued
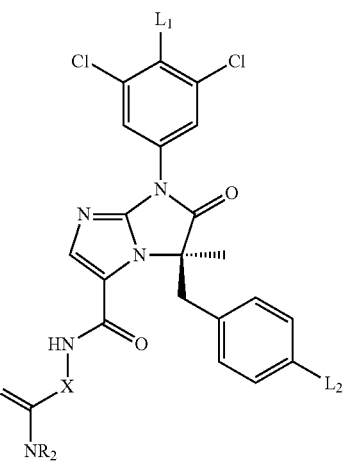
| Cpd # | NR2 | X | L1 | L2 |
|---|---|---|---|---|
| 28 | cyclopropyl-NH-(2-pyridyl) | CH(CH2CH2S(O)2CH3)- | H | CN |
| 29 | cyclopropyl-NH-(2-pyridyl) | CH(CH2OCH3)- | H | CN |
| 30 | CH(CH3)-NH-(2-pyridyl) | 1,1-cyclopropyl | H | OCF3 |
| 31 | cyclopropyl-NH-(2-pyridyl) | 1,1-cyclopropyl | H | CN |
| 32 | cyclopropyl-NH-(2-pyridyl) | CH(CH3)- | H | CN |

-continued
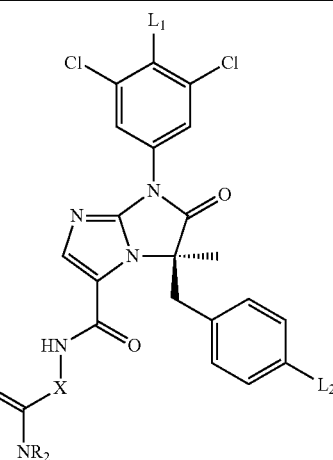
| Cpd # | NR2 | X | L1 | L2 |
|---|---|---|---|---|
| 33 | 1-(4-methoxypyridin-2-yl)cyclopropyl-NH– | cyclopropyl | H | CN |
| 34 | 1-(6-methoxypyridin-2-yl)cyclopropyl-NH– | cyclopropyl | H | CN |
| 35 | 1-(thiazol-2-yl)cyclopropyl-NH– | cyclopropyl | H | CN |
| 36 | 1-(1,3,4-thiadiazol-2-yl)cyclopropyl-NH– | cyclopropyl | H | CN |
| 37 | 1-(3-methyl-1,2,4-oxadiazol-5-yl)cyclopropyl-NH– | cyclopropyl | H | CN |

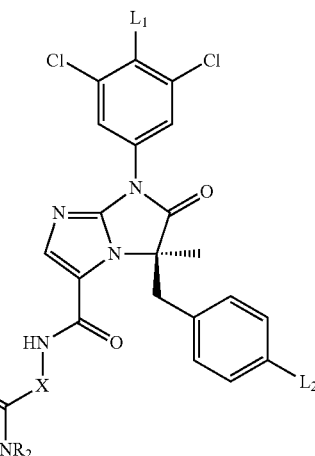
| Cpd # | NR2 | X | L1 | L2 |
|---|---|---|---|---|
| 38 | 1-(3-morpholino-1,2,4-oxadiazol-5-yl)cyclopropyl-NH- | cyclopropyl | H | CN |
| 39 | 1-(6-(dimethylamino)pyridin-3-yl)cyclopropyl-NH- | cyclopropyl | H | OCF3 |
| 40 | 1-(5-(dimethylamino)pyridin-2-yl)cyclopropyl-NH- | cyclopropyl | H | CN |
| 41 | 1-(1-methyl-1H-imidazol-4-yl)cyclopropyl-NH- | spirocyclopropyl | H | CN |

-continued
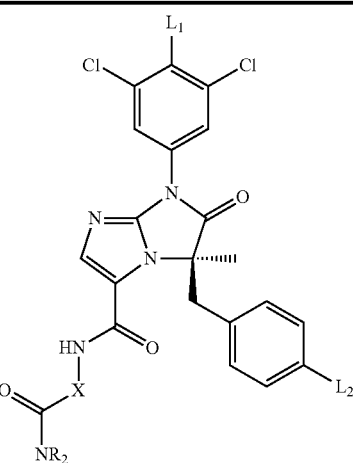
| Cpd # | NR₂ | X | L₁ | L₂ |
|---|---|---|---|---|
| 42 | 1-(4H-1,2,4-triazol-3-yl)cyclopropyl-NH– | cyclopropyl-1,1-diyl | H | CN |
| 43 | 1-(4-(aminomethyl)pyridin-2-yl)cyclopropyl-NH– | cyclopropyl-1,1-diyl | H | OCF3 |
| 44 | 1-(pyridin-2-yl)cyclopropyl-NH– | 1-acetylpiperidine-4,4-diyl | H | CN |
| 45 | 1-(4-(aminomethyl)pyridin-2-yl)cyclopropyl-NH– | cyclopropyl-1,1-diyl | H | CN |
| 46 | 1-(5-(dimethylamino)pyridin-2-yl)cyclopropyl-NH– | (1R,2R)-cyclopropane-1,2-diyl (methyl) | H | CN |

-continued
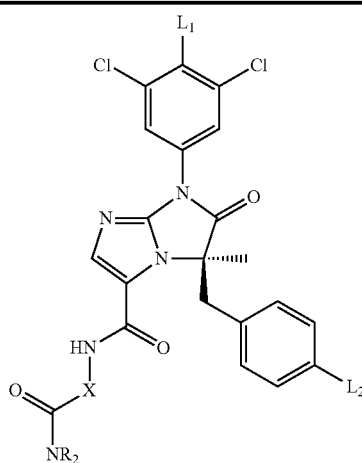
| Cpd # | NR₂ | X | L₁ | L₂ |
|---|---|---|---|---|
| 47 | 1-(5-(dimethylamino)pyridin-2-yl)cyclopropyl-NH- | -CH(CH₃)- | H | OCF3 |
| 48 | 1-(2-methylthiazol-4-yl)cyclopropyl-NH- | 1,1-cyclopropyl | H | CN |
| 49 | 1-(1H-1,2,4-triazol-3-yl)cyclopropyl-NH- | 1,1-cyclopropyl | H | OCF3 |
| 50 | 1-(oxazol-4-yl)cyclopropyl-NH- | 1,1-cyclopropyl | H | CN |
| 51 | 1-(pyridin-2-yl)cyclopropyl-NH- | 3,3-oxetanyl | H | CN |

-continued
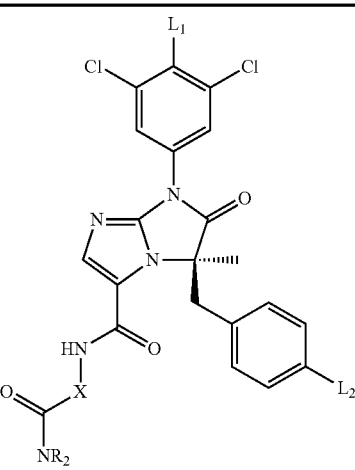
| Cpd # | NR₂ | X | L₁ | L₂ |
|---|---|---|---|---|
| 52 | 1-(6-aminopyridin-2-yl)cyclopropyl-NH- | cyclopropyl | H | OCF3 |
| 53 | 1-(6-aminopyridin-2-yl)cyclopropyl-NH- | cyclopropyl | H | CN |
| 54 | 1-(5-cyclopropyl-4H-1,2,4-triazol-3-yl)cyclopropyl-NH- | cyclopropyl | H | CN |
| 55 | 1-(pyridin-2-yl)cyclopropyl-NH- | CH(CH₃) | F | CN |
| 56 | 1-(pyridin-2-yl)cyclopropyl-NH- | cyclopropyl | F | CN |

-continued

| Cpd # | NR₂ | X | L₁ | L₂ |
|---|---|---|---|---|
| 57 | 1-(5-aminopyridin-2-yl)cyclopropyl-NH- | cyclopropyl | F | CN |
| 58 | 1-(4-methoxypyridin-2-yl)cyclopropyl-NH- | cyclopropyl | F | CN |
| 59 | 1-(6-methoxypyridin-2-yl)cyclopropyl-NH- | cyclopropyl | F | CN |
| 60 | 1-(thiazol-2-yl)cyclopropyl-NH- | cyclopropyl | F | CN |
| 61 | 1-(1,3,4-thiadiazol-2-yl)cyclopropyl-NH- | cyclopropyl | F | CN |

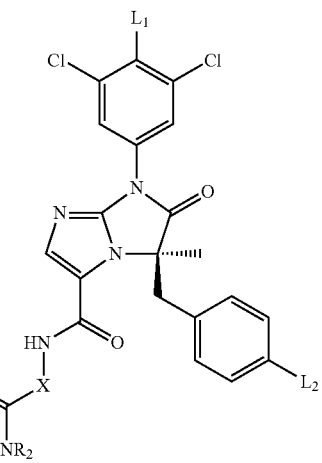
| Cpd # | NR₂ | X | L₁ | L₂ |
|---|---|---|---|---|
| 62 | cyclopropyl-NH with 4H-1,2,4-triazol-3-yl | cyclopropyl | F | CN |
| 63 | cyclopropyl-NH with 4-(aminomethyl)pyridin-2-yl | cyclopropyl | F | CN |
| 64 | cyclopropyl-NH with 3-methyl-1,2,4-oxadiazol-5-yl | cyclopropyl | F | CN |
| 65 | 3,3-difluoroazetidin-1-yl | cyclopropyl | H | OCF3 |
| 66 | (1-(pyridin-2-yl)ethyl)NH | CH(CH3) | H | OCF3 |

-continued
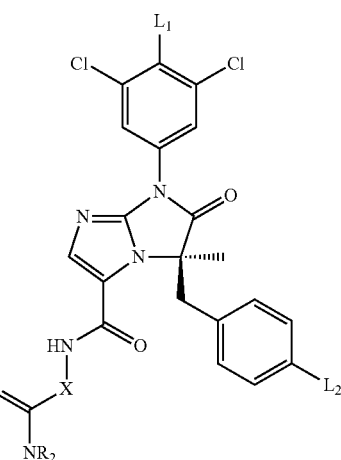
| Cpd # | NR2 | X | L1 | L2 |
|---|---|---|---|---|
| 67 | 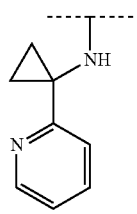 | 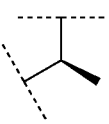 | H | OCF3 |
| 68 | 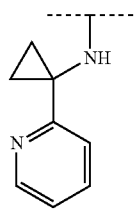 | 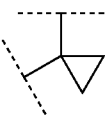 | H | OCF3 |
| 69 | 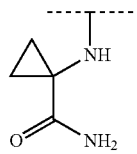 | 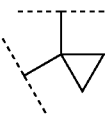 | H | OCF3 |
| 70 | 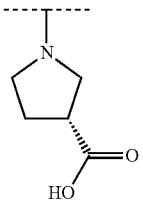 | 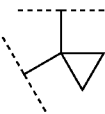 | H | OCF3 |
| 71 | 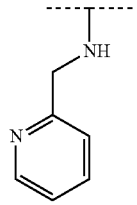 | 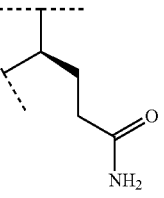 | H | CN |

-continued
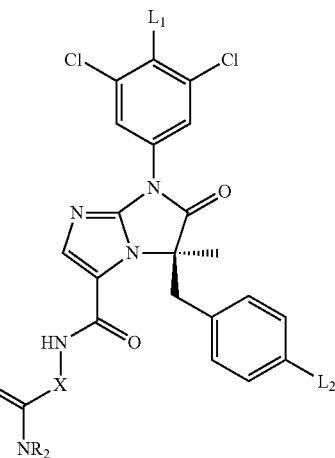
| Cpd # | NR₂ | X | L₁ | L₂ |
|---|---|---|---|---|
| 72 | 1-carbamoylcyclopropyl-NH- | cyclopropyl | H | CN |
| 73 | (1S,3R)-3-carbamoylcyclopentyl-NH- | cyclopropyl | H | CN |
| 74 | (3S)-3-cyanopyrrolidin-1-yl | cyclopropyl | H | CN |
| 75 | (3R)-3-(ethoxycarbonyl)piperidin-1-yl | isopropyl | H | CN |
| 76 | (3S)-3-(2H-tetrazol-5-yl)pyrrolidin-1-yl | cyclopropyl | H | CN |

-continued
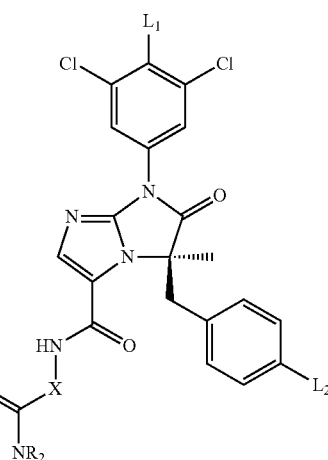
| Cpd # | NR₂ | X | L₁ | L₂ |
|---|---|---|---|---|
| 77 | (S)-pyrrolidin-3-yl-1,2,4-thiadiazol-5(4H)-one | cyclopropyl | H | OCF3 |
| 78 | piperidine-3-carboxamide | -CH(CH₂CH₂C(O)NH₂)- | H | CN |
| 79 | (S)-pyrrolidin-3-yl-1,2,4-thiadiazol-5(4H)-one | cyclopropyl | H | CN |
| 80 | (S)-pyrrolidin-3-yl-5-hydroxy-1H-pyrazole | cyclopropyl | H | CN |

-continued
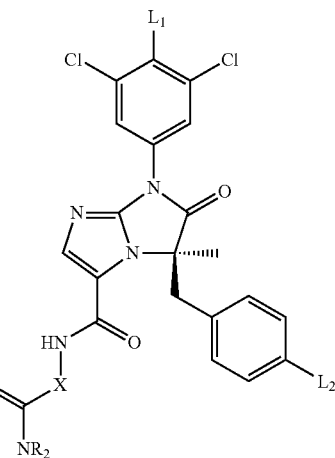
| Cpd # | NR₂ | X | L₁ | L₂ |
|---|---|---|---|---|
| 81 | pyrrolidin-1-yl with 3-COOH | cyclopropyl | H | CN |
| 82 | piperidin-1-yl with 3-CH₂OH | isopropyl | H | CN |
| 83 | piperidin-1-yl with 3-C(O)NH₂ | isopropyl | H | CN |
| 84 | pyrrolidin-1-yl with 3-OH | cyclopropyl | H | OCF₃ |
| 85 | NH-CH(CH₃)-thiazol-2-yl | isopropyl | H | CN |

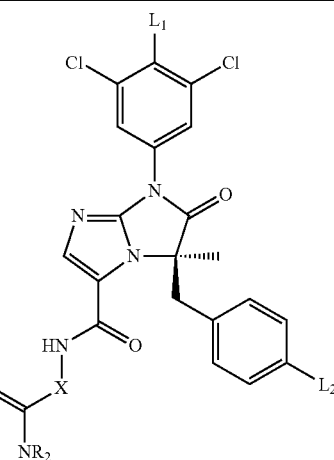
| Cpd # | NR2 | X | L1 | L2 |
|---|---|---|---|---|
| 86 | piperidine-tetrazole | isopropyl | H | phenyl |
| 87 | methyl cyclopentanecarboxylate-NH | isopropyl | H | CN |
| 88 | pyridin-2-ylmethyl-NH | isopropyl | H | CN |
| 89 | methyl cyclopentanecarboxylate-NH | cyclopropyl | H | CN |
| 90 | H2N-C(O)-CH(CH3)-NH | isopropyl | H | CN |
| 91 | pyridin-2-ylmethyl-NH | cyclopropyl | H | CN |

-continued
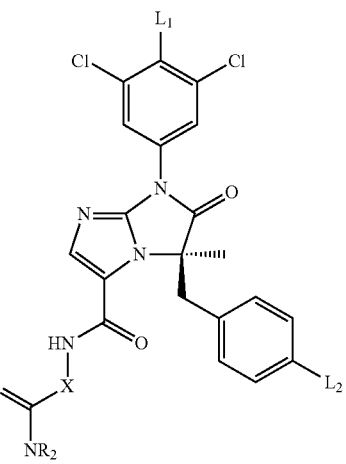
| Cpd # | NR₂ | X | L₁ | L₂ |
|---|---|---|---|---|
| 92 | cyclopentyl with C(=O)NH₂ and NH | isopropyl | H | CN |
| 93 | 1-methylpyrazol-5-yl-NH | isopropyl | H | CN |
| 94 | CH(CH₃)C(=O)NH₂ via NH | cyclopropyl | H | CN |
| 95 | cyclopentyl with CO₂Me and NH | isopropyl | H | CN |
| 96 | cyclopentyl with C(=O)NH₂ and NH | cyclopropyl | H | CN |
| 97 | pyridin-4-ylmethyl-NH | isopropyl | H | CN |

-continued
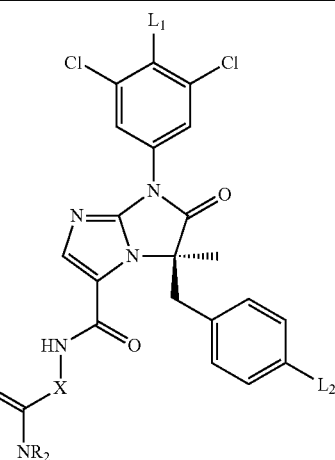
| Cpd # | NR₂ | X | L₁ | L₂ |
|---|---|---|---|---|
| 98 | methyl (1R,3S)-3-aminocyclopentane-1-carboxylate (MeO-C(=O)-cyclopentyl-NH–) | 1,1-cyclopropyl | H | CN |
| 99 | (1R,3S)-3-aminocyclopentane-1-carboxylic acid (HO-C(=O)-cyclopentyl-NH–) | CH(CH₃) | H | CN |
| 100 | (pyridin-3-ylmethyl)amino | CH(CH₃) | H | CN |
| 101 | 5-amino-1-methyl-1H-pyrazole-4-carboxamide | 1,1-cyclopropyl | H | CN |
| 102 | (furan-2-ylmethyl)amino | CH(CH₃) | H | CN |
| 103 | (3-amino-3-oxopropyl)amino | CH(CH₃) | H | CN |

-continued
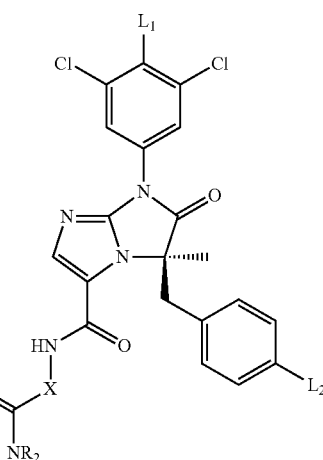
| Cpd # | NR₂ | X | L₁ | L₂ |
|---|---|---|---|---|
| 104 | cyclopentane with CONH₂ and NH | CH(CH₃) | H | CN |
| 105 | cyclopentane with CONH₂ and NH | cyclopropane | H | CN |
| 106 | thiophene-CH₂-NH | CH(CH₃) | H | CN |
| 107 | cyclopropane with NH and COOH | CH(CH₃) | H | CN |
| 108 | C(CH₃)₂(CONH₂)-NH | cyclopropane | H | CN |
| 109 | cyclopentane with COOMe and NH | cyclopropane | H | CN |

-continued
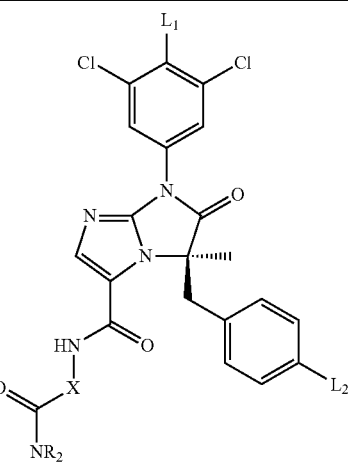
| Cpd # | NR₂ | X | L₁ | L₂ |
|---|---|---|---|---|
| 110 | benzylamine (PhCH₂NH–) | CH(CH₃)– | H | CN |
| 111 | 2-aminothiazole (thiazol-2-yl-NH–) | CH(CH₃)– | H | CN |
| 112 | 2-(1H-tetrazol-5-yl)ethylamine | CH(CH₃)– | H | OCF3 |
| 113 | (S)-alaninamide (H₂NC(O)CH(CH₃)NH–) | CH(CH₃)– | H | CN |
| 114 | 2-aminocyclopentanecarboxamide | CH(CH₃)– | H | CN |
| 115 | methyl 3-aminocyclopentanecarboxylate | CH(CH₃)– | H | CN |

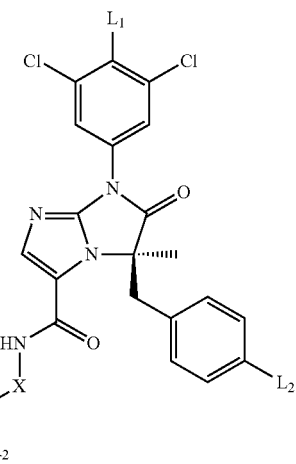
| Cpd # | NR2 | X | L1 | L2 |
|---|---|---|---|---|
| 116 | NH-CH2CH2-(1H-tetrazol-5-yl) | C(CH3)2 | H | OCF3 |
| 117 | NH-C(CH3)2-C(O)NH2 | CH(CH3) | H | CN |
| 118 | NH-C(CH3)2-phenyl | CH(CH3) | H | OCF3 |
| 119 | N(CH3)-CH2CH2-(1H-tetrazol-5-yl) | CH(CH3) | H | OCF3 |
| 120 | N(CH3)-CH2CH2-C(O)NH2 | CH(CH3) | H | CN |

-continued

| Cpd # | NR₂ | X | L₁ | L₂ |
|---|---|---|---|---|
| 121 | (1S,3R)-3-aminocyclopentane-1-carboxamide | isopropyl | H | CN |
| 122 | 1-amino-cyclopropanecarboxylic acid | isopropyl | H | CN |
| 123 | (1H-tetrazol-5-yl)methylamine | cyclopropyl | H | CN |
| 124 | (R)-1-phenylethylamine | isopropyl | H | CN |
| 125 | (3-hydroxyisoxazol-5-yl)methylamine | cyclopropyl | H | CN |
| 126 | 4-amino-1-methyl-1H-pyrazole-5-carboxamide | cyclopropyl | H | CN |

-continued

| Cpd # | NR₂ | X | L₁ | L₂ |
|---|---|---|---|---|
| 127 | (1S,3R)-methyl 3-aminocyclopentanecarboxylate (MeO-C(O)-cyclopentyl-NH-) | CH(CH₃) | H | CN |
| 128 | 2-(2H-tetrazol-5-yl)-N-methylethylamine (tetrazole-CH₂CH₂-N(CH₃)-) | C(CH₃)₃ | H | OCF₃ |
| 129 | (1-methyl-1H-pyrazol-5-yl)-NH- | CH(CH₃) | H | CN |
| 130 | (R)-1-phenylethyl-NH- | CH(CH₃) | H | OCF₃ |
| 131 | (3-hydroxyisoxazol-5-yl)methyl-NH- | CH(CH₃) | H | CN |
| 132 | 2-amino-2-methylpropanoic acid (HOOC-C(CH₃)₂-NH-) | CH(CH₃) | H | CN |

-continued
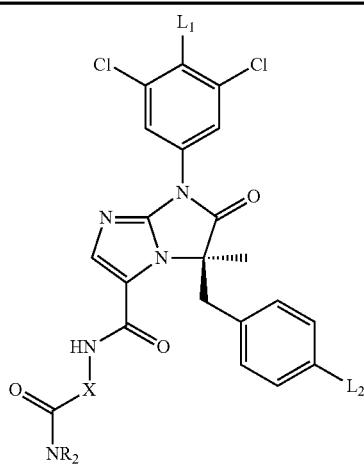
| Cpd # | NR₂ | X | L₁ | L₂ |
|---|---|---|---|---|
| 133 | ethylenediamine-acetamide (NH-CH₂CH₂-NH-C(O)CH₃) | cyclopropyl | H | CN |
| 134 | NH-CH₂CH₂-(2H-tetrazol-5-yl) | CH(CH₃) | H | OCF3 |
| 135 | NH-C(CH₃)₂-COOH | CH(CH₃) | H | CN |
| 136 | NH-(5-methyl-1,3,4-oxadiazol-2-yl) | CH(CH₃) | H | CN |
| 137 | 2-(NH)-4-methyl-thiazole-5-C(O)NH-CH₂CH₂OH | cyclopropyl | H | CN |
| 138 | NH-CH₂-(1,4-dioxan-2-yl) | CH(CH₃) | H | CN |

-continued
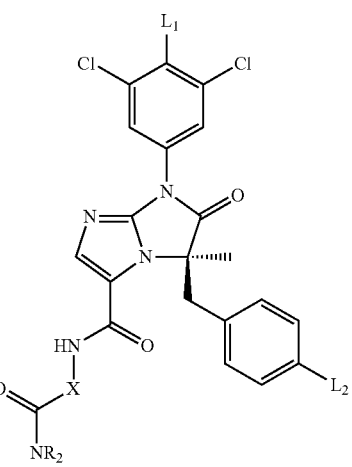
| Cpd # | NR₂ | X | L₁ | L₂ |
|---|---|---|---|---|
| 139 | tetrazol-5-ylmethyl-NH- | CH(CH₃)- | H | CN |
| 140 | 2-(1H-tetrazol-5-yl)ethyl-N(CH₃)- | CH(CH₃)- | H | CN |
| 141 | benzyl-NH- | CH(CH₃)- | H | OCF3 |
| 142 | (3-carbamoylcyclopentyl)-NH- | 1-cyclopropyl- | H | CN |
| 143 | (1-acetylpiperidin-4-yl)-NH- | 1-cyclopropyl- | H | CN |

-continued
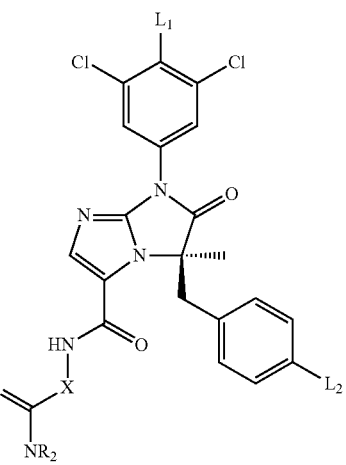
| Cpd # | NR2 | X | L1 | L2 |
|---|---|---|---|---|
| 144 | 5-(2-aminoethyl)-2H-tetrazole | | H | CN |
| 145 | 5-(2-aminoethyl)-1H-tetrazole | | H | CN |
| 146 | 2-amino-1,3,4-thiadiazole | | H | CN |
| 147 | (R)-1-phenylethylamine | | H | CN |
| 148 | (R)-1-phenylethylamine | | H | OCF3 |

-continued
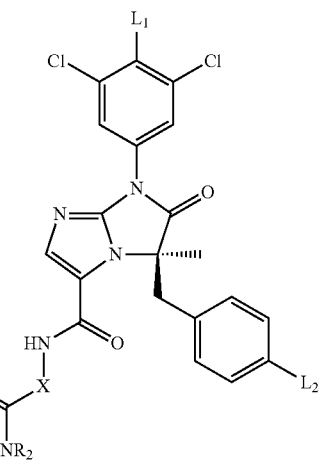
| Cpd # | NR₂ | X | L₁ | L₂ |
|---|---|---|---|---|
| 149 | glycinamide-NH- | CH(CH₃)- | H | CN |
| 150 | 2-(2-hydroxyethoxy)ethyl-NH- | CH(CH₃)- | H | CN |
| 151 | 2-(4-methyl-5-carbamoylthiazolyl)-NH- | cyclopropyl | H | CN |
| 152 | N-methyl-N-[2-(1H-tetrazol-5-yl)ethyl]amino- | cyclopropyl | H | CN |
| 153 | 2-(1H-tetrazol-5-yl)ethyl-NH- | C(CH₃)₂- | H | CN |

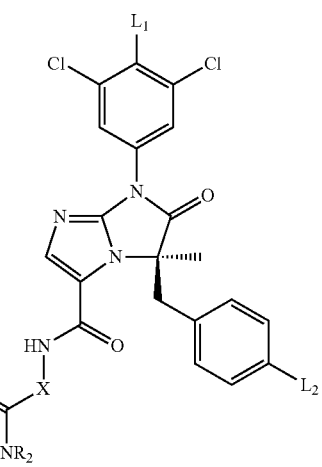
| Cpd # | NR₂ | X | L₁ | L₂ |
|---|---|---|---|---|
| 154 | 3-amino-1H-pyrazole-4-carboxamide-NH | cyclopropyl | H | CN |
| 155 | N,N-dimethyl-2-(2H-tetrazol-5-yl)ethanamine | cyclopropyl | H | OCF3 |
| 156 | methyl (1S,3S)-3-aminocyclopentane-1-carboxylate | cyclopropyl | H | CN |
| 157 | 1-(3-aminopropyl)pyrrolidin-2-one | isopropyl | H | CN |
| 158 | N-(2-aminoethyl)acetamide | isopropyl | H | CN |

-continued
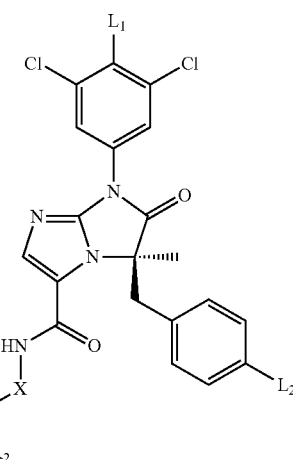
| Cpd # | NR₂ | X | L₁ | L₂ |
|---|---|---|---|---|
| 159 | 3-carbamoylcyclopentylamino (trans) | CH(CH₃) | H | CN |
| 160 | (3S)-3-hydroxypyrrolidin-1-yl | 1,1-cyclopropyl | H | CN |
| 161 | (3R)-3-(2H-tetrazol-5-yl)pyrrolidin-1-yl | C(CH₃)₂ | H | OCF3 |
| 162 | 3-(N-ethylacetamido)pyrrolidin-1-yl | 1,1-cyclopropyl | H | CN |
| 163 | (3R)-3-(2H-tetrazol-5-yl)piperidin-1-yl | CH₂CH₂ | H | OCF3 |

-continued
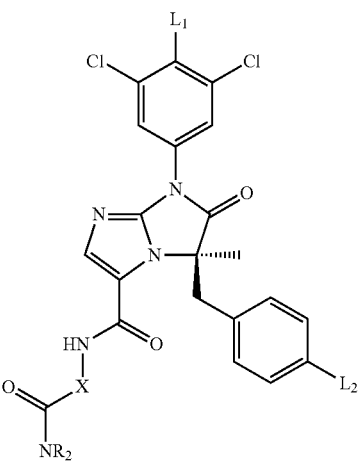
| Cpd # | NR₂ | X | L₁ | L₂ |
|---|---|---|---|---|
| 164 | (S)-pyrrolidin-3-yl carboxamide | 1,1-cyclopropyl | H | CN |
| 165 | 3-(1H-tetrazol-5-yl)piperidin-1-yl | CH(CH₃) | H | Br |
| 166 | 4-(hydroxymethyl)piperidin-1-yl | CH(CH₃) | H | CN |
| 167 | 3-(2H-tetrazol-5-yl)piperidin-1-yl | CH(CH₃) | H | OCF₃ |
| 168 | 3-(2H-tetrazol-5-yl)piperidin-1-yl | CH(CH₃) | H | CN |

-continued

| Cpd # | NR₂ | X | L₁ | L₂ |
|---|---|---|---|---|
| 169 | (R)-3-(tetrazol-5-yl)pyrrolidin-1-yl | isopropyl (CH(CH₃)) | H | OCF3 |
| 170 | 4-hydroxypiperidin-1-yl | CH(CH₃) | H | CN |
| 171 | 3-methyl-3-(tetrazol-5-yl)pyrrolidin-1-yl | 1,1-cyclopropyl | H | OCF3 |
| 172 | 4-acetyl-2-carboxypiperazin-1-yl | 1,1-cyclopropyl | H | CN |
| 173 | 3-methyl-3-(tetrazol-5-yl)pyrrolidin-1-yl | 1,1-cyclopropyl | H | CN |

-continued
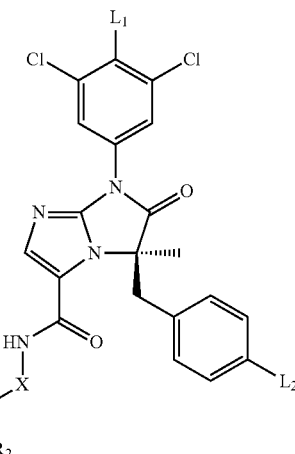
| Cpd # | NR₂ | X | L₁ | L₂ |
|---|---|---|---|---|
| 174 | 3-hydroxypyrrolidin-1-yl | 1,1-cyclopropyl | H | CN |
| 175 | 3-(tetrazol-5-yl)-1-methylpyrrolidine | tert-butyl (C(CH₃)₂) | H | CN |
| 176 | 3-(hydroxymethyl)piperidin-1-yl | 1,1-cyclopropyl | H | CN |
| 177 | 1-methylpiperidine-3-carboxylic acid | CH(CH₃) | H | CN |
| 178 | 3-(5-hydroxy-1H-pyrazol-3-yl)pyrrolidin-1-yl | 1,1-cyclopropyl | H | OCF₃ |

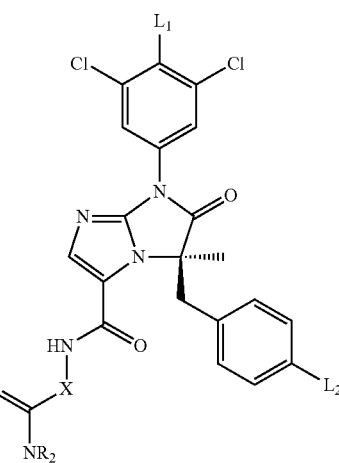
| Cpd # | NR₂ | X | L₁ | L₂ |
|---|---|---|---|---|
| 179 | N-piperidin-3-ol | | H | CN |
| 180 | 4-acetamidopiperidin-1-yl | | H | CN |
| 181 | ethyl piperidine-3-carboxylate N-yl | | H | CN |
| 182 | prolinamide N-yl | | H | CN |
| 183 | 3-(2H-tetrazol-5-yl)piperidin-1-yl | | H | CN |

-continued
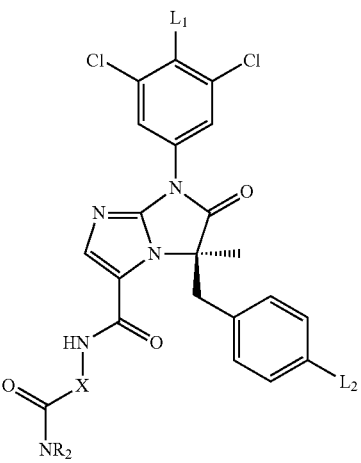
| Cpd # | NR₂ | X | L₁ | L₂ |
|---|---|---|---|---|
| 184 | 3-(tetrazol-5-yl)piperidin-1-yl | CH(CH₃) | H | 4-fluorophenyl |
| 185 | 3-(methylsulfonyl)pyrrolidin-1-yl | cyclopropyl | H | CN |
| 186 | 3-(tetrazol-5-yl)pyrrolidin-1-yl | C(CH₃)₂ | H | OCF₃ |
| 187 | 3-(N-ethylacetamido)pyrrolidin-1-yl | cyclopropyl | H | OCF₃ |
| 188 | 3,3-difluoroazetidin-1-yl | CH(CH₃) | H | CN |

-continued
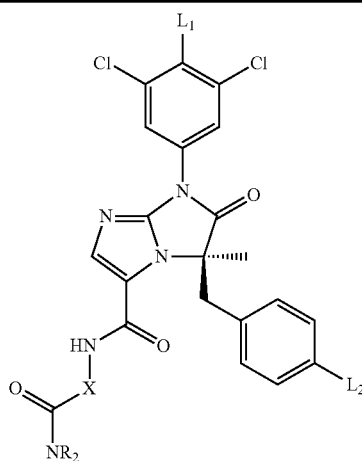
| Cpd # | NR₂ | X | L₁ | L₂ |
|---|---|---|---|---|
| 189 | 4-acetamido-piperidin-1-yl | 1,1-cyclopropyl | H | CN |
| 190 | 4-carbamoyl-piperidin-1-yl | isopropyl | H | CN |
| 191 | (3R)-3-carbamoyl-pyrrolidin-1-yl | isopropyl | H | CN |
| 192 | (3R)-3-carbamoyl-pyrrolidin-1-yl | 1,1-cyclopropyl | H | CN |
| 193 | 3-acetamido-piperidin-1-yl | isopropyl | H | CN |

-continued
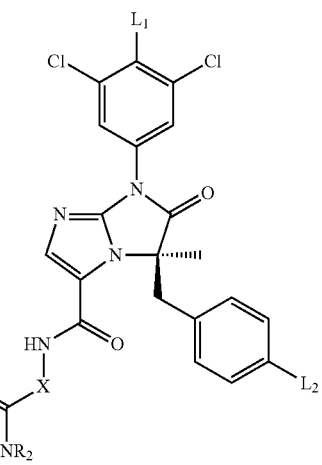
| Cpd # | NR2 | X | L1 | L2 |
|---|---|---|---|---|
| 194 | 4-acetamidopiperidin-1-yl | 1,1-cyclopropyl | H | OCF3 |
| 195 | 3-hydroxyazetidin-1-yl | CH(CH3) | H | CN |
| 196 | 3-carbamoylpiperidin-1-yl | 1,1-cyclopropyl | H | CN |
| 197 | (3R)-3-(2H-tetrazol-5-yl)pyrrolidin-1-yl | CH(CH3) | H | CN |
| 198 | 3,5-dicarbamoylpiperidin-1-yl | CH(CH3) | H | CN |

-continued
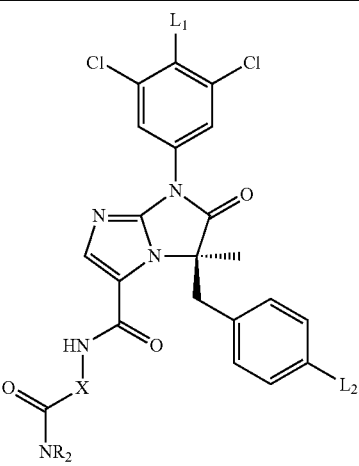
| Cpd # | NR₂ | X | L₁ | L₂ |
|---|---|---|---|---|
| 199 | 3-(2H-tetrazol-5-yl)piperidin-1-yl | 1,1-cyclopropyl | H | OCF3 |
| 200 | 4-carbamoylpiperidin-1-yl | 1,1-cyclopropyl | H | CN |
| 201 | 3-acetamidopiperidin-1-yl | 1,1-cyclopropyl | H | CN |
| 202 | (3R)-3-(2H-tetrazol-5-yl)piperidin-1-yl | 1,1-cyclopropyl | H | OCF3 |
| 203 | (3S)-3-acetamidopyrrolidin-1-yl | CH(CH₃) | H | CN |

-continued
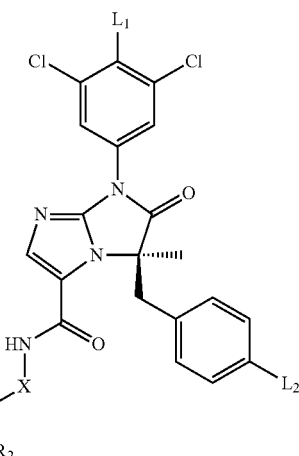
| Cpd # | NR₂ | X | L₁ | L₂ |
|---|---|---|---|---|
| 204 | (S)-3-(2-tert-butyl-tetrazol-5-yl)pyrrolidin-1-yl | isopropyl (R) | H | CN |
| 205 | (S)-2-(hydroxymethyl)pyrrolidin-1-yl | isopropyl (R) | H | CN |
| 206 | (R)-3-(2H-tetrazol-5-yl)piperidin-1-yl | isopropyl (R) | H | OCF3 |
| 207 | 3-acetamidopiperidin-1-yl | 1-cyclopropyl | H | OCF3 |
| 208 | (R)-3-(5-oxo-4,5-dihydroisoxazol-3-yl)piperidin-1-yl | isopropyl | H | OCF3 |

-continued
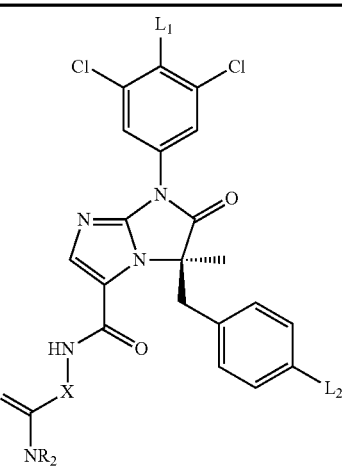
| Cpd # | NR₂ | X | L₁ | L₂ |
|---|---|---|---|---|
| 209 | pyrrolidinyl-tetrazole (3S) | CH(CH₃)CH— | H | OCF3 |
| 210 | pyrrolidinyl-tetrazole (3R) | CH(CH₃)CH— | H | OCF3 |
| 211 | pyrrolidinyl-methylsulfonyl | cyclopropyl | H | OCF3 |
| 212 | N-methyl-pyrrolidinyl-acetamide | CH(CH₃)CH— | H | OCF3 |
| 213 | pyrrolidinyl-tetrazole | cyclobutyl | H | OCF3 |

-continued

| Cpd # | NR₂ | X | L₁ | L₂ |
|---|---|---|---|---|
| 214 | 1-acetylpiperidin-4-ylamino | cyclopropylidene | H | OCF3 |
| 215 | (2-(hydroxymethyl)pyrrolidin-1-yl) | isopropyl | H | CN |
| 216 | 4-acetyl-3-carboxypiperazin-1-yl | cyclopropylidene | H | CN |
| 217 | (3-carbamoylpyrrolidin-1-yl) | isopropyl | H | CN |
| 218 | (3-acetamidopiperidin-1-yl) | isopropyl | H | OCF3 |

-continued
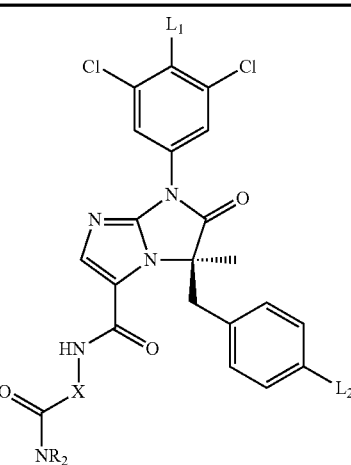
| Cpd # | NR₂ | X | L₁ | L₂ |
|---|---|---|---|---|
| 219 | 3-methyl-3-(2H-tetrazol-5-yl)pyrrolidin-1-yl | CH(CH(CH₃)) | H | CN |
| 220 | 4-(1H-tetrazol-5-yl)piperazin-1-yl | 1,1-cyclopropyl | H | CN |
| 221 | (3S)-3-(dimethylamino)pyrrolidin-1-yl | 1,1-cyclopropyl | H | OCF3 |
| 222 | 3-(3-hydroxyisoxazol-5-yl)piperidin-1-yl | CH(CH(CH₃)) | H | OCF3 |
| 223 | (3S)-3-(2H-tetrazol-5-yl)pyrrolidin-1-yl | cyclopropyl | H | OCF3 |

-continued
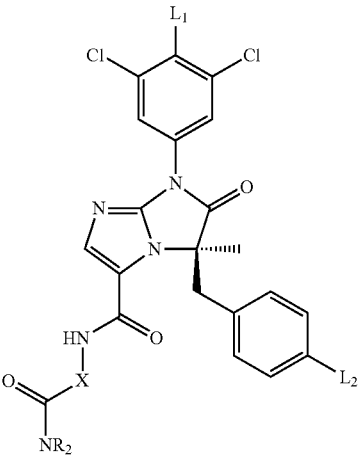
| Cpd # | NR₂ | X | L₁ | L₂ |
|---|---|---|---|---|
| 224 | 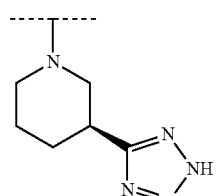 | 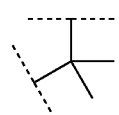 | H | OCF3 |
| 225 |  |  | H | CN |
| 226 | 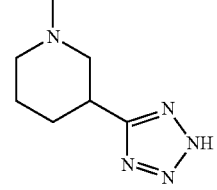 | 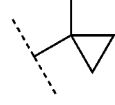 | H | CN |
| 227 |  |  | H | OCF3 |
| 228 | 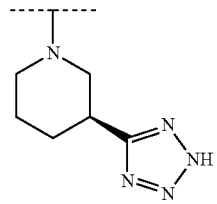 | 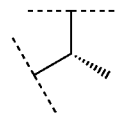 | H | OCF3 |

-continued
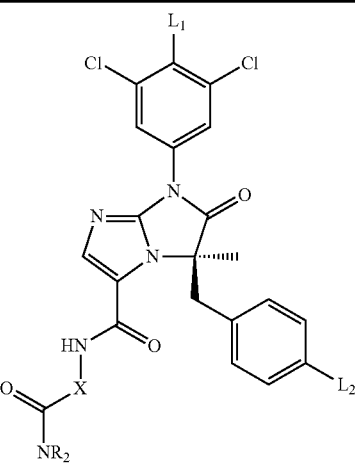
| Cpd # | NR₂ | X | L₁ | L₂ |
|---|---|---|---|---|
| 229 | 3-(N-methylacetamido)pyrrolidin-1-yl | cyclopropyl (trans) | H | CN |
| 230 | 3-methyl-3-(2H-tetrazol-5-yl)pyrrolidin-1-yl | cyclopropyl (trans) | H | OCF3 |
| 231 | (3S)-3-(dimethylamino)pyrrolidin-1-yl | 1,1-cyclopropyl | H | OCF3 |
| 232 | (3R)-3-carboxypyrrolidin-1-yl | 1,1-cyclopropyl | H | CN |
| 233 | 4-acetamidopiperidin-1-yl | cyclopropyl (trans) | H | OCF3 |

-continued
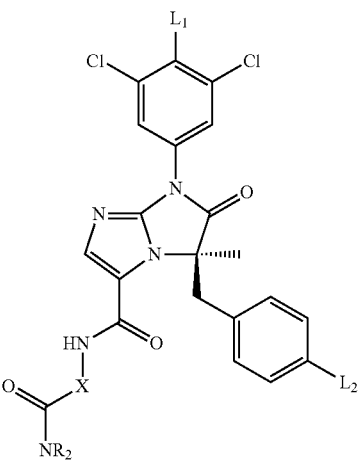
| Cpd # | NR₂ | X | L₁ | L₂ |
|---|---|---|---|---|
| 234 | (S)-3-(dimethylamino)pyrrolidin-1-yl | 1,1-cyclopropyl | H | CN |
| 235 | 3,3-difluoroazetidin-1-yl | CH(CH₃) | H | OCF3 |
| 236 | (R)-3-(2H-tetrazol-5-yl)pyrrolidin-1-yl | CH(CH₃) | H | CN |
| 237 | (R)-3-(2H-tetrazol-5-yl)piperidin-1-yl | C(CH₃)₂ | H | CN |
| 238 | (R)-3-(2H-tetrazol-5-yl)piperidin-1-yl | CH₂CH₂ | H | OCF3 |

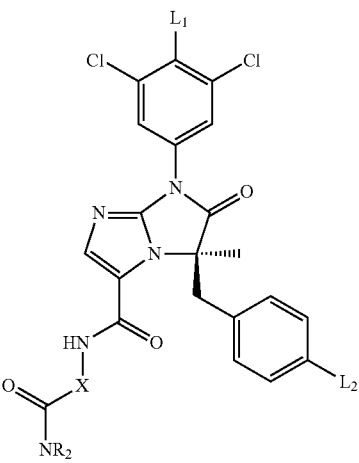
| Cpd # | NR₂ | X | L₁ | L₂ |
|---|---|---|---|---|
| 239 | pyrrolidine-N-, 3-NHC(O)CH₃ | CH(CH₃) | H | CN |
| 240 | pyrrolidine-N-, 3-NHC(O)CH₃ | CH(CH₃) | H | OCF3 |
| 241 | pyrrolidine-N-, 3-N(CH₃)₂ | cyclopropyl | H | CN |
| 242 | pyrrolidine-N-, 3-(tetrazol-5-yl) | CH(CH₃) | H | CN |
| 243 | piperidine-N-, 3-(tetrazol-5-yl) | CH(CH₃) | H | CN |

-continued
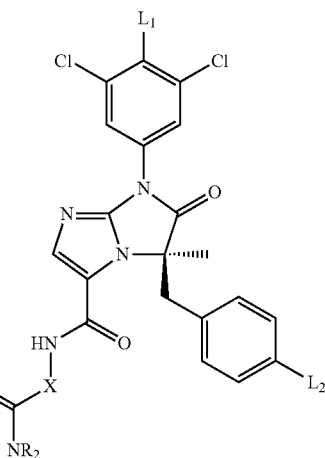
| Cpd # | NR₂ | X | L₁ | L₂ |
|---|---|---|---|---|
| 244 | 3-cyano-piperidin-1-yl | (isopropyl) | H | Br |
| 245 | 3-(2-tert-butyl-tetrazol-5-yl)-pyrrolidin-1-yl | (isopropyl) | H | OCF₃ |
| 246 | 3,3-difluoro-azetidin-1-yl | CH(CH₂C(O)NH₂) | H | CN |
| 247 | (1-(pyridin-2-yl)ethyl)-NH | (isopropyl) | H | CN |
| 248 | ((6-methylpyridin-2-yl)methyl)-NH | (isopropyl) | H | CN |

-continued
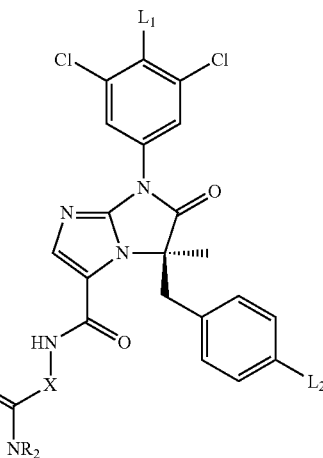
| Cpd # | NR₂ | X | L₁ | L₂ |
|---|---|---|---|---|
| 249 | 1-(furan-2-yl)ethyl-NH- | isopropyl | H | CN |
| 250 | (1-thiocarbamoylethyl)-NH- | isopropyl | H | CN |
| 251 | 1-(1,3,4-oxadiazol-2-yl)ethyl-NH- | isopropyl | H | CN |
| 252 | (pyridin-2-ylmethyl)-NH- | isopropyl | H | OCF3 |
| 253 | (pyridin-2-ylmethyl)-NH- | cyclopropyl | H | OCF3 |

-continued
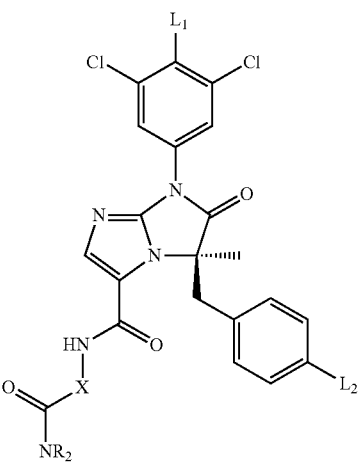
| Cpd # | NR₂ | X | L₁ | L₂ |
|---|---|---|---|---|
| 254 | *N-methyl-1-(pyridin-2-yl)ethylamine* | cyclopropyl | H | CN |
| 255 | *2,2,2-trifluoro-1-(pyridin-2-yl)ethylamine* | cyclopropyl | H | CN |
| 256 | *1-(thiocarbamoyl)cyclopropylamine* | cyclopropyl | H | CN |
| 257 | *1-(thiocarbamoyl)cyclopropylamine* | cyclopropyl | F | CN |
| 258 | *N-methyl-2-(1H-tetrazol-5-yl)ethylamine* | tert-butyl | H | CN |

-continued
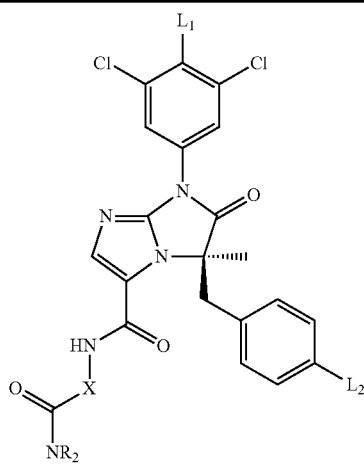
| Cpd # | NR₂ | X | L₁ | L₂ |
|---|---|---|---|---|
| 259 | ethyl-morpholine-NH- | isopropyl | H | CN |
| 260 | (3-carboxycyclopentyl)NH- | cyclopropyl | H | CN |
| 261 | 1-(3-oxo-3-ethoxypropanoyl)piperidin-3-yl | isopropyl | H | OCF3 |
| 262 | (2-phenylpropan-2-yl)NH- | isopropyl | H | CN |
| 263 | (2-(1H-tetrazol-5-yl)ethyl)NH- | cyclopropyl | H | CN |

-continued

| Cpd # | NR₂ | X | L₁ | L₂ |
|---|---|---|---|---|
| 264 | 2-(1H-tetrazol-5-yl)ethylamino | CH₂CH₂ | H | CN |
| 265 | (1S,3R)-3-amino-cyclopentanecarboxylic acid | CH(CH₃) | H | CN |
| 266 | 3-(1H-imidazol-1-yl)propylamino | CH(CH₃) | H | CN |
| 267 | 5-carbamoyl-1-methyl-1H-pyrazol-4-ylamino | cyclopropyl | H | CN |
| 268 | 4-carbamoyl-1H-imidazol-5-ylamino | cyclopropyl | H | CN |
| 269 | (1S,3R)-3-amino-cyclopentanecarboxylic acid | cyclopropyl | H | CN |

-continued
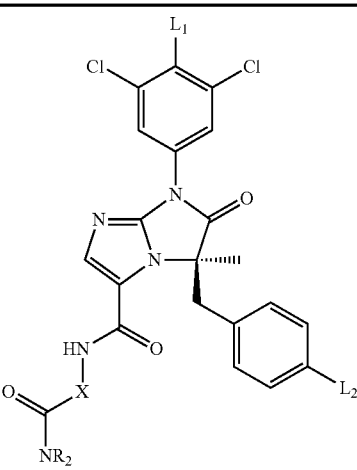
| Cpd # | NR₂ | X | L₁ | L₂ |
|---|---|---|---|---|
| 270 | (1S,3R)-3-aminocyclopentane-1-carboxylic acid | sec-butyl | H | CN |
| 271 | N-methyl-2-(1H-tetrazol-5-yl)ethanamine | cyclopropyl | H | CN |
| 272 | 5-amino-4-carbamoyl-3-methylisoxazole | 1,1-cyclopropyl | H | CN |
| 273 | (1S,3R)-3-aminocyclopentane-1-carboxylic acid | 1,1-cyclopropyl | H | CN |
| 274 | (3R)-3-(1H-tetrazol-5-yl)pyrrolidine | cyclopropyl | H | CN |
| 275 | (3R)-3-(1H-tetrazol-5-yl)piperidine | tert-butyl | H | CN |

-continued
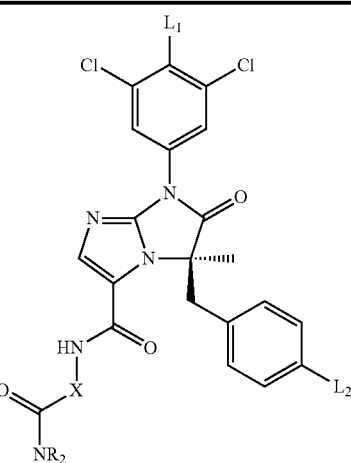
| Cpd # | NR₂ | X | L₁ | L₂ |
|---|---|---|---|---|
| 276 | 1-methyl-3-methylpyrrolidine with tetrazole | branched | H | CN |
| 277 | piperidine with CF₂F (4-CF₃) | branched | H | CN |
| 278 | piperidine-3-carboxylic acid | branched | H | CN |
| 279 | piperidine-3-yl tetrazole | linear | H | CN |
| 280 | pyrrolidin-3-yl tetrazole | linear | H | CN |

-continued
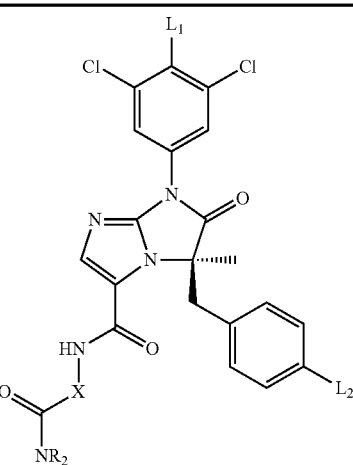
| Cpd # | NR₂ | X | L₁ | L₂ |
|---|---|---|---|---|
| 281 | 3-cyanopiperidin-1-yl | CH(CH₃) | H | Br |
| 282 | NH-CH(CH₃)-(pyridin-2-yl) | CH(CH₃) | H | OCF3 |
| 283 | NH-CH₂-(6-methylpyridin-2-yl) | CH(CH₃) | H | OCF3 |
| 284 | NH-CH(CH₃)-(thiophen-2-yl) | CH(CH₃) | H | CN |
| 285 | NH-CH(CH₃)-(4-ethyl-4H-1,2,4-triazol-3-yl) | CH(CH₃) | H | CN |
| 286 | NH-(thiazol-2-yl) | CH(CH₃) | H | CN |

-continued
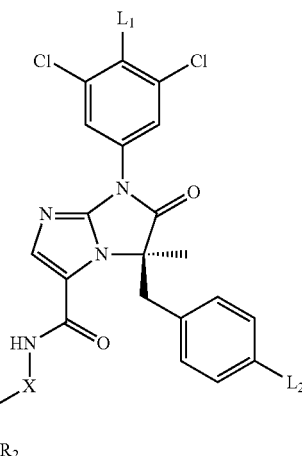
| Cpd # | NR_2 | X | L_1 | L_2 |
|---|---|---|---|---|
| 287 | 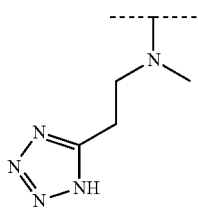 | 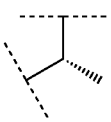 | H | CN |
| 288 | 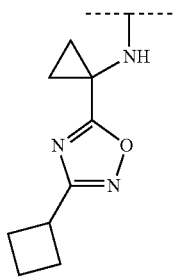 | 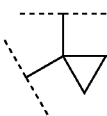 | H | CN |
| 289 | 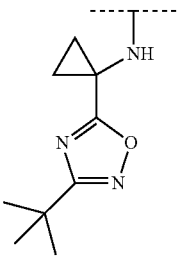 | 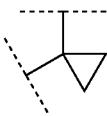 | H | CN |
| 290 | 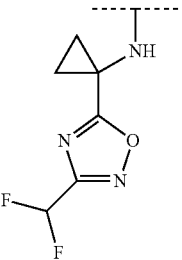 | 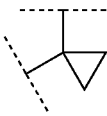 | H | CN |

-continued
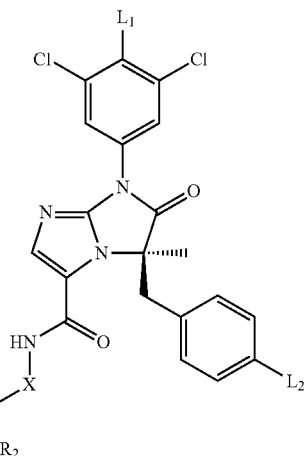
| Cpd # | NR2 | X | L1 | L2 |
|---|---|---|---|---|
| 291 | 1-(oxazolo[5,4-b]pyridin-2-yl)cyclopropyl-NH- | cyclopropyl | F | CN |
| 292 | 1-(benzoxazol-2-yl)cyclopropyl-NH- | cyclopropyl | F | CN |
| 293 | 1-(pyrido[2,3-d]pyrimidin-2-yl)cyclopropyl-NH- | cyclopropyl | F | CN |
| 294 | 1-(1,8-naphthyridin-2-yl)cyclopropyl-NH- | cyclopropyl | F | CN |

-continued
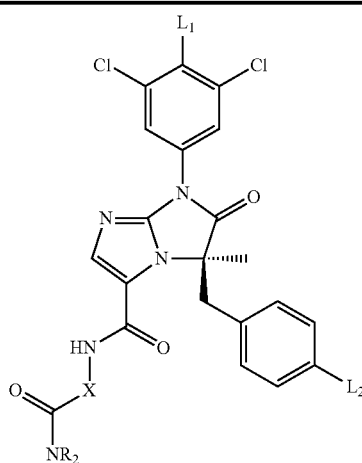
| Cpd # | NR₂ | X | L₁ | L₂ |
|---|---|---|---|---|
| 295 | cyclopropyl-NH linked to quinolin-2-yl | cyclopropyl | F | CN |
| 296 | cyclopropyl-NH linked to 1,7-naphthyridin-2-yl | cyclopropyl | F | CN |
| 297 | cyclopropyl-NH linked to quinazolin-2-yl | cyclopropyl | F | CN |
| 298 | cyclopropyl-NH linked to 6-chloroquinazolin-2-yl | cyclopropyl | F | CN |

-continued

| Cpd # | NR₂ | X | L₁ | L₂ |
|---|---|---|---|---|
| 299 | 1-(4-iodopyridin-2-yl)cyclopropylamino | cyclopropyl | H | CN |
| 300 | 1-(pyridin-3-yl)cyclopropylamino | CH(CH₃) | F | CN |
| 301 | 1-(1H-tetrazol-5-yl)cyclopropylamino | cyclopropyl | H | CN |
| 302 | 1-(pyridin-2-yl)cyclopropylamino | CH(CH₂CH₂NH₂) | H | CN |
| 303 | 1-(pyridin-2-yl)cyclopropylamino | CH(CH₂CH₂C(O)O-tBu) | F | OCF₃ |

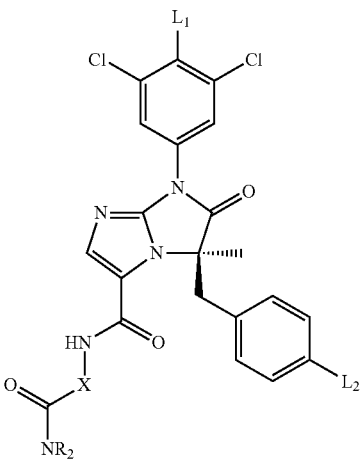
| Cpd # | NR₂ | X | L₁ | L₂ |
|---|---|---|---|---|
| 304 | cyclopropyl-NH- attached to pyridine with COOH | cyclopropyl | F | CN |
| 305 | cyclopropyl-NH- attached to 1-isopropylimidazole | cyclopropyl | F | CN |
| 306 | cyclopropyl-NH- attached to 5-methyl-1H-1,2,4-triazole | cyclopropyl | H | CN |
| 307 | cyclopropyl-NH- attached to 5-methyl-1H-1,2,4-triazole | cyclopropyl | F | CN |

-continued
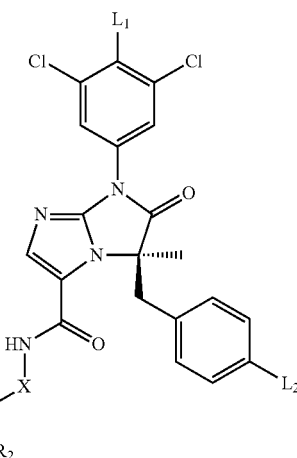
| Cpd # | NR₂ | X | L₁ | L₂ |
|---|---|---|---|---|
| 308 | 1-(1H-imidazol-4-yl)cyclopropyl-NH- | cyclopropyl | F | CN |
| 309 | 1-(pyrimidin-2-yl)cyclopropyl-NH- | 1,1-dioxidotetrahydro-2H-thiopyran-4-yl | F | CN |
| 310 | 1-(pyrimidin-2-yl)cyclopropyl-NH- | 1-acetylpiperidin-4-yl | F | CN |
| 311 | 1-(pyrimidin-2-yl)cyclopropyl-NH- | 4-amino-4-oxobutan-2-yl | F | CN |
| 312 | 1-(pyrimidin-2-yl)cyclopropyl-NH- | 1-(1-methyl-1H-imidazol-4-yl)propan-2-yl | F | CN |

-continued
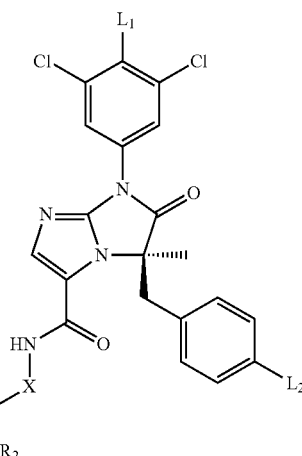
| Cpd # | NR₂ | X | L₁ | L₂ |
|---|---|---|---|---|
| 313 | 1-(pyrimidin-2-yl)cyclopropyl-NH- | -CH(-)-CH₂-(1-methylimidazol-5-yl) | F | CN |
| 314 | 1-(pyrimidin-2-yl)cyclopropyl-NH- | 4-(cyclopropanecarbonyl)piperidin-4-yl | F | CN |
| 315 | 1-(pyrimidin-2-yl)cyclopropyl-NH- | -CH(-)-CH₂-CH₂-N(CH₃)₂ | F | CN |
| 316 | 1-(pyrimidin-2-yl)cyclopropyl-NH- | 4-(propanoyl)piperidin-4-yl | H | CN |
| 317 | 1-(pyrimidin-2-yl)cyclopropyl-NH- | 4-(acetyl)piperidin-4-yl | H | CN |

-continued
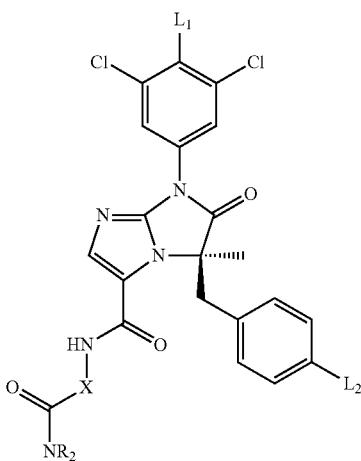
| Cpd # | NR2 | X | L1 | L2 |
|---|---|---|---|---|
| 318 | | | H | CN |
| 319 | | | F | CN |
| 320 | | | F | CN |
| 321 | | | H | OCF3 |

-continued
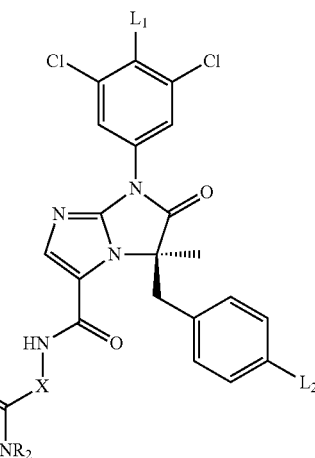
| Cpd # | NR2 | X | L1 | L2 |
|---|---|---|---|---|
| 322 | cyclopropyl-NH- with 3-cyclopropyl-1,2,4-oxadiazol-5-yl | cyclopropyl | F | CN |
| 323 | cyclopropyl-NH- with 3-cyclopropyl-1,2,4-oxadiazol-5-yl | cyclopropyl | H | OCF3 |
| 324 | cyclopropyl-NH- with 5-(trifluoromethyl)pyridin-2-yl | cyclopropyl | H | CN |
| 325 | cyclopropyl-NH- with pyridin-2-yl | cyclopropyl | H | CF3CF2- |

-continued
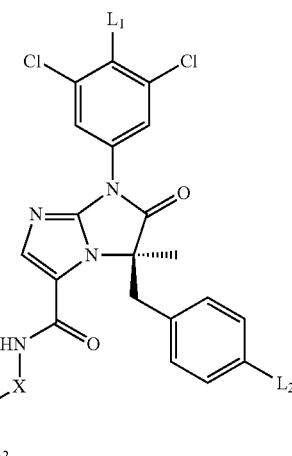
| Cpd # | NR2 | X | L1 | L2 |
|---|---|---|---|---|
| 326 | 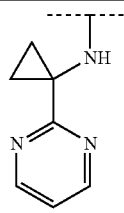 | 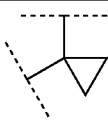 | H | 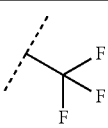 |
| 327 | 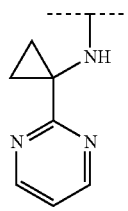 | 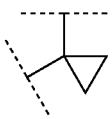 | H | OCF3 |
| 328 | 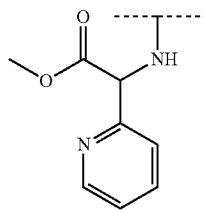 | 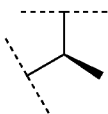 | H | CN |
| 329 | 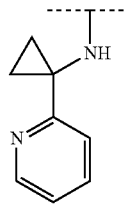 | 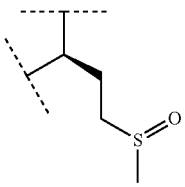 | H | CN |
| 330 | 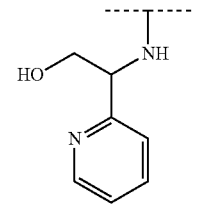 | 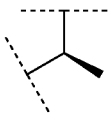 | H | CN |

-continued
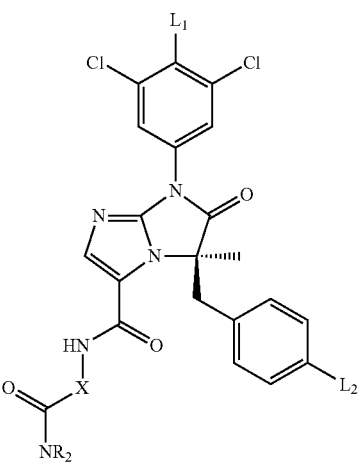
| Cpd # | NR₂ | X | L₁ | L₂ |
|---|---|---|---|---|
| 331 | 1-(4-(trifluoromethyl)-1H-imidazol-2-yl)cyclopropyl-NH- | cyclopropyl | H | CN |
| 332 | (1-(1H-pyrrolo[2,3-b]pyridin-2-yl)propyl)-NH- | cyclopropyl | H | CN |
| 333 | N-methyl-1-(1H-pyrrolo[2,3-b]pyridin-6-yl)cyclopropyl-NH- | cyclopropyl | F | CN |
| 334 | 1-(pyridin-2-yl)cyclopropyl-NH- | 4-(dimethylamino)butan-2-yl | H | CN |

-continued
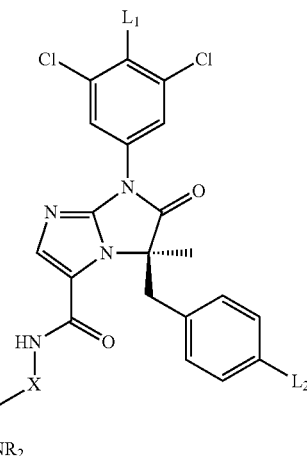
| Cpd # | NR2 | X | L1 | L2 |
|---|---|---|---|---|
| 335 | cyclopropyl-NH with 2-pyridyl | acetyl-pyrrolidine spiro | H | CN |
| 336 | cyclopropyl-NH with 5-(aminomethyl)pyridin-2-yl | spirocyclopropyl | H | CN |
| 337 | cyclopropyl-NH with 5-((dimethylamino)methyl)pyridin-2-yl | spirocyclopropyl | H | CN |
| 338 | cyclopropyl-NH with 2-cyclopropyl-oxazol-4-yl | spirocyclopropyl | H | CN |

-continued
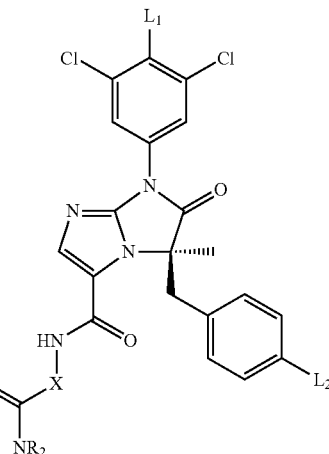
| Cpd # | NR₂ | X | L₁ | L₂ |
|---|---|---|---|---|
| 339 | 1-(5-methylpyridin-2-yl)cyclopropyl-NH- | cyclopropyl | H | CN |
| 340 | 1-(5-(hydroxymethyl)pyridin-2-yl)cyclopropyl-NH- | cyclopropyl | H | CN |
| 341 | 1-(2-isopropyloxazol-4-yl)cyclopropyl-NH- | cyclopropyl | H | CN |
| 342 | 1-(2-isopropyloxazol-4-yl)cyclopropyl-NH- | cyclopropyl | F | CN |

-continued
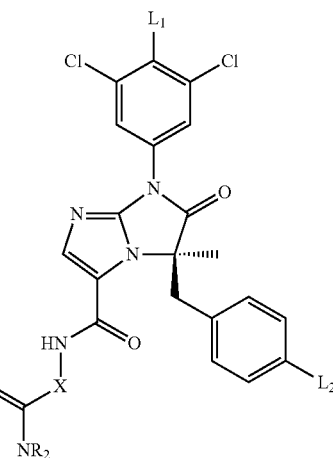
| Cpd # | NR2 | X | L1 | L2 |
|---|---|---|---|---|
| 343 | 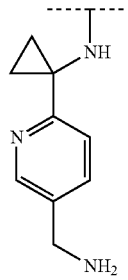 | 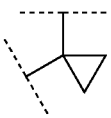 | F | CN |
| 344 | 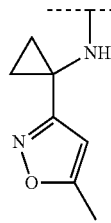 | 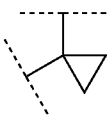 | H | CN |
| 346 | 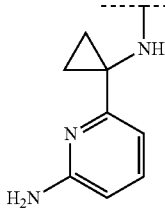 | 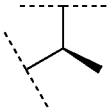 | H | CN |
| 347 | 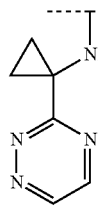 | 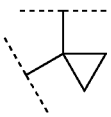 | H | CN |

-continued
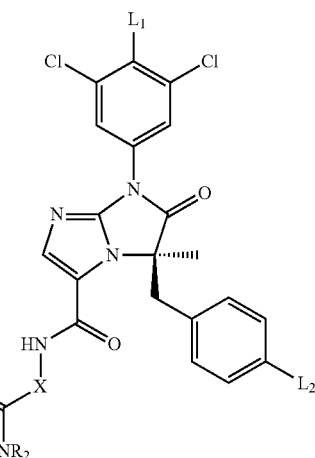
| Cpd # | NR₂ | X | L₁ | L₂ |
|---|---|---|---|---|
| 348 | cyclopropyl-NH-(pyrimidin-2-yl) | cyclopropyl | H | CN |
| 349 | cyclopropyl-NH-(pyrazin-2-yl) | cyclopropyl | H | CN |
| 350 | cyclopropyl-NH-(pyridazin-3-yl) | cyclopropyl | H | CN |
| 351 | cyclopropyl-NH-(pyrimidin-2-yl) | cyclopropyl | F | CN |
| 352 | cyclopropyl-NH-(pyrimidin-2-yl) | CH(CH₃) | F | CN |

-continued
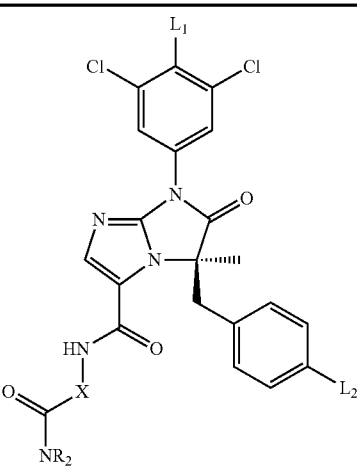
| Cpd # | NR₂ | X | L₁ | L₂ |
|---|---|---|---|---|
| 353 | 1-(pyridazin-3-yl)cyclopropyl-NH- | cyclopropyl | F | CN |
| 354 | 1-(6-chloropyridin-2-yl)cyclopropyl-NH- | CH(CH₃) | H | CN |
| 355 | 1-(5-methylpyrazin-2-yl)cyclopropyl-NH- | cyclopropyl | H | CN |
| 356 | 1-(4-aminopyrimidin-2-yl)cyclopropyl-NH- | cyclopropyl | H | CN |
| 357 | 1-(1-oxidopyridazin-3-yl)cyclopropyl-NH- | cyclopropyl | F | CN |

-continued
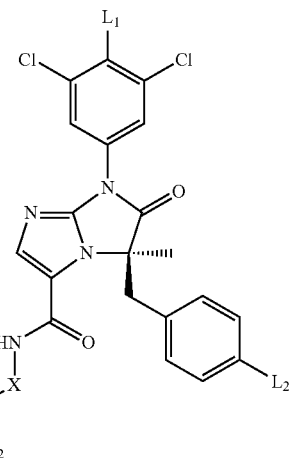
| Cpd # | NR₂ | X | L₁ | L₂ |
|---|---|---|---|---|
| 358 | 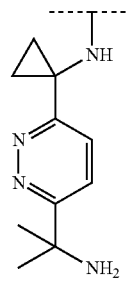 | 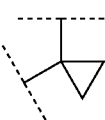 | F | CN |
| 359 | 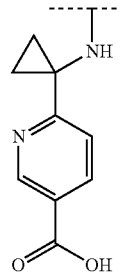 | 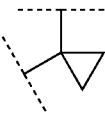 | H | CN |
| 360 | 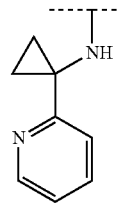 | 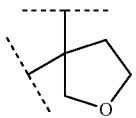 | H | CN |
| 361 | 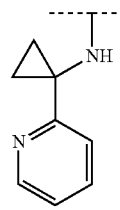 | 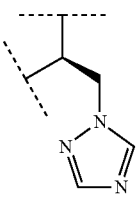 | H | CN |

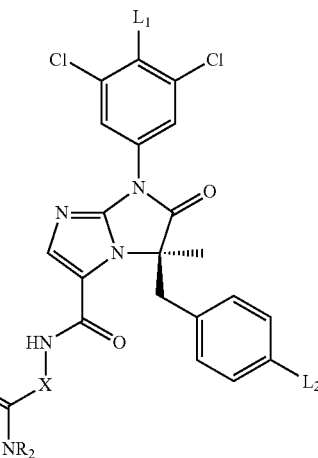
| Cpd # | NR₂ | X | L₁ | L₂ |
|---|---|---|---|---|
| 362 | cyclopropyl-NH with 2-pyridyl | tetrahydropyran-4-yl (spiro) | H | CN |
| 363 | cyclopropyl-NH with 2-pyridyl | cyclohexyl | H | CN |
| 365 | cyclopropyl-NH with 3-(5-cyclopropyl-1,2,4-oxadiazol-3-yl) | cyclopropyl | H | CN |
| 366 | cyclopropyl-NH with 5-(3-(2-hydroxyethyl)-1,2,4-oxadiazol-5-yl) | cyclopropyl | H | CN |

-continued
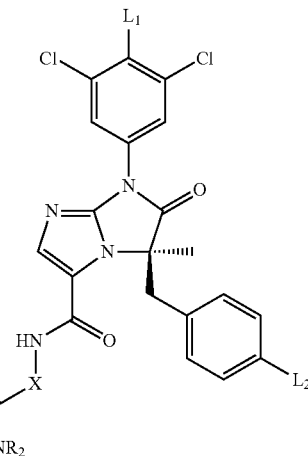
| Cpd # | NR₂ | X | L₁ | L₂ |
|---|---|---|---|---|
| 367 | 1-(5-methyl-1,2,4-oxadiazol-3-yl)cyclopropyl-NH- | spiropentyl | H | CN |
| 368 | 1-(5-isopropyl-1,2,4-oxadiazol-3-yl)cyclopropyl-NH- | spiropentyl | H | CN |
| 369 | 1-(3-(2,2,2-trifluoroethyl)-1,2,4-oxadiazol-5-yl)cyclopropyl-NH- | spiropentyl | H | CN |
| 370 | 1-(3-ethyl-1,2,4-oxadiazol-5-yl)cyclopropyl-NH- | spiropentyl | H | CN |

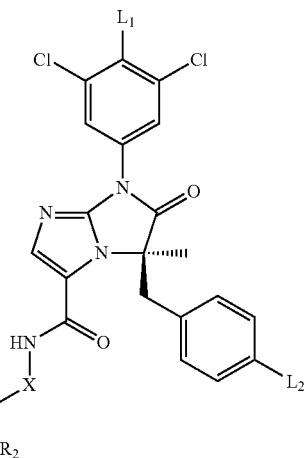
| Cpd # | NR₂ | X | L₁ | L₂ |
|---|---|---|---|---|
| 371 | cyclopropyl-NH attached to 1,2,4-oxadiazole with CH₂CH(OH)CH₃ | cyclopropyl | H | CN |
| 372 | cyclopropyl-NH attached to 1,2,4-oxadiazole with N(CH₃)₂ | cyclopropyl | H | CN |
| 373 | cyclopropyl-NH with 2-pyridyl | CH(CH₃) | H | CH₂Br |
| 374 | cyclopropyl-NH with 2-pyridyl | cyclopropyl | H | CH₂-(1,2,4-triazol-1-yl) |

-continued
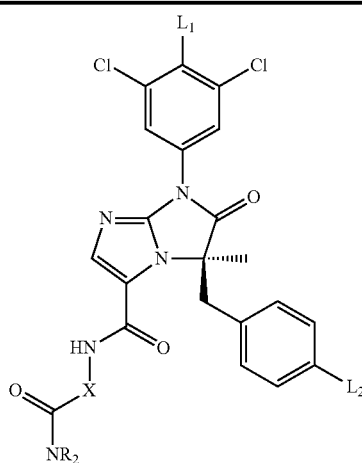
| Cpd # | NR₂ | X | L₁ | L₂ |
|---|---|---|---|---|
| 375 | 1-(pyridin-2-yl)cyclopropyl-NH– | cyclopropyl | H | Cl |
| 376 | 1-(pyridin-2-yl)cyclopropyl-NH– | cyclopropyl | H | 1,2,3-triazol-1-yl |
| 377 | 1-(pyridin-2-yl)cyclopropyl-NH– | cyclopropyl | H | 1,2,3-triazol-2-yl |
| 378 | 1-(pyridin-2-yl)cyclopropyl-NH– | CH(CH(OH)CH₃) | F | CN |
| 379 | 1-(5-iodopyridin-2-yl)cyclopropyl-NH– | spiro-bicyclopropyl | F | CN |

-continued
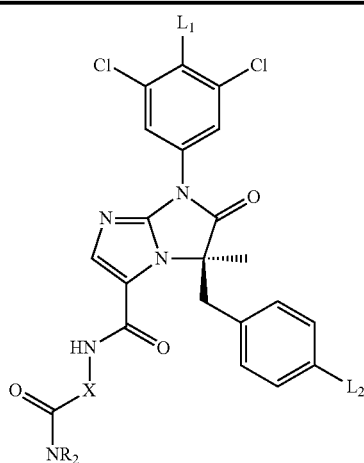
| Cpd # | NR₂ | X | L₁ | L₂ |
|---|---|---|---|---|
| 380 | 1-(pyridin-2-yl)cyclopropyl-NH- | -CH(CH₂OP(O)(OH)₂)- | F | CN |
| 381 | 1-(pyridin-2-yl)cyclopropyl-NH- | -CH(CH₂CH₂C(O)OH)- | F | OCF3 |
| 383 | 1-(4H-1,2,4-triazol-3-yl)cyclopropyl-NH- | -CH(CH₃)- | H | CN |
| 384 | 1-(5-cyclopropyl-4H-1,2,4-triazol-3-yl)cyclopropyl-NH- | spirocyclopropyl | F | CN |

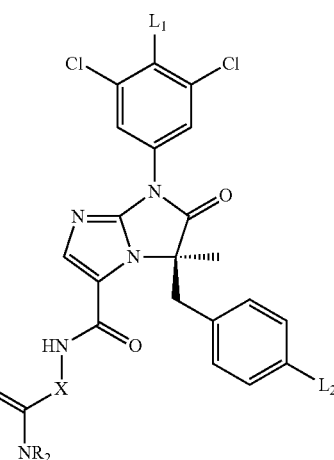
| Cpd # | NR₂ | X | L₁ | L₂ |
|---|---|---|---|---|
| 385 | cyclopropyl-NH attached to 5-cyclopropyl-4H-1,2,4-triazol-3-yl | CH(CH₃) | F | CN |
| 386 | 1-(6-methylpyridin-2-yl)cyclopropyl-NH | 1,1-cyclopropylene | H | CN |
| 387 | 1-(6-bromopyridin-2-yl)cyclopropyl-NH | 1,1-cyclopropylene | H | CN |
| 388 | 1-(1,6-naphthyridin-2-yl)cyclopropyl-NH | 1,1-cyclopropylene | F | CN |

-continued
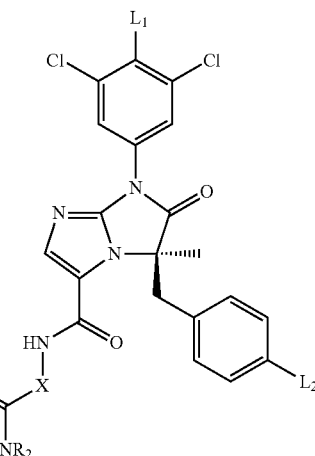
| Cpd # | NR₂ | X | L₁ | L₂ |
|---|---|---|---|---|
| 389 | 1-(3-cyclopropyl-1,2,4-oxadiazol-5-yl)cyclopropylamino | cyclopropylidene | H | CN |
| 393 | 1-(pyridin-2-yl)cyclobutylamino | cyclopropylidene | H | CN |
| 394 | 1-(pyridin-2-yl)cyclopropylamino | cyclopropylidene | F | pyrimidin-5-yl |
| 395 | 1-(2-(4-methylsulfonamido)pyridin-2-yl)cyclopropylamino | cyclopropylidene | H | CN |

-continued
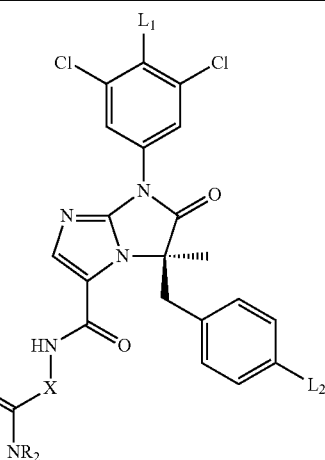
| Cpd # | NR₂ | X | L₁ | L₂ |
|---|---|---|---|---|
| 396 | cyclopropyl-NH- linked to pyridine with 5-SO₂Me | cyclopropyl | H | OCF3 |
| 397 | cyclopropyl-NH- linked to 1,5-naphthyridine | cyclopropyl | F | CN |
| 400 | cyclopropyl-NH- linked to oxazole with 4-C(O)NH₂ | cyclopropyl | H | CN |
| 401 | cyclopropyl-NH- linked to 1,2,4-oxadiazole with 5-CF₃ | cyclopropyl | F | CN |

-continued
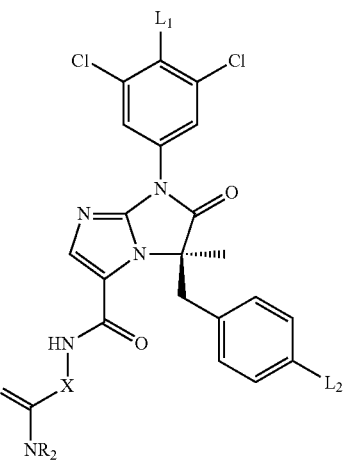
| Cpd # | NR₂ | X | L₁ | L₂ |
|---|---|---|---|---|
| 402 | 1-(pyrimidin-2-yl)cyclopropyl-NH- | -CH(CH₂CH₂S(O)₂CH₃)- | F | CN |
| 403 | 1-(pyrimidin-2-yl)cyclopropyl-NH- | -CH(CH₂OH)- | F | CN |
| 404 | 1-(pyrimidin-2-yl)cyclopropyl-NH- | -CH(CH₂OCH₃)- | F | CN |
| 405 | 1-(pyrimidin-2-yl)cyclopropyl-NH- | -CH(CH(OH)CH₃)- | F | CN |
| 406 | 1-(4-cyanopyridin-2-yl)cyclopropyl-NH- | 1-cyclopropyl-cyclopropyl | H | CN |

-continued
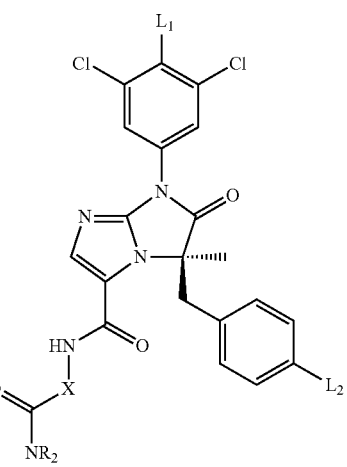
| Cpd # | NR₂ | X | L₁ | L₂ |
|---|---|---|---|---|
| 407 | 1-(3-cyclopropyl-1,2,4-oxadiazol-5-yl)cyclopropylamino | cyclopropylidene | F | CN |
| 408 | 1-(3-cyclopropyl-1,2,4-oxadiazol-5-yl)cyclopropylamino | (S)-sec-butyl | H | OCF3 |
| 409 | 1-(pyrimidin-2-yl)cyclopropylamino | (R)-1-(2H-1,2,3-triazol-2-yl)ethylmethyl | F | CN |
| 410 | 1-(5-acetylpyridin-2-yl)cyclopropylamino | cyclopropylidene | H | CN |

-continued
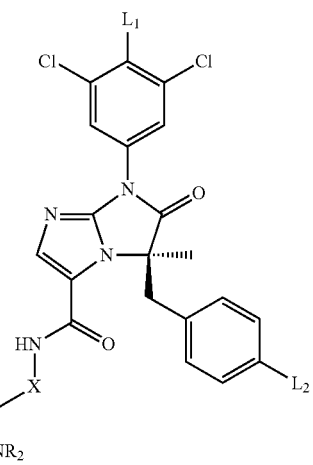
| Cpd # | NR₂ | X | L₁ | L₂ |
|---|---|---|---|---|
| 411 | cyclopropyl-NH- linked to pyrimidin-4-yl | cyclopropyl | H | CN |
| 413 | cyclopropyl-NH- linked to 4-(hydroxymethyl)pyridin-2-yl | cyclopropyl | H | CN |
| 414 | cyclopropyl-NH- linked to 5-bromopyridin-2-yl | cyclopropyl | F | CN |
| 415 | cyclopropyl-NH- linked to 4-carboxypyridin-2-yl | cyclopropyl | H | CN |

-continued
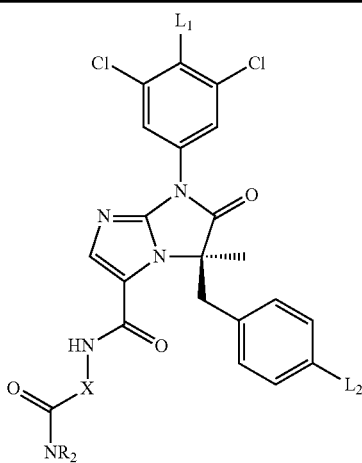
| Cpd # | NR₂ | X | L₁ | L₂ |
|---|---|---|---|---|
| 416 | 1-(5-carboxypyridin-2-yl)cyclopropyl-NH- | cyclopropyl | H | CN |
| 417 | 1-(5-carboxypyridin-2-yl)cyclopropyl-NH- | cyclopropyl | F | CN |
| 418 | 1-(5-carboxypyridin-2-yl)cyclopropyl-NH- | cyclopropyl | F | OCF3 |
| 419 | 1-(1,8-naphthyridin-2-yl)cyclopropyl-NH- | CH(OH)CH(CH3) | F | CN |

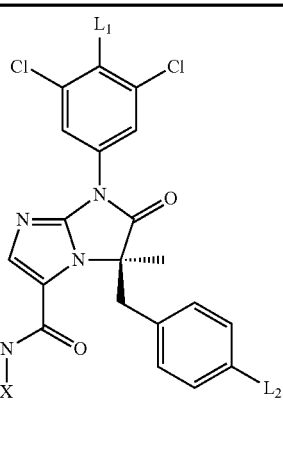
| Cpd # | NR₂ | X | L₁ | L₂ |
|---|---|---|---|---|
| 420 | cyclopropyl-NH-(1,8-naphthyridin-2-yl) | CH(CH₂OH) | F | CN |
| 422 | cyclopropyl-NH-[2-(4-(pyrrolidin-1-ylmethyl)pyridin-3-yl)] | cyclopropyl | H | OCF₃ |
| 423 | cyclopropyl-NH-[2-(4-(morpholinomethyl)pyridin-3-yl)] | cyclopropyl | H | CN |
| 424 | cyclopropyl-NH-[2-(4-(azetidin-1-ylmethyl)pyridin-3-yl)] | cyclopropyl | H | CN |
| 425 | cyclopropyl-NH-[2-(4-((3-hydroxyazetidin-1-yl)methyl)pyridin-3-yl)] | cyclopropyl | H | CN |

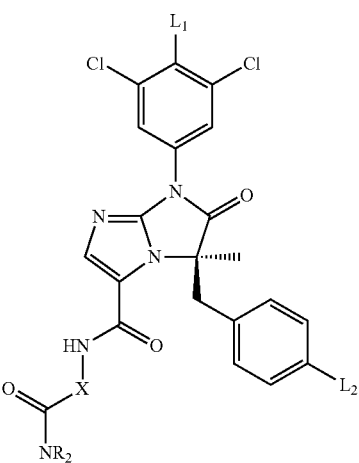
| Cpd # | NR2 | X | L1 | L2 |
|---|---|---|---|---|
| 426 | cyclopropyl-NH- linked to 2-pyridyl with 4-CH2NHC(O)CH3 | cyclopropyl | H | CN |
| 427 | cyclopropyl-NH- linked to 2-pyridyl with 4-CH2NHS(O)2CH3 | cyclopropyl | H | CN |
| 428 | cyclopropyl-NH- linked to 2-pyridyl with 4-CH2NHC(O)NH2 | cyclopropyl | H | CN |
| 429 | cyclopropyl-NH- linked to 2-pyridyl with 4-CH2NHC(O)-cyclopropyl | cyclopropyl | H | CN |

-continued
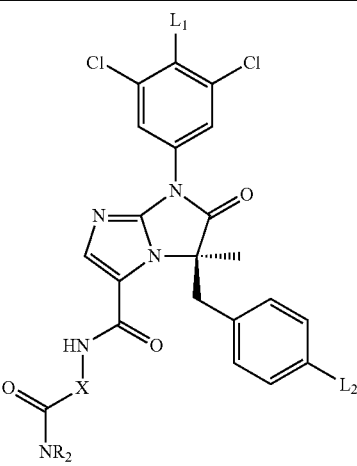
| Cpd # | NR₂ | X | L₁ | L₂ |
|---|---|---|---|---|
| 430 | 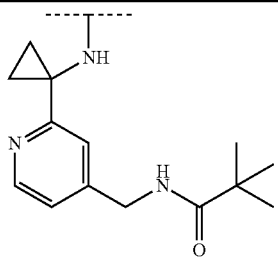 | 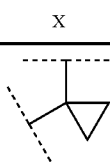 | H | CN |
| 431 | 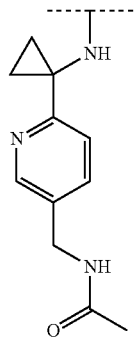 | 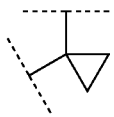 | H | CN |
| 432 | 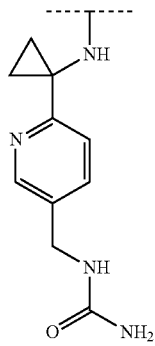 | 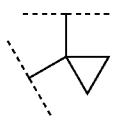 | H | CN |

-continued
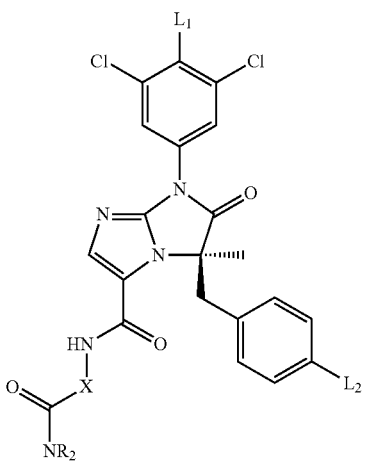
| Cpd # | NR₂ | X | L₁ | L₂ |
|---|---|---|---|---|
| 433 | cyclopropyl-NH-[pyridin-2-yl]-CH₂-NH-S(O)₂-CH₃ | cyclopropyl | H | CN |
| 434 | cyclopropyl-NH-[pyridin-2-yl]-CH₂-NH-C(O)-cyclopropyl | cyclopropyl | H | CN |
| 435 | cyclopropyl-NH-[pyridin-2-yl]-CH₂-NH-C(O)-C(CH₃)₃ | cyclopropyl | H | CN |

-continued
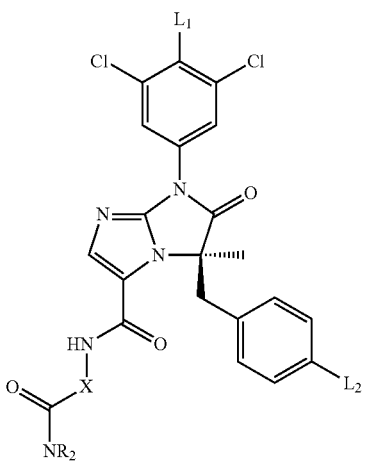
| Cpd # | NR₂ | X | L₁ | L₂ |
| --- | --- | --- | --- | --- |
| 436 | cyclopropyl-NH-pyridine-CH₂-NH-SO₂-cyclopropyl | cyclopropyl | H | CN |
| 437 | cyclopropyl-NH-pyridine-CH₂-NH-SO₂-CH₃ | cyclopropyl | F | CN |
| 438 | cyclopropyl-NH-pyridine-CH₂-NH-SO₂-cyclopropyl | cyclopropyl | F | CN |

-continued
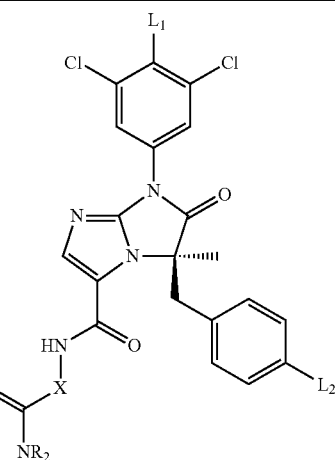
| Cpd # | NR2 | X | L1 | L2 |
|---|---|---|---|---|
| 439 | 1-(1,8-naphthyridin-2-yl)cyclopropyl-NH- | CH(CH3)- | F | CN |
| 440 | 1-(1,5-naphthyridin-2-yl)cyclopropyl-NH- | CH(CH3)- | F | CN |
| 441 | 1-(1,8-naphthyridin-2-yl)cyclopropyl-NH- | cyclopropyl | F | OCF3 |
| 442 | 1-(quinazolin-2-yl)cyclopropyl-NH- | CH(CH3)- | F | CN |

-continued
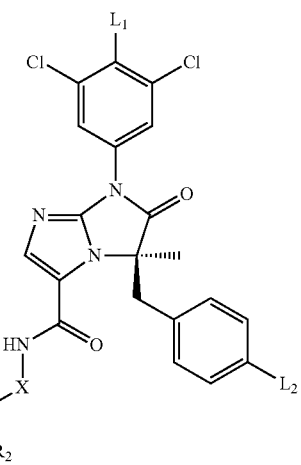
| Cpd # | NR₂ | X | L₁ | L₂ |
|---|---|---|---|---|
| 443 | 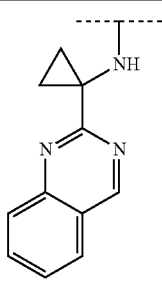 | 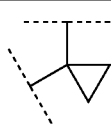 | F | OCF3 |
| 445 | 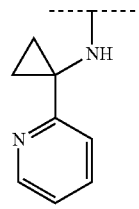 | 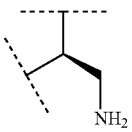 | H | CN |
| 446 | 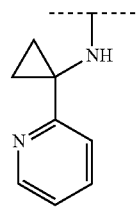 | 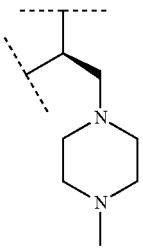 | H | CN |
| 447 | 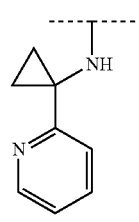 | 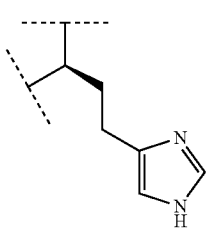 | H | CN |

-continued

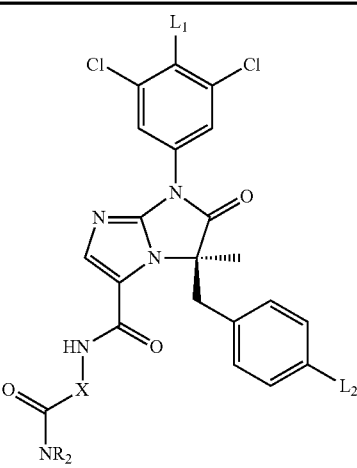

| Cpd # | NR₂ | X | L₁ | L₂ |
|---|---|---|---|---|
| 448 | 1-(pyridin-2-yl)cyclopropyl-NH- | -CH(CH₂OH)- | F | CN |
| 449 | 1-(pyridin-2-yl)cyclopropyl-NH- | -CH(CH₂OSO₃H)- | F | CN |
| 450 | 1-(pyridin-2-yl)cyclopropyl-NH- | -CH(CH₂CH₂C(O)O-tBu)- | F | CN |
| 451 | 1-(pyridin-2-yl)cyclopropyl-NH- | -CH(CH₂CH₂C(O)OH)- | F | CN |

General Synthetic Methods

The compounds of the invention may be prepared by the methods described below. In each of the schemes below, the groups $R^1$-$R^{10}$ are as defined above for general formula I unless noted otherwise. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) or HPLC-MS if desired. Intermediates and products may be purified by chromatography on silica gel, recrystallization and/or reverse phase HPLC. HPLC purification methods used anywhere from 0-100% acetonitrile in water containing 0.1% formic acid or 0.1% TFA and used one of the following columns:

a) Waters Sunfire OBD C18 5 μM 30×150 mm column
b) Waters XBridge OBD C18 5 μM 30×150 mm column
c) Waters ODB C8 5 μM 19×150 mm column.
d) Waters Atlantis ODB C18 5 μM 19×50 mm column.
e) Waters Atlantis T3 OBD 5 μM 30×100 mm column
f) Phenomenex Gemini Axia C18 5 μM 30×100 mm column Starting materials and reagents are either commercially available or may be prepared by one skilled in the art using methods described in the chemical literature.

Compounds of formula I may be prepared from intermediate II as illustrated in Scheme I. The synthesis of intermediate II is reported by the following U.S. Pat. Nos. 6,492,408, 6,414,161, 6,844,360, 6,852,748 and also US Application Publications 2006/0025447 and 2007/0173517. The desired $R^1$ on formula II compounds may be obtained by selection of the appropriately substituted reagents as described in Wu et al., U.S. Pat. No. 6,492,408 and Frutos et al., U.S. Pat. No. 6,414,161.

The synthesis of compounds of formula I from intermediate II is illustrated in Scheme I.

Scheme I

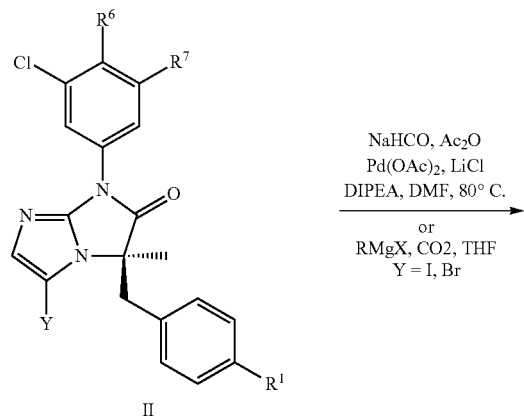

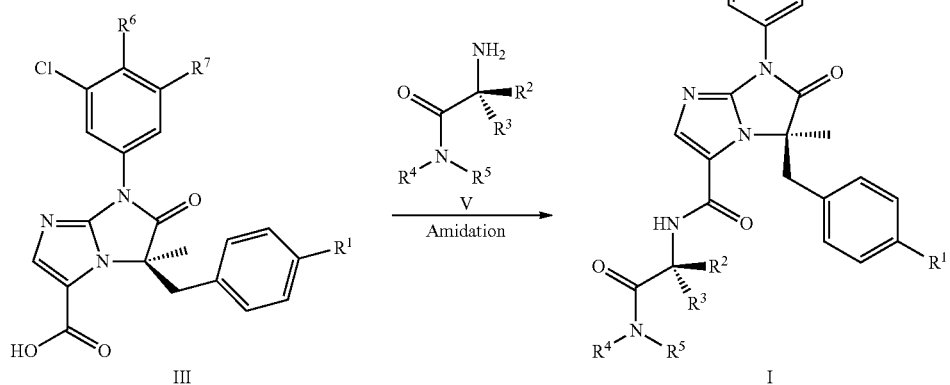

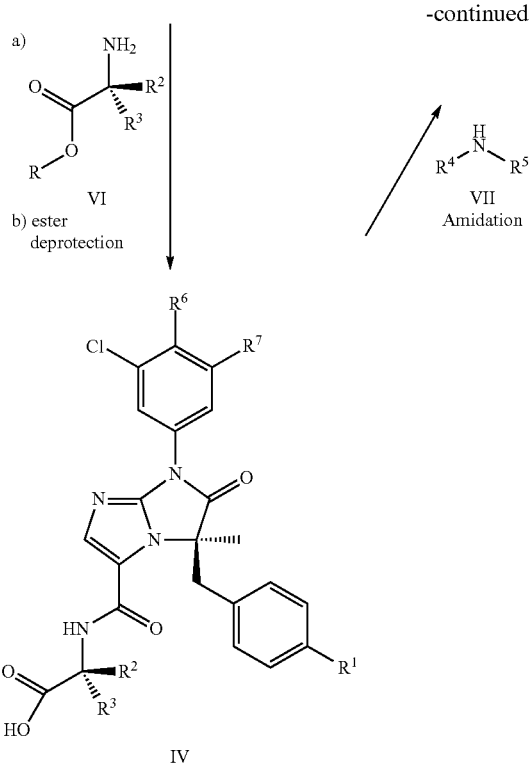

As illustrated above, II is transformed into III under Grignard conditions and trapping with $CO_2$ or Pd catalyzed carboxylation. Carboxylic acid III provides I by either amide formation with a suitably functionalized intermediate V or a three step procedure which forms intermediate IV prior to final amide forming reaction. Intermediates (V, VI and VII) are either commercially available, readily prepared from commercially available starting materials by methods known in the art or disclosed herein. The initial product of formula I may be further modified by methods known in the art to provide additional compounds of the invention. Several examples are provided in the Synthetic Examples section.

Synthetic Examples

Synthesis of Intermediates (R)-5-Pyrrolidin-3-yl-2H-pyrazol-3-ol

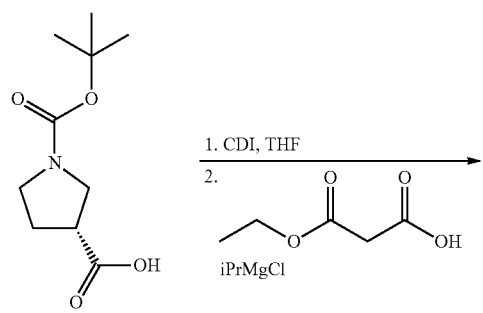

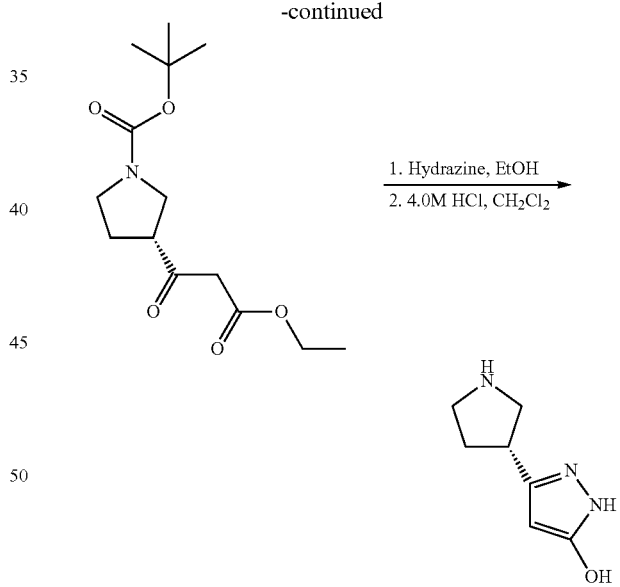

To a solution of (R)-pyrrolidine-1,3-dicarboxylic acid 1-tert-butyl ester (1 g, 4.65 mmol) in THF (5 mL) was added CDI (0.9 g, 5.58 mmol). The reaction mixture was stirred at room temperature for 12 h to yield a crude solution of (R)-3-(imidazole-1-carbonyl)-pyrrolidine-1-carboxylic acid tert-butyl ester.

A solution of the malonate (0.92 g, 6.97 mmol) in THF (5 mL) was cooled to 0° C. under $N_2$. Isopropylmagnesium chloride (6.97 mL, 2.0 M) was added and the reaction was stirred for 30 min at 0° C., 30 min at room temperature and 30 min at 40° C. The solution was then cooled to 0° C. and the crude solution of (R)-3-(imidazole-1-carbonyl)-pyrrolidine- 1-carboxylic acid tert-butyl ester was added via cannula. A thick precipitate formed. The reaction was warmed to room temperature and stirred under $N_2$ for 12 h. The reaction mixture was cooled to 0° C. and ice-cold 1.0 M $H_3PO_4$ (20 mL) was added to the mixture. After 5 min, the reaction was extracted with EtOAc (3×20 mL). The combined organic extracts were washed with sat. $NaHCO_3$ (15 mL) and brine (15 mL), dried over $MgSO_4$ and concentrated to afford crude (R)-3-(2-ethoxycarbonyl-acetyl)-pyrrolidine-1-carboxylic acid tert-butyl ester (0.91 g, crude 69%). The material was used without further purification.

To a solution of (R)-3-(2-ethoxycarbonyl-acetyl)-pyrrolidine-1-carboxylic acid tert-butyl ester (150 mg, 0.53 mmol) in ethanol (3 mL) was added hydrazine (18 μL, 0.58 mmol).

The reaction mixture was stirred at room temperature for 4.5 h. The solvent was evaporated in vacuo and the residue was purified using flash chromatography on silica gel (1-5% MeOH/$CH_2Cl_2$) to afford (R)-3-(5-hydroxy-1H-pyrazol-3-yl)-pyrrolidine-1-carboxylic acid tert-butyl ester (70 mg, 53%) as a white solid.

To a solution of (R)-3-(5-hydroxy-1H-pyrazol-3-yl)-pyrrolidine-1-carboxylic acid tert-butyl ester (44 mg, 0.17 mmol) in $CH_2Cl_2$ (1 mL) was added HCl in dioxane (0.2 mL, 4.0 M). The reaction mixture was stirred for 48 h. Solvent was removed at reduced pressure to afford crude (R)-5-pyrrolidin-3-yl-2H-pyrazol-3-ol as a white solid. The material was used without further purification.

(R)-5-Piperidin-3-yl-2H-pyrazol-3-ol was prepared using a procedure analogous to that described above.

(1S,3R)-3-Amino-cyclopentanecarboxylic acid methyl ester

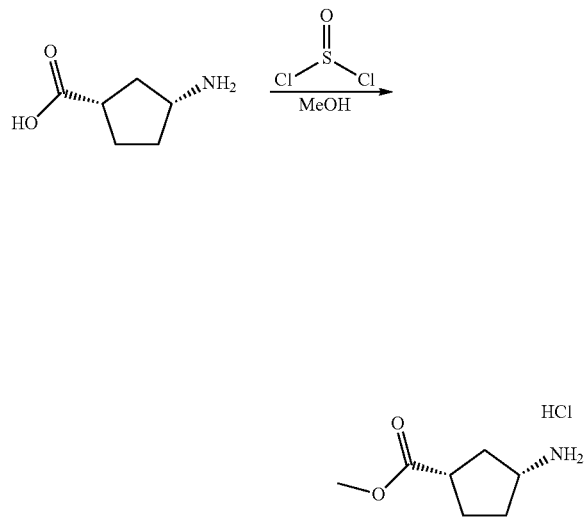

To a solution of (1S,3R)-3-aminocyclopentanecarboxylic acid (1.0 g, 7.4 mmol) in dry MeOH (10 mL) under $N_2$ at 0° C. was added thionyl chloride (2.7 mL, 36.8 mmol) dropwise. The reaction mixture was slowly warmed to room temperature and stirred overnight. The reaction was concentrated in vacuo. The resultant residue was washed with anhydrous diethyl ether (3×30 mL) and dried under high vacuum to afford 1.87 g of (1S,3R)-3-amino-cyclopentanecarboxylic acid methyl ester as the HCl salt that was used without further purification.

(R)-3-Pyrrolidin-3-yl-4H-1,2,4-oxadiazol-5-one

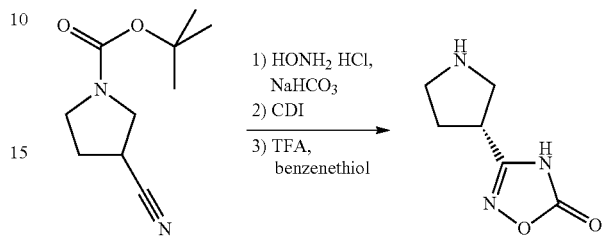

(R)-3-Cyano-pyrrolidine-1-carboxylic acid tert-butyl ester (1.02 g, 5.2 mmol), hydroxylamine hydrochloride (396 mg, 5.7 mmol) and $NaHCO_3$ (487 mg, 5.8 mmol) were added to MeOH (12 mL) and the solution was heated to reflux. After 4 h, the reaction was concentrated in vacuo. The residue was partitioned between EtOAc and brine. The layers were separated and the organic layer was dried over $Na_2SO_4$, filtered and concentrated to yield 927 mg of crude (R)-3-(N-hydroxycarbamimidoyl)-pyrrolidine-1-carboxylic acid tert-butyl ester as a yellow foam.

Crude (R)-3-(N-hydroxycarbamimidoyl)-pyrrolidine-1-carboxylic acid tert-butyl ester (887 mg, 3.86 mmol) and CDI (94 mg, 5.8 mmol) were dissolved in dioxane (30 mL) and heated to reflux. After 1 h, the reaction was concentrated in vacuo. The crude reaction mixture was dissolved in $CH_2Cl_2$ and the pH was adjusted to 3 by adding 1M HCl to the solution. The layers were separated and the aqueous layer was extracted with $CH_2Cl_2$. The combined organic layers were washed with water and brine, dried over $MgSO_4$, filtered and concentrated in vacuo to yield 872 mg of crude (R)-3-(5-oxo-4,5-dihydro-1,2,4-oxadiazol-3-yl)-pyrrolidine-1-carboxylic acid tert-butyl ester.

Crude (R)-3-(5-oxo-4,5-dihydro-1,2,4-oxadiazol-3-yl)-pyrrolidine-1-carboxylic acid tert-butyl ester (872 mg, 3.41 mmol), $CH_2Cl_2$ (5 mL) and thiophenol (0.7 mL, 6.8 mmol) were combined and diluted with TFA (5 mL). After 24 h, the reaction was concentrated in vacuo. The residue was partitioned between $CH_2Cl_2$ and water. The layers were separated and the $CH_2Cl_2$ layer was extracted with water. The combined aqueous layers were concentrated in vacuo. Reverse phase HPLC purification yielded 482 mg of (R)-3-pyrrolidin-3-yl-4H-1,2,4-oxadiazol-5-one as a tan oil (~50% pure) that was used without further purification.

2-(1H-Tetrazol-5-yl)-ethylamine formiate

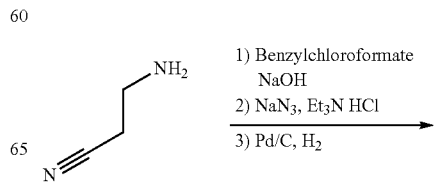

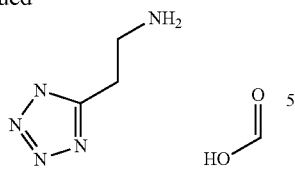

Aminopropionitrile fumarate (6.6 g, 53.4 mmol) was dissolved in water and basified to pH 10 with solid NaOH. A solution of benzylchloroformate (8.0 mL, 53.4 mmol) in $Et_2O$ (15 mL) was then added with vigorous stirring. The pH was continually adjusted to pH 10 by addition of 2M NaOH. After 2 h, the reaction was diluted with $Et_2O$ and the layers were separated. The aqueous layer was extracted with $Et_2O$. The combined organic layers were washed with water and brine, dried over $MgSO_4$, filtered and concentrated in vacuo. The resulting solid was dissolved in hot $Et_2O$ and filtered to yield 1 g of (2-cyano-ethyl)-carbamic acid benzyl ester as a white solid. Another 3.35 g of (2-cyano-ethyl)-carbamic acid benzyl ester was obtained by repetitive crystallization of the mother liquor from $Et_2O$.

A mixture of (2-cyano-ethyl)-carbamic acid benzyl ester (2.6 g, 12.7 mmol), sodium azide (2.48 g, 38 mmol) and triethylamine hydrochloride (2.62 g, 19 mmol) in NMP (96 mL) was stirred at 100° C. under Ar. After 24 h, the reaction was cooled to room temperature. Additional sodium azide (1.24 g, 19 mmol) and triethylamine hydrochloride (1.3 g, 9.5 mmol) was added to the reaction mixture and the solution was heated to 100° C. under Ar. After 18 h, the reaction was diluted with water (100 mL). 1M HCl was added dropwise until the pH was slightly acidic (~pH 4). The solution was extracted with EtOAc (3×100 mL). The combined organic layers were washed with water (3×100 mL) and brine (100 mL), dried over $MgSO_4$, filtered and concentrated in vacuo to yield a brown oil. Flash chromatography on silica gel (0-15% MeOH in $CH_2Cl_2$) yielded 1.1 g of crude 2-(1H-tetrazol-5-yl)-ethyl]-carbamic acid benzyl ester (~70% pure).

Crude 2-(1H-tetrazol-5-yl)-ethyl]carbamic acid benzyl ester (1.0 g, 4.04 mmol) was dissolved in MeOH (35 mL). The flask was purged with Ar and then 10% Pd/C (100 mg) was added. The flask was purged with $H_2$ (balloon). After 6 h, the reaction was purged with Ar and the heterogeneous solution was filtered through diatomaceous earth. The Pd/C was washed with MeOH. The filtrate was concentrated in vacuo to yield 470 mg of a yellow solid. The solid was purified via reverse phase HPLC, yielding 310 mg of 2-(1H-tetrazol-5-yl)-ethylamine formiate as a colorless oil which solidified upon standing.

(R)-3-Pyrrolidin-3-yl-4H-[1,2,4]thiadiazol-5-one

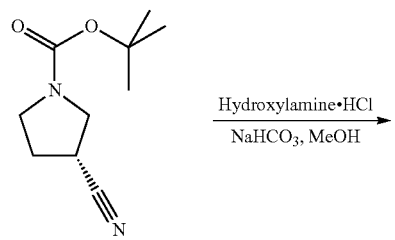

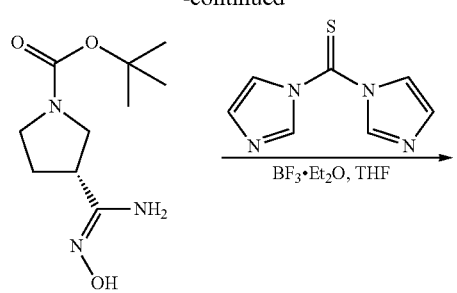

(R)-3-Cyano-pyrrolidine-1-carboxylic acid tert-butyl ester (2.04 g, 10.4 mmol), hydroxylamine hydrochloride (0.79 g, 11.4 mmol) and $NaHCO_3$ (0.97 g, 11.6 mmol) were added to MeOH (24 mL) and the solution was heated to reflux. After 4 h, the reaction was cooled to room temperature and filtered through a fritted funnel. The solution was concentrated in vacuo. The residue was purified by reverse phase HPLC to afford (R)-3-(N-hydroxycarbamimidoyl)-pyrrolidine-1-carboxylic acid tert-butyl ester (1.28 g, 5.58 mmol, 54%) as a yellow foam.

(R)-3-(N-Hydroxycarbamimidoyl)-pyrrolidine-1-carboxylic acid tert-butyl ester (0.54 g, 2.36 mmol) and di-imidazol-1-yl-methanethione (0.70 g, 3.53 mmol) were dissolved in THF (15 mL) and stirred for 30 min. The reaction was diluted with water (50 mL) and extracted with EtOAc (50 mL×3). The combined organic layers were dried by $MgSO_4$ and concentrated in vacuo. The residue was dissolved in THF (20 mL) and $BF_3.Et_2O$ (0.89 ml, 7.06 mmol) was added dropwise. After 1 h of stirring, the reaction was diluted with water (50 mL) and extracted with EtOAc (50 mL×3). The combined organic layers were dried with $MgSO_4$ and concentrated in vacuo. The crude material was purified by flash chromatography on silica gel (20-50% EtOAc/Hexane) to give (R)-3-(5-oxo-4,5-dihydro-[1,2,4]thiadiazol-3-yl)-pyrrolidine-1-carboxylic acid tert-butyl ester (0.42 g, 1.55 mmol, 66%) as a white solid.

(R)-3-(5-Oxo-4,5-dihydro-[1,2,4]thiadiazol-3-yl)-pyrrolidine-1-carboxylic acid tert-butyl ester (420 mg, 1.55 mmol) was dissolved in methanol (15 mL). 4M HCl in dioxane (0.70 mL, 2.80 mmol) was then added. The solution was stirred overnight. The reaction was concentrated in vacuo. The resi- (R)-5-Pyrrolidin-3-yl-2H-tetrazole

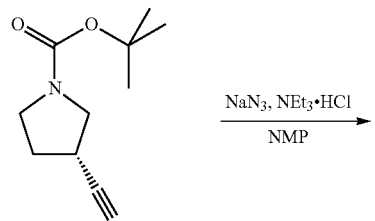

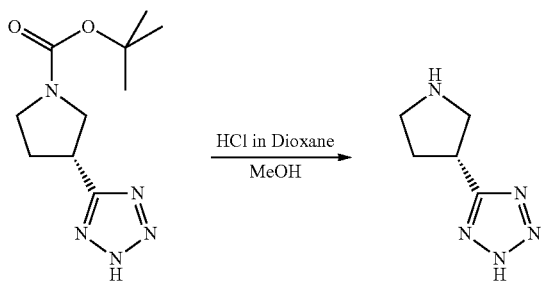

A mixture of (R)-3-cyano-pyrrolidine-1-carboxylic acid tert-butyl ester (1.0 g, 5.10 mmol), sodium azide (0.99 g, 15.3 mmol) and triethylamine hydrochloride (1.05 g, 7.64 mmol) in NMP (40 mL) was stirred at 140° C. for 6 h under Ar. The reaction was cooled to room temperature and diluted with water (50 mL). 1M HCl was added dropwise until the pH of the solution was slightly acidic (approx pH 4). The solution was then extracted with EtOAc (3×100 mL). The combined organic layers were washed with brine (50 mL), dried over MgSO$_4$, filtered and concentrated to yield 3 g of tan oil. Reverse phase HPLC purification afforded (R)-3-(2H-tetrazol-5-yl)-pyrrolidine-1-carboxylic acid tert-butyl ester (620 mg, 2.59 mmol, 51%) as a yellow oil.

(R)-3-(2H-Tetrazol-5-yl)-pyrrolidine-1-carboxylic acid tert-butyl ester (600 mg, 2.51 mmol) was dissolved in methanol (20 mL), 4M HCl in dioxane (1.13 ml, 4.52 mmol) was then added dropwise. The solution was stirred overnight. The reaction was concentrated in vacuo. The residue was purified by reverse phase HPLC to afford (R)-5-pyrrolidin-3-yl-2H-tetrazole (220 mg, 1.58 mmol, 63%) as a white solid.

The following tetrazoles were synthesized using procedures analogous to that described above:
(S)-5-Pyrrolidin-3-yl-2H-tetrazole, 5-(3-Methyl-pyrrolidin-3-yl)-2H-tetrazole, 3-(2H-Tetrazol-5-yl)-piperidine, (S)-3-(2H-Tetrazol-5-yl)-piperidine, (R)-3-(2H-Tetrazol-5-yl)-piperidine 2-Methyl-5-(R)-pyrrolidin-3-yl-2H-tetrazole trifluoroacetic acid salt

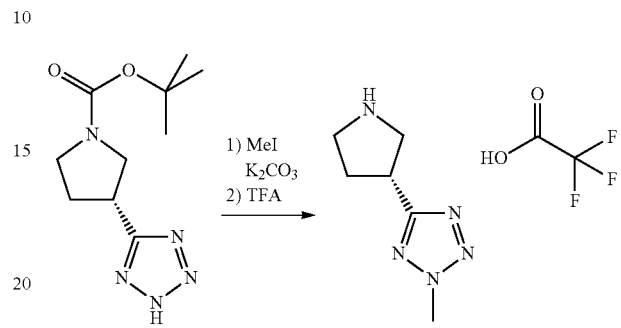

(R)-3-(2H-Tetrazol-5-yl)-pyrrolidine-1-carboxylic acid tert-butyl ester (500 mg, 2.1 mmol) was dissolved in acetone (20 mL). K$_2$CO$_3$ (579 mg, 4.2 mmol) and MeI (0.14 mL, 2.19 mmol) were added sequentially. After 8 h the crude reaction was filtered and the filtrate was concentrated. The residue was purified via reverse phase HPLC and yielded 145 mg of (R)-3-(1-methyl-1H-tetrazol-5-yl)-pyrrolidine-1-carboxylic acid tert-butyl ester as a white solid (eluted first) and 243 mg of (R)-3-(2-methyl-2H-tetrazol-5-yl)-pyrrolidine-1-carboxylic acid tert-butyl ester as a pale yellow oil.

(R)-3-(2-methyl-2H-tetrazol-5-yl)-pyrrolidine-1-carboxylic acid tert-butyl ester was dissolved in CH$_2$Cl$_2$ (3.5 mL) and diluted with TFA (3.5 mL). After 18 h, the reaction was concentrated in vacuo and yielded 260 mg of 2-methyl-5-(R)-pyrrolidin-3-yl-2H-tetrazole trifluoroacetic acid salt as a tan oil.

2-tert-Butyl-5-(R)-pyrrolidin-3-yl-2H-tetrazole trifluoroacetic acid salt

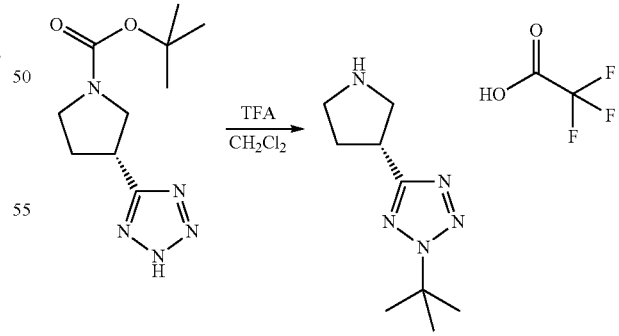

(R)-3-(2H-Tetrazol-5-yl)-pyrrolidine-1-carboxylic acid tert-butyl ester (840 mg, 3.51 mmol) was dissolved in CH$_2$Cl$_2$ (20 mL) and TFA (4 mL) was added dropwise. The reaction was stirred overnight at 25° C. The solution was concentrated in vacuo to give the crude product. It was determined that the mixture contained 2-tert-butyl-5-(R)-pyrrolidin-3-yl-2H-tetrazole and (R)-5-pyrrolidin-3-yl-2H-tetrazole (3:1) as trifluoroacetic acid salts. The mixture was used without further purification.

(1-Carbamoyl-1-methyl-ethyl)-carbamic acid tert-butyl ester

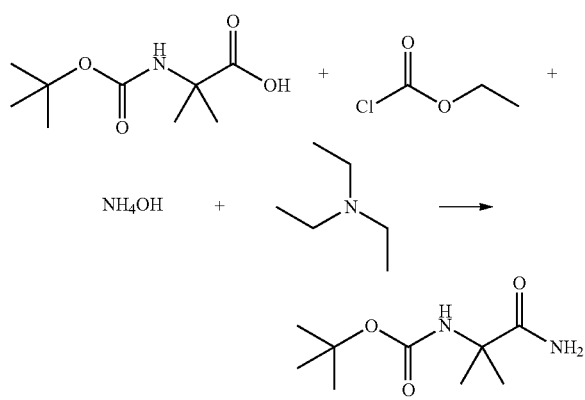

To a cooled (−10° C.) solution of 2-tert-butoxycarbonylamino-2-methyl-propionic acid (1.00 g, 4.92 mmol) and triethylamine (686 μL, 4.92 mmol) in tetrahydrofuran (20 mL) was added ethyl chloroformate (470 μL, 4.92 mmol). The reaction mixture was stirred for 1 h. The ammonium hydroxide (1.20 mL, 19.7 mmol) was added and the solution was stirred at room temperature for 16 h. The product was then filtered through a Buchner funnel and dried in vacuo to afford 945 mg of the title compounds as a white solid, m/z 203.3 [M+1]$^+$.

The following compound was prepared using similar procedures as described above:

(1-Carbamoyl-cyclopropyl)-carbamic acid tert-butyl ester, m/z 201.2 [M+1]$^+$

2-Amino-2-methyl-propionamide trifluoroacetic acid salt

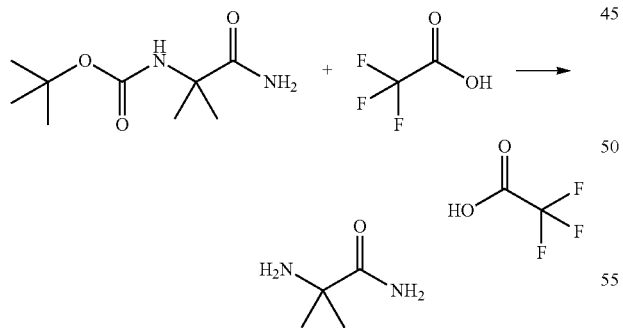

To a solution of (1-carbamoyl-1-methyl-ethyl)-carbamic acid tert-butyl ester (945 mg, 4.67 mmol) in dichloromethane (20 mL) was added trifluoroacetic acid (10.0 mL, 64 mmol). The reaction mixture was stirred at room temperature for 4 h. The reaction mixture was then concentrated in vacuo to afford 882 mg of the title compound as a white solid, isolated as the TFA salt, m/z 103.2 [M+1]$^+$.

The following compound was prepared using similar procedures as described above:

1-Amino-cyclopropanecarboxylic acid amide, m/z 101.1 [M+1]$^+$ (R)-2-Amino-thiopropionamide hydrochloride

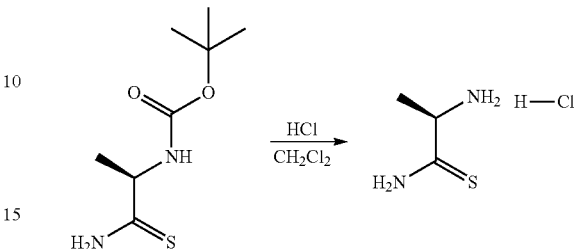

To a suspension of the ((R)-1-thiocarbamoyl-ethyl)-carbamic acid tert-butyl ester[1] (600 mg, 2.94 mmol) in 10 mL of $CH_2Cl_2$ was added HCl in dioxane (4 M, 3.67 mL, 14.7 mmol). The reaction mixture became clear within a few minutes, followed by the formation of a white precipitate. The cloudy reaction mixture was stirred at room temperature for 5 h and then diluted with 25 mL of $Et_2O$ and filtered, washing with $Et_2O$. (R)-2-Amino-thiopropionamide hydrochloride was obtained as a sticky white solid after drying under high vacuum, 393 mg (95%). This material was used without further purification.

[1]Xia, Z.; Smith, C. D. J. Org. Chem. 2001, 66, 3459-3466.

1-Amino-cyclopropanecarbothioic acid amide hydrochloride

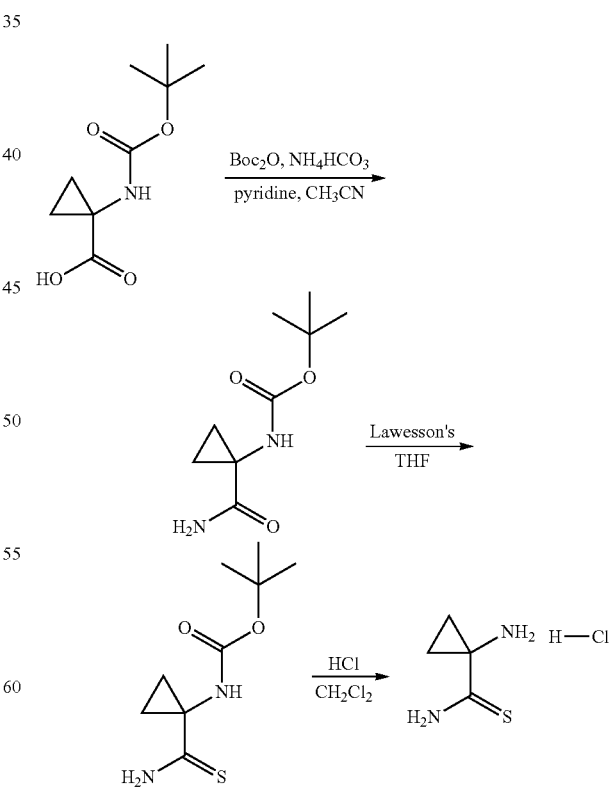

To a mixture of 1-tert-butoxycarbonylamino-cyclopropanecarboxylic acid (2.00 g, 9.94 mmol), Boc anhydride (2.82 g, 12.9 mmol), ammonium bicarbonate (0.982 g, 12.4 mmol) in 30 mL of acetonitrile at room temperature was added pyridine (0.482 mL, 5.96 mmol). The cloudy, colorless reaction mixture was stirred at room temperature for 16 h and then concentrated under reduced pressure. The residue was partitioned between 100 mL of ethyl acetate and 30 mL of 1 M HCl. The organic phase was washed with 30 mL of saturated. NaHCO$_3$ solution and brine, dried over Na$_2$SO$_4$, filtered, and concentrated in vacuo to give 1.80 g (90%) of (1-carbamoyl-cyclopropyl)-carbamic acid tert-butyl ester as a white solid.

To a suspension of (1-carbamoyl-cyclopropyl)-carbamic acid tert-butyl ester (1.00 g, 4.99 mmol) in 6 mL of THF was added Lawesson's reagent (1.01 g, 2.50 mmol). The pale yellow cloudy reaction mixture was stirred at room temperature for 6 h and then partitioned between 40 mL of ethyl acetate and 15 mL of 0.5 M NaOH solution. The organic phase was washed with 15 mL each of water and brine, dried over Na$_2$SO$_4$, filtered, and concentrated in vacuo. The crude was purified by flash chromatography on silica gel, eluting with 20-60% EtOAc/hexanes, to give 864 mg (80%) of (1-thiocarbamoyl-cyclopropyl)-carbamic acid tert-butyl ester as a white solid.

To a suspension of (1-thiocarbamoyl-cyclopropyl)-carbamic acid tert-butyl ester (864 mg, 3.99 mmol) in 15 mL of CH$_2$Cl$_2$ was added HCl in dioxane (4 M, 5.00 mL, 20.0 mmol). The reaction mixture became clear within a few minutes, followed by the formation of a white precipitate. The cloudy reaction mixture was stirred at room temperature for 5 h and then diluted with 40 mL of Et$_2$O and filtered, washing with Et$_2$O. 1-Amino-cyclopropanecarbothioic acid amide hydrochloride was obtained as an off-white solid after drying under high vacuum, 597 mg (98%). This material was used without further purification.

1-(6-Methoxy-pyridin-2-yl)-cyclopropylamine

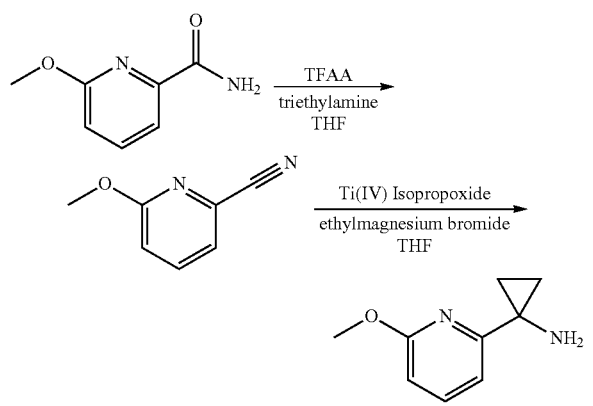

To an ice cold solution of 6-methoxy-pyridine-2-carboxylic acid amide (300 mg, 1.97 mmol) in THF (3 mL) were added triethylamine (1.25 mL, 8.68 mmol) and dropwise added TFAA (0.61 mL, 4.34 mmol). The reaction mixture was allowed to warm to room temperature and stirred overnight. The volatiles were concentrated in vacuo and the liquid residue was added dropwise to a vigorously stirred, ice cold, pH 7 phosphate buffer solution (5 mL). After 15 min of further stirring the yellowish solid was filtered and air dried for 1 h to yield 250 mg (95%) of 6-methoxy-pyridine-2-carbonitrile as yellowish solid, m/z 135.4 [M+1]$^+$.

To a solution of 6-methoxy-pyridine-2-carbonitrile (1.50 g, 11.2 mmol) in THF (75 mL) at room temperature was added Ti(OiPr)$_4$ (7.21 mL, 24.6 mmol). EtMgBr (14.9 mL, 44.7 mmol) was added dropwise. and the clear brown solution became heterogeneous. The reaction mixture was stirred for 1 h at room temperature. The reaction was diluted with water (10 mL), extracted with EtOAc (3×25 mL) and dried with MgSO$_4$. After filtration, the solvent was removed in vacuo. The residue was purified by reverse phase HPLC to afford 380 mg (22%) of 1-(6-methoxy-pyridin-2-yl)-cyclopropylamine, m/z 166.3 [M+1]$^+$.

The following compound was prepared using similar procedures as described above:

1-(4-Methoxy-pyridin-2-yl)-cyclopropylamine (33%), m/z 165.4 [M+1]$^+$ 1-1,3,4-Thiadiazol-2-yl-cyclopropylamine hydrobromide

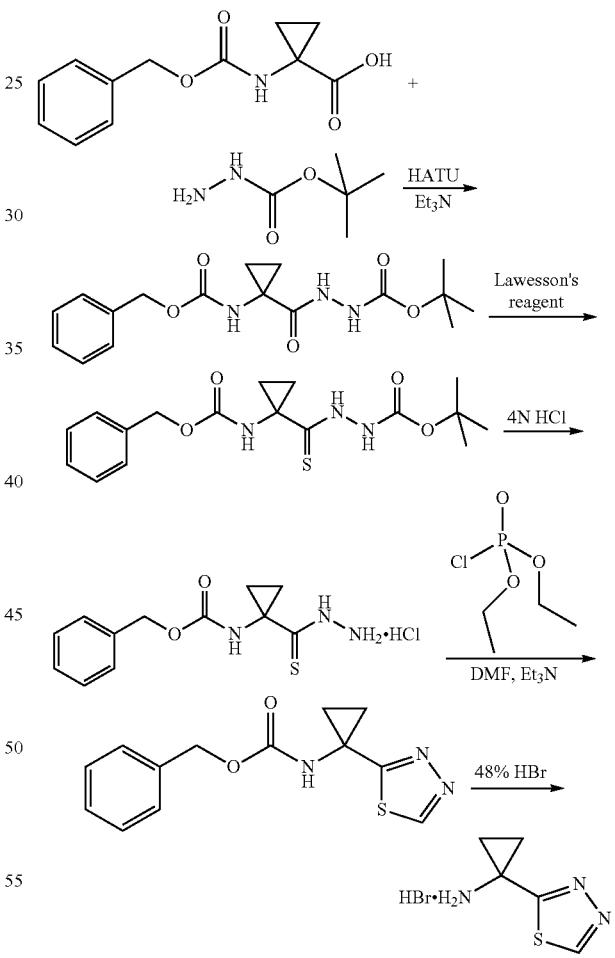

To a solution of 1-benzoylamino-cyclopropanecarboxylic acid (5.0 g, 21.3 mmol) in DMF (5 mL) was added Et$_3$N (2.94 mL, 21.3 mmol) and HATU (8.08 g, 21.3 mmol). The reaction mixture was allowed to stir for 10 min then hydrazinecarboxylic acid tert-butyl ester (2.81 g, 21.3 mmol) was added. The reaction was allowed to stir at room temperature overnight. The mixture was diluted with water and extracted with EtOAc (3×50 mL). The combined extracts were washed with saturated NaHCO₃, 2N HCl, brine and dried with MgSO₄. The mixture was filtered, concentrated in vacuo, and purified by silica gel chromatography (25-100% EtOAc in hexanes) to give the N'-(1-benzyloxy-carbonylamino-cyclopropyl)-hydrazinecarboxylic acid tert-butyl ester (6.2 g, 17.7 mmol) as a white solid, m/z 250.6 [M−101]⁺.

To a solution of N'-(1-benzyloxycarbonylamino-cyclopropyl)-hydrazinecarboxylic acid tert-butyl ester (2.0 g, 5.72 mmol) in toluene (20 mL) was added Lawesson's reagent (2.31 g, 5.72 mmol) and the reaction mixture heated at 90° C. for 12 h. The reaction was cooled to room temperature and diluted with 2N NaOH. The mixture was extracted with EtOAc (3×100 mL) and the combined extracts were washed with water, brine and dried with MgSO₄. The mixture was filtered, concentrated in vacuo, and purified by silica gel chromatography (12-100% EtOAc in hexanes) to give N'-(1-benzyloxythiocabonyl-amino-cyclopropyl)-hydrazinecarboxylic acid tert-butyl ester (0.8 g, 2.19 mmol) as a white solid, m/z 310.6 [M−57]⁺.

N'-(1-benzyloxythiocarbonylamino-cyclopropyl)-hydrazinecarboxylic acid tert-butyl ester (0.25 g, 0.684 mmol) was dissolved in 4N HCl in dioxane (4 mL) and the reaction allowed to stir at room temperature overnight. The mixture was triturated with Et₂O and the resulting precipitate collected by filtration. The precipitate was washed with Et₂O to give (1-hydrazino-cyclopropyl)-thiocarbamic acid O-benzyl ester hydrochloride (0.15 g, 0.48 mmol) as a white solid, m/z 266.5 [M+H]⁺.

To a suspension of (1-hydrazino-cyclopropyl)-thiocarbamic acid O-benzyl ester hydrochloride (0.3 g, 0.99 mmol) was added phosphorochloridic acid diethyl ester (0.14 mL, 0.99 mmol) and Et₃N (0.14 mL, 0.99 mmol). The reaction was stirred at room temperature for 2 h and then diluted with MeOH. The crude reaction mixture was then purified directly by reverse phase HPLC to give (1-1,3,4-thiadiazol-2-yl-cyclopropyl)-carbamic acid benzyl ester (0.24 g, 0.87 mmol) as a clear oil, m/z 276.3 [M+H]⁺.

(1-1,3,4-Thiadiazol-2-yl-cyclopropyl)-carbamic acid benzyl ester (0.2 g, 0.73 mmol) was dissolved in 48% HBr in acetic acid (5 mL) and allowed to stir for 30 min. Et₂O was then added and the majority of the liquid decanted off. The remaining residue was concentrated under reduced pressure to give 1-1,3,4-thiadiazol-2-yl-cyclopropylamine hydrobromide (0.12 g, 0.54 mmol) as an orange gum, m/z 142.4 [M+H]⁺.

N-Hydroxy-morpholine-4-carboxamidine

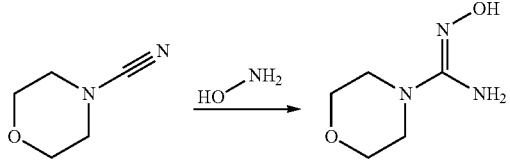

A mixture of hydroxylamine (4.0 mL, 65 mmol) and morpholine-4-carbonitrile (5.00 g, 44.6 mmol) was heated at 80° C. for 24 h. After cooling to room temperature, the reaction mixture was diluted with MeOH and Et₂O, then allowed to stand at room temperature for 2 days. The resultant precipitate was collected by filtration to give 9.02 g of the desired product as a white solid.

3,N-Dihydroxy-butyramidine

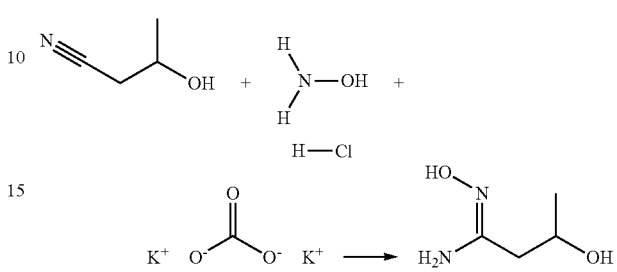

To a slurry of 3-hydroxybutyronitrile (1.00 g, 11.8 mmol) and K₂CO₃ (3.25 g, 23.5 mmol) in 15 mL of ethanol was added hydroxylamine hydrochloride (1.63 g, 23.5 mmol). The reaction mixture was stirred at reflux for 20 h and then cooled to room temperature and filtered, washing with 40 mL of EtOH. The filtrates were concentrated to an oily white solid that was treated with 30 mL of EtOH. The precipitate was filtered, washing with 30 mL of ethanol, and the filtrates were concentrated to a yellow, oily solid. The crude product was triturated with 30 mL of 10% MeOH/dichloromethane and filtered, washing with 10 mL of 10% MeOH/dichloromethane. The filtrates were concentrated to give 1.32 g of the product as a pale yellow oil.

The following compounds were prepared using similar procedures as described above: 3,N-Dihydroxy-propionamidine, N-Hydroxy-propionamidine, 3,3,3-Trifluoro-N-hydroxy-propionamidine, N-Hydroxy-dimethylamine-1-carboxamidine, [1-(N-Hydroxy-carbamimidoyl)-cyclopropyl]-carbamic acid tert-butyl ester; (1-Cyano-cyclopropyl)-carbamic acid tert-butyl ester was prepared from 1-tert-butoxycarbonylamino-cyclopropanecarboxylic acid according to literature procedures (Demko, Z. P.; Sharpless, K. B. Org. Lett. 2002, 4, 2525).

1-(3-Methyl-[1,2,4]oxadiazol-5-yl)-cyclopropylamine hydrochloride

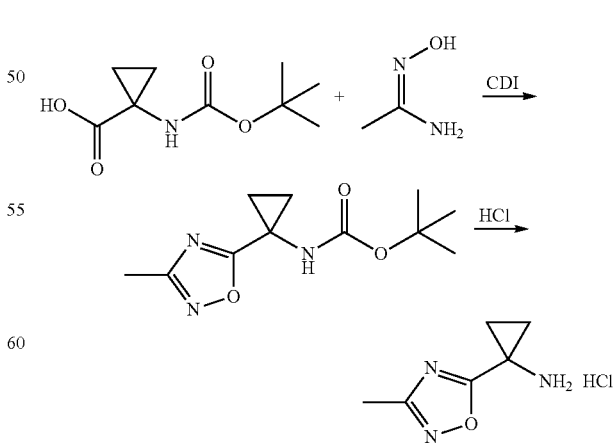

To a solution of N-boc-amino-cyclopropanecarboxylic acid (1.01 g, 5.00 mmol) in 2 mL of DMF was added carbonyldiimidazole (0.812 g, 5.01 mmol). This reaction mixture was stirred at room temperature for 6 h. N-Hydroxy-acetamidine (0.374 g, 5.05 mmol) was added. This reaction mixture was stirred at room temperature for 2 h then heated at 100° C. for 16 h. After cooling to room temperature, the reaction mixture was diluted with water. The resultant precipitate was collected by filtration was washed with acetonitrile and water, air-dried to give [1-(3-methyl-1,2,4-oxadiazol-5-yl)-cyclopropyl]-carbamic acid tert-butyl ester as 1.05 g of white solid, m/z 240 [M+1]$^+$. [1-(3-Methyl-1,2,4-oxadiazol-5-yl)-cyclopropyl]-carbamic acid tert-butyl ester (80 mg, 0.33 mmol) was dissolved in HCl in 1,4-dioxane (4.0 M, 1.0 mL, 4.0 mmol). After standing at room temperature for 1 h, the solvent was removed by a stream of nitrogen. The title compound was isolated and used without further purification.

The following compounds were prepared using similar procedures as described above:
1-(3-Morpholin-4-yl-[1,2,4]oxadiazol-5-yl)-cyclopropylamine hydrochloride;
1-(3-Cyclobutyl-[1,2,4]oxadiazol-5-yl)-cyclopropylamine hydrochloride;
1-(3-tert-Butyl-[1,2,4]oxadiazol-5-yl)-cyclopropylamine hydrochloride;
1-(3-Difluoromethyl-[1,2,4]oxadiazol-5-yl)-cyclopropylamine hydrochloride,
1-(3-cyclopropyl-[1,2,4]oxadiazol-5-yl)-cyclopropylamine hydrochloride;

1-[5-(1-Amino-cyclopropyl)-1,2,4-oxadiazol-3-yl]-propan-2-ol hydrochloride

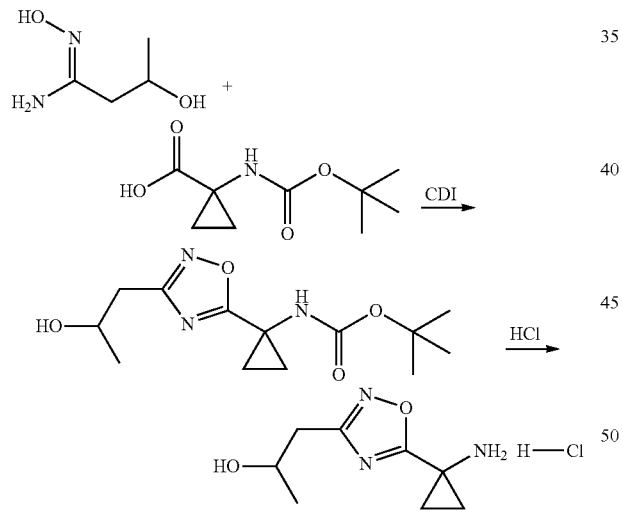

To a solution of N-boc-amino-cyclopropanecarboxylic acid (500 mg, 2.49 mmol) in 2 mL of DMF at 0° C. was added carbonyldiimidazole (403 mg, 2.49 mmol). The reaction mixture was stirred at room temperature for 30 min, and 3,N-dihydroxy-butyramidine (480 mg, 4.06 mmol) was added as a solution in 2 mL of DMF. The pale yellow, faintly cloudy reaction mixture was stirred at room temperature for 30 min and then heated at 100° C. for 15 h. After cooling to room temperature, the reaction mixture was diluted with 15 mL of water and extracted with 50 mL of ethyl acetate. The organics were washed with 2×15 mL of water and 15 mL of brine, dried over Na$_2$SO$_4$, filtered, and concentrated. The crude was purified by flash chromatography on silica gel (0-8% MeOH/CH$_2$Cl$_2$) to afford 242 mg (34%) of {1-[3-(2-hydroxy-propyl)-1,2,4-oxadiazol-5-yl]-cyclopropyl}-carbamic acid tert-butyl ester as a pale yellow oil.

To a solution of {1-[3-(2-hydroxy-propyl)-1,2,4-oxadiazol-5-yl]-cyclopropyl}-carbamic acid tert-butyl ester (242 mg, 0.854 mmol) in 5 mL of dichloromethane was added HCl in dioxane (1.07 mL, 4 M, 4.27 mmol) at room temperature. A white precipitate formed after a several minutes. The cloudy reaction mixture was stirred at room temperature for 17 h and then concentrated in vacuo. The residue was dissolved in 10% MeOH/CH$_2$Cl$_2$ and concentrated (2×) to afford 217 mg of product as an orange oil.

The following compounds were prepared using similar procedures as described above: [5-(1-Amino-cyclopropyl)-1,2,4-oxadiazol-3-yl]-dimethyl-amine hydrochloride, 2-[5-(1-Amino-cyclopropyl)-1,2,4-oxadiazol-3-yl]-ethanol hydrochloride, 1-[3-(2,2,2-Trifluoro-ethyl)-1,2,4-oxadiazol-5-yl]-cyclopropylamine hydrochloride, 1-(3-Ethyl-1,2,4-oxadiazol-5-yl)-cyclopropylamine hydrochloride, 1-(3-Isopropyl-1,2,4-oxadiazol-5-yl)-cyclopropylamine hydrochloride, 1-(5-Methyl-1,2,4-oxadiazol-3-yl)-cyclopropylamine hydrochloride, 1-(5-Isopropyl-1,2,4-oxadiazol-3-yl)-cyclopropylamine hydrochloride, 1-(5-Cyclopropyl-1,2,4-oxadiazol-3-yl)-cyclopropylamine hydrochloride.

6-(1-Amino-cyclopropyl)-pyridin-3-ylamine

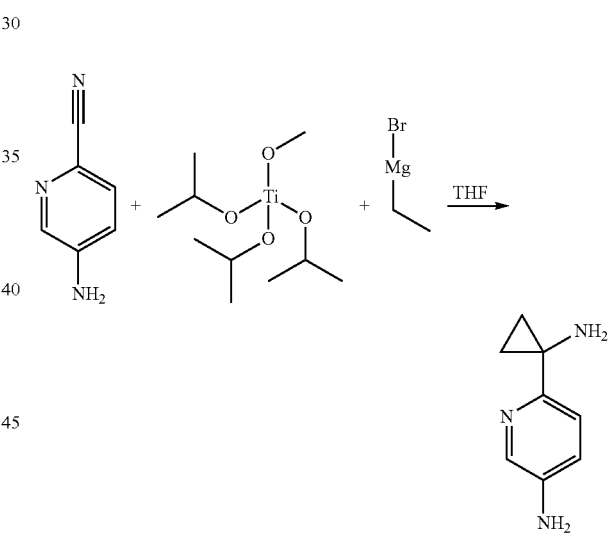

To a solution of 5-amino-2-cyanopyridine (1.0 g, 8.06 mmol) in dry THF (50 mL) was added titanium(IV) isopropoxide (5.2 mL, 17.7 mmol). EtMgBr (3.0M in Et$_2$O, 10.7 mL, 32.2 mmol) was then added dropwise. The reaction mixture was stirred for 23 h, then diluted with water (100 mL) and 1N HCl (5 mL), and stirred for 5 min. The mixture was filtered and the filtrate was concentrated in vacuo to afford 6-(1-amino-cyclopropyl)-pyridin-3-ylamine as brown oil (10 g) which was used without further purification.

The following compounds were prepared using procedures similar to those described above:

[6-(1-Amino-cyclopropyl)-pyridin-3-yl]-dimethyl-amine, 1-(1-Methyl-1H-imidazol-4-yl)-cyclopropylamine, 1-(2-Methyl-thiazol-4-yl)-cyclopropylamine, m/z 155.5 [M+1]$^+$, 1-Oxazol-4-yl-cyclopropylamine, m/z 125.5 [M+1]$^+$, 1-(5-

Trifluoromethyl-pyridin-2-yl)-cyclopropylamine, 1-(4-Iodo-pyridin-2-yl)-cyclopropylamine, 1-(5-Iodo-pyridin-2-yl)-cyclopropylamine;

5-Iodo-pyridine-2-carbonitrile

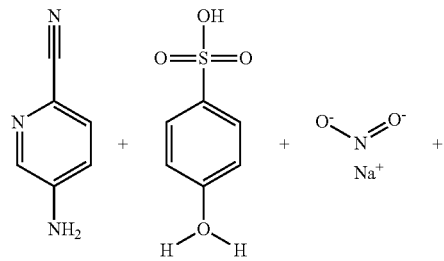

lated as a 94:6 mixture with the corresponding carboxylic acid from hydrolysis of the product nitrile.

Cyclopropanecarboxylic acid [6-(1-amino-cyclopropyl)-pyridin-3-yl]amide dihydrochloride

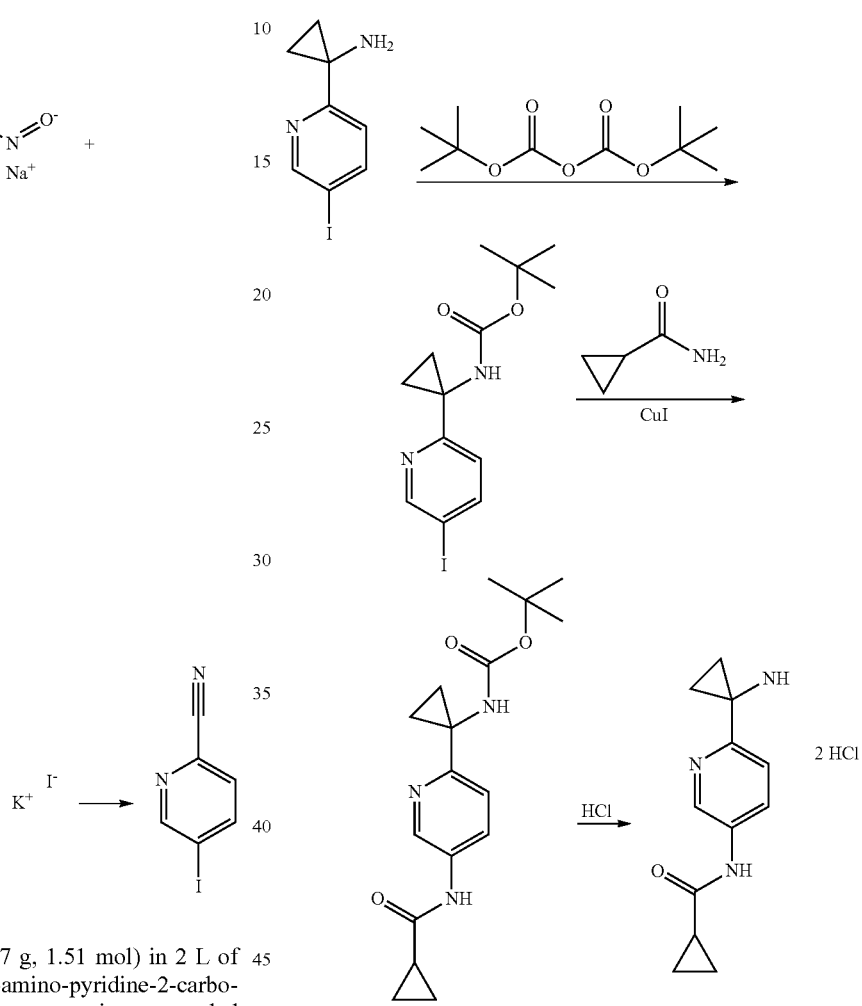

To a solution of TsOH.H$_2$O (287 g, 1.51 mol) in 2 L of CH$_3$CN in a 5 L flask was added 5-amino-pyridine-2-carbonitrile (60 g, 504 mmol). The resulting suspension was cooled to 5° C. A solution of NaNO$_2$ (69.5 g, 1.01 mol) and KI (209 g, 1.30 mol) in 300 mL of water was added slowly in small portions. Vigorous gas evolution and foaming was observed during the addition. The resulting brown/black mixture was stirred 10 min and was then warmed to room temperature and stirred for 4 h. The reaction was diluted with water and NaHCO$_3$ solution (saturated) until pH 9-10 was achieved. Sodium thiosulfate solution (saturated, 800 mL) was added until the solution changed from a dark red to light orange in color, and the solution was stirred for 30 min. The solution was diluted with EtOAc to dissolve the solids. The layers were separated and the aqueous layer was extracted with EtOAc. The combined organics were washed with satd. NaHCO$_3$ solution (2×) and brine (1×), dried over MgSO$_4$ and concentrated in vacuo. The residue was taken up in CH$_2$Cl$_2$ and the orange suspension was stirred at room temperature to break up the large particles. The mixture was filtered, and the filtrates were concentrated to afford 84 g of 5-iodo-pyridine-2-carbonitrile (73%) as an orange oil. The product was iso- 1-(5-Iodo-pyridin-2-yl)-cyclopropylamine (1.0 g, 3.9 mmol), Boc2O (839 mg, 3.9 mmol) and triethylamine (0.5 mL, 3.9 mmol) were combined in THF (20 mL) and allowed to stir at room temperature for 3 h. The mixture was diluted with water and extracted with EtOAc (3×100 mL). The combined extracts were washed with water, brine and dried with MgSO$_4$, concentrated to yield 1.45 g of [1-(5-Iodo-pyridin-2-yl)-cyclopropyl]-carbamic acid tert-butyl ester as a yellow solid, m/z=361.6 [M+1]$^+$.

A mixture of 0.20 g (0.56 mmol) of [1-(5-iodo-pyridin-2-yl)-cyclopropyl]-carbamic acid tert-butyl ester, 22 mg (0.12 mmol) of CuI, 0.035 mL (0.22 mmol) of 1,2-trans-di(methylamino)cychlohexane, 0.090 mg (1.1 mmol) of cyclopropanecarboxamide, and 0.24 mg (1.1 mmol) of K$_3$PO$_4$ in 1 mL of 1,4-dioxane was heated under an N$_2$ atmosphere for overnight at 110° C. The mixture was cooled, diluted with 10 mL of EtOAc, and washed with aq. NH$_4$Cl/NH$_4$OH (pH 8), then with aq. NH$_4$Cl. The organic layer was dried over Na$_2$SO$_4$, filtered, and concentrated. The residue was triturated with acetonitrile to provide 98 mg (56%) of {1-[5-(cyclopropanecarbonyl-amino)-pyridin-2-yl]-cyclopropyl}-carbamic acid tert-butyl ester as an off-white powder.

The synthesis of the title compound was completed by the HCl deprotection method used in the synthesis of 1-[5-(1-Amino-cyclopropyl)-1,2,4-oxadiazol-3-yl]-propan-2-ol hydrochloride.

[6-(1-Amino-cyclopropyl)-pyridin-2-yl]-bis-(4-methoxy-benzyl)-amine

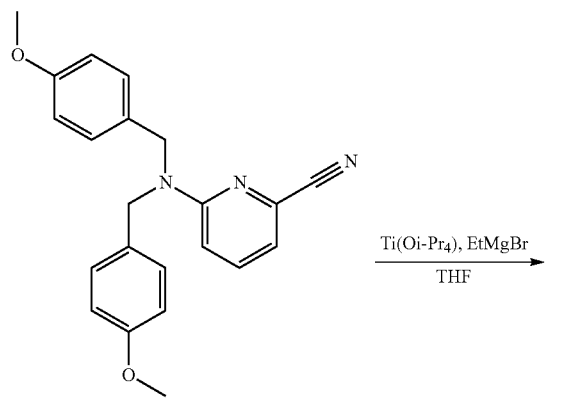

To a solution of 6-[bis-(4-methoxy-benzyl)-amino]-pyridine-2-carbonitrile (1.83 g, 5.09 mmol) in anhydrous THF (64 mL) was added Ti(Oi-Pr)$_4$ (1.79 mL, 6.11 mmol) in one portion followed by EtMgBr (3.0 M solution in THF, 4.07 mL, 12.2 mmol) slowly over 5 min. The reaction was stirred at room temperature overnight. Additional Ti(Oi-Pr)$_4$ (0.5 mL, 1.7 mmol) and EtMgBr (1.2 mL, 3.60 mmol) were added and stirring was continued for 2 h. Additional Ti(Oi-Pr)$_4$ (1.8 mL, 6.1 mmol) and EtMgBr (3 M, 4.1 mL, 12 mmol) were added and stirring was continued for 3 h. Water (12 mL) was added to the reaction mixture causing the formation of a precipitate. The mixture was filtered through a pad of diatomaceous earth and the filtrate was concentrated in vacuo to give an orange/red oil. The concentrate was re-dissolved in CH$_2$Cl$_2$, causing precipitation of a white solid. After filtration, the filtrate was concentrated in vacuo and purified via iterative flash chromatography on silica gel (1→10% MeOH/CH$_2$Cl$_2$) to give 381 mg of the title compound as a light orange viscous oil, m/z 391.08 [M+2]$^+$.

(6-Bromo-pyridin-2-yl)-bis-(4-methoxy-benzyl)-amine

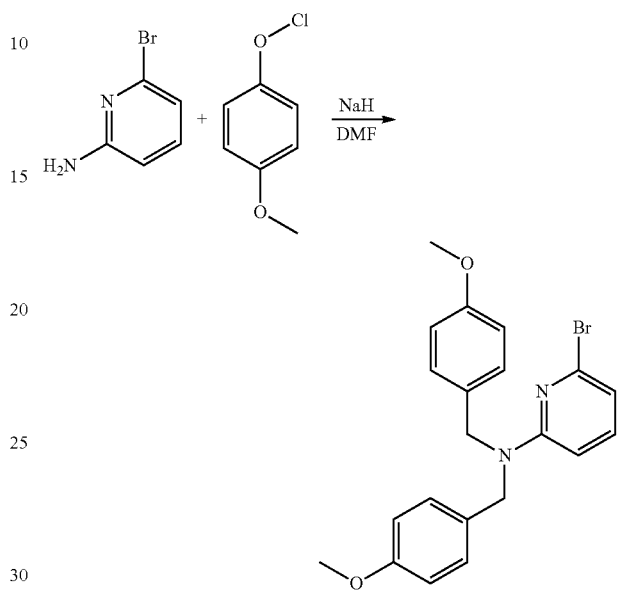

To a solution of 6-bromo-pyridin-2-ylamine (1.00 g, 5.78 mmol) under a nitrogen atmosphere at room temperature was added 4-methoxybenzyl chloride (1.96 mL, 14.5 mmol) in one portion. To this mixture was added NaH (60% suspension in mineral oil, 694 mg, 17.3 mmol) in one portion. The reaction was stirred for 2 h then partitioned between aqueous NaHCO$_3$ and CH$_2$Cl$_2$. The layers were separated and the aqueous layer was further extracted with CH$_2$Cl$_2$. The combined organic layers were dried with MgSO$_4$ and concentrated in vacuo to give a light yellow oil. This oil was purified by flash chromatography on silica gel (1→15% EtOAc/hexanes) to give 2.55 g of the title compound as a colorless oil, m/z 413.9 [M−H]$^+$.

6-[Bis-(4-methoxy-benzyl)-amino]-pyridine-2-carbonitrile

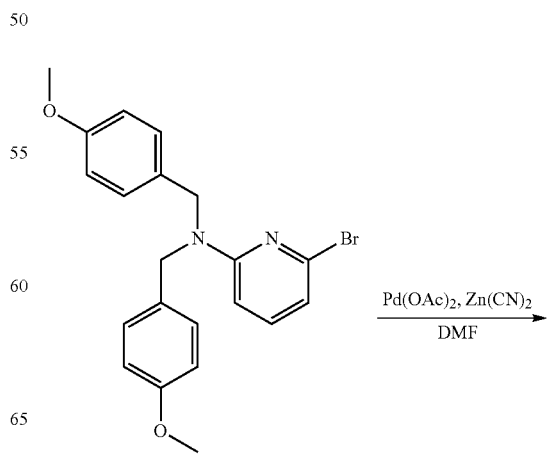

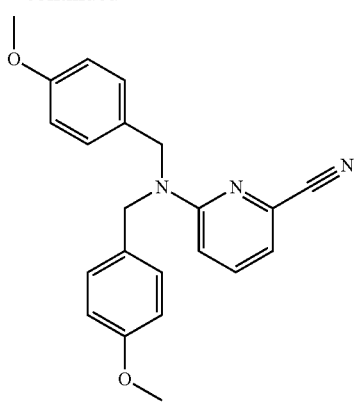

Polystyrene supported triphenylphosphine (250 mg, 0.544 mmol) and Pd(OAc)₂ (57 mg, 0.25 mmol) were combined in a glass vial along with DMF (5.5 mL). The vial was flushed with argon and a septum was affixed. The suspension was stirred for 1 h at room temperature. Solid Zn(CN)₂ (426 mg, 3.63 mmol) and a solution of (6-bromo-pyridin-2-yl)-bis-(4-methoxy-benzyl)-amine (1.50 g, 3.63 mmol) in DMF (5.5 mL) were then added. The vial was flushed with argon, sealed, and heated at 140° C. in a microwave for 30 min. The reaction mixture was filtered and the volatiles were removed in vacuo. The residue was purified by flash chromatography on silica gel (10→50% EtOAc/hexanes) to give the title compound as a colorless oil, m/z 361.0 [M+2]⁺.

5-Dimethylamino-pyridine-2-carbonitrile

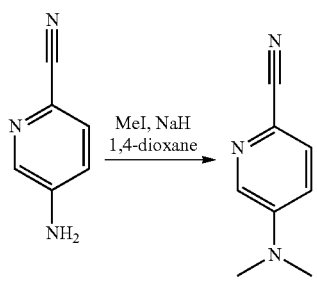

To the solution of 5-amino-2-cyanopyridine (15 g, 121 mmol) in dry 1,4-dioxane (200 mL) at 0° C. was added NaH (9.162 g, 362.6 mmol). This reaction mixture was stirred at 0° C. for 5 min then at room temperature for 30 min. MeI (53.3 mL, 846 mmol) was added slowly and the resultant reaction mixture was stirred at room temperature for 10 min. A condenser was added on the reaction flask and the reaction mixture was heated to 80° C. The reaction mixture was stirred at that temperature for 30 min then cooled to room temperature. After cooling to 0° C., the reaction was quenched by slowly adding MeOH (100 mL). The reaction mixture was then slowly warmed to room temperature and filtered through a pad of silica gel. The filtrate was concentrated in vacuo and the resultant crude product was purified by flash chromatography on silica gel using 1-5% MeOH/CH₂Cl₂ as the gradient to afford 6.5 g of 5-dimethylamino-pyridine-2-carbonitrile as a brown solid.

1-Methyl-1H-imidazole-4-carbonitrile

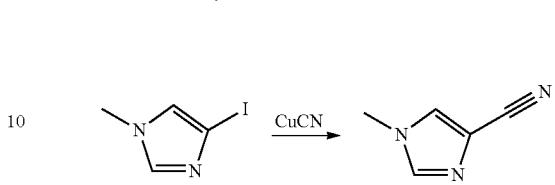

To a microwave tube was added 4-iodo-1-methyl-1H-imidazole (2.00 g, 9.62 mmol) and CuCN (1.03 g, 11.5 mmol) in DMA (12 mL). The reaction mixture was heated at 180° C. in a microwave reactor for 45 min. The reaction mixture was concentrated in vacuo. The residue was suspended in EtOAc/sat. NH₄Cl/NH₄OH (add NH₄OH to sat NH₄Cl to pH=9) and stirred for 30 min. The organic phase was separated, washed with brine, dried over anhydrous Na₂SO₄, filtered and concentrated to afford 580 mg of the title compound as a light brown solid.

[1-(4H-[1,2,4]Triazol-3-yl)-cyclopropyl]-carbamic acid benzyl ester

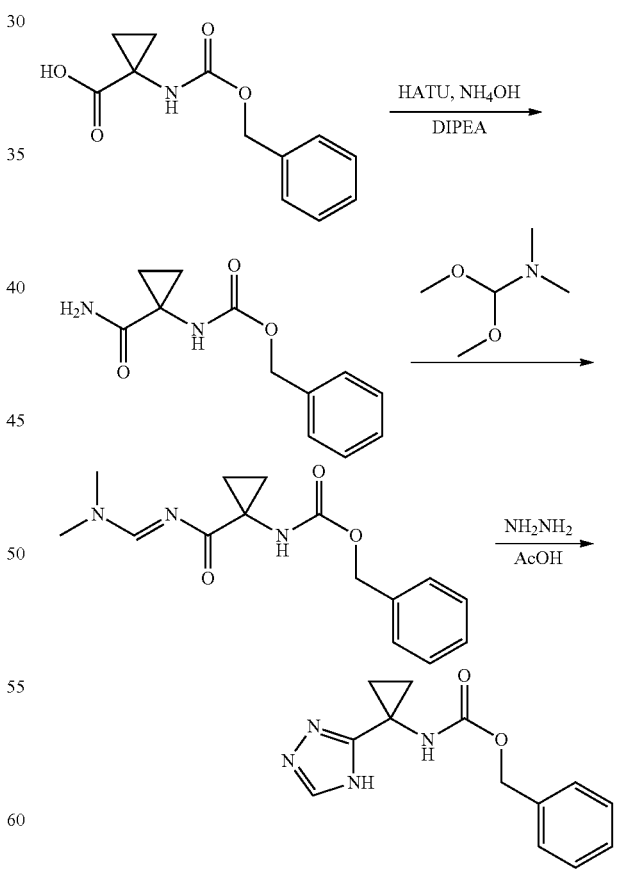

To a vial was added Cbz-1-aminocyclopropane-1-carboxylic acid (1.00 g, 4.25 mmol) in DMF (10 mL), followed by the addition of DIPEA (137 g, 10.6 mmol) and HATU (1.80 g, 4.73 mmol). The reaction mixture was stirred at room temperature for 15 min, followed by the addition of NH₄OH (4 mL). The reaction mixture was stirred at room temperature for 3 h. The reaction mixture was concentrated in vacuo. The yellow solid residue was dissolved in EtOAc/H₂O. The organic phase was separated, washed with water, brine, dried over anhydrous Na₂SO₄, filtered, concentrated and dried under high vacuum to afford 935 mg of (1-carbamoyl-cyclopropyl)-carbamic acid benzyl ester as a light yellow solid, m/z 235.8 [M+1]⁺.

To a round bottom flask was added (1-carbamoyl-cyclopropyl)-carbamic acid benzyl ester (935 mg, 4 mmol) in N,N-dimethylformamide dimethyl acetal (15 mL). The reaction mixture was stirred at 100° C. for 1 h. The solvent was concentrated in vacuo. The residue was dissolved in EtOAc/sat. NaHCO₃. The organic phase was separated, washed with brine, dried over anhydrous Na₂SO₄, filtered, concentrated and dried under high vacuum to afford 1.11 g of (1-{[1-dimethylamino-meth-(E)-ylidene]-carbamoyl}-cyclopropyl)-carbamic acid benzyl ester as a light brown oil, m/z 290.9 [M+1]⁺.

To a solution of (1-{[1-dimethylamino-meth-(E)-ylidene]-carbamoyl}-cyclopropyl)-carbamic acid benzyl ester (1.11 g, 3.83 mmol) in AcOH (6 ml) was added hydrazine dihydrochloride (803 mg, 7.65 mmol). The reaction mixture was stirred at 90° C. for 1.5 h. The reaction mixture was poured into EtOAc/water. The organic phase was separated, washed with water, sat. NaHCO₃, brine, dried over anhydrous Na₂SO₄, filtered, concentrated and dried under high vacuum to afford 677 mg of [1-(4H-[1,2,4]triazol-3-yl)-cyclopropyl]-carbamic acid benzyl ester as a off-white solid, m/z 259.6 [M+1]⁺.

1-(4H-[1,2,4]Triazol-3-yl)-cyclopropylamine

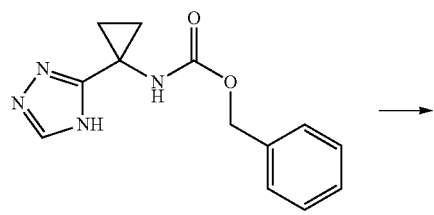

To a solution of [1-(4H-[1,2,4]triazol-3-yl)-cyclopropyl]-carbamic acid benzyl ester (60 mg, 0.23 mmol) in MeOH (5 mL) was added 10% Pd/C (60 mg). The reaction mixture was stirred under H₂ atmosphere (balloon) for 1.5 h. The reaction mixture was filtered through diatomaceous earth. The solvent was concentrated in vacuo and dried under high vacuum to afford 28 mg of the title compound, m/z 125.5 [M+1]⁺.

[2-(1-Amino-cyclopropyl)-pyridin-4-ylmethyl]-carbamic acid tert-butyl ester

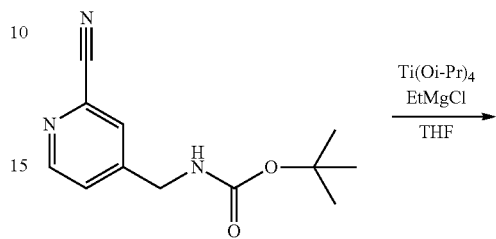

To a solution of (2-cyano-pyridin-4-ylmethyl)-carbamic acid tert-butyl ester (1.2 g, 5.1 mmol) in THF (100 mL) was added ethylmagnesium bromide (3 M, 3.3 mL, 10 mmol) and titanium isopropoxide (2.3 mL, 7.7 mmol). The reaction mixture was stirred at room temperature for 16 h. Water was added (5 mL) and the resulting solids filtered off. The organics were concentrated, then purified by flash chromatography on silica gel using 5-10% MeOH/CH₂Cl₂ to afford [2-(1-amino-cyclopropyl)-pyridin-4-ylmethyl]-carbamic acid tert-butyl ester as a solid, m/z 264.4 [M+1]⁺.

The following compounds were prepared via a method analogous to that described above:

1-(2-Isopropyloxazol-4-yl)cyclopropylamine; 1-(2-Cyclopropyloxazol-4-yl)cyclopropylamine; 1-(5-Methylisoxazol-3-yl)cyclopropylamine; 1-(5-Methylpyridin-2-yl)cyclopropylamine; [6-(1-Aminocyclopropyl)pyridin-3-ylmethyl] carbamic acid tert-butyl ester; 1-(5-Dimethylaminomethylpyridin-2-yl)cyclopropylamine; 1-[5-(tert-Butyldimethylsilanyloxymethyl)pyridin-2-yl] cyclopropylamine (Carbonitrile precursor was synthesized according to literature procedure: LecClerc et al. *J. Het. Chem.* 1993, 30, 631.); 1-[4-(tert-Butyl-dimethyl-silanyloxymethyl)-pyridin-2-yl]-cyclopropylamine (Carbonitrile precursor was synthesized according to literature procedure: LecClerc et al. *J. Het. Chem.* 1993, 30, 631.); 1-(5-Bromopyridin-2-yl)-cyclopropylamine; 1-(4-Iodo-pyridin-2-yl)- cyclopropylamine; [6-(1-Amino-cyclopropyl)-pyridin-3-yl]-dimethyl-amine; 1-(2-methyl-thiazol-4-yl)-cyclopropylamine:

1-[1,8]Naphthyridin-2-yl-cyclopropylamine dihydrochloride

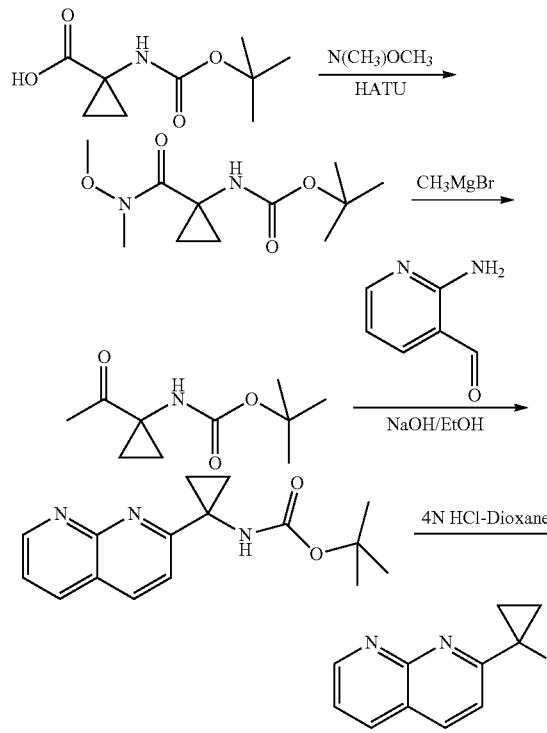

Boc-1-aminocyclopropane-1-carboxylic acid (25.0 g, 124.2 mmol), HATU (56.7 g, 149.1 mmol) and N,O-dimethylhydroxylamine hydrochloride (13.3 g, 136.7 mmol) were combined in DMF (200 mL). To this solution was added diisopropylethyl amine (108.2 mL, 621.3 mmol). The reaction was stirred for 2 h, diluted with EtOAc and poured into 1N NaOH. The aqueous phase was separated and extracted two more times with EtOAc. The organic layers were combined and washed with brine, dried ($Na_2SO_4$), decanted and concentrated in vacuo. The resultant solid was purified via $SiO_2$ flash chromatography (10-50% EtOAc-Hexanes) to afford the desired Weinreb amide as a white solid (30.4 g, 81%).

To a solution of the Weinreb amide (24.6 g, 100.7 mmol) in THF (300 mL) at 0° C. was slowly added methylmagnesium bromide as a 3.0M solution in ether (100.7 mL, 302.1 mmol). The reaction was allowed to slowly warm to 25° C. and stirred for 24 h then quenched by the addition of saturated aqueous $NH_4Cl$ (100 mL). EtOAc (200 mL) was added and the layers were separated. The aqueous phase was extracted two more times with EtOAc. The organic layers were combined, washed with Brine, dried ($Na_2SO_4$), decanted and concentrated to afford a solid. The solid was purified via $SiO_2$ flash chromatography (10-50% EtOAc-Heptane) to afford the desired ketone as a white solid (11.0 g, 55%).

Freshly ground NaOH (1.98 g, 49.5 mmol) was dissolved in absolute EtOH (250 mL). To this solution was added the ketone (4.2 g, 21.1 mmol) and 2-aminopyridine-3-carboxaldehyde (2.57 g, 21.1 mmol) simultaneously as a solution in EtOH (250 mL). The reaction was allowed to stir for 72 h and the volatiles were removed in vacuo. To the resultant crude solid was added $CH_2Cl_2$ (50 mL) and the suspension was filtered. The filtrate was absorbed onto $SiO_2$ and purified via $SiO_2$ flash chromatography (20-75% EtOAc-Hexane followed by 2-10% MeOH—$CH_2Cl_2$) to afford the desired Boc-protected 1,8-naphthyridine as a white solid (5.50 g, 91%).

The Boc-protected 1-[1,8]Naphthyridin-2-yl-cyclopropylamine (5.50 g, 19.3 mmol) was dissolved in 1,4-dioxane (30 mL) and to this solution was added 4N HCl in dioxane (70 mL, 280 mmol). The solution was stirred for 2 h. A ppt formed and the volatiles were removed in vacuo to afford 1-[1,8]naphthyridin-2-yl-cyclopropylamine dihydrochloride as an off-white solid (4.92 g, 99%).

The following amine dihydrochlorides were prepared by methods analogous to those described for 1-[1,8]naphthyridin-2-yl-cyclopropylamine dihydrochloride by employing the appropriate amino-carboxaldehyde substrate:
1-(1-quinolin-2-yl-cyclopropylamine dihydrochloride
1-[1,7]naphthyridin-2-yl-cyclopropylamine dihydrochloride
1-[1,6]naphthyridin-2-yl-cyclopropylamine dihydrochloride
1-[1,5]naphthyridin-2-yl-cyclopropylamine dihydrochloride
1-(1-pyrido[2,3-d]pyrimidin-2-yl-cycloamine dihydrochloride

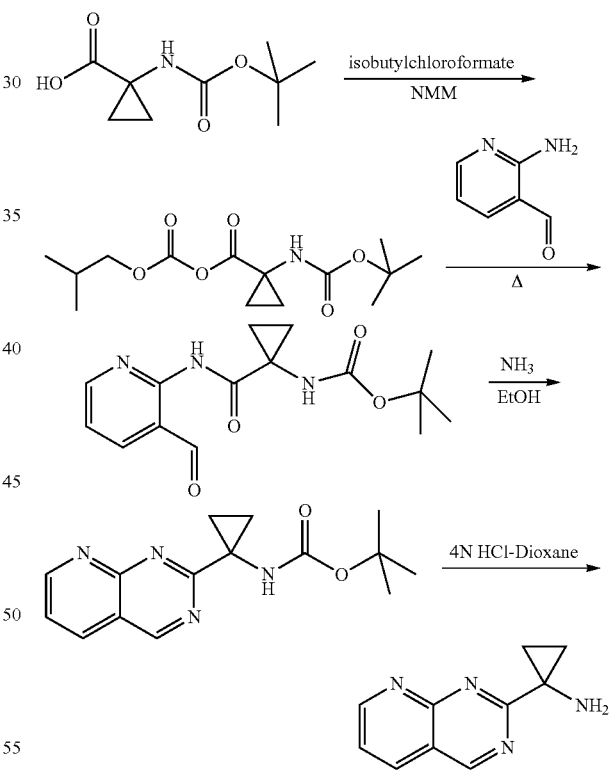

Boc-1-aminocyclopropane-1-carboxylic acid (1.00 g, 4.97 mmol) was dissolved in 1,2-DME (5.0 mL) and cooled to −15° C. To this solution was added N-methyl morpholine (0.552 mL, 5.02 mmol) followed by isobutylchloroformate (0.651 mL, 5.02 mmol). The solution was stirred for 5 min then the precipitated N-methyl morpholine hydrochloride was removed via vacuum filtration, washed with 2×5 mL 1,2-DME and the washings were combined with the filtrate. This solution of isobutyl mixed anhydride was kept under inert atmosphere and used directly.

To the solution of the isobutyl mixed anhydride (1.50 g, 4.98 mmol) in 1,2-DME (15 mL) was added 2-amino-3-pyridinecarboxaldehyde (0.669 g, 5.48 mmol) and the reaction was heated to 140° C. in a microwave reactor for 2 h, followed by additional thermal heating at 100° C. for 18 h. The reaction was allowed to cool to 25° C. and the volatiles were removed in vacuo to afford a yellow oil. The crude oil was purified via $SiO_2$ flash chromatography (25-100% EtOAc-Hexanes) to afford the desired pyridine amide-aldehyde as a tan solid (0.601 g, 40%).

Ammonia (1.00 mL) was condensed in a vessel submerged in $N_2(l)$. To this cold liquid ammonia was added a solution of pyridine amide-aldehyde (601 mg, 1.97 mmol) in absolute EtOH (10 mL). The reaction vessel was sealed and heated to 80° C. for 18 h. The vessel was allowed to cool to 25° C. and the volatiles were removed in vacuo. The resultant crude residue was purified via $SiO_2$ flash chromatography (25-100% EtOAc-Hexanes) to afford the Boc-protected 1-(1-pyrido[2,3-d]pyrimidin-2-yl-cycloamine as a tan solid (0.263 g, 47%).

The Boc-protected 1-(1-pyrido[2,3-d]pyrimidin-2-yl-cycloamine (0.263 g, 0.920 mmol) was dissolved in 1,4-dioxane (0.5 mL) and to this solution was added 4N HCl in dioxane (4.00 mL, 17.4 mmol). The solution was stirred for 2 h. A ppt formed and the volatiles were removed in vacuo to afford 1-(1-pyrido[2,3-d]pyrimidin-2-yl-cyclopropylamine dihydrochloride as a white solid (0.063 g, 27%).

The following amine dihydrochlorides were prepared by methods analogous to those described for 1-(1-pyrido[2,3-d]pyrimidin-2-yl-cyclopropylamine dihydrochloride by employing the appropriate aminocarboxaldehyde substrate:
1-(1-Quinolin-2-yl-cyclopropylamine dihydrochloride
1-[1-(6-Chloro-quinazolin-2-yl)-cyclopropylamine dihydrochloride
1-1,6-Naphthyridin-2-yl-cyclopropylamine
1-(1-oxazolo[4,5-b]pyridin-2-yl-cyclopropylamine hydrochloride

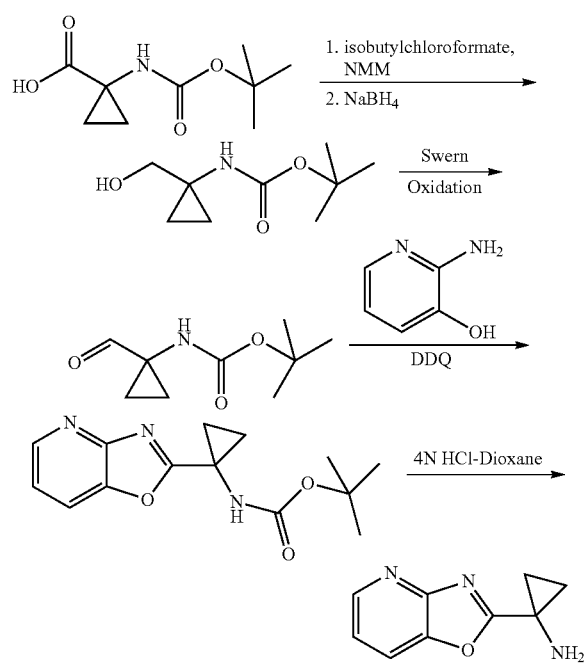

Boc-1-aminocyclopropane-1-carboxylic acid (5.0 g, 24.9 mmol) was dissolved in 1,2-DME (25 mL) and cooled to −15° C. To this solution was added N-methyl morpholine (2.76 mL, 25.1 mmol) followed by isobutylchloroformate (3.26 mL, 25.1 mmol). The solution was stirred for 5 min. The precipitated NMM hydrochloride was then removed via vacuum filtration, washed with 2×5 mL DME and the washings were combined with the filtrate in a flask and cooled in an ice-salt bath. An aqueous solution of sodium borohydride (4.01 g, 37.5 mmol, 10 mL $H_2O$) was added rapidly to the flask. Gas evolved vigorously and the reaction was stirred for another 10 min then quenched by the addition of water. The reaction was then diluted with EtOAc and the aqueous phase was separated and extracted two more times with EtOAc. The organic layers were combined, dried ($Na_2SO_4$), decanted and concentrated to afford the desired alcohol which was used without further purification (3.61 g, 78%).

To a solution of oxalyl chloride (2.01 mL, 23.1 mmol) in $CH_2Cl_2$ (50 mL) at −55° C. was added dropwise a solution of DMSO (1.64 mL, 23.1 mmol) in $CH_2Cl_2$ (10 mL). Upon complete addition, the reaction was stirred for 5 min then the Boc-protected amino alcohol (3.6 g, 19.2 mmol) was added as a solution in $CH_2Cl_2$ (10 mL) and stifling was continued for 15 min. Triethylamine (13.9 mL, 99.9 mmol) was added and the reaction was stirred for 5 min then allowed to slowly warm to room temperature. After 1 h, $H_2O$ (50 mL) was added and the reaction was poured into $CH_2Cl_2$. The aqueous phase was separated and extracted two more times with $CH_2Cl_2$. The organic layers were combined and washed with brine, dried ($Na_2SO_4$), decanted and concentrated. The resultant residue was purified via $SiO_2$ flash chromatography (10-40% EtOAc-Hexanes) to afford Boc-1-aminocyclopropane-1-carboxaldehyde as a white solid (2.5 g, 70%).

Boc-1-aminocyclopropane-1-carboxaldehyde (0.150 g, 0.81 mmol) and 2-amino-3-hydroxypyridine (0.094 g, 0.85 mmol) were combined in anhydrous methanol (2.5 mL). To this solution was added freshly activated 3 Å molecular sieves (~25 beads). The reaction vessel was sealed and heated to 45° C. for 18 h. The volatiles were removed in vacuo and the resultant residue was dissolved in $CH_2Cl_2$ (2.5 mL). To this solution was added DDQ (0.202 g, 0.89 mmol) and the reaction was stirred for 1 11. The reaction was diluted with saturated aqueous $NH_4Cl$ and poured into a separatory funnel. An additional 15 mL of $CH_2Cl_2$ was added. The aqueous phase was separated and extracted two more times with $CH_2Cl_2$. The organic layers were combined, dried ($Na_2SO_4$), decanted and concentrated. The crude residue was absorbed onto $SiO_2$ and purified via $SiO_2$ flash chromatography (25-75% EtOAc-Hexanes) to afford the Boc-protected 1-(1-oxazolo[4,5-b]pyridin-2-yl-cyclopropylamine as a tan solid (0.044 mg, 20%).

The Boc-protected 1-(1-oxazolo[4,5-b]pyridin-2-yl-cyclopropylamine (0.044 g, 0.160 mmol) was dissolved in 1,4-dioxane (0.5 mL) and to this solution was added 4N HCl in dioxane (2.50 mL, 10.9 mmol). The solution was stirred for 2 h. A ppt formed and the volatiles were removed in vacuo to afford 1-(1-oxazolo[4,5-b]pyridin-2-yl-cyclopropylamine dihydrochloride as a tan solid (0.023 g, 69%).

The following amine dihydrochloride was prepared by methods analogous to those described for 1-(1-oxazolo[4,5-b]pyridin-2-yl-cyclopropylamine dihydrochloride by employing 2-aminophenol as a substrate:

1-(1-benzooxazol-2-yl-cyclopropylamine dihydrochloride

1-(1H-Tetrazol-5-yl)-cyclopropylamine

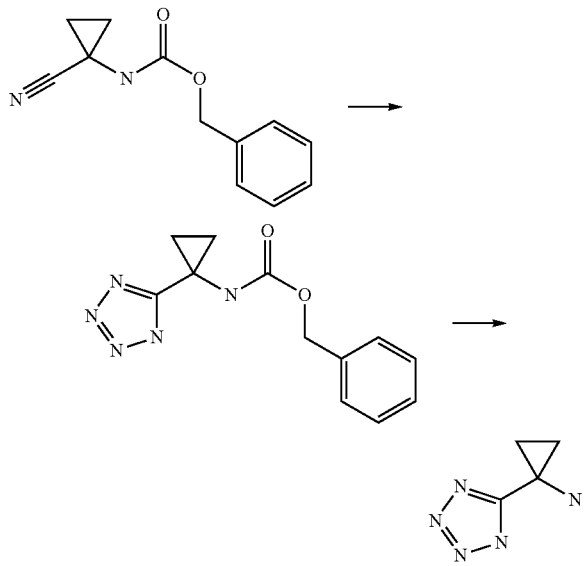

To a round bottom flask was added (1-cyano-cyclopropyl)-carbamic acid benzyl ester (500 mg, 2.31 mmol) in DMF (4 ml), followed by the addition of $NaN_3$ (195 mg, 3 mmol) and $NH_4Cl$ (161 mg, 3 mmol). The reaction mixture was stirred at 110° C. for 24 h. The reaction mixture was concentrated in vacuo. The residue was dissolved in EtOAc/water. The organic layer was separated, washed with brine, dried under any. $Na_2SO_4$, filtered and concentrated to afford 380 mg of [1-(1H-tetrazol-5-yl)-cyclopropyl]-carbamic acid benzyl ester as a off-white solid, m/z 260.8 $[M+1]^+$.

[1-(1H-tetrazol-5-yl)-cyclopropyl]-carbamic acid benzyl ester was dissolved in MeOH (5 ml). The solution was passed through a H-Cube hydrogenator at 0 bar, 30° C. and 1 ml/min with 10% Pd/C as a catalyst. The elute was concentrated to afford 48 mg of 1-(1H-tetrazol-5-yl)-cyclopropylamine as a solid product, m/z 126.5 $[M+1]^+$.

1-Amino-cyclopropanecarboxylic acid (1-oxazol-4-yl-cyclopropyl)-amide

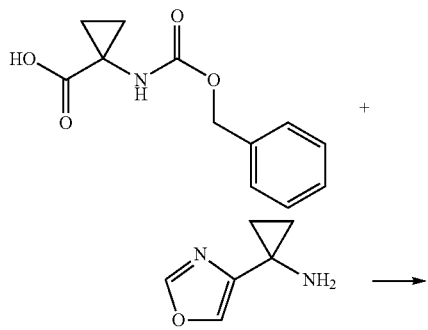

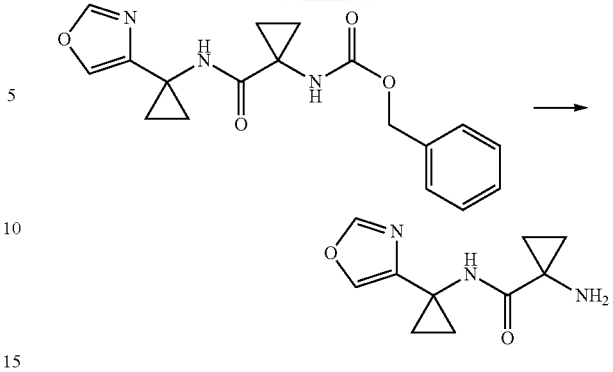

To a round bottom flask was added Z-1-aminocyclopropane-1-carboxylic acid (150 mg, 0.638 mmol) in DMF (10 ml), followed by the addition of Hunig's base (207 mg, 1.6 mmol) and HATU (270 mg, 0.71 mmol). The reaction mixture was stirred at room temperature for 15 min, followed by the addition of 1-Oxazol-4-yl-cyclopropylamine (200 mg, 1.6 mmol). The reaction mixture was stirred at room temperature for 18 h. The reaction mixture was concentrated in vacuo. The residue was purified by prepHPLC to afford 70 mg of [1-(1-oxazol-4-yl-cyclopropylcarbamoyl)-cyclopropyl]-carbamic acid benzyl ester, m/z 343 $[M+1]^+$.

[1-(1-oxazol-4-yl-cyclopropylcarbamoyl)-cyclopropyl]-carbamic acid benzyl ester (70 mg, 0.21 mmol) was dissolved in MeOH (10 ml), followed by the addition of 10% Pd/C (35 mg). The solution mixture was stirred under $H_2$ balloon for 1 h. The reaction mixture was filtered through celite. The solvent was concentrated under high vacuum pump to afford 42 mg of 1-amino-cyclopropanecarboxylic acid (1-oxazol-4-yl-cyclopropyl)-amide as a off-white solid product, m/z 208.8 $[M+1]^+$.

The following compounds were prepared using procedures similar to those described above using the appropriate starting material:

4-Amino-4-(1-pyrimidin-2-yl-cyclopropylcarbamoyl)-piperidine-1-carboxylic acid tert-butyl ester

1-Isopropyl-1H-imidazole-4-carbonitrile

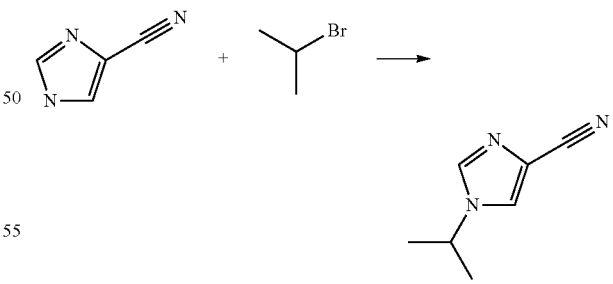

To a round bottom flask was added 1H-imidazole-4-carbonitrile (300 mg, 3.22 mmol), 2-bromopropane (794 mg, 6.44 mmol), and $K_2CO_3$ (890 mg, 6.44 mmol) in DMF (9 ml). The reaction mixture was stirred at room temperature for 18 h. The reaction mixture was filtered. The solvent was concentrated in vacuo. The residue was purified by prepHPLC to afford 310 mg of 1-Isopropyl-1H-imidazole-4-carbonitrile TFA salt and 71 mg of 3-isopropyl-3H-imidazole-4-carbonitrile TFA salt region-isomer.

1-Isopropyl-1H-imidazole-4-carbonitrile TFA salt was dissolved in EtOAc, washed with sat. NaHCO$_3$, brine, dried under anhy. Na$_2$SO$_4$, filtered and concentrated to afford 200 mg of 1-isopropyl-1H-imidazole-4-carbonitrile as a colorless oil, m/z 136.5 [M+1]$^+$.

1-(1H-Imidazol-4-yl)-cyclopropylamine

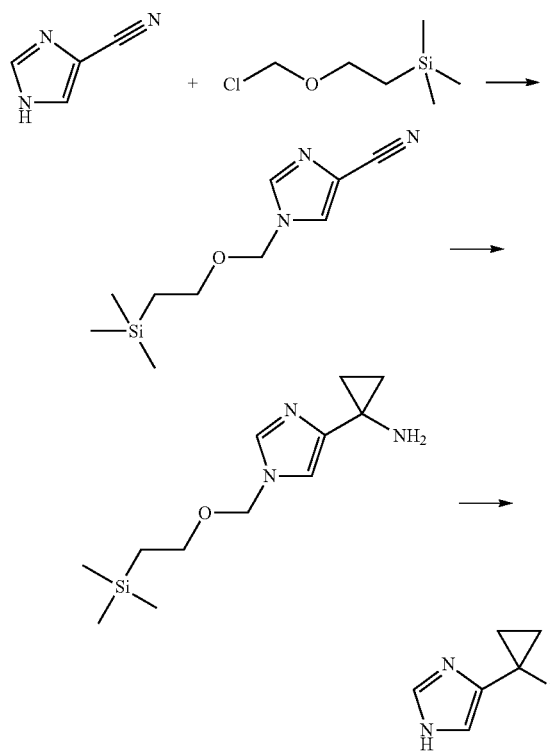

To a round bottom flask was added NaH (60% in mineral oil) (200 mg, 5.22 mmol) in dry THF (12 ml), followed by the addition of 1H-imidazole-4-carbonitrile (400 mg, 4.3 mmol), SEMCl (1433 mg, 8.6 mmol). The reaction mixture was stirred at room temperature for 18 h. The reaction mixture was concentrated in vacuo. The residue was dissolved in EtOAc/sat. NaHCO$_3$. The organic phase was separated, washed with water, brine, dried over anhy. Na$_2$SO$_4$, filtered and concentrated. The resulting residue was purified by flash chromatography on silica gel (0-3% MeOH/CH$_2$Cl$_2$). The product fractions were collected and concentrated to afford 355 mg of 1-(2-trimethylsilanyl-ethoxymethyl)-1H-imidazole-4-carbonitrile, m/z 224.6 [M+1]$^+$.

To a round bottom flask was added 1-(2-trimethylsilanyl-ethoxymethyl)-1H-imidazole-4-carbonitrile (310 mg, 3.19 mmol) in THF (10 ml), followed by the addition Ti(OiPr)$_4$ (0.9 ml, 3.05 mmol) Next, EtMgBr (3.0 M in ether) (1.85 ml, 5.55 mmol) was added slowly. The clear solution changed to dark and gas evolved was found. The reaction mixture was stirred at room temperature for 0.5 h. The reaction mixture was added with water (10 ml). The solid precipitate was filtered through celite. The filter cake was washed with THF (10 ml), EtOAc (10 ml). The combined solvent was concentrated to afford 400 mg of 1-[1-(2-trimethylsilanyl-ethoxymethyl)-1H-imidazol-4-yl]-cyclopropylamine, m/z 254.6 [M+1]$^+$.

To a round bottom flask was added 1-[1-(2-trimethylsilanyl-ethoxymethyl)-1H-imidazol-4-yl]-cyclopropylamine (400 mg, 1.58 mmol) in EtOH (20 ml) and 3N HCl (15 ml). The reaction mixture was stirred at 90° C. for 4 h. The reaction mixture was concentrated in vacuo. The residue was purified by prepHPLC by eluting with 0.5% acetonitrile/water to afford 267 mg of 1-(1H-imidazol-4-yl)-cyclopropylamine as a formic acid salt, m/z 124 [M+1]$^+$.

1-(5-Methyl-4H-[1,2,4]triazol-3-yl)-cyclopropylamine

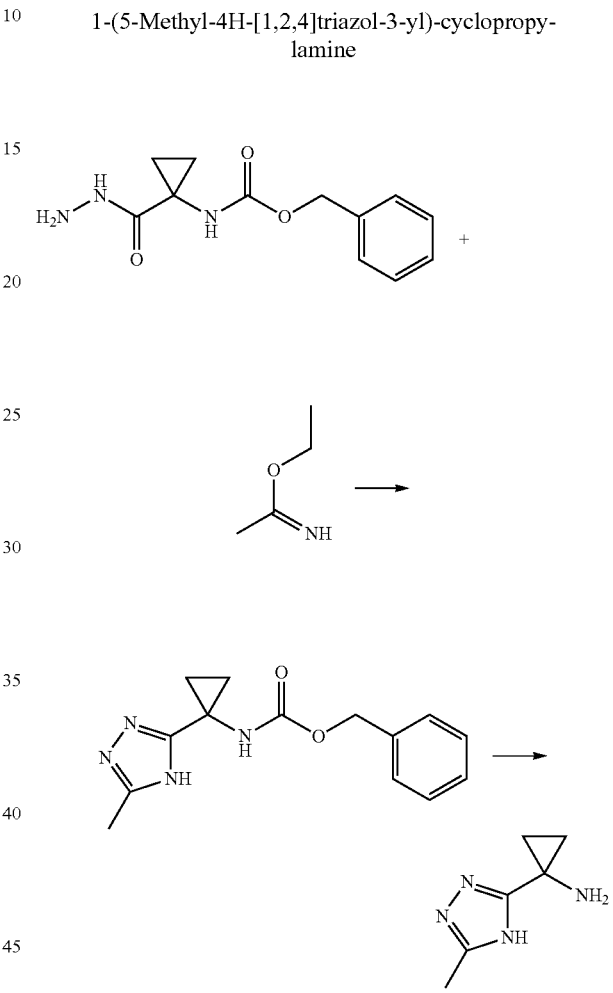

To a vial was added (1-hydrazinocarbonyl-cyclopropyl)-carbamic acid benzyl ester HCl salt (300 mg, 1.05 mmol), acetimidic acid ethyl ester HCl salt (195 mg, 1.58 mmol) and triethylamine (320 mg, 3.16 mmol) in toluene (8 ml). The reaction mixture was stirred at 120° C. for 18 h. The reaction mixture was concentrated in vacuo. The residue was dissolved in EtOAc/sat. NaHCO$_3$. The organic phase was separated, washed with brine, dried under anhy. Na$_2$SO$_4$, filtered and concentrated. The residue was purified by prepHPLC to afford 57 mg of [1-(5-methyl-4H-[1,2,4]triazol-3-yl)-cyclopropyl]-carbamic acid benzyl ester, m/z 273.6 [M+1]$^+$.

[1-(5-methyl-4H-[1,2,4]triazol-3-yl)-cyclopropyl]-carbamic acid benzyl ester (57 mg, 0.21 mmol) was dissolved in MeOH (5 ml), followed by the addition of 10% Pd/C (20 mg). The reaction mixture was stirred under H$_2$ balloon for 1.5 h. The reaction mixture was filtered through celite. The solvent was concentrated under high vacuum pump to afford 30 mg of 1-(5-methyl-4H-[1,2,4]triazol-3-yl)-cyclopropylamine, m/z 139.6 [M+1]$^+$.

((S)-2-Amino-propionylamino)-pyridin-2-yl-acetic acid methyl ester and (S)-2-Amino-N-(2-hydroxy-1-pyridin-2-yl-ethyl)-propionamide

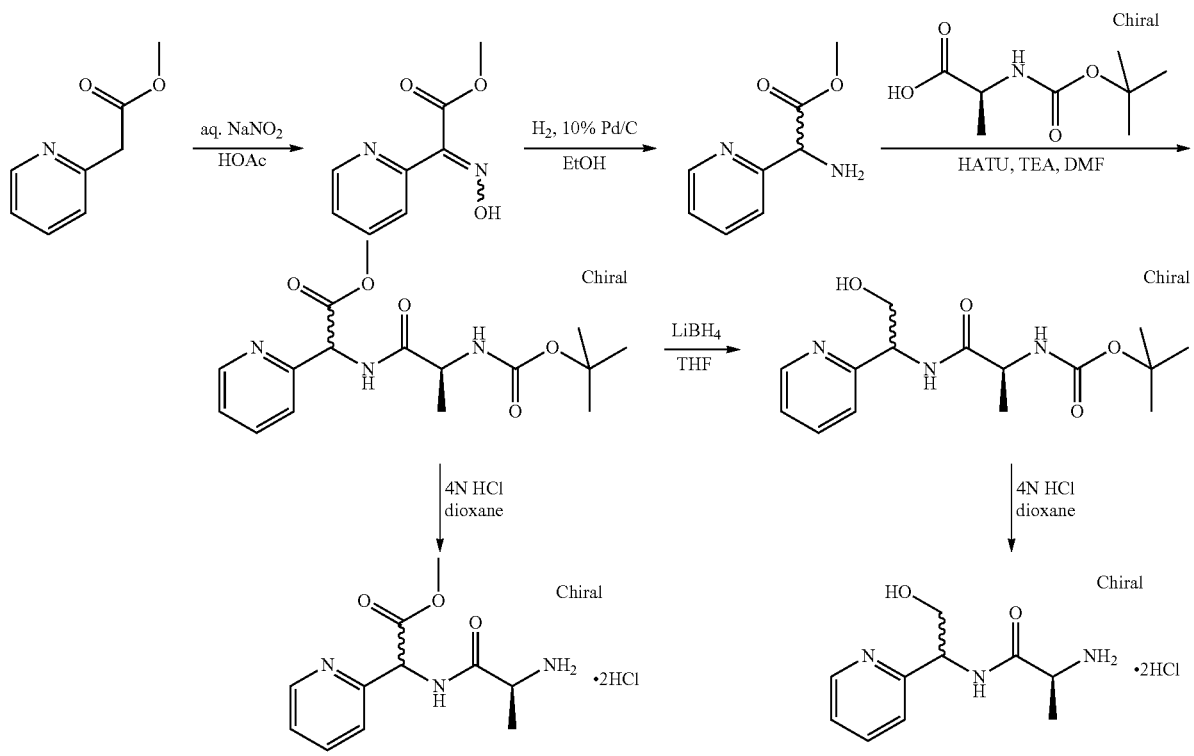

To a solution of pyridin-2-yl-acetic acid methyl ester (8.9 ml, 0.66 mmol) in AcOH (16 mL) at 0° C. with stirring, an aqueous solution of sodium nitrite (4.67 g, 0.66 mmol in 14 mL) was added portion wise. After addition was completed stirring was continued for 40 min at room temperature. Water (30 mL) was added and the mixture was stirred for additional 1 h. The mixture was concentrated to remove most of the AcOH and basidified to pH 8~9 with $Na_2CO_3$ aq. extracted with EtOAc (3×). The combined organics were dried over $MgSO_4$, filtered, and concentrated in vacuo. Drying in a vacuum oven affords Hydroxyimino-pyridin-2-yl-acetic acid methyl ester (11.6 g, 97%) as an off-white solid, m/z 181.6 $[M+1]^+$ A solution of Hydroxyimino-pyridin-2-yl-acetic acid methyl ester (2.0 g, 11.1 mmol) in ethanol (50 mL) was placed in a round bottom flask. The flask was evacuated under vacuum and filled with $Ar_2$ three times. Then 200 mg of 10% Pd on Carbon was added in one portion. The flask was evacuated again under vacuum and filled with Hydrogen three times. The reaction was stirred at room temperature under a balloon containing $H_2$ for 16 h. The mixture was filtered through a pad of celite and rinsed with DCM three times. The combined organics were concentrated down to give Amino-pyridin-2-yl-acetic acid methyl ester (1.8 g) as a yellow oil which was used immediately in next step without further purification, m/z 167.55 $[M+1]^+$ To (S)-2-tert-Butoxycarbonylamino-propionic acid (1.54 g, 8.12 mmol), Amino-pyridin-2-yl-acetic acid methyl ester (1.35 g, 8.12 mmol) and HATU (3.1 g, 8.12 mmol) was added the DMF (20 mL) and $Et_3N$ (2.26 ml, 16.20 mmol) and the solution was stirred for 2 h. The mixture was concentrated to remove most of the DMF was removed. The resulting oil was dissolved in EtOAc, washed with water, 0.1 N HCl aq., 1 N $NaHCO_3$ aq., followed by Brine. The combined organics were dried over $MgSO_4$, filtered, and concentrated in vacuo to provide ((S)-2-tert-Butoxycarbonylamino-propionylamino)-pyridin-2-yl-acetic acid methyl ester (2.7 g, 98%) as a yellow oil, m/z 338.61 $[M+1]^+$ To a solution of ((S)-2-tert-Butoxycarbonylamino-propionylamino)-pyridin-2-yl-acetic acid methyl ester (337 mg, 1.00 mmol) in dioxane (2 mL) was added 4 N HCl in dioxane (1.00 mL, 4.00 mmol). The reaction was stirred at room temperature for 1 h. Removal of solvents in vacuo provided the title compound ((S)-2-Amino-propionylamino)-pyridin-2-yl-acetic acid methyl ester (270 mg) as a HCl salt, m/z 210.96 $[M+1]^+$ To a suspension of ((S)-2-tert-Butoxycarbonylamino-propionylamino)-pyridin-2-yl-acetic acid methyl ester (1.12 g, 3.32 mmol) in 15 mL of THF was added $LiBH_4$ (2 M in THF, 1.66 mL, 3.32 mmol) drop wise and the reaction was stirred at room temperature for 16 h. The reaction was carefully quenched by water, neutralized with 0.1 N HCl aq., extracted with EtOAc, washed with aq. $NaHCO_3$ and Brine. Dried over $Na_2SO_4$, filtered and concentrated in vacuo to afford [(S)-1-(2-Hydroxy-1-pyridin-2-yl-ethylcarbamoyl)-ethyl]-carbamic acid tert-butyl ester (770 mg, 77%) as a white foam, m/z 310.60 $[M+1]^+$ To a solution of [(S)-1-(2-Hydroxy-1-pyridin-2-yl-ethylcarbamoyl)-ethyl]-carbamic acid tert-butyl ester (556 mg, 1.79 mmol) in dioxane (1 mL) was added 4 N HCl in dioxane (2.24 m, 8.95 mmol). The reaction was stirred at room temperature for 1 h. Removal of solvents in vacuo provided the title compound (S)-2-Amino-N-(2-hydroxy-1-pyridin-2-yl-ethyl)-propionamide (580 mg) as a HCl salt. m/z 210.96 [M+1]$^+$

1-(4-Trifluoromethyl-1H-imidazol-2-yl)-cyclopropylamine

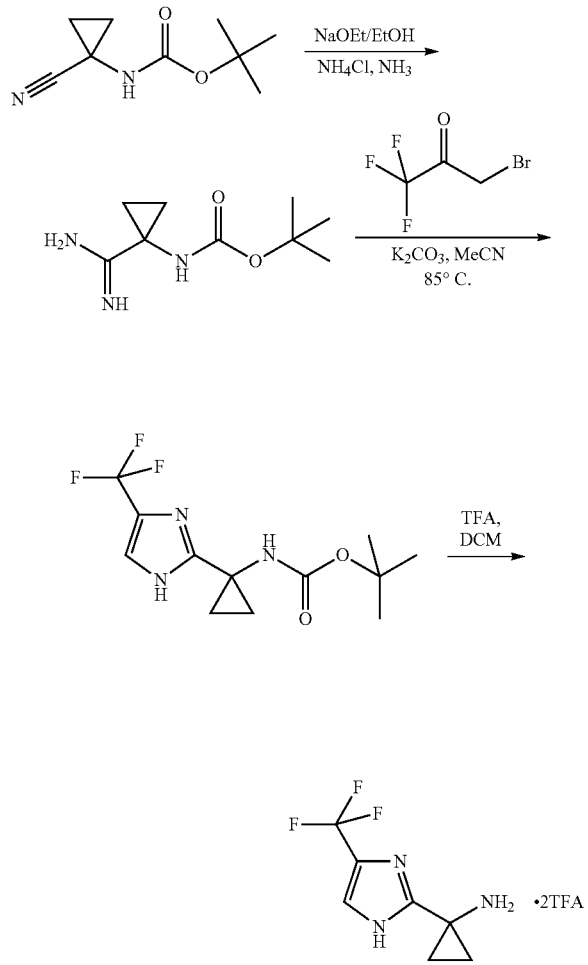

(1-Cyano-cyclopropyl)-carbamic acid tert-butyl ester (2.44 g, 13.40 mmol) was dissolved in dry EtOH (33 mL). Sodium ethoxide (21 wt % in EtOH solution, 10.70 mL, 22.80 mmol)) was added and the reaction was stirred for 1 h at room temperature under an atmosphere of dry argon. To the light yellow solution was added solid NH$_4$Cl (2.94 g, 55 mmol) followed by 7 M NH$_3$ in MeOH (8.08 mL, 56.60 mmol). The reaction was capped and allowed to stir for 16 h. The turbid suspension was filtered using MeOH to rinse. The filtrate was concentrated in vacuo and the solid residue was re-suspended in dry EtOH. The solids were filtered off, rinsing with EtOH. The filtrate was concentrated to give 2.91 g of (1-Carbamimidoyl-cyclopropyl)-carbamic acid tert-butyl ester as a light yellow solid. m/z 200.48 [M+1]$^+$ To a suspension of (1-Carbamimidoyl-cyclopropyl)-carbamic acid tert-butyl ester (488 mg, 2.45 mmol) and K$_2$CO$_3$ (676 mg, 4.90 mmol) in MeCN (14 mL) at 85° C. was added a solution of 3-Bromo-1,1,1-trifluoro-propan-2-one (400 mg, 2.09 mmol) in MeCN (10 mL) drop wise over 30 min. The dilute reaction mixture (0.1 N) was stirred at 85° C. for 3 h before cooled to room temperature. Diluted with EtOAc and extracted three times, washed with water and Brine. Dried over MgSO$_4$, filtered and concentrated down in vacuo. The mixture was purified by reverse phase preparation HPLC to give 32 mg of [1-(4-Trifluoromethyl-1H-imidazol-2-yl)-cyclopropyl]-carbamic acid tert-butyl ester as a yellow solid, m/z 292.42 [M+1]$^+$ To a solution of [1-(4-Trifluoromethyl-1H-imidazol-2-yl)-cyclopropyl]-carbamic acid tert-butyl ester (32 mg, 0.11 mmol) in DCM (1 mL) was added TFA (500 uL). The clear solution was stirred at room temperature for overnight. Solvents were removed and the resulting materials were re-suspended in Toluene (15 mL) and concentrated down to dryness to provide the title compound 1-(4-Trifluoromethyl-1H-imidazol-2-yl)-cyclopropylamine as a TFA salt, m/z 192.41 [M+1]$^+$

1-(1H-Pyrrolo[2,3-b]pyridin-6-yl)-cyclopropylamine

1-(1H-Pyrrolo[2,3-b]pyridin-6-yl)-propylamine

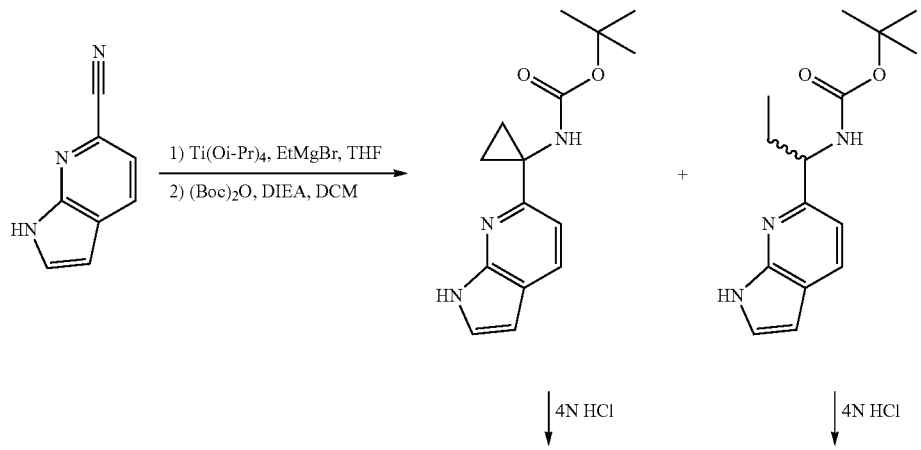

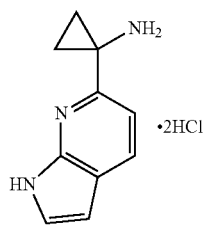

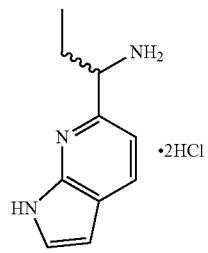

To a solution of 1H-Pyrrolo[2,3-b]pyridine-6-carbonitrile (500 mg, 3.49 mmol) in THF (80 mL) was added Titanium (IV) isopropoxide (2.05 mL, 6.98 mmol) followed by EtMgBr (4.66 mL, 13.97 mmol) dropwise. The mixture was stirred at room temperature for 3 h. The dark color reaction mixture was quenched with 10 mL of $H_2O$ and stirred efficiently for 30 min. The resulting yellow suspension was filtered through a plug of celite, washed the celite cake with EtOAc followed by 10% $MeOH/CH_2Cl_2$. Solvents were removed and the resulting brown oil was suspended in Toluene (2×10 mL) to removed residual water. After evaporation of the solvent the crude amine products were obtained as a brownish solid. To a mixture of these crude amines and DIEA (801 uL, 4.60 mmol) in DCM (15 mL) was added $Boc_2O$ (810 mg, 3.71 mmol). The mixture was stirred at room temperature for 16 h. The reaction was diluted with DCM and washed with water, followed by Brine. Dried over $MgSO_4$, filtered and concentrated down to provide crude material which was purified by silica gel chromatography (5% to 50% EtOAc in hexane) to give 80 mg of [1-(1H-Pyrrolo[2,3-b]pyridin-6-yl)-cyclopropyl]-carbamic acid tert-butyl ester (m/z 274.40 $[M+1]^+$) and 230 mg of [1-(1H-Pyrrolo[2,3-b]pyridin-6-yl)-propyl]-carbamic acid tert-butyl ester m/z 276.41 $[M+1]^+$ To a solution of [1-(1H-Pyrrolo[2,3-b]pyridin-6-yl)-cyclopropyl]-carbamic acid tert-butyl ester (80 mg, 0.32 mmol) in dioxane (1 mL) was added 4N HCl in dioxane (500 uL, 2.00 mmol). The reaction was stirred at room temperature for 1 h. Solvents were removed and the resulting brown oil was suspended in Toluene (3 mL×2). Removal of solvents to dryness affords 79 mg of the title compound 1-(1H-Pyrrolo[2,3-b]pyridin-6-yl)-cyclopropylamine as a HCl salt, m/z 174.40 $[M+1]^+$ To a solution of [1-(1H-Pyrrolo[2,3-b]pyridin-6-yl)-propyl]-carbamic acid tert-butyl ester (230 mg, 0.84 mmol) in dioxane (2 mL) was added 4N HCl in dioxane (500 uL, 2.00 mmol). The reaction was stirred at room temperature for 1 h. Solvents were removed and the resulting brown oil was suspended in Toluene (3 mL×2). Removal of solvents to dryness affords 197 mg of the title compound 1-(1H-Pyrrolo[2,3-b]pyridin-6-yl)-propylamine as a HCl salt, m/z 176.40 $[M+1]^+$.

5-Methyl-isoxazole-3-carbonitrile

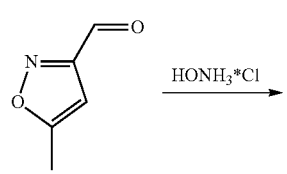

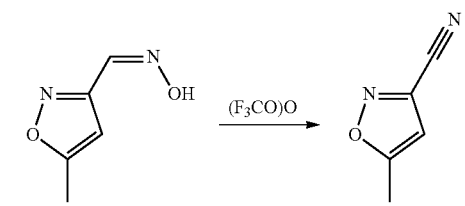

To a solution of 5-methyl-3-isoxazolecarboxaldehyde (1.00 g, 9.00 mmol) in DCM (5 mL) was added subsequently pyridine (0.73 mL, 9.00 mmol) and hydroxylamine hydrochloride (0.63 g, 9.00 mmol). After being stirred at room temperature for 12 h, the reaction mixture was diluted with methylene chloride (50 mL) and extracted with water (2×50 mL). The organic extracts were dried ($MgSO_4$), filtered, and concentrated under reduced pressure to provide a white solid. The crude product, obtained as a mixture of syn- and anti-oximes, was used in the next reaction without further purification.

The 5-methyl-isoxazole-3-carbaldehyde oxime (0.89 g, 7.07 mmol) was dissolved in dioxane (25 mL) and anhydrous pyridine (18 mL). The solution was cooled to 0° C. before trifluoroacetic anhydride (1.08 mL, 7.78 mmol) were added dropwise so that the reaction temperature did not rise above 7° C. The reaction mixture was warmed to room temperature and stirred for 12 h. The reaction was not complete (~50% conversion) and therefore the mixture was cooled to 0° C. and an additional equivalent of TFA-anhydride was added. The mixture was stirred for 12 h at rt before 100 mL of methylene chloride was added and washed with 8×35 mL of water. The organic extracts were washed with brine (35 mL), dried (MgSO4), filtered, and concentrated under reduced pressure to provide 5-methyl-isoxazole-3-carbonitrile as a yellow solid (514 mg, >90% pure).

2-Cyclopropyloxazole-4-carbonitrile

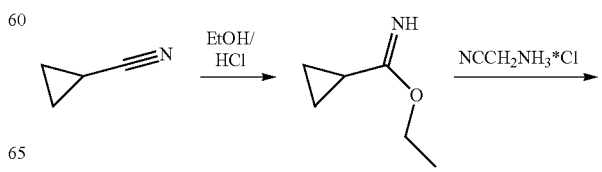

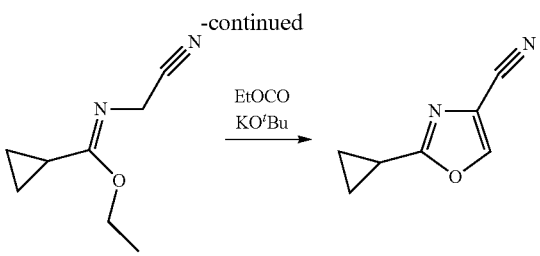

Through a solution of cyclopropylcarbonitrile (10 g, 0.15 mmol) in 50 ml of ethanol was bubbled HCl-gas for 15 min. The reaction mixture was stirred at room temperature for 2 hours and then put in the refrigerator for 24 h. After evaporation of the solvent the product was obtained as an off-white solid (6.00 g).

To a suspension of ethyl cyclopropylacetimidate hydrochloride (6.0 g, 53 mmol) in ether (50 mL) was added anhydrous potassium carbonate (7.3 g, 53 mmol). After stirring for 5 min, a solution of aminoacetonitrile hydrochloride (4.9 g, 53 mmol) in water (40 mL) was added and the mixture stirred for additional 90 min. The reaction was diluted with water (100 mL) and extracted with ether (2×300 mL). The combined organic fractions were dried (Na$_2$SO$_4$), filtered, and concentrated to give N-cyanomethyl-cyclopropanecarboximidic acid ethyl ester as a liquid (4.54 g).

To a solution of N-cyanomethyl-cyclopropanecarboximidic acid ethyl ester (4.54 g, 14.9 mmol) in THF (10 mL) at −10° C. were added potassium tert-butoxide (1.67 g, 14.9 mmol) and ethyl formate (1.2 mL, 14.9 mmol) successively. After being stirred at −10° C. for 3 h, the reaction mixture was left in the refrigerator overnight and then diluted with ether. The precipitated brown solid was filtered and dried under vacuum. The vacuum-dried solid was added to boiling acetic acid (45 mL) and refluxed for 2 min. The reaction mixture was cooled to room temperature, diluted with water, and adjusted to pH 7 by adding 1 N sodium hydroxide. The reaction mixture was extracted with ether (2×1 L). The combined organic fractions were dried (MgSO$_4$), filtered, and concentrated. The crude brownish solid was chromatographed (silica gel, 0-50% EtOAc in Hexane, detection KMnO$_4$ spray, R$_f$=0.3 in 10% EtOAc/Hexane) to give 2-cyclopropyl-oxazole-4-carbonitrile as a colorless liquid (463 mg).

2-Isopropyloxazole-4-carbonitrile was prepared using the same procedure starting from iso-propylcarbonitrile.

(1-Cyano-cyclopropyl)-carbamic acid tert-butyl ester

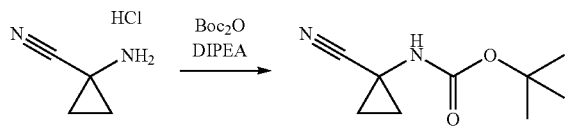

To a suspension of 1-amino-cyclopropylcarbonitrile.HCl (4.50 g, 38.0 mmol) in CH$_2$Cl$_2$ (50 mL) was added DIPEA (20 mL, 114.8 mmol) followed by (Boc)$_2$O (13.0 g, 59.6 mmol). The mixture was stirred at room temperature for 88 h and then diluted with EtOAc (300 mL). The solution was washed with HCl(aq) (1 N, 120 mL), followed by NaHCO$_3$ (saturated aq) (100 mL) and then brine (100 mL). The organic layer was dried over Na$_2$SO$_4$ and concentrated to give a yellow liquid that was purified by flash chromatography (silica, 15→100% EtOAc/hexanes) giving 3.0 g of the title compound as a white crystalline solid, m/z 183.46 [M+1]$^+$.

(1-Carbamimidoyl-cyclopropyl)-carbamic acid tert-butyl ester hydrochloride

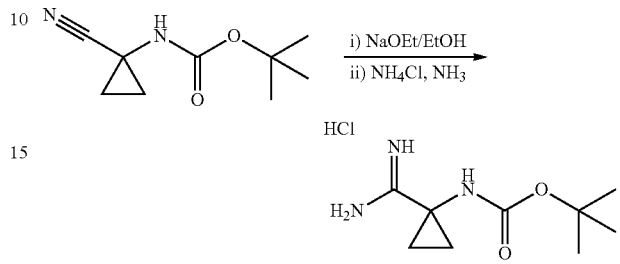

(1-Cyano-cyclopropyl)-carbamic acid tert-butyl ester (2.12 g, 11.6 mmol) was dissolved in anhydrous EtOH (29 mL) and NaOEt (21 wt % in EtOH, 6.5 mL, 17.5 mmol) was added via syringe in one portion. The yellow solution was stirred at room temperature for 1 h. An additional amount of NaOEt (21 wt % in EtOH, 2.2 mL, 2.9 mmol) was added and stirring was continued for 2 h. To the reaction was added solid NH$_4$Cl (2.5 g, 47 mmol) followed by NH$_3$ (7N in MeOH, 1.7 mL, 12 mmol). The flask was sealed and the suspension was allowed to stir for 88 h. The solids were filtered off, using anhydrous EtOH to rinse. The filtrate was concentrated and re-suspended in EtOAc (10 mL). This mixture was heated to reflux for 30 min then allowed to cool to room temperature. The solids were collected by filtration to give 2.22 g of the title compound as a white powder, m/z 200.44 [M+1]$^+$.

(1-Pyrimidin-2-yl-cyclopropyl)-carbamic acid tert-butyl ester

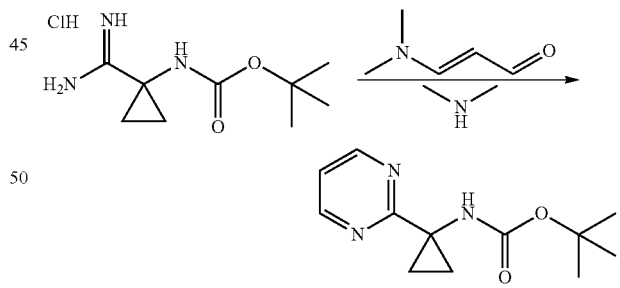

To a solution of (1-Carbamimidoyl-cyclopropyl)-carbamic acid tert-butyl ester hydrochloride (3.62 g, 15.4 mmol) in anhydrous EtOH (62 mL) was added dimethylaminoacrolein (3.6 mL, 36. mmol) and dimethylamine (2 M in THF, 10. mL, 20. mmol). The reaction was heated at 70° C. for 18 h. The EtOH was removed in vacuo and the residue was dissolved in EtOAc (150 mL) and washed with water (3×100 ml). The organic phase was dried with Na$_2$SO$_4$ and concentrated to give a red oil. The product was crystallized from the oil using warm hexanes (30 mL) and the light orange solids were collected by filtration. The filtrate was re-processed in the same manner two additional times. In total 2.23 g of the title compound was isolated as a light orange powder, m/z 236.40 [M+1]+

1-Pyrimidin-2-yl-cyclopropylamine dihydrochloride

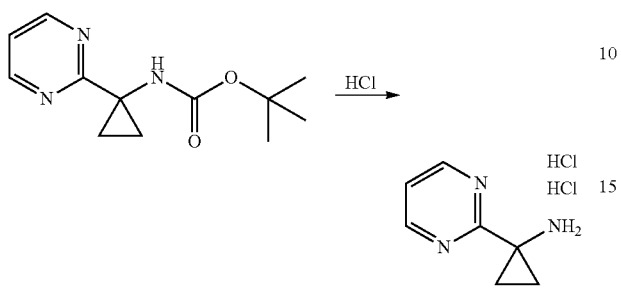

(1-Pyrimidin-2-yl-cyclopropyl)-carbamic acid tert-butyl ester (1.60 g, 6.80 mmol) was dissolved in CH$_2$Cl$_2$ (10 mL). HCl solution (4M in 1,4-dioxane, 17 mL, 68 mmol) was added via in one portion via syringe and the solution immediately became cloudy. The reaction was allowed to stir for 3 h. Solvents were removed in vacuo yielding a solid mass that was dried under vacuum to give 1.12 g of the title compound as a light yellow solid, m/z 136.32 [M+1]+.

(1-1,2,4-Triazin-3-yl-cyclopropyl)-carbamic acid tert-butyl ester

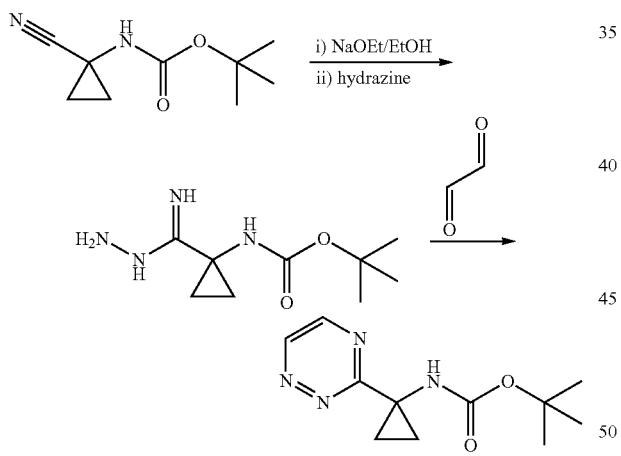

(1-Cyano-cyclopropyl)-carbamic acid tert-butyl ester (50 mg, 0.27 mmol) was dissolved in anhydrous EtOH (1.1 mL) and NaOEt (21 wt % in EtOH, 0.22 mL, 0.59 mmol) was added via syringe in one portion. The yellow solution was stirred at room temperature for 1 h. The solvent was removed in vacuo and the residue was suspended in CHCl$_3$ (4 mL) and anhydrous hydrazine (0.06 mL, 2 mmol). After 3 min of stirring the reaction was filtered to remove a white precipitate and the filtrate was allowed to stir for 87 h. The solvents were removed under a stream of N$_2$ to give the crude amidine-type intermediate as a white solid, m/z 215.60 [M+1]+.

To a solution of the crude intermediate in EtOH (0.5 mL) was added glyoxal (40% in water, 0.5 mL, 4 mmol). The mixture was stirred for 20 h and the solvent was removed under stream of N$_2$. The residue was purified by flash chromatography (silica, 50→80% EtOAc/hexanes) and then by reversed phase HPLC (20→95% MeCN/H$_2$O+0.1% TFA) to give 9 mg of the title compound as an orange solid, m/z 181.38 [M-t-Bu]+.

1-1,2,4-Triazin-3-yl-cyclopropylamine dihydrochloride was obtained by a method analogous to that described for 1-Pyrimidin-2-yl-cyclopropylamine dihydrochloride, m/z 137.12 [M+1]+.

1-Pyrazin-2-yl-cyclopropanecarbonitrile

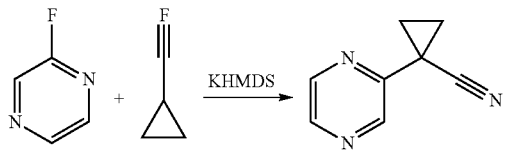

In a dry flask under argon, 2-fluoropyrazine (1.95 g, 19.9 mmol) and cyclopropanecarbonitrile (1.5 mL, 20. mmol) were dissolved in dry toluene (25 mL). The solution was cooled to 0° C. and potassium bis(trimethylsilyl)amide (1.0 M in THF, 20 mL, 20 mmol) was added slowly over 5 min via syringe. The black, opaque reaction mixture was allowed to warm to room temperature and stir for 4 h. The reaction was diluted with H$_2$O (200 mL) and EtOAc (200 mL) and the layers were separated. The aqueous layer was back extracted with EtOAc (2×100 mL). The combined organic layers were dried over Na$_2$SO4, filtered and concentrated to give a black oil. The oil was purified by flash chromatography (silica, 20→60% EtOAc/hexanes) to give 849 mg of the title compound as a light yellow oil, m/z 146.17 [M+1]+.

1-Pyrazin-2-yl-cyclopropanecarboxylic acid

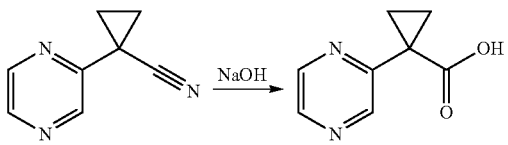

1-Pyrazin-2-yl-cyclopropanecarbonitrile (849 mg, 5.85 mmol) was dissolved in MeOH (7 mL) and NaOH solution (20 wt % in water, 2.0 mL, 10 mmol) was added via syringe in one portion. The orange mixture was heated to 75° C. for 22 h, cooled to room temperature, and acidified to pH 2-3 with 6N HCl. The mixture was filtered through a pad of celite using MeOH and the filtrate was concentrated. The residue was suspended in EtOAc, dried with Na$_2$SO$_4$, filtered and concentrated to give 111 mg of the title compound as an orange solid, m/z 165.28 [M+1]$^+$.

(1-Pyrazin-2-yl-cyclopropyl)-carbamic acid allyl ester

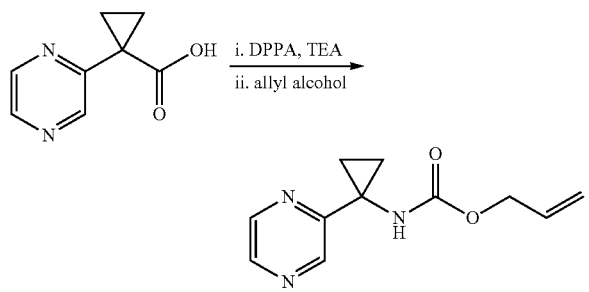

To a solution of 1-Pyrazin-2-yl-cyclopropanecarboxylic acid (111 mg, 0.676 mmol) in dry toluene (1.5 mL) was added TEA (0.11 mL, 0.81 mmol) followed by diphenylphosphoryl azide (DPPA, 0.16 mL, 0.74 mmol). The reaction was stirred for 1 h at rt. Allyl alcohol (0.2 mL) was added via syringe and the reaction was heated to 90° C. for 3 h. After cooling to room temperature, the reaction was diluted with water (6 mL) and EtOAc (4 mL). The layers were separated and the water layer was extracted with EtOAc (3×4 mL). The combined organic layers were dried over Na$_2$SO$_4$ and concentrated to give a black residue that was purified by flash chromatography (silica, 40→50% EtOAc/hexanes) to give 67 mg of the title compound as a light orange oil, m/z 220.52 [M+1]$^+$.

1-Pyrazin-2-yl-cyclopropylamine

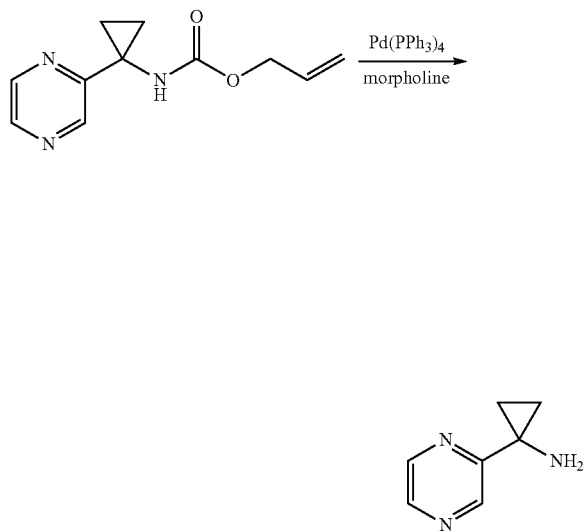

To a solution of (1-Pyrazin-2-yl-cyclopropyl)-carbamic acid allyl ester (67 mg, 0.31 mmol) and morpholine (0.31 mL, 3.1 mmol) in THF (3 mL) was added Pd(PPh$_3$)$_4$ (27 mg, 0.02 mmol) and the yellow mixture was stirred at 50° C. for 3 h. The solvent was removed under a stream of N$_2$ and the residue was purified by flash chromatography (silica, 4→7% MeOH/CH$_2$Cl$_2$) to give 6 mg of the title compound as an orange oil, m/z 136.04 [M+1]$^+$.

(1-Furan-2-yl-cyclopropyl)-carbamic acid tert-butyl ester

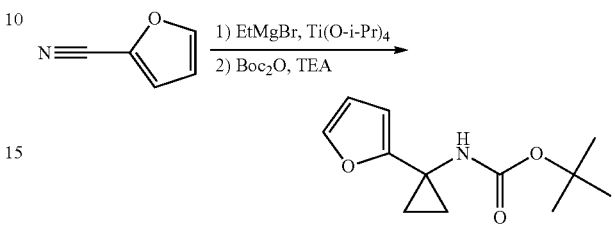

Ti(O-i-Pr)$_4$ (97.4 mL, 322 mmol) was added to a solution of 2-furonitrile (25 g, 269 mmol) in dry Et$_2$O (150 mL) at room temperature. The ethyl magnesium bromide (3M in Et$_2$O, 215 mL, 645 mmol) was added dropwise via addition funnel over 1.5 h. The reaction was stirred 2 h and then BF$_3$ etherate (52 mL, 403 mmol) was slowly added via additional funnel over 20 min. The reaction was cooled 0° C. and water (250 mL) was added. The resulting mixture was filtered through a pad of diatomaceous earth, rinsing with CH$_2$Cl$_2$, and the filtrate was concentrated in vacuo to give a red liquid. To a solution of the resulting oil in THF (150 mL) was added TEA (75 mL, 537 mmol) followed by Boc$_2$O (41.0 g, 188 mmol) and the mixture was stirred for 20 h. The reaction mixture was concentrated in vacuo and diluted with aqueous HCL (1N, 1 L). This was extracted with EtOAc (1×1.5 L). The organic layer was washed with saturated NaHCO$_3$ solution (1×1 L), dried with Na$_2$SO$_4$ and concentrated in vacuo to give a red liquid. This was purified by iterative flash chromatography (silica, 0→20% EtOAc/hexanes) to give 7.0 g of the title compound as a white solid that is best stored in the freezer, m/z 224.53 [M+1]$^+$.

(1-Pyridazin-3-yl-cyclopropyl)-carbamic acid tert-butyl ester

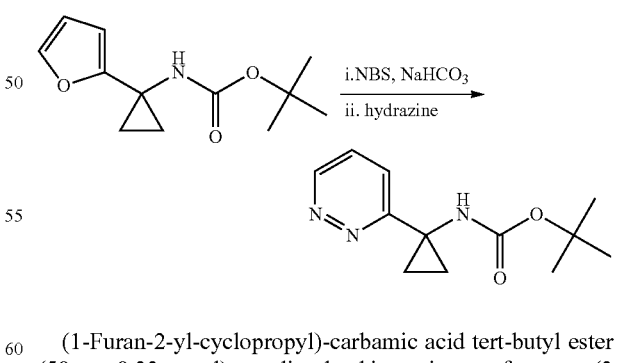

(1-Furan-2-yl-cyclopropyl)-carbamic acid tert-butyl ester (50 mg, 0.22 mmol) was dissolved in a mixture of acetone (2 mL) and water (0.2 mL) and cooled to −20° C. To this solution was added solid NaHCO$_3$ (38 mg, 0.45 mmol) and NBS (52 mg, 0.29 mmol) and stirring was continued for 2 h. Furan (100 uL) was added via syringe and the reaction was allowed to warm to 0° C. over 30 min. The volatiles were removed under a stream of N$_2$ and to the residue was added i-PrOH (2 mL)

and of hydrazine hydrate (300 uL). The mixture was stirred for 18 h and then the solvents were removed under a stream of $N_2$.

The residue was purified by flash chromatography (silica, 0→3% MeOH/$CH_2Cl_2$) to give 10 mg of the title compound as a yellow oily residue, m/z 236.46 [M+1]$^+$.

1-Pyridazin-3-yl-cyclopropylamine dihydrochloride was obtained by a method analogous to that described for 1-Pyrimidin-2-yl-cyclopropylamine dihydrochloride, m/z 136.23 [M+1]$^+$.

1-(6-Chloro-pyridin-2-yl)-cyclopropylamine

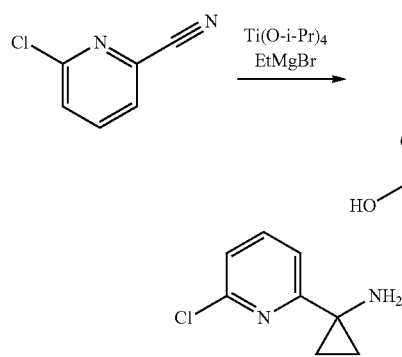

To a solution of 6-Chloro-pyridine-2-carbonitrile (500 mg, 3.61 mmol) in THF (45 mL) was added titanium isopropoxide (1.59 mL, 5.41 mmol) in one portion followed by ethylmagnesium bromide (3 M in $Et_2O$, 3.6 mL, 11 mmol) slowly over 5 min. The reaction was stirred for 4 then quenched by the addition of water (5 mL). The mixture was filtered through a pad of diatomaceous earth and the filtrate was concentrated. The resulting material was purified first by flash chromatography (silica, 5→10% MeOH/$CH_2Cl_2$) and then by reversed phase HPLC (1→95% MeCN/$H_2O$+0.1% TFA) to give 86 mg of the title compound presumably as the bis-TFA salt, m/z 169.59 [M+1]$^+$.

[1-(5-Methyl-pyrazin-2-yl)-cyclopropyl]-carbamic acid tert-butyl ester

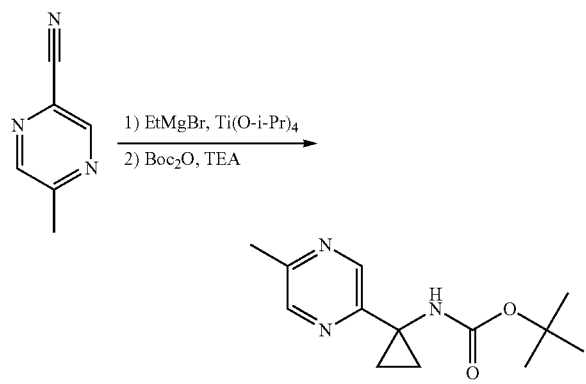

Ti(O-i-Pr)$_4$ (14.8 mL, 50.4 mmol) was added to a solution of 5-Methyl-pyrazine-2-carbonitrile (5.0 g, 42 mmol) in dry THF (66 mL) at room temperature. The ethyl magnesium bromide (3M in $Et_2O$, 28.7 mL, 86.0 mmol) was added dropwise via syringe over 10 min. The reaction was stirred 19 h and then water (15 mL) was added. The resulting mixture was filtered through a pad of diatomaceous earth, rinsing with $CH_2Cl_2$, and the filtrate was concentrated in vacuo to give a red sludge. To a solution of the resulting sludge in THF (100 mL) was added DIPEA (14.6 mL, 83.9 mmol) followed by $Boc_2O$ (11.5 g, 52.5 mmol) and the mixture was stirred for 3 h. The reaction mixture was concentrated in vacuo and diluted with EtOAc (200 mL). This was washed with aqueous citric acid (10 wt %, 2×200 mL) and then brine (1×100 mL). The organic phase was dried with $Na_2SO_4$ and concentrated in vacuo to give a black oil. This was purified by flash chromatography (silica, 0→2.5% MeOH/$CH_2Cl_2$) and then by reverse phase HPLC to give 416 mg of the title compound as a red solid, m/z 250.48 [M+1]$^+$.

1-(5-Methyl-pyrazin-2-yl)-cyclopropylamine was obtained by a method analogous to that described for 1-Pyrimidin-2-yl-cyclopropylamine dihydrochloride, m/z 150.34 [M+1]$^+$.

[1-(4-Amino-pyrimidin-2-yl)-cyclopropyl]-carbamic acid tert-butyl ester

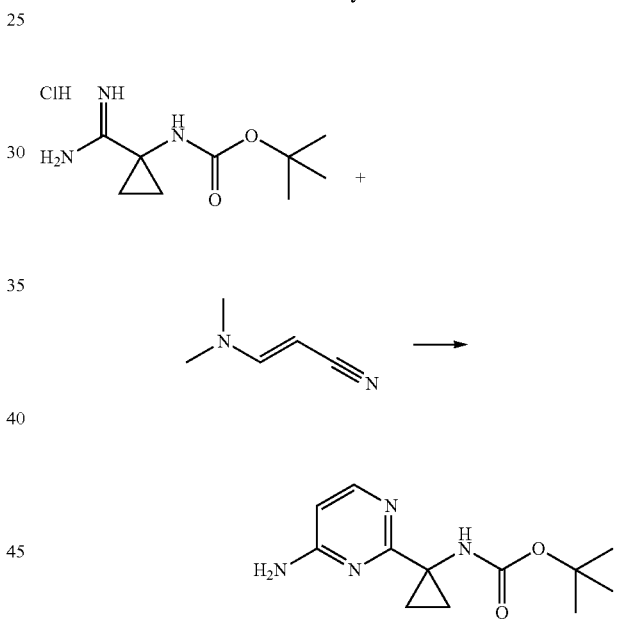

3-Dimethylamino-acrylonitrile (0.05 mL, 0.50 mmol) was dissolved in EtOH (1 mL) and NaOEt solution (21 wt % in EtOH, 0.19 mL, 0.50 mmol) was added. This was stirred for 1 h and then (1-Carbamimidoyl-cyclopropyl)-carbamic acid tert-butyl ester hydrochloride (50 mg, 0.25 mmol) was added. The reaction was stirred for 1.5 h at 60° C. and then solid $NH_4Cl$ (27 mg, 0.50 mmol) and $NH_3$ (7 M in MeOH, 0.50 mL, 3.5 mmol) were added and stirring was continued at 60° C. for 1 h and then at 100° C. for 17 h. Additional 3-dimethylamino-acrylonitrile (0.1 mL, 0.87 mmol) was added to the reaction and stirring was continued at 100° C. for 22 h. The solvent was removed under a stream of $N_2$ and the residue was directly purified by reversed phase HPLC (20% MeCN/$H_2O$+ 0.1% TFA) to give a red semisolid that was neutralized by dissolving in EtOAc (5 mL) and washing with saturated aqueous $NaHCO_3$ (2×5 mL). The organic phase was dried with $Na_2SO_4$ and concentrated to give 29 mg of the title compound as a red semisolid, m/z 251.44 [M+1]$^+$.

2-(1-Amino-cyclopropyl)-pyrimidin-4-ylamine dihydrochloride was obtained by a method analogous to that described for 1-Pyrimidin-2-yl-cyclopropylamine dihydrochloride.

[1-(5-Cyano-furan-2-yl)-cyclopropyl]-carbamic acid tert-butyl ester

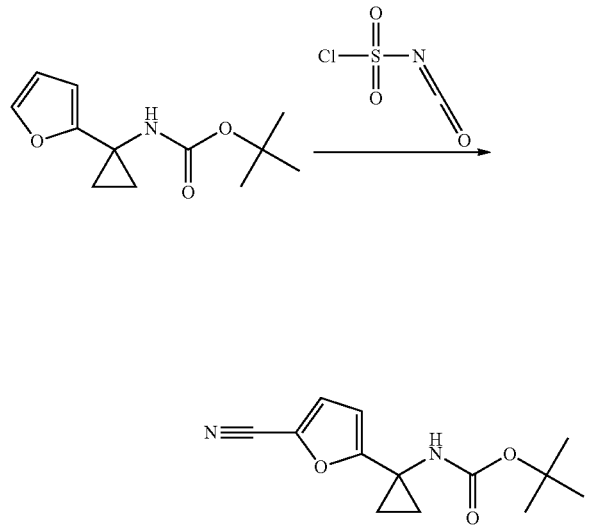

(1-Furan-2-yl-cyclopropyl)-carbamic acid tert-butyl ester (765 mg, 3.43 mmol) was dissolved in MeCN (7.7 mL) and cooled to −40° C. in an acetone/dry ice bath. Chloroulfonyl isocyante (0.45 mL, 5.1 mmol) was added in one portion via syringe and the reaction was allowed to stir at a temperature between −40 and −30° C. for 45 min. Anhydrous DMF (1.2 mL) was then added and stirring continued at room temperature for 30 min. The reaction was diluted with saturated aqueous NaHCO$_3$ (100 ml) and extracted with EtOAc (3×50 mL). The combined organic layers were concentrated to a red liquid and chromatographed (silica, 5→25% EtOAc/hexanes) to give 400 mg of the title compound as a white solid, m/z 234.35 [M-t-Bu+MeCN]$^+$.

{1-[5-(1-Benzyloxycarbonylamino-1-methyl-ethyl)-furan-2-yl]-cyclopropyl}-carbamic acid tert-butyl ester

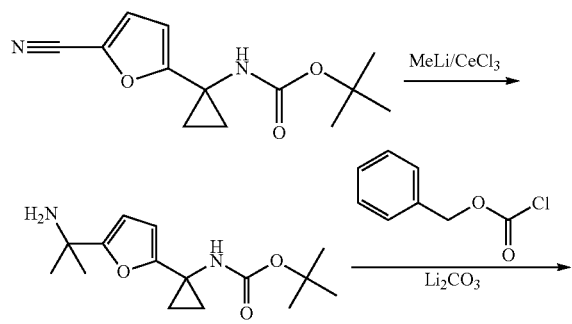

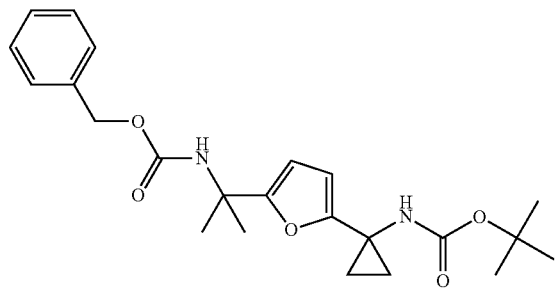

To an oven-dried flask under N$_2$ was added anhydrous cerium(III) chloride (2.00 g, 8.04 mmol) and anhydrous THF (10 mL). The mixture sonicated (1 min) to help break up the chunks of CeCl$_3$ and then stirred at rt for 30 min. The reaction was cooled −78° C. and methyl lithium (1.6 M in Et$_2$O, 5.0 mL, 8.0 mmol) was added in one portion via syringe. The mixture was stirred at −78° C. for 30 min and then [1-(5-Cyano-furan-2-yl)-cyclopropyl]-carbamic acid tert-butyl ester (399 mg, 1.61 mmol) in anhydrous THF (10 mL) was added in one portion via syringe. The reaction was stirred at −78° C. for 15 min then allowed to warm to room temperature and stir for an additional 2.25 h. The flask was cooled to −40° C. and NH$_4$OH (30 wt % in water, 1.8 mL) was added via syringe. After warming to room temperature, the thick mixture was filtered through a short pad of diatomaceous earth using CH$_2$Cl$_2$ to rinse. The filtrate was dried over Na$_2$SO$_4$ and concentrated to give 451 mg of crude {1-[5-(1-amino-1-methyl-ethyl)-furan-2-yl]-cyclopropyl}-carbamic acid tert-butyl ester as an orange oil, m/z 264.51 [M-NH$_2$]$^+$.

To a solution of crude {1-[5-(1-amino-1-methyl-ethyl)-furan-2-yl]-cyclopropyl}-carbamic acid tert-butyl ester (451 mg, 1.61 mmol) in a mixture of THF (8.0 mL) and water (1.6 mL), was added Li$_2$CO$_3$ (297 mg, 4.02 mmol) followed by benzyl chloroformate (0.57 mL, 4.0 mmol). This was stirred for 2.5 h then diluted with water (50 mL) and extracted EtOAc (3×50 mL). The combined organic layers were dried with Na$_2$SO$_4$ and concentrated to give a red residue. The residue was purified by flash chromatography (silica, 20->40% EtOAc/hexanes) to give 324 mg of the title compound as a yellow oil, m/z 437.64 [M+Na]$^+$.

{1-[6-(1-Benzyloxycarbonylamino-1-methyl-ethyl)-pyridazin-3-yl]-cyclopropyl}-carbamic acid tert-butyl ester

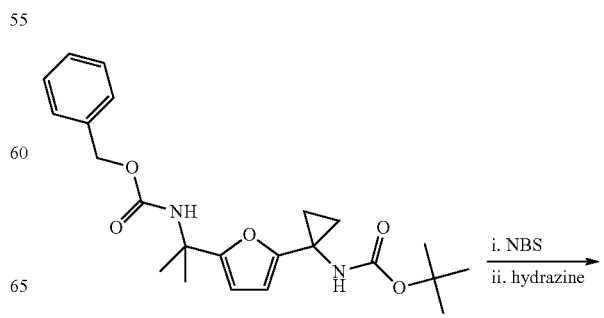

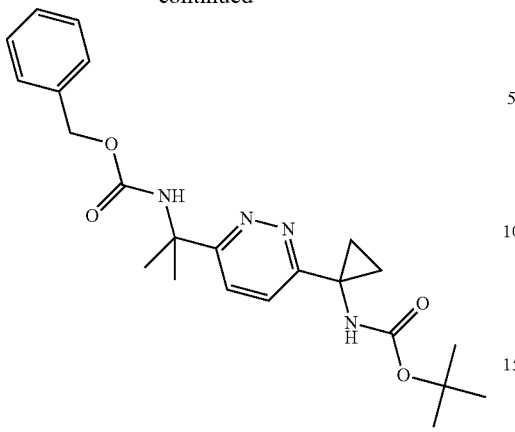

{1-[5-(1-Benzyloxycarbonylamino-1-methyl-ethyl)-furan-2-yl]-cyclopropyl}-carbamic acid tert-butyl ester (324 mg, 0.782 mmol) was dissolved in THF (13.5 mL) and water (1.4 mL) and cooled to −40° C. in a dry ice/acetone bath. To this slurry was added NBS (153 mg, 0.860 mg) as a solid in one portion. The reaction was stirred for 15 min at this temperature and then anhydrous hydrazine (0.2 mL, 6 mmol) was added in one portion via syringe. The ice bath was removed and the reaction was allowed to stir at room temperature for 49 h. The THF was removed in vacuo and the resulting liquid was diluted with water (150 mL) and extracted EtOAc (3×60 mL). The combined organic layers were dried over Na$_2$SO$_4$ and purified by flash chromatography (silica, 1→3.5% MeOH/CH$_2$Cl$_2$). Collected 32 mg of the title compound as a light yellow colored oil, m/z 427.63 [M+1]$^+$.

{1-[6-(1-Amino-cyclopropyl)-pyridazin-3-yl]-1-methyl-ethyl}-carbamic acid benzyl ester dihydrochloride dihydrochloride was obtained by a method analogous to that described for 1-Pyrimidin-2-yl-cyclopropylamine dihydrochloride, m/z 327.65 [M+1]$^+$.

(1-Propynoyl-cyclopropyl)-carbamic acid tert-butyl ester

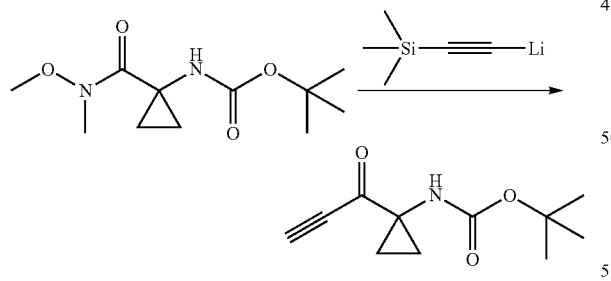

To a solution of [1-(Methoxy-methyl-carbamoyl)-cyclopropyl]-carbamic acid tert-butyl ester (5.0 g, 20. mmol) in anhydrous THF (50 mL) at −78° C., was slowly added lithium (trimethylsilyl)acetylide (0.5 M in THF, 81 mL, 41 mmol). The reaction stirred at this temperature for 2 h then an additional amount of lithium (trimethylsilyl)acetylide (0.5 M in THF, 81 mL, 41 mmol) was added and stirring continued for 3 h at −78° C. The reaction was diluted with saturated aqueous NH$_4$Cl and extracted with EtOAc. The organic layer was washed with brine, dried over Na$_2$SO$_4$, and concentrated in vacuo. The material was purified by flash chromatography (silica, 15% EtOAc/petroleum ether) to give 550 mg of the title compound as a brown syrup, m/z 154.18 [M-t-Bu]$^+$.

[1-((E)-3-Dimethylamino-acryloyl)-cyclopropyl]-carbamic acid tert-butyl ester

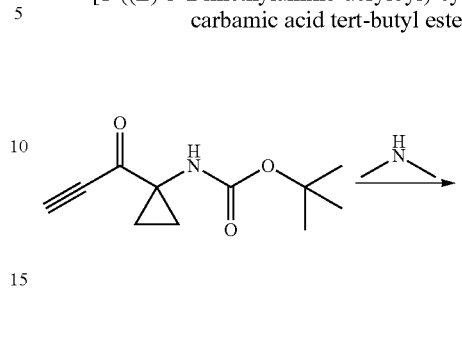

(1-Propynoyl-cyclopropyl)-carbamic acid tert-butyl ester (2.2 g, 10.5 mmol) was dissolved in a solution of Me$_2$NH (2 M in THF, 21 mL, 42 mmol) at 0° C. The reaction mixture was stirred at room temperature for 2 h and then the volatiles were removed in vacuo to give a crude solid. The solid was purified by washing with n-pentane and Et$_2$O to give 1.8 g of the title compound as a yellow solid, m/z 255.36 [M+1]$^+$.

(1-Pyrimidin-4-yl-cyclopropyl)-carbamic acid tert-butyl ester

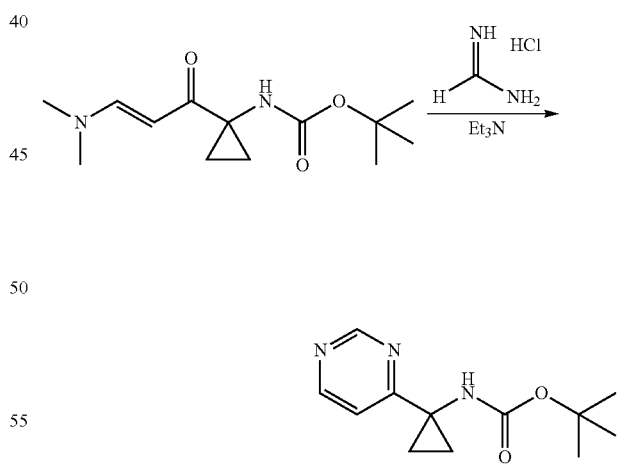

To a solution of [1-((E)-3-Dimethylamino-acryloyl)-cyclopropyl]-carbamic acid tert-butyl ester (600 mg, 2.4 mmol) was added triethylamine (1.3 mL, 9.4 mmol) and formamidine hydrochloride (570 mg, 7.1 mmol) at room temperature. The reaction was stirred at 75-80° C. for 14 h. The volatiles were removed in vacuo to give a crude solid mass that was purified by preparative reversed phase HPLC to give 115 mg of the title compound as a light yellow solid, m/z 236.36 [M+1]$^+$.

1-Pyrimidin-4-yl-cyclopropylamine dihydrochloride was obtained by a method analogous to that described for 1-Pyrimidin-2-yl-cyclopropylamine dihydrochloride, m/z 136.02 [M+1]$^+$.

1-(5-Cyclopropyl-4H-[1,2,4]triazol-3-yl)-cyclopropylamine

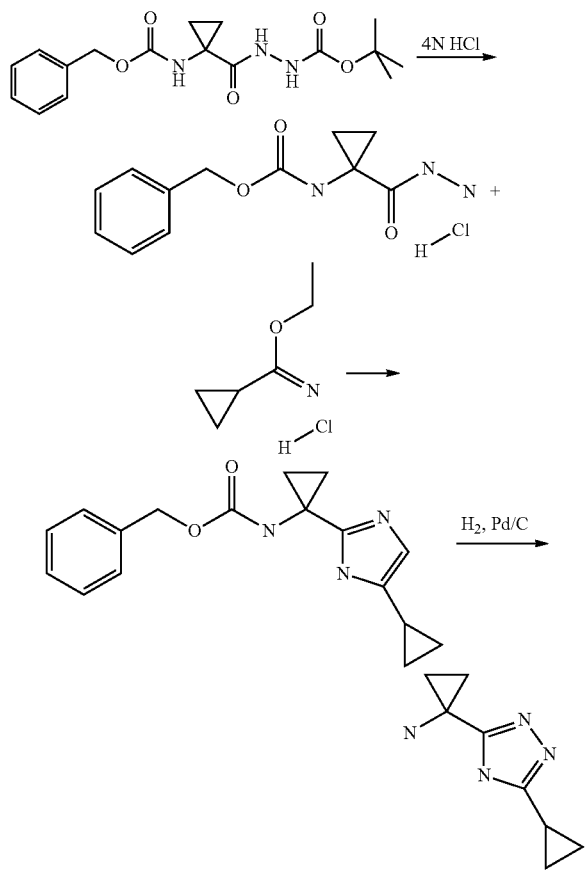

N'-(1-Benzyloxycarbonylamino-cyclopropanecarbonyl)-hydrazinecarboxylic acid tert-butyl ester (450 mg, 1.29 mmol) was dissolved in 4N HCl in Dioxane (8 ml, 32 mmol).

The mixture was allowed to stir at RT for 2 h. Diluted with Et$_2$O (20 mL) and the mixture concentrated under high vacuum to give (1-Hydrazinocarbonyl-cyclopropyl)-carbamic acid benzyl ester; hydrochloride (340 mg, 1.19 mmol, 92.4%) as white solids.

(1-Hydrazinocarbonyl-cyclopropyl)-carbamic acid benzyl ester; hydrochloride (916 mg, 3.2 mmol) and Cyclopropanecarboximidic acid ethyl ester; hydrochloride (480 mg, 3.2 mmol) and triethylamine (0.89 mL, 6.4 mmol) were combined in DMF (10 mL) and heated in the oil bath at 120° C. for 45 minutes. LCMS shows ~50% conversion to the product. The reaction was loaded directly onto a prep HPLC (mass-triggered Waters, Column: Sunfire C18 30×150 mm, Mobile phase: 95% water to 65% water, retention time of product=15.4 min) and after concentrating in vacuo, yielded [1-(5-Cyclopropyl-4H-[1,2,4]triazol-3-yl)-cyclopropyl]-carbamic acid benzyl ester (220 mg, 0.74 mmol, 23.0%) as white solids.

[1-(5-Cyclopropyl-4H-[1,2,4]triazol-3-yl)-cyclopropyl]-carbamic acid benzyl ester (220 mg, 0.74 mmol) was dissolved in MeOH (40 mL) followed by the addition of 10% Pd/C. The solution mixture was stirred under H$_2$ balloon for 1.5 hours. The reaction mixture was filtered through celite. The solvent was concentrated under high vacuum pump to afford 1-(5-Cyclopropyl-4H-[1,2,4]triazol-3-yl)-cyclopropylamine (120 mg, 0.73 mmol, 99.1%) as off-white solids.

1-Pyridin-2-yl-cyclobutylamine

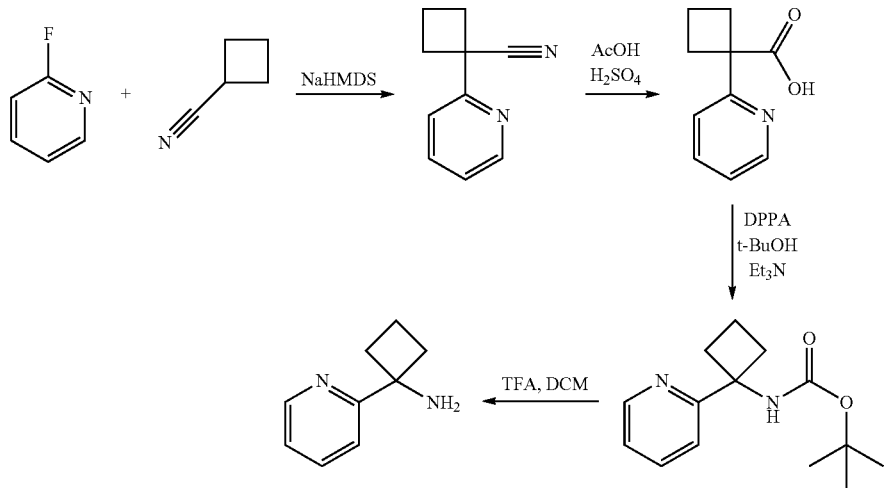 [SMILES: Fc1ccccn1 ; N#CC1CCC1 ; N#CC1(c2ccccn2)CCC1 ; O=C(O)C1(c2ccccn2)CCC1 ; NC1(c2ccccn2)CCC1 ; CC(C)(C)OC(=O)NC1(c2ccccn2)CCC1]

In a dry flask under Ar, 2-fluoropyridine (3.18 ml, 37 mmol) and cyclobutanecarbonitrile (3.0 g, 37 mmol) were dissolved in toluene (55 mL). The solution was cooled to 0° C. A 1M solution of sodium bis(trimethylsilyl)amide in THF (40.7 mL, 40.7 mmol) was added slowly over 5 min. After 1 h, the solution was warmed to room temperature. After another 19 h, the reaction was diluted with NH$_4$Cl (aq) and DCM. The layers were separated. The aqueous layer was extracted with DCM. The combined organic layers were dried over MgSO$_4$, filtered and concentrated to yield 4.68 g (80%) of 1-pyridin-2-yl-cyclobutanecarbonitrile as a pale yellow oil, m/z=159.7 [M+1]$^+$.

1-Pyridin-2-yl-cyclobutanecarbonitrile (4.92 g, 31.1 mmol) was combined with water (5 mL), AcOH (5 mL) and sulfuric acid (5 mL). The homogeneous solution was heated to reflux. After 2.5 h, the solution was cooled to room temperature and poured into water (20 mL) and Et$_2$O. The layers were separated and the Et$_2$O layer was discarded. The aqueous layer was basified to pH 4.5-5 with 10% NaOH and extracted with DCM (2×100 mL). The combined organic layers were washed with brine, dried over MgSO$_4$, filtered and concentrated to yield 3.28 g (59%) of 1-pyridin-2-yl-cyclobutanecarboxylic acid as pale yellow solid, m/z=178.5 [M+1]$^+$.

1-Pyridin-2-yl-cyclobutanecarboxylic acid (2.0 g, 11.3 mmol) was combined with t-BuOH 50 mL), Et$_3$N (1.78 mL, 12.4 mmol) and diphenylphosphoryl azide (2.7 mL, 12.4 mmol). The reaction was heated to reflux for 1.5 h. The t-BuOH was removed in vacuo to yield 7.0 g of crude (1-pyridin-2-yl-cyclobutyl)-carbamic acid tert-butyl ester as a pink-black oil. The crude product was used in subsequent reactions without further purification.

Crude (1-pyridin-2-yl-cyclobutyl)-carbamic acid tert-butyl ester (7.0 g, 5.64 mmol) was dissolved in DCM (20 mL) and TFA (20 mL) was added dropwise. After 6 h, the reaction was concentrated in vacuo and partitioned between DCM (100 mL) and water (20 mL). The aqueous layer was extracted with DCM (2×50 mL). The aqueous layer was then concentrated in vacuo. The brown oil was dissolved in water (3 mL) and purified via Mass-directed reverse phase HPLC purification which yielded 322 mg of 1-pyridin-2-yl-cyclobutylamine as a formic acid salt (yellow solid), m/z=149.5 [M+1]$^+$.

1-(5-Methanesulfonyl-pyridin-2-yl)-cyclopropylamine

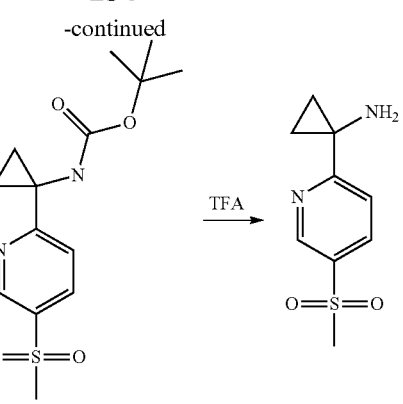

In a Biotage microwave vial was placed [1-(5-iodo-pyridin-2-yl)-cyclopropyl]-carbamic acid tert-butyl ester (500 mg, 1.39 mmol), sodium thiomethoxide (292 mg, 4.17 mmol) and Xantphos (80 mg, 0.14 mmol). The vial was flushed with Ar. 1,4-Dioxane (7.5 ml) and Et$_3$N (0.48 mL, 2.78 mmol) were added. Ar was bubbled through the reaction solution for 15 minutes. Pd$_2$(dba)$_3$ (65 mg, 0.07 mmol) was added and the reaction was thermally heated to 100° C. After 8 h, the reaction was transferred to a separatory funnel, diluted with saturated NaHCO$_3$ and brine, and extracted with EtOAc (2×50 mL). The combined organic layers were dried, filtered and evaporated to give a black oil. Flash chromatography (10 g silica, 0-10% MeOH in DCM) yielded 300 mg of [1-(5-methylsulfanyl-pyridin-2-yl)-cyclopropyl]-carbamic acid tert-butyl ester as a dark oil.

[1-(5-Methylsulfanyl-pyridin-2-yl)-cyclopropyl]-carbamic acid tert-butyl ester (150 mg, 0.54 mmol) was dissolved in DCM (5 mL) and m-chloroperbenzoic acid (253 mg, 1.1 mmol) was added in one portion. After 4 h, 1 g of TBD-polymethyl styrene (loading: 2.5 mmol/g) was added and the reaction was shaken for 2 h. The reaction was filtered and the resin was washed with 10% MeOH in DCM. The filtrate was concentrated to yield 148 mg (89%) of [1-(5-methanesulfonyl-pyridin-2-yl)-cyclopropyl]-carbamic acid tert-butyl ester as a pale yellow solid, m/z=313.6 [M+1]$^+$.

[1-(5-Methanesulfonyl-pyridin-2-yl)-cyclopropyl]-carbamic acid tert-butyl ester (148 mg, 0.47 mmol) was dissolved in DCM (4 mL). TFA (2 mL) was added dropwise. After 4 h, the reaction was concentrated in-vacuo to yield 250 mg of crude 1-(5-methanesulfonyl-pyridin-2-yl)-cyclopropylamine as a TFA salt (dark oil), m/z=213.3 [M+1]$^+$. The product was used in subsequent reactions without further purification.

2-(1-amino-cyclopropyl)-oxazole-4-carboxylic acid amide hydrobromide

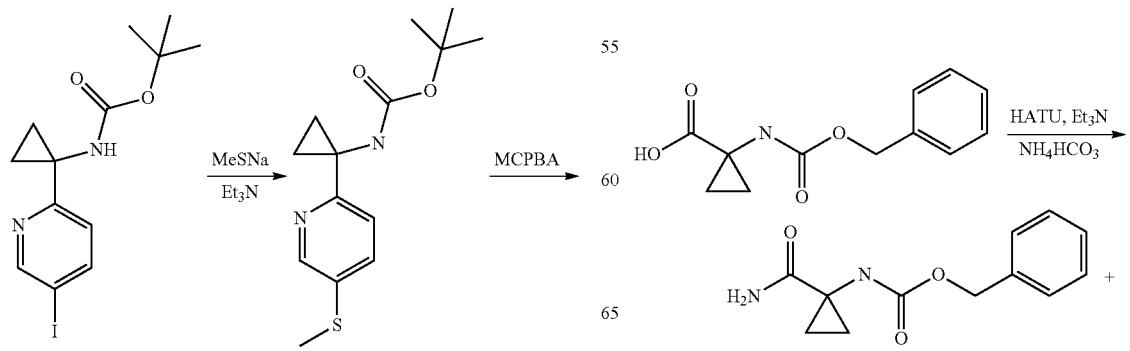

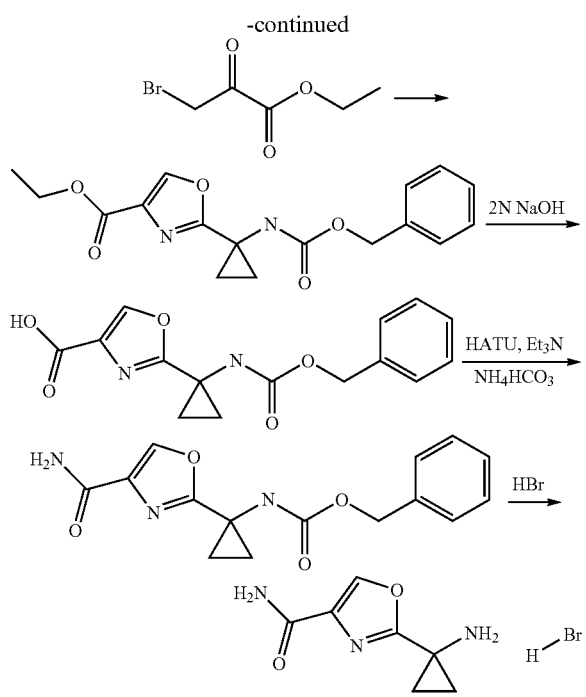

To a solution of 1-benzyloxycarbonylamino-cyclopropanecarboxylic acid (7.0 g, 29.8 mmol) in DMF (30 mL) was added HATU (11.3 g, 29.8 mmol) and Et₃N (4.3 mL, 29.8 mmol). The mixture was allowed to stir at room temperature for 20 min, then ammonium hydrogen carbonate (7.06 g, 89.3 mmol) was added in one portion. The reaction was heated at 60° C. for 12 h. The mixture was cooled to room temperature, diluted with water and extracted with EtOAc (2×100 mL). The combined extracts were washed with satd NaHCO₃, water, brine and dried with MgSO₄. The mixture was filtered and the solvent removed to give (1-carbamoyl-cyclopropyl)-carbamic acid benzyl ester (5.5 g, 24.5 mmol) as a white solid.

To a solution of (1-carbamoyl-cyclopropyl)-carbamic acid benzyl ester (3.0 g, 8.1 mmol) in THF (100 mL) was added NaHCO₃ (9.7 g, 120 mmol) and 3-bromo-2-oxo-propionic acid ethyl ester (8.1 mL, 64.0 mmol). The reaction was heated at 70° C. for 15 h. The resulting orange suspension was filtered through celite and concentrated under reduced pressure. The resulting orange oil was dissolved in THF (10 mL) and to this was added trifluoroacetic anhydride (1 mL). The mixture was stirred at room temperature for 24 h. The reaction was quenched with satd NaHCO₃ and extracted with EtOAc (3×50 mL). The combined extracts were washed with water, brine and dried with MgSO₄. The mixture was filtered, concentrated and purified by reverse phase HPLC. The combined HPLC fractions were extracted with EtOAc (3×100 mL). The extracts were washed with water, brine and dried with MgSO₄. The mixture was filtered and concentrated to give 2-(1-benzyloxycarbonylamino-cyclopropyl)-oxazole-4-carboxylic acid ethyl ester (1.3 g, 3.9 mmol) as a white solid.

2-(1-Benzyloxycarbonylamino-cyclopropyl)-oxazole-4-carboxylic acid ethyl ester (0.44 g, 1.3 mmol) was dissolved in THF (10 mL) and to this solution was added 2N NaOH (2.0 mL, 4.0 mmol). The mixture was heated at 70° C. for 17 h. The mixture was neutralized with 2N HCl and extracted with EtOAc (3×100 mL). The combined extracts were washed with water, brine and dried with MgSO₄. The mixture was filtered and concentrated to give 2-(1-benzyloxycarbonylamino-cyclopropyl)-oxazole-4-carboxylic acid (0.22 g, 0.73 mmol) as a brown solid.

To a solution of 2-(1-benzyloxycarbonylamino-cyclopropyl)-oxazole-4-carboxylic acid (0.20 g, 0.66 mmol) in DMF (3 mL) was added HATU (0.25 g, 0.66 mmol) and Et₃N (0.16 g, 2.0 mmol). Ammonium hydrogen carbonate was then added and the reaction vessel sealed. The mixture was heated at 60° C. for 18 h. The reaction was allowed to cool to room temperature and diluted with water. The mixture was extracted with EtOAc (3×100 mL) and the combined extracts were washed with water, brine and dried with MgSO₄. The mixture was filtered and concentrated to give [1-(4-carbamoyl-oxazol-2-yl)-cyclopropyl]-carbamic acid benzyl ester (0.17 g, 0.55 mmol).

1-(4-Carbamoyl-oxazol-2-yl)-cyclopropyl]-carbamic acid benzyl ester (0.14 g, 0.47 mmol) was dissolved in 33% HBr in acetic acid (3.0 mL) and allowed to stir at room temperature for 30 min. The solution was diluted with Et₂O resulting in the precipitation of a white solid. The majority of the liquid was decanted off and the residue concentrated under reduced pressure. The material was treated with Et₂O and concentrated again to give 2-(1-amino-cyclopropyl)-oxazole-4-carboxylic acid amide hydrobromide (0.11 g, 0.44 mmol) as an orange solid.

1-(5-Trifluoromethyl-1,2,4-oxadiazol-3-yl)-cyclopropylamine hydrobromide

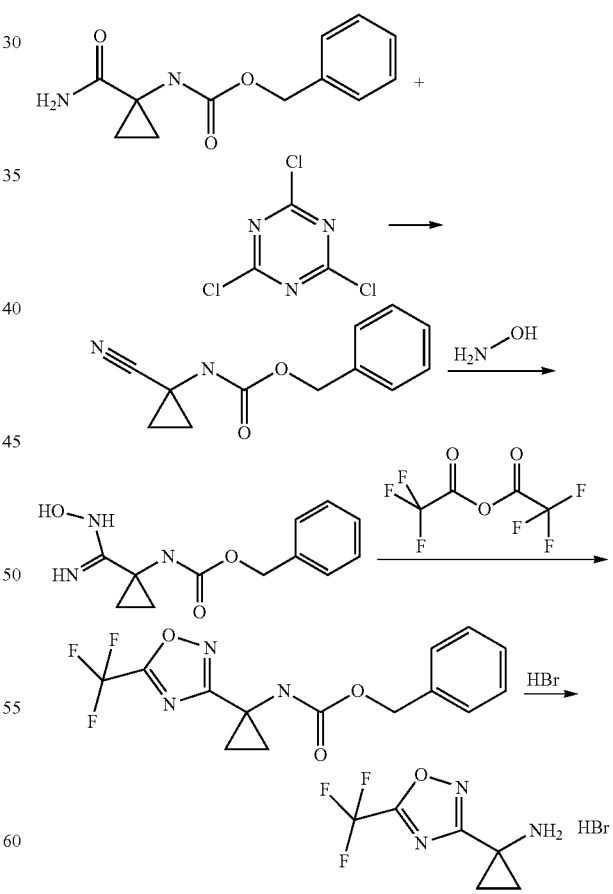

To a 0° C. solution of (1-carbamoyl-cyclopropyl)-carbamic acid benzyl ester (1.8 g, 7.7 mmol) in DMF (20 mL) was added cyanuric chloride in one portion. The reaction was allowed to warm to room temperature overnight. The reaction was quenched with water and extracted with EtOAc (3×100 mL). The combined extracts were washed with water (3×50 mL), brine and dried with MgSO₄. The mixture was filtered and concentrated. The resulting crude residue was dissolved in 30% EtOAc in hexanes (90 mL) and filtered through a plug of silica gel. The filtrate was concentrated to give (1-cyano-cyclopropyl)-carbamic acid benzyl ester (1.4 g, 6.5 mmol) as a white foam.

To a solution of (1-cyano-cyclopropyl)-carbamic acid benzyl ester (3.7 g, 17.11 mmol) in EtOH (40 mL) was added hydroxylamine hydrochloride (3.6 g, 51 mmol) and K₂CO₃ (9.5 g, 68 mmol). The reaction mixture was heated at reflux for 24 h. The resulting white suspension was cooled to RT and concentrated under reduced pressure. The residue was diluted with water and extracted with EtOAc (3×100 mL). The combined extracts were washed with water, brine and dried with MgSO₄. The mixture was filtered, concentrated and purified by reverse phase HPLC to give [1-(N-hydroxycarbamimidoyl)-cyclopropyl]-carbamic acid benzyl ester (0.68 g, 2.7 mmol) as a white solid.

To a solution of [1-(N-hydroxycarbamimidoyl)-cyclopropyl]-carbamic acid benzyl ester (0.30 g, 1.0 mmol) in dioxane (10 mL) was added Et₃N (0.33 mL, 2.4 mmol) and TFAA (0.14 mL, 1.0 mmol). The reaction was allowed to stir at RT for 30 min, then BF₃.OEt₂ (0.4 mL) was added and the reaction heated at 110'C for 20 h. The resulting yellow solution was cooled to RT, diluted with water and extracted with EtOAc (3×100 mL). The combined extracts were washed with water, brine and dried with MgSO₄. The mixture was filtered, concentrated and the residue purified by silica gel chromatography (0-100% EtOAc in hexanes) to give [1-(5-trifluoromethyl-1,2,4-oxadiazol-3-yl)-cyclopropyl]-carbamic acid benzyl ester (0.24 g, 0.73 mmol) as a yellow oil.

[1-(5-Trifluoromethyl-1,2,4-oxadiazol-3-yl)-cyclopropyl]-carbamic acid benzyl ester (0.22 g, 0.67 mmol) was dissolved in 33% HBr in acetic acid (0.5 mL) and the reaction allowed to stir for 30 min at RT. The mixture was diluted with Et₂O resulting is formation of a white precipitate. The majority of the liquid was decanted off and the residue concentrated under reduce pressure to give 1-(5-trifluoromethyl-1,2,4-oxadiazol-3-yl)-cyclopropylamine hydrobromide (0.19 g, 0.69 mmol) as an orange solid.

(2S,3R)-2-Amino-3-tert-butoxy-N-(1-pyrimidin-2-yl-cyclopropyl)-butyramide trifluoro-acetic acid

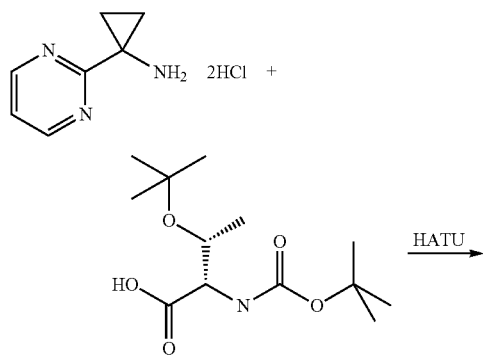

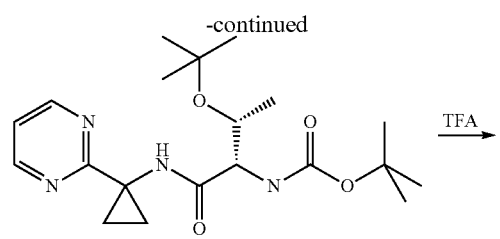

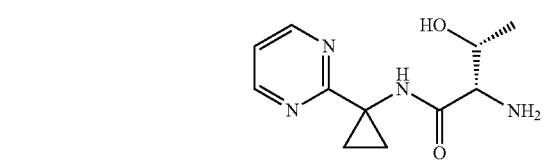

To a solution of (2S,3R)-3-tert-butoxy-2-tert-butoxycarbonylamino-butyric acid (0.20 g, 0.72 mmol) in DMF (1 mL) was added HATU (0.27 g, 0.72 mmol), Et₃N (0.30 mL, 2.2 mmol) and 1-pyrimidin-2-yl-cyclopropylamine dihydrochloride (0.15 g, 0.72 mmol.). The reaction was allowed to stir at RT for 24 h. The mixture was diluted with water and extracted with EtOAc (3×50 mL). The combined extracts were washed with satd NaHCO₃, 2N HCl, water and brine. The solution was dried with MgSO₄, filtered and concentrated to give [(1S,2R)-2-tert-butoxy-1-(1-pyrimidin-2-yl-cyclopropylcarbamoyl)-propyl]-carbamic acid tert-butyl ester (0.23 g, 0.59 mmol).

[(1S,2R)-2-tert-butoxy-1-(1-pyrimidin-2-yl-cyclopropylcarbamoyl)-propyl]-carbamic acid tert-butyl ester (0.17 g, 0.45 mmol) was dissolved in DCM (1 mL) and to this was added TFA (0.2 mL). The reaction was allowed to stir at RT for 24 h. The solvent was removed under reduced pressure and the residue triturated with Et₂O to give (2S,3R)-2-amino-3-tert-butoxy-N-(1-pyrimidin-2-yl-cyclopropyl)-butyramide trifluoro-acetic acid (0.16 g, 0.45 mmol) as a white solid.

[1-(5-Acetyl-pyridin-2-yl)-cyclopropyl]-carbamic acid tert-butyl ester

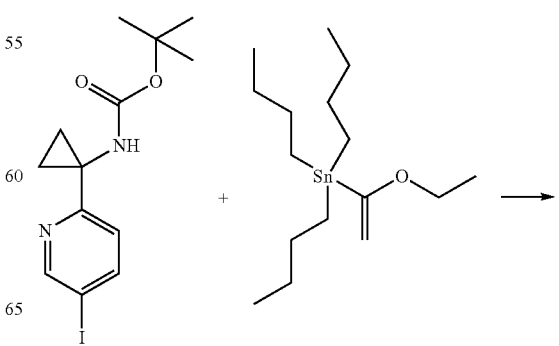

-continued

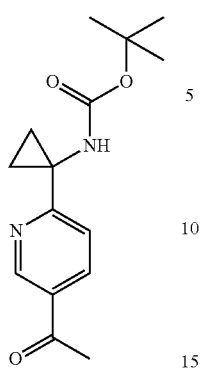

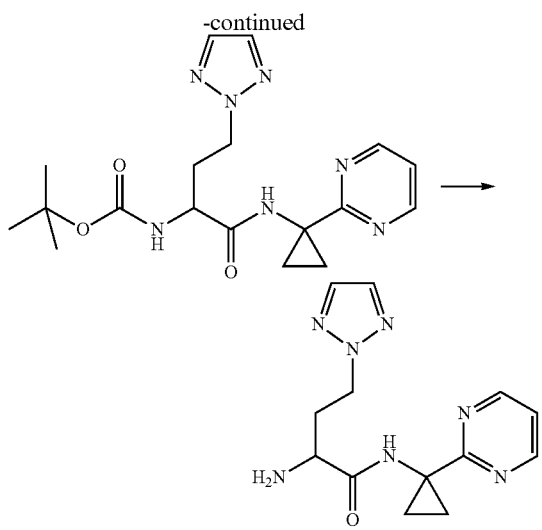

To a solution of [1-(5-Iodo-pyridin-2-yl)-cyclopropyl]-carbamic acid tert-butyl ester (100 mg, 0.278 mmol) in anhydrous DMF (1 mL) was added tributyl-(1-ethoxy-vinyl)-stannane (0.103 mL, 0.305 mmol) followed by tetrakis (triphenylphosphane)palladium (0) (32.1 mg, 0.028 mmol). The mixture was stirred at 100° C. under an atmosphere of argon. After 16 h, pyridinium p-toluenesulfonate (77.0 mg, 0.306 mmol) was added along with 0.5 mL of water and the mixture was stirred at rt for 1 h. The reaction was diluted with 10 mL of 10% citric acid and was extracted with EtOAc (3×30 mL). The combined organic layers were washed with brine, dried over MgSO$_4$, filtered, and concentrated in vacuo. The product was purified by column chromatography (10 g biotage SNAP column, 5-40% EtOAc in hexanes) to give the title compound as a yellow solid (74.7 mg, 97%).

Preparation of 2-Amino-N-(1-pyrimidin-2-yl-cyclopropyl)-4-1,2,3-triazol-2-yl-butyramide trifluoroacetate

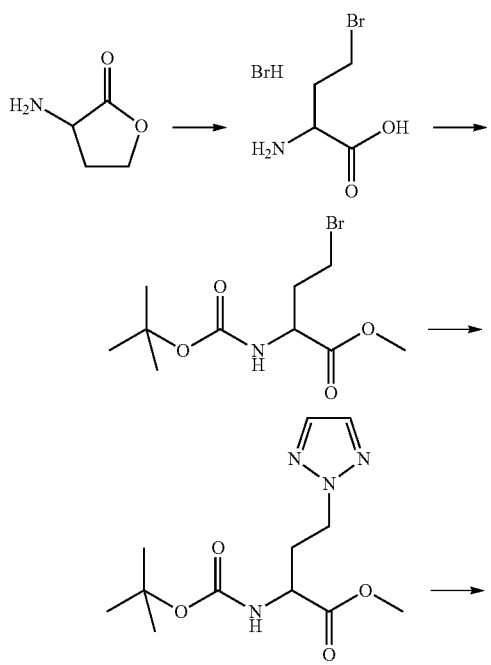

A suspension of α-amino-γ-butyrolactone hydrobromide in 30% HBr in HOAc was heated at 100° C. in a sealed tube for 5 days. The mixture was concentrated to give a white solid that was washed with Et$_2$O to provide 23.1 g (64%) of 2-amino-4-bromo-butyric acid hydrobromide.

Acetyl chloride (61 mL, 860 mmol) was added dropwise to 200 mL of MeOH at 0° C. The mixture was stirred at room temperature for 30 min, and 22.5 g (124 mmol) of 2-amino-4-bromo-butyric acid hydrobromide was added. The mixture was stirred overnight and concentrated. The residue was washed with Et$_2$O to provide 23.5 g (82%) of methyl 4-bromo-2-amino-butyrate hydrochloride. A solution of 27.7 g (330 mmol) of NaHCO$_3$ in 100 mL of water was slowly added to 19.2 g (82.5 mmol) of this material along with 21.6 g (99.0 mmol) of Boc$_2$O in 140 mL of 1,4-dioxane at 0° C., The mixture was warmed to room temperature and stirred overnight. N,N-dimethylpropane-1,3-diamine (5 mL) was added to the mixture, and stirring was continued for 20 min. The mixture was diluted with water then extracted twice with EtOAc. The extracts were washed with water, 1M NaHSO$_4$, and brine, and then combined, dried with Na$_2$SO$_4$, filtered, and concentrated to provide 21.5 g (88%) of 4-bromo-2-tert-butoxycarbonylamino-butyric acid methyl ester as a white solid.

To a solution of 0.87 g (8.4 mmol) of 2-chloroimidazole in 14 mL of DMF was added 0.40 g (10 mmol) of 60% NaH in mineral oil. After 20 min of stirring, 2.5 g (8.4 mmol) of 4-bromo-2-tert-butoxycarbonylamino-butyric acid methyl ester in 5 mL of DMF was added. The reaction mixture was heated to 80° C. for 1 h. The mixture was diluted with EtOAc (150 mL), washed with water, brine, dried over MgSO4, filtered, and concentrated. The residue was purified by flash chromatography (0-5% MeOH in CH2Cl2) to provide 2.1 g (78%) of 2-tert-butoxycarbonylamino-4-1,2,3-triazol-2-yl-butyric acid methyl ester.

A mixture of 0.50 g (1.6 mmol) of 2-tert-butoxycarbonylamino-4-1,2,3-triazol-2-yl-butyric acid methyl ester in 1.0 mL of MeOH and 3.0 mL (9.0 mmol) of 3M aq. NaOH is stirred at 80° C. for 60 min The mixture was cooled to rt and washed with EtOAc (1×10 mL). After adjusting the pH to 4 with 3M HCl, the mixture is extracted with EtOAc (3×) and the extracts are washed with brine, then dried with Na2SO4, filtered, and concentrated to provide 0.42 g (87%) of 2-tert-butoxycarbonylamino-4-1,2,3-triazol-2-yl-butyric acid as a white solid.

To a solution of the 2-tert-butoxycarbonylamino-4-1,2,3-triazol-2-yl-butyric acid (0.1 g, 0.37 mmol) in DMF (2 mL) was added 1-pyrimidin-2-yl-cyclopropylamine dihydrochloride (50 mg, 0.24 mmol) followed by Et₃N (0.1 ml, 0.74 mmol) and HATU (211 mg, 0.55 mmol). The mixture was stirred at room temperature for 1 h. The mixture was diluted with water and EtOAc. The layers were separated and the organic layer was washed with water (3×30 mL), brine (2×30 mL), dried over MgSO₄, filtered, and concentrated in vacuo to yield crude [1-(1-pyrimidin-2-yl-cyclopropyl-carbamoyl)-3-1,2,3-triazol-2-yl-propyl]-carbamic acid tert-butyl ester. The product was not purified and was used in subsequent reactions.

To a solution of the [1-(1-pyrimidin-2-yl-cyclopropyl-carbamoyl)-3-1,2,3-triazol-2-yl-propyl]-carbamic acid tert-butyl ester (143 mg, 0.37 mmol) in CH₂Cl₂ (5 mL) was added TFA (0.14 mL, 1.85 mmol) and the mixture was stirred at rt for 2 h. The mixture was concentrated in vacuo and 106 mg of crude 2-amino-N-(1-pyrimidin-2-yl-cyclopropyl)-4-1,2,3-triazol-2-yl-butyramide trifluoroacetate. The title compound was used in subsequent reactions without further purification.

1-Amino-cyclopropanecarboxylic acid [1-(4-pyrrolidin-1-ylmethyl-pyridin-2-yl)-cyclopropyl]-amide

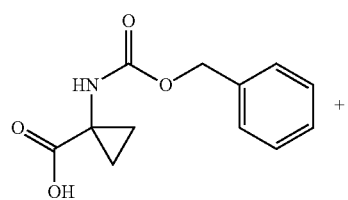

+

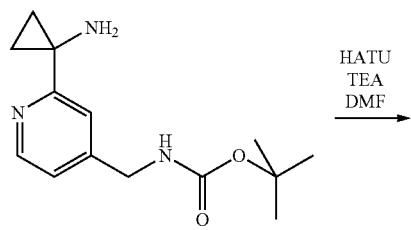

HATU
TEA
DMF

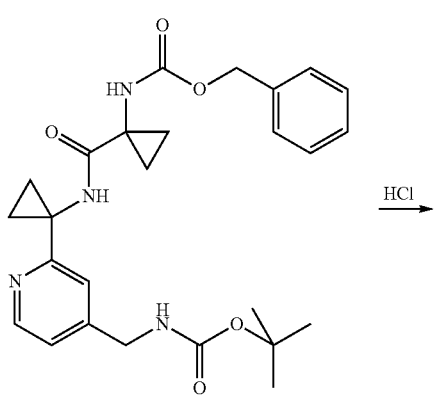

HCl

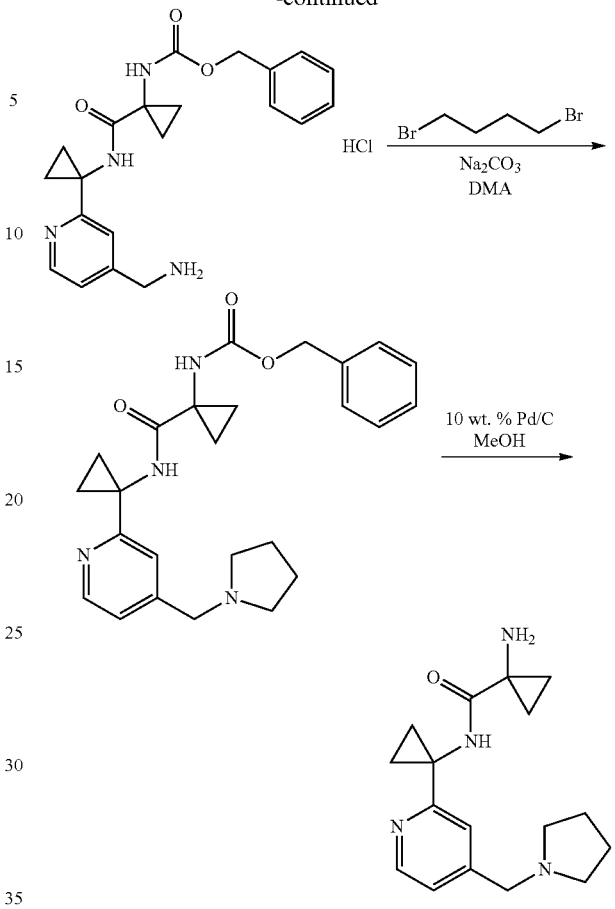

1-Benzyloxycarbonylamino-cyclopropanecarboxylic acid (1.251 g, 5.316 mmol) and HATU (2.527 g, 6.645 mmol) were dissolved in dry DMF (15 mL) and stirred for 5 min. This solution was added to the solution of [2-(1-Aminocyclopropyl)-pyridin-4-ylmethyl]-carbamic acid tert-butyl ester (2.8 g, 10.633 mmol) in dry DMF (5 mL). TEA (2.2 mL, 16 mmol) was then added and the reaction was stirred at room temperature for 25 min. The reaction was diluted with EtOAc (450 mL) and then acidified with 1N HCl (20 mL) to pH 1. Without separation of the layers, the mixture was basified with saturated NaHCO₃ (140 mL) to pH 8.5. Layers were separated. The organic layer was further washed with water (3×350 mL). The organics was dried with anhydrous Na₂SO₄, filtered, and concentrated to afford 3.73 g of the crude product which was purified by Biotage flash column using 0-2% MeOH/DCM as the gradient to afford 1.447 g of (1-{1-[4-(tert-Butoxycarbonylamino-methyl)-pyridin-2-yl]-cyclopropylcarbamoyl}-cyclopropyl)-carbamic acid benzyl ester as a light brown foam.

4M HCl solution in 1,4-dioxane (15 mL) was added to (1-{1-[4-(tert-Butoxycarbonylamino-methyl)-pyridin-2-yl]-cyclopropylcarbamoyl}-cyclopropyl)-carbamic acid benzyl ester (1.403 g, 2.92 mmol). The resultant mixture was allowed to stir at RT for 6 h. The mixture was concentrated to afford a light brown solid. This solid was washed with diethyl ether and dried in vacuo to afford 1.271 g of {1-[1-(4-Aminomethyl-pyridin-2-yl)-cyclopropylcarbamoyl]-cyclopropyl}-carbamic acid benzyl ester di-hydrochloric acid salt.

{1-[1-(4-Aminomethyl-pyridin-2-yl)-cyclopropylcarbamoyl]-cyclopropyl}-carbamic acid benzyl ester dihydrochloride (200 mg, 0.441 mmol) was dissolved in dry DMA (5 mL). 1,4-Dibromobutane (0.264 mL, 2.206 mmol) was added followed by Na2CO3 (0.234 g, 2.206 mmol). The reaction mixture was heated at 80° C. in a microwave reactor for 20 min. The reaction mixture was diluted with MeCN (4 mL) and water (1 mL) and filtered. The resultant crude product was purified by mass triggered LCMS using 5-35% MeCN/water as the gradient to afford 67 mg of {1-[1-(4-Pyrrolidin-1-ylmethyl-pyridin-2-yl)-cyclopropylcarbamoyl]-cyclopropyl}-carbamic acid benzyl ester.

In a 100 mL one neck round bottom flask, {1-[1-(4-Pyrrolidin-1-ylmethyl-pyridin-2-yl)-cyclopropylcarbamoyl]-cyclopropyl}-carbamic acid benzyl ester (67 mg, 0.154 mmol) was dissolved in MeOH (10 mL). 10 Wt. % Pd/C (15 mg) was then added. Nitrogen gas was bubbled through the suspension for 10 min. The reaction flask was evacuated and then filled with $H_2$. This purging process was repeated twice and then the reaction was allowed to stir for 16 h under $H_2$ (1 atm). The reaction mixture was filtered through celite. The filtrate was concentrated in vacuo to afford 39.3 mg of the title compound as a white solid.

The following compound was prepared using similar procedures as described above:

1-Amino-cyclopropanecarboxylic acid [1-(4-morpholin-4-ylmethyl-pyridin-2-yl)-cyclopropyl]-amide 3,5-Dichloro-4-fluoro-phenylamine

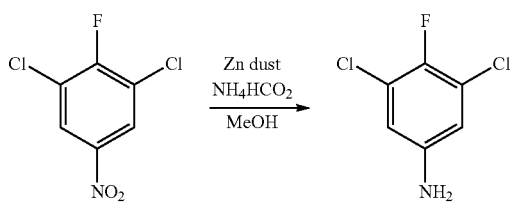 [SMILES: "MeOH" ; O=[N+]([O-])c1cc(Cl)c(F)c(Cl)c1 ; Nc1cc(Cl)c(F)c(Cl)c1]

To a solution of 1,3-dichloro-2-fluoro-5-nitro-benzene (71.4 g, 340 mmol) in methanol (1.5 L) was added a solution of ammonium formate (180.2 g, 2.86 mol) in water (300 mL). Zinc dust (93.4 g, 1.43 mol) was then added in four equal portions over 20 min. The reaction was stirred for 1 h and then allowed to cool to room temperature. The reaction mixture was filtered through diatomaceous earth and the filtrate was concentrated in vacuo. Ethyl acetate (300 mL) and water (300 mL) were added and the mixture was again filtered through diatomaceous earth. The layers were separated, and the aqueous layer was further extracted with ethyl acetate (350 mL). The combined organics were washed with 500 mL of brine, dried over $Na_2SO_4$, filtered, and concentrated to afford 56.4 g of the title compound as a brown solid, m/z 180.2 [M+H]$^+$. This material was used without any further purification.

[(R)-1-(3,5-Dichloro-4-fluoro-phenylcarbamoyl)-ethyl]-carbamic acid tert-butyl ester

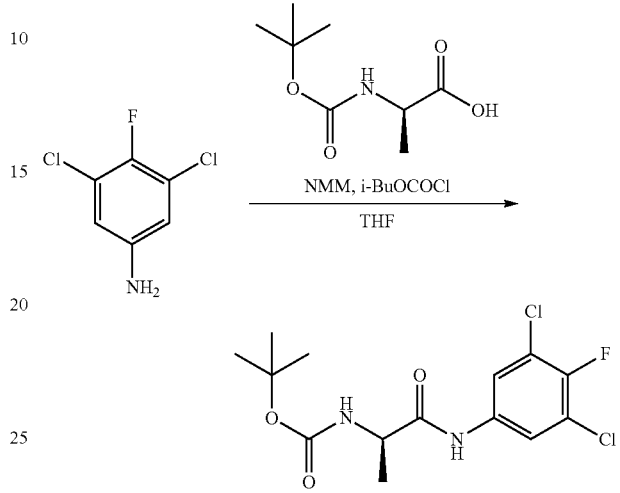

To a cooled (−20° C.) solution of (R)-2-tert-butoxycarbonylamino-propionic acid (57.2 g, 302 mmol) in anhydrous THF (582 mL) was added N-methyl-morpholine (34.9 mL, 317 mmol) at a rate to keep the internal temperature at −15° C. Isobutyl chloroformate (42.0 mL, 317 mmol) was then added over a 20 min period and the resulting mixture was stirred for 30 min. A solution of 3,5-dichloro-4-fluoro-phenylamine (54.4 g, 302 mmol) in THF (160 mL) was then added over 40 min. The reaction mixture was warmed to 20° C. and stirred for 20 h. The reaction mixture was filtered and concentrated in vacuo. To the resulting oil was added MeOH (200 mL) and the solution was concentrated to provide the title compound as a tan colored solid, m/z 295.3 [M−t−Bu]$^+$. This material was used without further purification.

(R)-2-Amino-N-(3,5-dichloro-4-fluoro-phenyl)-propionamide

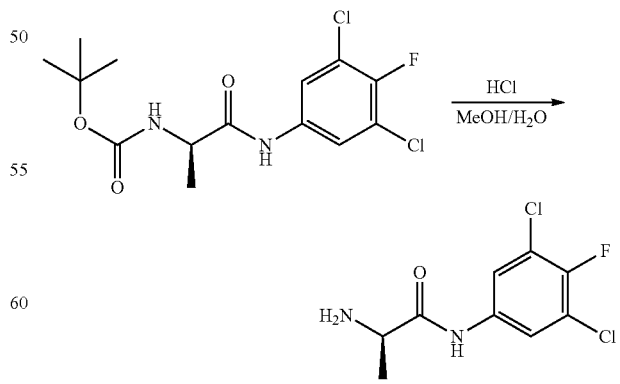

To a solution of hydrochloric acid (12 M, 266 mL, 3.19 mol) in water (272 mL) and MeOH (135 mL) was added a solution of crude [(R)-1-(3,5-dichloro-4-fluoro-phenylcarbamoyl)-ethyl]-carbamic acid tert-butyl ester (208.6 g, max. 594 mmol) in MeOH (600 mL) via an addition funnel over 30 min. CH$_2$Cl$_2$ (300 mL) was then added and the reaction mixture was stirred at room temperature overnight. An additional portion of HCl (12 M, 100 mL) was added and stirring was continued for another 20 h. The volatile solvents were removed in vacuo and the remaining aqueous mixture was cooled to −15 to −20° C. Toluene (400 mL) was added followed by the addition of NaOH solution (50% aqueous, 300 mL), which was added at a rate to keep the internal temperature below 25° C. The layers were separated and the aqueous layer was extracted with toluene (2×1 L). The combined organic layers were dried with Na$_2$SO$_4$ and concentrated to give 158.3 g of the title compound as a dark brown oil that solidifies slowly in the freezer, m/z 251.1 [M+H]$^+$. This crude material was used without further purification.

(2S,5R)-2-tert-Butyl-3-(3,5-dichloro-4-fluoro-phenyl)-5-methyl-1-(2,2,2-trifluoro-acetyl)-imidazolidin-4-one

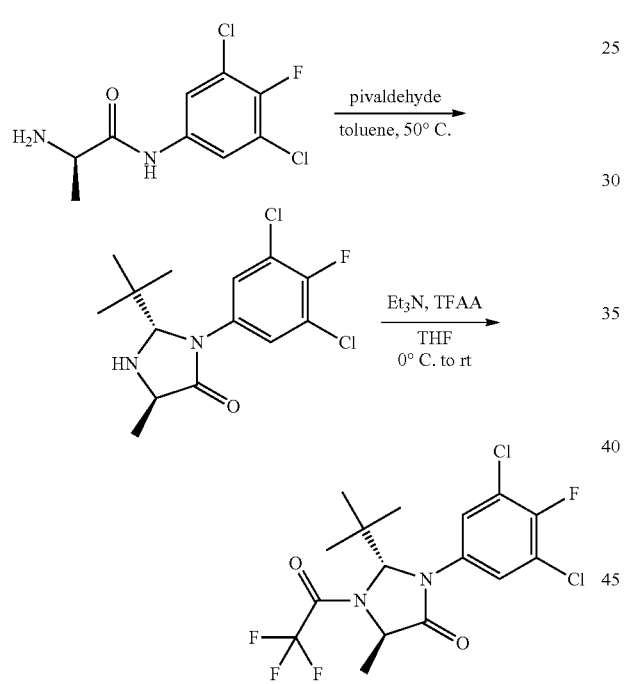

To a solution of (R)-2-amino-N-(3,5-dichloro-4-fluoro-phenyl)-propionamide (149.1 g crude, max 594 mmol) in toluene (743 mL) at 40° C., was added pivalaldehyde (67.1 mL, 618 mmol) in one portion. The reaction was stirred at 50° C. for 22 h and then all volatiles were removed in vacuo to give a viscous brown oil. Hexane (500 mL) was added and the resulting suspension was stirred at room temperature for 30 min. The mixture was filtered and the solids rinsed with cold hexane. The filtrate was concentrated in vacuo and reprocessed in a similar manner to obtain additional precipitate. The remaining filtrate was diluted with hexane until a black oil separated from the solution. The hexane layer was decanted from this black oil and concentrated in vacuo. The residue was re-dissolved in warm diethyl ether (300 mL) and stored in the freezer for 1.5 h over which time crystal growth was observed. The solids were filtered, and the filtrate reprocessed in a similar manner to obtain additional crystals. All of the collected solids were combined to give 112.2 g of (2S,5R)-2-tert-butyl-3-(3,5-dichloro-4-fluoro-phenyl)-5-methyl-imidazolidin-4-one as a tan solid. To a solution of this solid in toluene (639 mL) at 0° C. was added triethylamine (73.5 mL, 527 mmol) in one portion. Trifluoroacetic anhydride (58.6 mL, 422 mmol) was added to the reaction mixture over 1 h at a rate to keep the internal temperature below 5° C. The reaction mixture was stirred at 0° C. for 1 h and then warmed to 20° C. over 1 h. The mixture was then cooled to 10° C. and water (1.2 L) was added. The layers were separated and the organic layer was washed with water (1.2 L and then 0.6 L). The combined aqueous layers were extracted with toluene (0.6 L). The combined organic layers were dried over MgSO$_4$ and concentrated in vacuo to give 149.4 g of the title compound as a tan solid, m/z 456.4 [M+MeCN+H]$^+$.

4-[(2R,4R)-2-tert-Butyl-1-(3,5-dichloro-4-fluoro-phenyl)-4-methyl-5-oxo-3-(2,2,2-trifluoro-acetyl)-imidazolidin-4-ylmethyl]-benzonitrile

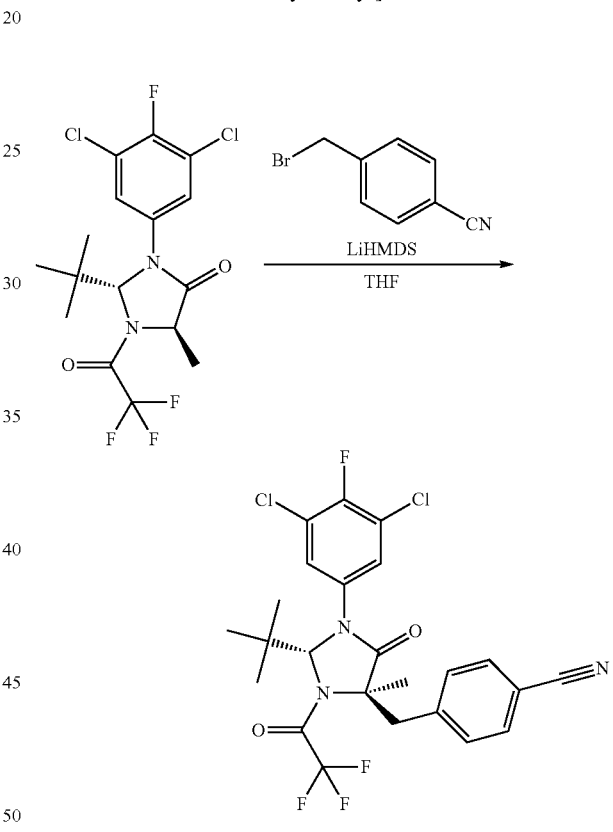

To a solution of (2S,5R)-2-tert-butyl-3-(3,5-dichloro-4-fluoro-phenyl)-5-methyl-1-(2,2,2-trifluoro-acetyl)-imidazolidin-4-one (158.4 g, 0.382 mol) in anhydrous THF (382 mL) under a nitrogen atmosphere at −20° C. was added a solution of LiHMDS (1.0 M in THF, 401 mL, 0.401 mol) over 50 min. The internal temperature increased to −5° C. over the course of this addition. Stirring was continued at this temperature for an additional hour. The reaction was cooled to −10° C. and a solution of 4-cyanobenzyl bromide (78.5 g, 401 mmol) in anhydrous THF (400 mL) was added over 50 min. The reaction temperature had increased to 0° C. over the course of the addition. Stirring was continued for 2 h while the reaction was allowed to warm to 10° C. To the reaction mixture was added saturated aqueous NH$_4$Cl (200 mL), water (800 mL), and EtOAc (1 L). The layers were separated and the aqueous layer was extracted with EtOAc (1 L). The combined organic layers were dried with MgSO$_4$ and concentrated in vacuo to give 214.2 g of the title compound as a tan/brown solid, m/z 571.3 [M+MeCN+H]$^+$.

(R)-2-(4-Cyano-phenyl)-1-(3,5-dichloro-4-fluoro-phenylcarbamoyl)-1-methyl-ethyl-ammonium toluene-4-sulfonate

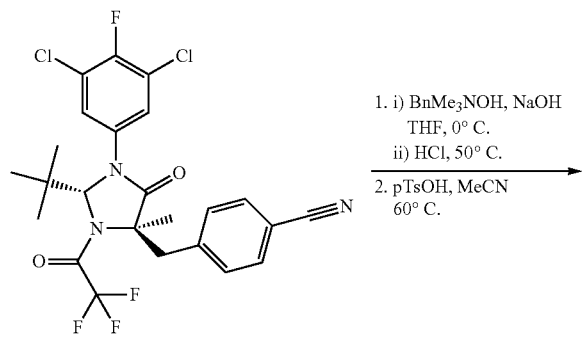

To a solution of 4-[(2R,4R)-2-tert-butyl-1-(3,5-dichloro-4-fluoro-phenyl)-4-methyl-5-oxo-3-(2,2,2-trifluoro-acetyl)-imidazolidin-4-ylmethyl]-benzonitrile (121.3 g, 228.7 mmol) in THF (457 mL) at 0° C. was added an aqueous solution of BnMe$_3$NOH (40 wt % in water, 135.3 mL, 343.1 mmol) over 30 min followed by aqueous NaOH (50 wt %, 21.5 mL, 407.4 mmol). Both reagents were added at a rate sufficient to keep the internal temperature at 0° C. The reaction mixture was stirred at this temperature for 6.5 h. HCl solution (6N, 234 mL, 1.40 mol) was then added to the reaction mixture at a rate sufficient to keep the internal temperature below 15° C. The reaction was heated to 50° C. and stirred at this temperature for 1.5 h. A portion of the solvent (~350 mL) was removed in vacuo and CH$_2$Cl$_2$ (300 mL) was added. The mixture was cooled in an ice bath and a NaOH solution (2N) was added at a rate to keep the internal temperature below 20° C. until the pH of aqueous layer reached 14. The mixture was transferred to a separatory funnel using CH$_2$Cl$_2$ and H$_2$O to ensure the transfer all of the solid material. The layers were separated and the aqueous layer was extracted with CH$_2$Cl$_2$ (2×500 mL). The combined organic layers were washed once with brine (300 mL), dried with Na$_2$SO$_4$, and concentrated in vacuo to give 83.8 g of a red/black viscous oil. This material was dissolved in MeCN (600 mL) and heated to 60° C. with stirring. p-Toluenesulfonic acid monohydrate (50.1 g, 263 mmol) was added to the solution causing a precipitate to form. Additional MeCN (200 mL) was added and mixture was filtered to collect the solids. The filter cake washed with 600 mL of MeCN and dried to give 106 g of the title compound as a white solid, m/z 366.6 [M]$^+$.

(R)-3-(4-Cyano-phenyl)-N-(3,5-dichloro-4-fluoro-phenyl)-2-[3-(2,2-dimethoxy-ethyl)-ureido]-2-methyl-propionamide

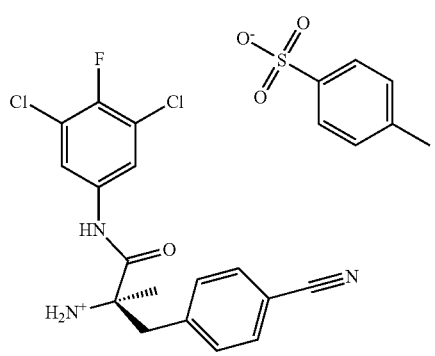

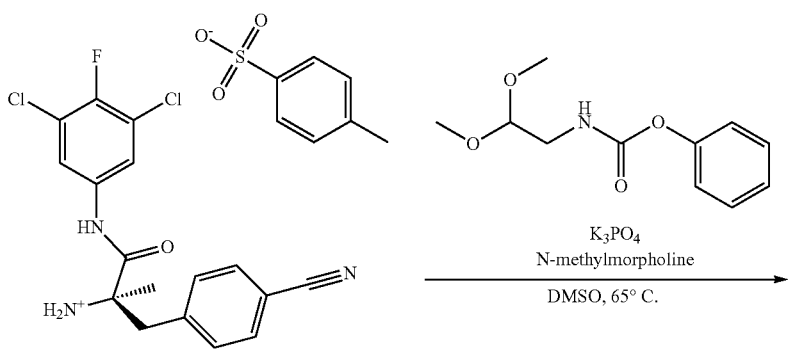

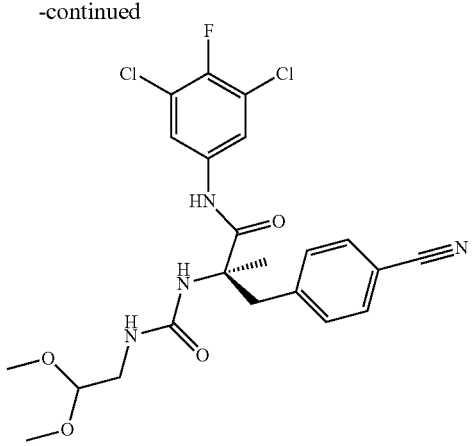

To a solution of (R)-2-(4-cyano-phenyl)-1-(3,5-dichloro-4-fluoro-phenylcarbamoyl)-1-methyl-ethyl-ammonium toluene-4-sulfonate (87.7 g, 162.9 mmol) and (2,2-dimethoxy-ethyl)-carbamic acid phenyl ester (40.4 g, 179 mmol) in DMSO (162 mL) was added $Na_3PO_4$ (29.4 g, 179 mmol) and N-methylmorpholine (3.04 mL, 27.7 mmol). The solution was heated to 65° C. and stirred for 6 h. The solution was cooled to 20° C. and transferred to a separatory funnel with aqueous $Na_2CO_3$ (3 wt %, 500 mL) and EtOAc (500 mL), forming a triphasic system after shaking. The bottom two layers were removed. The top organic layer was washed with 3% NaCl (500 mL), dried with $Na_2SO_4$ and concentrated in vacuo keeping internal temperature lower than 40° C. A mixture of heptane and EtOAc (10:1 heptane:EtOAc, 20 mL) was added and the resulting slurry was stirred at 22° C. for 16 h. The slurry was filtered and the solids were washed with a 10:1 mixture of heptane/EtOAc (2×100 mL) to give 61.6 g of the title compound as a white solid, m/z 497.7 $[M+H]^+$.

4-[(R)-1-(3,5-Dichloro-4-fluoro-phenyl)-3-methyl-2-oxo-2,3-dihydro-1H-imidazo[1,2-a]imidazol-3-ylmethyl]-benzonitrile

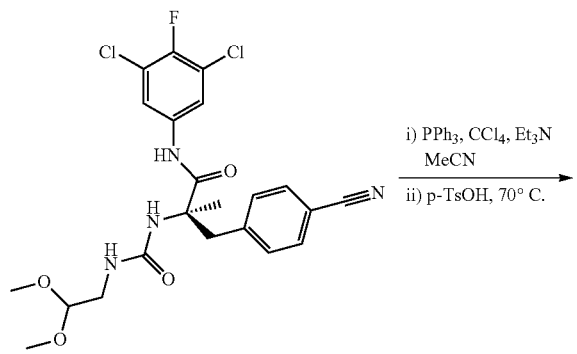

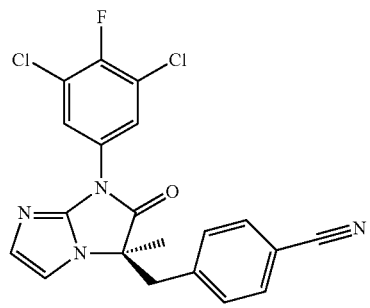

To a room temperature suspension of (R)-3-(4-cyano-phenyl)-N-(3,5-dichloro-4-fluoro-phenyl)-2-[3-(2,2-dimethoxy-ethyl)-ureido]-2-methyl-propionamide (62.6 g, 125.9 mmol), $PPh_3$ (51.98 g, 198.17 mmol), and $Et_3N$ (29.35 mL, 210.6 mmol) in MeCN (250 mL) was added $CCl_4$ (20.3 mL, 210.6 mmol) in one portion. The reaction was stirred for 2 h and then cooled to 0° C. To this solution was added p-toluenesulfonic acid monohydrate (37.7 g, 198.2 mmol) and the reaction was heated at 70° C. for 2 h. The volatiles were evaporated in vacuo, and the residue was diluted with isopropyl acetate (i-PrOAc) (500 mL) and water (500 mL). The water layer was removed and the organic layer was washed with aqueous $Na_2CO_3$ (5 wt %, 500 mL) and then aqueous NaCl (3 wt %, 500 mL). The organic layer was dried over $Na_2SO_4$ and concentrated in vacuo to give an oily solid. A mixture of Heptane/i-PrOAc (150 mL, 80:20 heptane:i-PrOAc) was added causing precipitation of a solid. The resulting slurry was stirred overnight and then filtered. The filtrate was evaporated in vacuo to give a brown oil. The oil was re-processed using the same conditions 3 more times. The remaining brown oil from the filtrate was then purified by flash chromatography on silica gel (20-50% EtOAc/hexanes) to give 48.0 g of the title compounds as a white solid, m/z 415.7 [M+H]+.

4-[(R)-1-(3,5-Dichloro-4-fluoro-phenyl)-5-iodo-3-methyl-2-oxo-2,3-dihydro-1H-imidazo[1,2-a]imidazol-3-ylmethyl]-benzonitrile

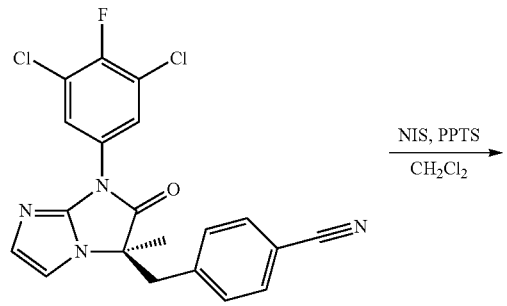

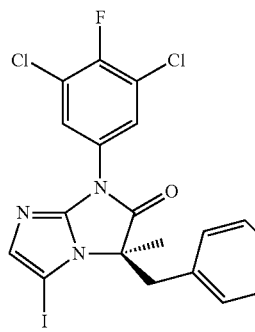

An aluminum foil covered flask containing a solution of 4-[(R)-1-(3,5-dichloro-4-fluoro-phenyl)-3-methyl-2-oxo-2,3-dihydro-1H-imidazo[1,2-a]imidazol-3-ylmethyl]-benzonitrile (48.8 g, 117.5 mmol) in CH₂Cl₂ (900 mL) was partially submerged in an ice water bath. To this solution was added a solid mixture of N-iodosuccinimide (29.1 g, 129 mmol) and pyridinium p-toluenesulfonate (2.95 g, 11.7 mmol) in four separate portions over a 30 min period. The reaction was allowed to stir in the thawing ice bath for 1 h and then the bath was removed. Stirring was continued overnight. Saturated aqueous Na₂S₂O₃ (300 mL) was added to the reaction and the mixture was transferred to a separatory funnel using CH₂Cl₂ (200 mL) and water (1 L). The layers were separated and the aqueous layer was further extracted with CH₂Cl₂ (2×500 mL) and EtOAc (500 mL). The combined organic layers were dried over MgSO₄ and concentrated in vacuo to give a yellow oil. This oil was purified by flash chromatography on silica gel (0-2.5% EtOAc/toluene) to give 52 g of the title compound as a white solid, m/z 541.3 [M+H]+.

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid

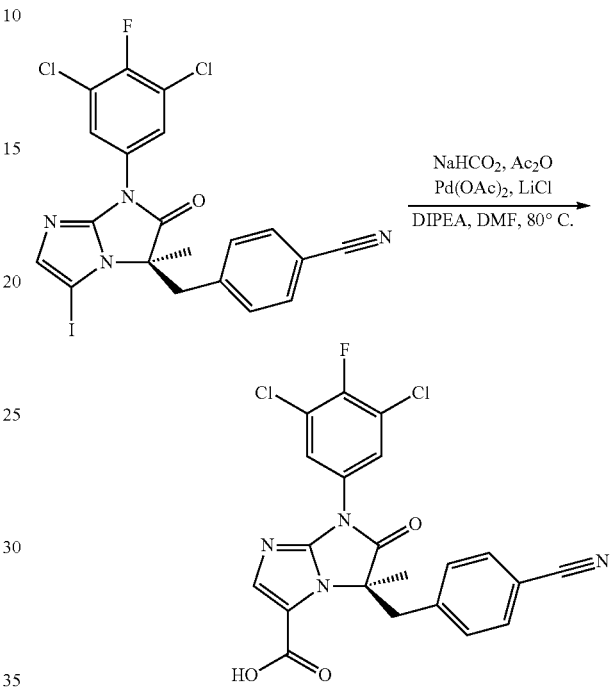

Acetic anhydride (14.0 mL, 148 mmol), sodium formate (15.1 g, 222 mmol) and Hunig's base (25.8 mL, 148 mmol) were suspended in anhydrous DMF (50 mL) in a 1000 mL screw-top glass pressure-vessel. This was sealed with the screw cap and allowed to stir for 45 min at room temperature. To this mixture was added a solution of 4-[(R)-1-(3,5-dichloro-4-fluoro-phenyl)-5-iodo-3-methyl-2-oxo-2,3-dihydro-1H-imidazo[1,2-a]imidazol-3-ylmethyl]-benzonitrile (40.0 g, 73.9 mmol) in anhydrous DMF (200 mL) followed by Pd(OAc)₂ (830 mg, 3.70 mmol) and anhydrous LiCl (9.40 g, 221 mmol). The vessel was capped tightly and allowed to stir at 80° C. for 20 h. In a well ventilated fume hood, the reaction was cooled to room temperature and the screw cap was slowly removed allowing for gas release. The reaction was transferred to a seperatory funnel containing a solution of aqueous HCl (2N, 1 L) using EtOAc (1 L). The layers were separated and the organic phase was washed with aqueous 2N HCl (1 L). The combined aqueous phase was extracted with EtOAc (2×1 L). The combined organic phase was dried with MgSO₄ and concentrated in vacuo. Toluene was added to the dark colored residue causing precipitation of a solid. The solid was filtered and washed with 1:1 toluene:hexanes followed by hexanes. The filtrate was concentrated and re-processed in a similar manner to give additional solids. A total of 29.4 g of the title compound was obtained as an off-white solid, m/z. 459.4 [M+H]+.

The following compounds were prepared using procedures similar to those described above:
(R)-5-(4-Cyano-benzyl)-7-(3,5-dichloro-phenyl)-5-methyl-6-oxo-6,7-dihydro-5H-imidazo[1,2-a]imidazole-3-carboxylic acid (R)-7-(3,5-Dichloro-phenyl)-5-methyl-6-oxo-5-(4-trifluoromethoxy-benzyl)-6,7-dihydro-5H-imidazo[1,2-a]imidazole-3-carboxylic acid (R)-7-(3,5-Dichloro-phenyl)-5-methyl-6-oxo-5-(4-trifluoromethyl-benzyl)-6,7-dihydro-5H-imidazo[1,2-α]imidazole-3-carboxylic acid, m/z 484.5 [M+1]+

1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid

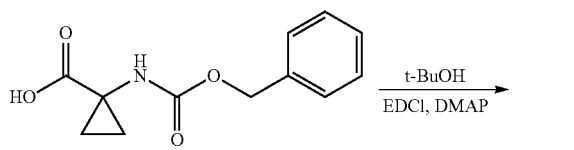

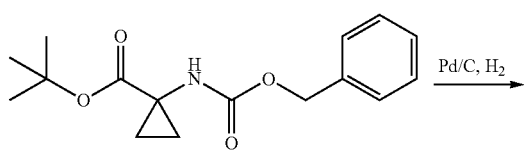

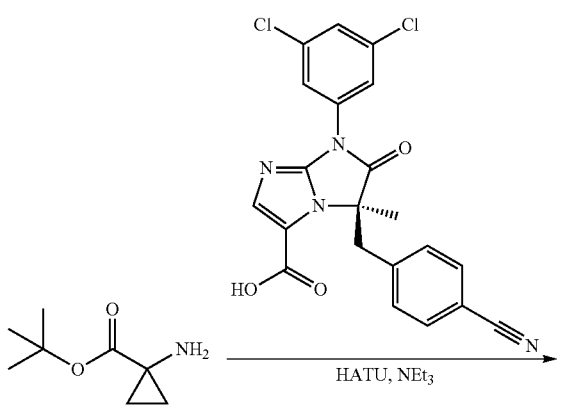

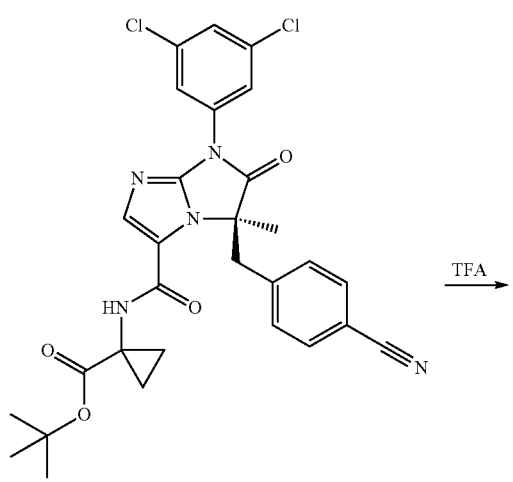

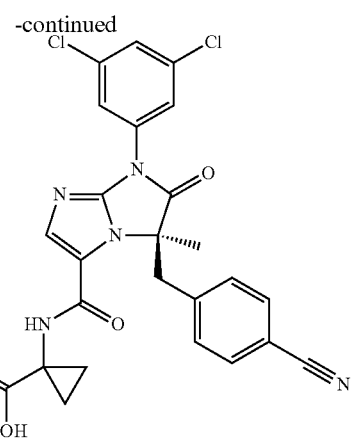

1-Benzyloxycarbonylamino-cyclopropanecarboxylic acid (10 g, 42.5 mmol), t-butanol (4.78 mL, 50.0 mmol) and DMAP (2.60 g, 21.2 mmol) in CH$_2$Cl$_2$ (160 mL) were cooled to 0° C. EDCI (9.20 g, 48.0 mmol) was then added to the mixture. The reaction was stirred at 0° C. for 2 h and then at room temperature overnight. The solution was dried in vacuo and the residue was dissolved in EtOAc (200 mL) and water (50 mL) The organic layer was separated and washed by saturated aqueous NaHCO$_3$ (1×100 mL) and brine (1×100 mL). The organic fraction was concentrated in vacuo and the residue was purified by flash chromatography on silica gel (20% EtOAc/Hexanes). 1-Benzyloxycarbonyl-amino-cyclopropanecarboxylic acid tert-butyl ester (5.3 g, 17.5 mmol, 41%) was isolated.

1-Benzyloxycarbonylamino-cyclopropanecarboxylic acid tert-butyl ester (5.1 g, 17.5 mmol) was dissolved in MeOH (50 mL). The solution was degassed with Ar for 15 min. Pd/C (370 mg) was then added to the solution. The mixture was degassed with Ar again. The flask was flushed with H$_2$. After 3 h, the reaction was then filtered through diatomaceous earth and 1-amino-cyclopropanecarboxylic acid tert-butyl ester (2.3 g, 14.6 mmol, 84%) was collected as pale yellow oil.

(R)-5-(4-Cyano-benzyl)-7-(3,5-dichloro-phenyl)-5-methyl-6-oxo-6,7-dihydro-5H-imidazo[1,2-a]imidazole-3-carboxylic acid (3.3 g, 7.48 mmol), 1-amino-cyclopropane-carboxylic acid tert-butyl ester (1.8 g, 11.4 mmol) and HATU (4.27 g, 11.2 mmol) were dissolved in anhydrous DMF (20 mL). The mixture was stirred for 15 min. Et$_3$N (2.95 mL, 20.4 mmol) was then added to the reaction. After 30 min, the crude reaction was concentrated in vacuo. The residue was purified by flash chromatography on silica gel (10% to 30% EtOAc/Hexanes) to give 1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid tert-butyl ester (3.8 g, 6.55 mmol, 87.5%) as a white solid, m/z 580.5 [M+1]+.

1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid tert-butyl ester (3.8 g, 6.55 mmol) was dissolved in CH$_2$Cl$_2$ (100 mL), and. TFA (20 mL) was then added dropwise to the solution. The mixture was stirred overnight. After evaporation of the solvent in vacuo, the residue was purified by flash chromatography on silica gel (5% MeOH/CH$_2$Cl$_2$) to give 1-{[(R)-

5-(4-cyano-benzyl)-7-(3,5-dichloro-phenyl)-5-methyl-6-oxo-6,7-dihydro-5H-imidazo[1,2-α]imidazole-3-carbonyl]-amino}-cyclopropane-carboxylic acid (3.4 g, 6.48 mmol, 99.0%) as a white solid, m/z 524.3 [M+1]$^+$.

The following compounds were prepared using procedures similar to those described above using either (R)-5-(4-cyano-benzyl)-7-(3,5-dichloro-phenyl)-5-methyl-6-oxo-6,7-dihydro-5H-imidazo[1,2-a]imidazole-3-carboxylic acid, (R)-7-(3,5-dichloro-phenyl)-5-methyl-6-oxo-5-(4-trifluoromethoxy-benzyl)-6,7-dihydro-5H-imidazo[1,2-a]imidazole-3-carboxylic acid, or (R)-5-(4-cyano-benzyl)-7-(3,5-dichloro-4-fluoro-phenyl)-5-methyl-6-oxo-6,7-dihydro-5H-imidazo[1,2-a]imidazole-3-carboxylic acid as starting materials:

(S)-2-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-propionic acid (S)-2-{[(R)-5-(4-Cyano-benzyl)-7-(3,5-dichloro-4-fluoro-phenyl)-5-methyl-6-oxo-6,7-dihydro-5H-imidazo[1,2-a]imidazole-3-carbonyl]-amino}-propionic acid 1-{[(R)-5-(4-Cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropanecarboxylic acid 1-{[(R)-7-(3,5-Dichloro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarboxylic acid (S)-2-{[(R)-7-(3,5-Dichloro-phenyl)-5-methyl-6-oxo-5-(4-trifluoromethoxy-benzyl)-6,7-dihydro-5H-imidazo[1,2-a]imidazole-3-carbonyl]-amino}-propionic acid The following two intermediates were made using a similar procedure to Example 12 using either 1-{[(R)-7-(3,5-dichloro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarboxylic acid or 1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid as the starting material:

(R)-7-(3,5-Dichloro-phenyl)-5-methyl-6-oxo-5-(4-trifluoromethoxy-benzyl)-6,7-dihydro-5H-imidazo[1,2-a]imidazole-3-carboxylic acid [1-(1-{6-[bis-(4-methoxy-benzyl)-amino]-pyridin-2-yl}-cyclopropylcarbamoyl)-cyclopropyl]-amide, m/z 956.21 [M+2]$^+$ (R)-5-(4-cyano-benzyl)-7-(3,5-dichloro-phenyl)-5-methyl-6-oxo-6,7-dihydro-5H-imidazo[1,2-a]imidazole-3-carboxylic acid [1-(1-{6-[bis-(4-methoxy-benzyl)-amino]-pyridin-2-yl}-cyclopropylcarbamoyl)-cyclopropyl]-amide, m/z 897.2 [M+3]$^+$ Synthesis of Final Compounds Example 1

(3R)-3-(4-Cyanobenzyl)-1-(3,5-dichlorophenyl)-3-methyl-N-{(1S)-1-methyl-2-oxo-2-[(3R)-3-(2H-tetrazol-5-yl)piperidin-1-yl]ethyl}-2-oxo-2,3-dihydro-1H-imidazo[1,2-a]imidazole-5-carboxamide

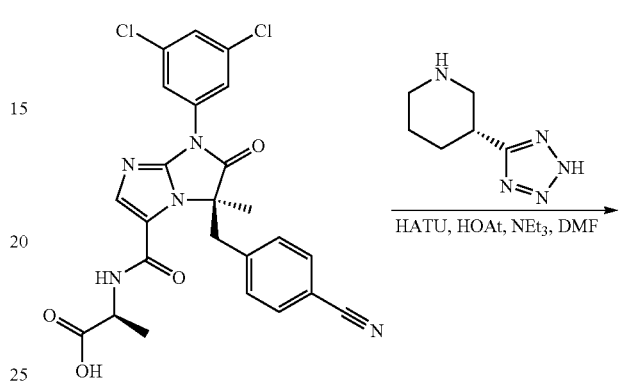

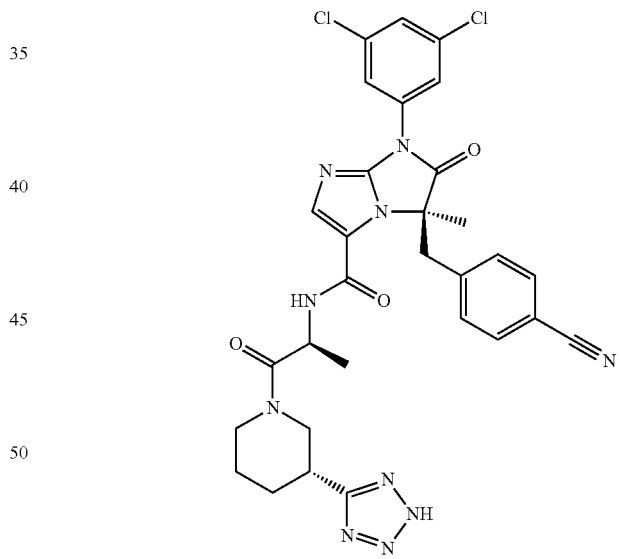

To a solution of (S)-2-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-propionic acid (60 mg, 0.117 mmol) and (R)-3-(2H-tetrazol-5-yl)-piperidine (35.8 mg, 0.234 mmol) in anhydrous DMF (1 mL) was added Et$_3$N (33.8 μl, 0.234 mmol) at 0° C. HOAt (47.8 mg, 0.351 mmol) was then added to the reaction. After 10 min of stirring at 0° C., HATU (53.4 mg, 0.140 mmol) was added. The reaction was slowly warmed to 25° C. and stirred overnight. The crude reaction was purified by reverse phase HPLC to afford 55 mg of (3R)-3-(4-cyanobenzyl)-1-(3,5-dichlorophenyl)-3-methyl-N-{(1S)-1-methyl-2-oxo-2-[(3R)-3-(2H-tetrazol-5-yl)piperidin-1-yl]ethyl}-2-oxo-2,3-dihydro-1H-imidazo[1,2-a]imidazole-5-carboxamide as a white solid, m/z 647.5 [M+1]+.

Example 2

(R)-5-(4-Cyano-benzyl)-7-(3,5-dichloro-phenyl)-5-methyl-6-oxo-6,7-dihydro-5H-imidazo[1,2-a]imidazole-3-carboxylic acid [(S)-1-((R)-1-thiocarbamoyl-ethylcarbamoyl)-ethyl]-amide

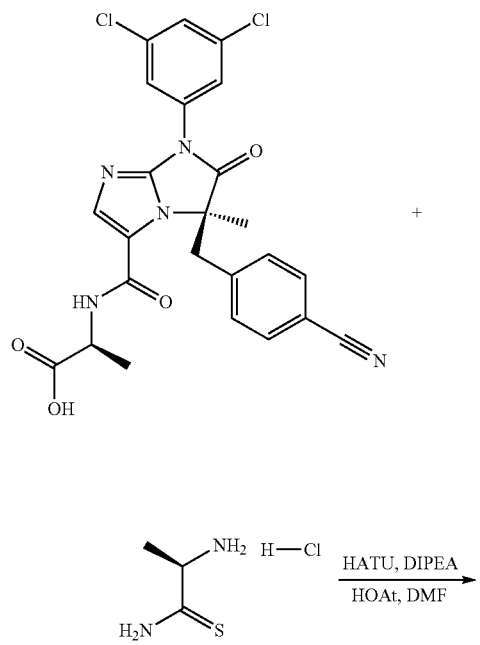

A solution of (S)-2-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-propionic acid, (129 mg, 0.25 mmol), (R)-2-amino-thiopropionamide hydrochloride (53 mg, 0.38 mmol) and diisopropylethylamine (0.175 mL, 1.01 mmol) in DMF (1 mL) was stirred at room temperature for 10 min. After cooling to 0° C., HOAt (69 mg, 0.50 mmol) and HATU (105 mg, 0.25 mmol) were added. The clear yellow reaction mixture was allowed to warm to room temperature slowly overnight. The reaction mixture was partitioned between ethyl acetate (35 mL) and 1 M HCl (10 mL). The organic phase was washed with saturated NaHCO3 solution and brine, dried over Na2SO4, filtered, and concentrated in vacuo. The residue was purified by flash chromatography on silica gel (0-10% MeOH in dichloromethane) to afford 154 mg of the title compound as a white foam, m/z 598.4 [M+1]+.

Example 3

(R)-5-(4-Cyano-benzyl)-7-(3,5-dichloro-phenyl)-5-methyl-6-oxo-6,7-dihydro-5H-imidazo[1,2-a]imidazole-3-carboxylic acid [(S)-1-(5-methyl-1,3,4-oxadiazol-2-ylcarbamoyl)-ethyl]-amide

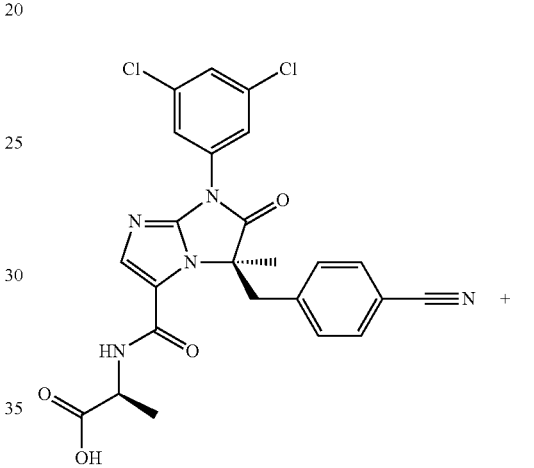

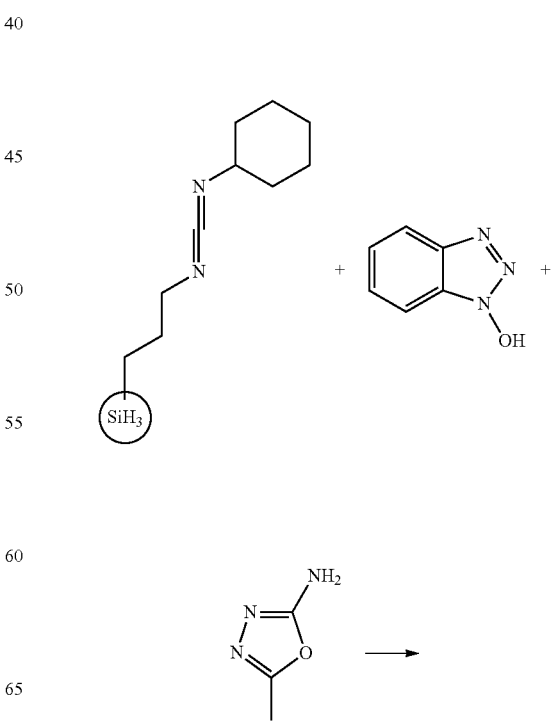

-continued

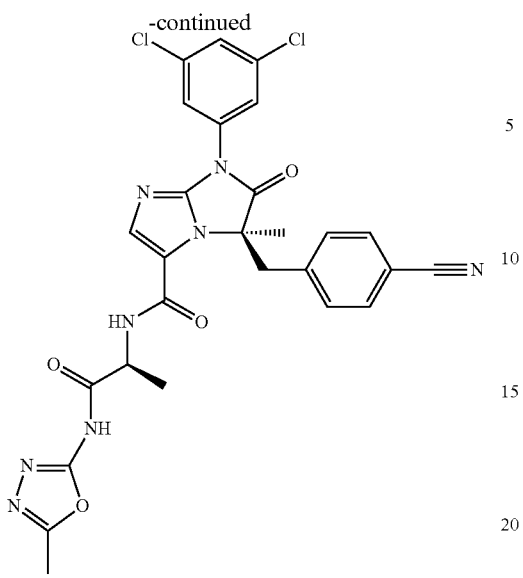

To a solution of (S)-2-{[(R)-5-(4-cyano-benzyl)-7-(3,5-dichloro-phenyl)-5-methyl-6-oxo-6,7-dihydro-5H-imidazo[1,2-c]imidazole-3-carbonyl]-amino}-propionic acid (40 mg, 0.078 mmol) in dichloromethane (1 mL) were added SiliaBond Carbodiimide (205 mg, 0.234 mmol, Silicycle-R70530B, loading 1.14 mmol/g) and HOBt (16 mg, 0.117 mmol). The reaction mixture was stirred at room temperature for 1 h and the 5-methyl-1,3,4-oxadiazol-2-ylamine (31 mg, 0.312 mmol) was added. The reaction mixture was stirred at room temperature for 16 h. The reaction mixture was then filtered through a glass frit and the solution was concentrated in vacuo. The resulting residue was purified by reverse phase HPLC to afford 10 mg of the title compound as a white solid, m/z 593.4 [M+1]$^+$.

Example 4

(3R)-3-(4-Cyanobenzyl)-1-(3,5-dichlorophenyl)-3-methyl-N-{(1S)-1-methyl-2-[(1-methyl-1H-pyrazol-5-yl)amino]-2-oxoethyl}-2-oxo-2,3-dihydro-1H-imidazo[1,2-a]imidazole-5-carboxamide and (3R)-3-(4-cyanobenzyl)-1-(3,5-dichlorophenyl)-3-methyl-N-{(1R)-1-methyl-2-[(1-methyl-1H-pyrazol-5-yl)amino]-2-oxoethyl}-2-oxo-2,3-dihydro-1H-imidazo[1,2-a]imidazole-5-carboxamide

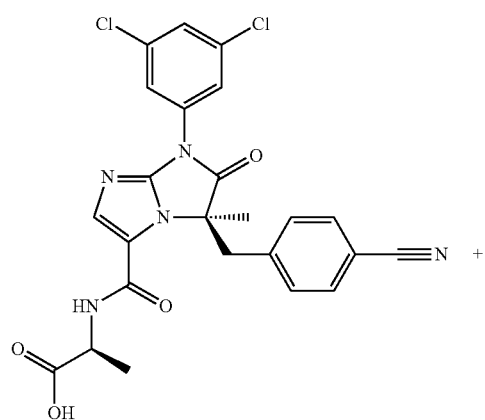

-continued

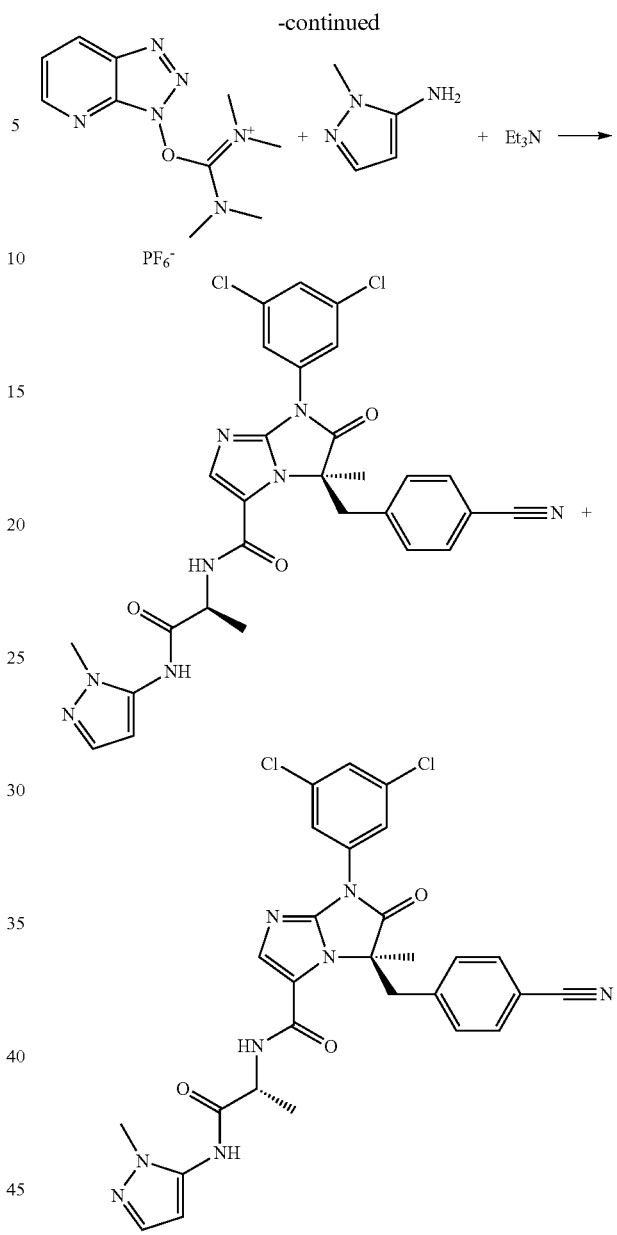

To a solution of (S)-2-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-propionic acid (100 mg, 0.195 mmol), [dimethylamino-(1,2,3-triazolo[4,5-b]pyridin-3-yloxy)-methylene]-dimethyl-ammonium hexafluoro phosphate (111 mg, 0.293 mmol) and 2-methyl-2H-pyrazol-3-ylamine (75 mg, 0.781 mmol) in DMF (1 mL) was added triethylamine (136 µL, 0.976 mmol). The reaction mixture was stirred at room temperature for 4 h. The reaction mixture was then diluted with water and extracted with dichloromethane (×3). The combined organic layers were then washed with water (×3). The organic phase was dried over anhydrous Na$_2$SO$_4$ and concentrated in vacuo. The resulting diastereomers were purified and separated by reverse phase HPLC to afford 22 mg and 21 mg, respectively, of the title compounds as white solids, m/z 591.5 [M+1]$^+$.

The following compounds were prepared using procedures similar to those described above using either 1-{[(R)-5-(4-cyano-benzyl)-7-(3,5-dichloro-phenyl)-5-methyl-6-oxo-6, 7-dihydro-5H-imidazo[1,2-a]imidazole-3-carbonyl]-amino}-cyclopropanecarboxylic acid, 1-{[(R)-7-(3,5-dichloro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarboxylic acid, (S)-2-{[(R)-7-(3,5-Dichloro-phenyl)-5-methyl-6-oxo-5-(4-trifluoromethoxy-benzyl)-6,7-dihydro-5H-imidazo[1,2-a]imidazole-3-carbonyl]-amino}-propionic acid, (S)-2-{[(R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carbonyl]-amino}-propionic acid, 1-{[(R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarboxylic acid, 1-{[(R)-5-(4-Cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropanecarboxylic acid or (S)-2-{[(R)-5-(4-Cyano-benzyl)-7-(3,5-dichloro-4-fluoro-phenyl)-5-methyl-6-oxo-6,7-dihydro-5H-imidazo[1,2-a]imidazole-3-carbonyl]-amino}-propionic acid as a starting material:

Compound 243, m/z 647.5 [M+1]+
Compound 168, m/z 647.5 [M+1]+
Compound 226, m/z 647.5 [M+1]+
Compound 7, m/z 706.5 [M+1]+
Compound 227, m/z 706.5 [M+1]+
Compound 167, m/z 706.5 [M+1]+
Compound 206, m/z 706.5 [M+1]+
Compound 276, m/z 647.6 [M+1]+
Compound 219, m/z 647.6 [M+1]+
Compound 230, m/z 706.6 [M+1]+
Compound 197, m/z 633.5 [M+1]+
Compound 169, m/z 692.6 [M+1]+
Compound 191, m/z 608.4 [M+1]+
Compound 217, m/z 608.4 [M+1]+
Compound 285, m/z 634.4 [M+1]+
Compound 251, m/z 607.4 [M+1]+
Compound 261, m/z 752.1 [M+1]+
Compound 131, m/z 608 [M+1]+
Compound 139, m/z 593 [M+1]+
Compound 170, m/z 595.6 [M+1]+
Compound 179, m/z 595.6 [M+1]+
Compound 180, m/z 636.6 [M+1]+
Compound 188, m/z 587.4 [M+1]+
Compound 193, m/z 636.5 [M+1]+
Compound 203, m/z 622.5 [M+1]+
Compound 212, m/z 681.5 [M+1]+
Compound 218, m/z 695.6 [M+1]+
Compound 233, m/z 695.6 [M+1]+
Compound 235, m/z 646.5 [M+1]+
Compound 240, m/z 681.5 [M+1]+
Compound 239, m/z 622.5 [M+1]+
Compound 103, m/z 582.4 [M+1]+
Compound 120, m/z 596.4 [M+1]+
Compound 127, m/z 637.0 [M+1]+
Compound 95, m/z 636.9 [M+1]+
Compound 115, m/z 637.2 [M+1]+
Compound 87, m/z 637.2 [M+1]30
Compound 146, m/z 595.5 [M+1]+
Compound 113, m/z 582.4 [M+1]+
Compound 90, m/z 582.4 [M+1]+
Compound 111, m/z 594.5 [M+1]+
Compound 286, m/z 594.5 [M+1]+
Compound 107, m/z 595.4 [M+1]+
Compound 122, m/z 595.4 [M+1]+
Compound 132, m/z 597.6 [M+1]+
Compound 135, m/z 597.6 [M+1]+
Compound 2, m/z 616.5 [M+1]+
Compound 114, m/z 622.5 [M+1]+
Compound 21, m/z 622.6 [M+1]+
Compound 82, m/z 609.4 [M+1]+
Compound 88, m/z 602.4 [M+1]+
Compound 166, m/z 609.4 [M+1]+
Compound 97, m/z 602.4 [M+1]+
Compound 100, m/z 603.4 [M+2]+
Compound 102, m/z 591.5 [M+1]+
Compound 182, m/z 608.2 [M+1]+
Compound 190, m/z 622.6 [M+1]+
Compound 195, m/z 567.5 [M+1]+
Compound 106, m/z 609.2 [M+3]+
Compound 205, m/z 595.3 [M+1]+
Compound 117, m/z 596.4 [M+1]+
Compound 215, m/z 596.9 [M+2]+
Compound 138, m/z 611.4 [M+1]+
Compound 229, m/z 636.6 [M+1]+
Compound 149, m/z 568.4 [M+1]+
Compound 150, m/z 598.9 [M+1]+
Compound 157, m/z 636.2 [M+1]+
Compound 158, m/z 596.2 [M+1]+
Compound 259, m/z 624.4 [M+1]+
Compound 277, m/z 647.5 [M+1]+
Compound 266, m/z 620.2 [M+2]+
Compound 75, m/z 651.3 [M+1]+
Compound 181, m/z 651.3 [M+1]+
Compound 141, m/z 660.5 [M+1]+
Compound 148, m/z 674.5 [M+1]+
Compound 130, m/z 674.5 [M+1]+
Compound 118, m/z 688.5 [M+1]+
Compound 66, m/z 675.5 [M+1]+
Compound 282, m/z 675.5 [M+1]+
Compound 67, m/z 687.5 [M+1]+
Compound 283, m/z 675.5 [M+1]+
Compound 252, m/z 661.5 [M+1]+
Compound 204, m/z 689.2 [M+1]+
Compound 245, m/z 748.0 [M+1]+
Compound 145, m/z 607.5 [M+1]+
Compound 140, m/z 621.5 [M+1]+
Compound 65, m/z 658.1 [M+1]+
Compound 198, m/z 665.6 [M+1]+
Compound 336, m/z 669.9 [M+1]+
Compound 337, m/z 697.9 [M+1]+
Compound 338, m/z 670.5 [M+1]+
Compound 339, m/z 654.5 [M+1]+
Compound 340, m/z 670.5 [M+1]+
Compound 341, m/z 672.5 [M+1]+
Compound 342, m/z 690.5 [M+1]+
Compound 343, m/z 688.4 [M+1]+
Compound 344, m/z 644.4 [M+1]+ Compound 61, m/z 665.7 [M+1]+ Compound 400, m/z 673.6 [M+1]+
Compound 401, m/z 717.6 [M+1]+ Compound 405, m/z 677.5 [M+1]+
Compound 299, m/z 766.4 [M+1]+
Compound 413, m/z 670.4 [M+1]+
Compound 414, m/z 736.2 [M+1]+
Compound 320, m/z 741.5 [M+1]+

Compound 408, m/z 720 [M+1]+ Compound 407, m/z 691.7 [M+1]+

Example 5

(R)-5-(4-Cyano-benzyl)-7-(3,5-dichloro-phenyl)-5-methyl-6-oxo-6,7-dihydro-5H-imidazo[1,2-a]imidazole-3-carboxylic acid [(S)-1-(1-thiazol-2-yl-ethyl-carbamoyl)-ethyl]-amide

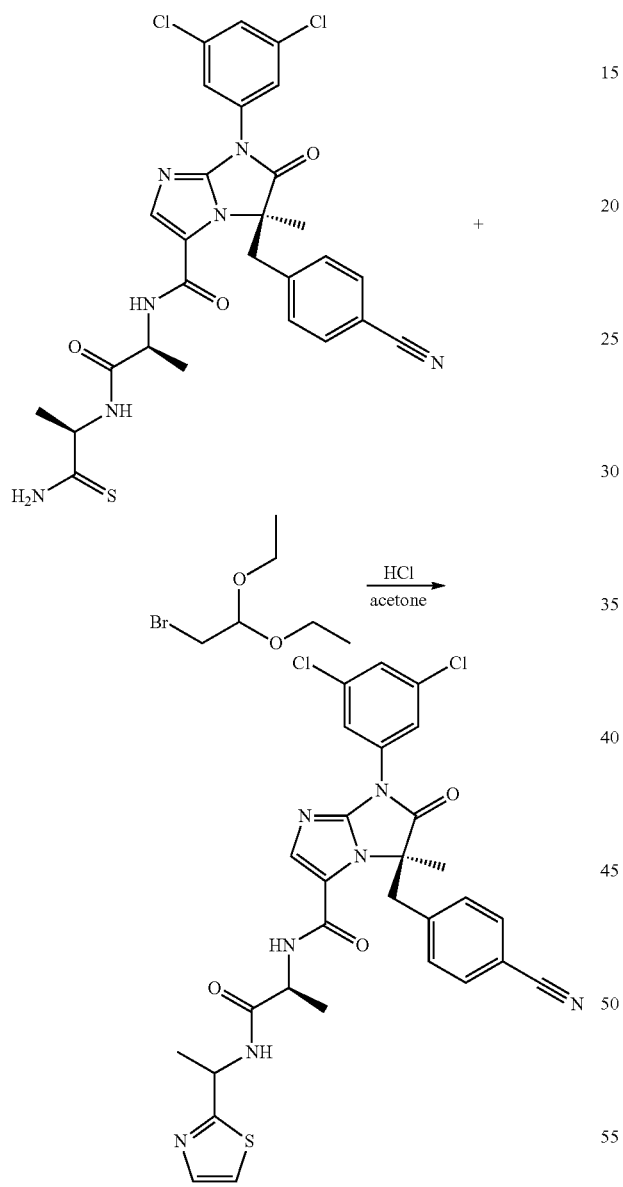

To a solution of (R)-5-(4-cyano-benzyl)-7-(3,5-dichloro-phenyl)-5-methyl-6-oxo-6,7-dihydro-5H-imidazo[1,2-a] imidazole-3-carboxylic acid [(S)-1-((R)-1-thiocarbamoyl-ethylcarbamoyl)-ethyl]-amide (132 mg, 0.22 mmol) in 1 mL of acetone was added bromoacetaldehyde diethyl acetal (0.166 mL, 1.10 mmol) and HCl in dioxane (4 M, 0.003 mL, 0.01 mmol). The reaction mixture was heated at reflux for 5 h, and then cooled to room temperature and concentrated in vacuo. The residue was dissolved in 25 mL of ethyl acetate and washed with 10 mL of saturated NaHCO$_3$ solution. The organic phase was washed with water and brine (10 mL each), dried over Na$_2$SO$_4$, filtered, and concentrated in vacuo to a pale brown oil. The crude product was purified by flash chromatography on silica gel, eluting with 0-5% MeOH in CH$_2$Cl$_2$, to furnish 122 mg (89%) of the title compound as a pale brown foam, obtained as a 1:1 mixture of thiazole α-methyl diastereomers, m/z 622.3 [M+1]+.

Example 6

(3R)-1-(3,5-dichlorophenyl)-N-{2-[(3R)-3-(3-hydroxy-1H-pyrazol-5-yl)piperidin-1-yl]-1-methyl-2-oxoethyl}-3-methyl-2-oxo-3-[4-(trifluoromethoxy)-benzyl]-2,3-dihydro-1H-imidazo[1,2-a]imidazole-5-carboxamide

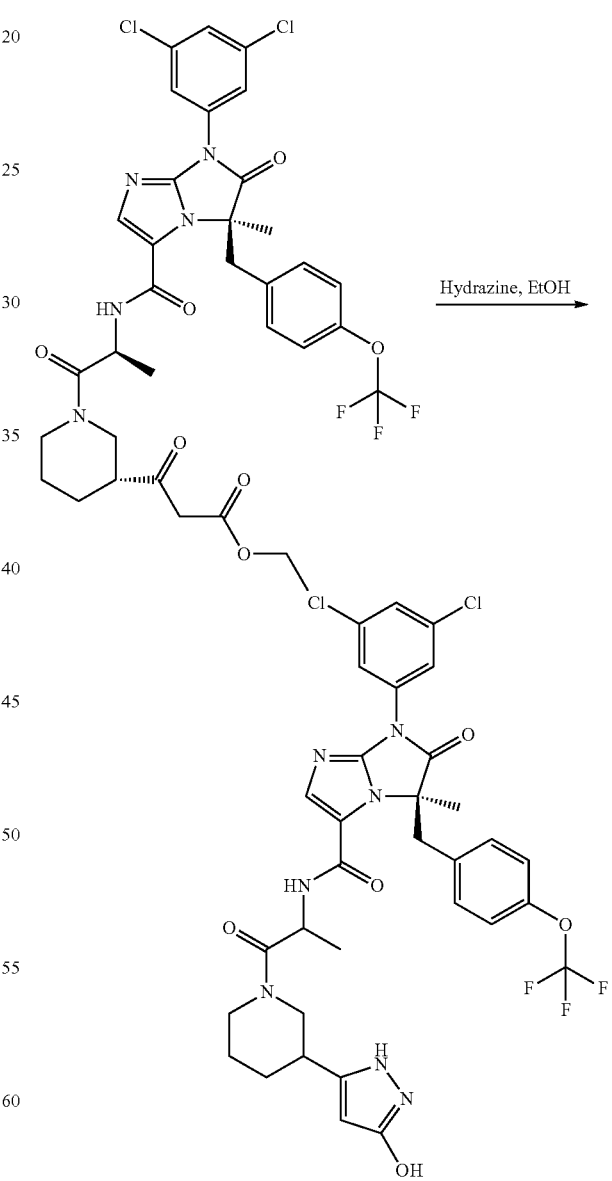

To a solution of 3-[(R)-1-((S)-2-{[(R)-7-(3,5-dichloro-phenyl)-5-methyl-6-oxo-5-(4-trifluoromethoxy-benzyl)-6,7-dihydro-5H-imidazo[1,2-a]imidazole-3-carbonyl]- amino}-propionyl)-piperidin-3-yl]-3-oxo-propionic acid ethyl ester (40 mg, 0.05 mmol) in ethanol (2 mL) was added hydrazine (8.5 µL, 0.26 mmol). The reaction mixture was stirred at room temperature for 1.5 h. The solvent was evaporated in vacuo, and the residue was purified using reverse phase HPLC to afford the title compound (27 mg, 71%) as a white solid, m/z 720.6 [M+1]⁺.

Example 7

(3R)-1-(3,5-Dichlorophenyl)-N-{2-[(3R)-3-(3-hydroxyisoxazol-5-yl)piperidin-1-yl]-1-methyl-2-oxoethyl}-3-methyl-2-oxo-3-[4-(trifluoromethoxy)-benzyl]-2,3-dihydro-1H-imidazo[1,2-a]imidazole-5-carboxamide and (3R)-1-(3,5-dichlorophenyl)-3-methyl-N-{1-methyl-2-oxo-2-[(3R)-3-(5-oxo-4,5-dihydroisoxazol-3-yl)piperidin-1-yl]ethyl}-2-oxo-3-[4-(trifluoromethoxy)benzyl]-2,3-dihydro-1H-imidazo[1,2-a]imidazole-5-carboxamide(.

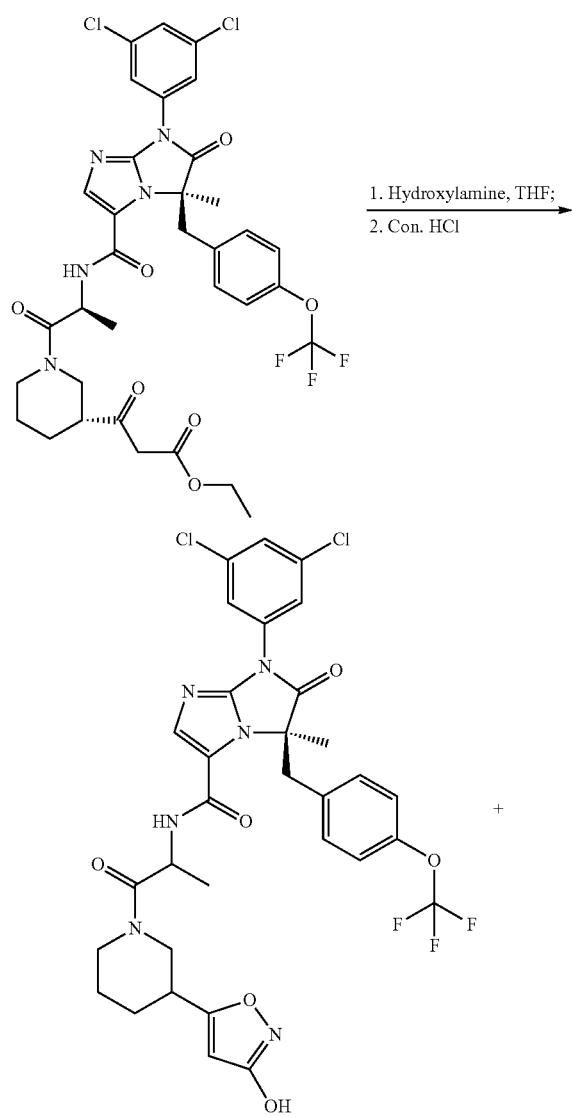

1. Hydroxylamine, THF;
2. Con. HCl

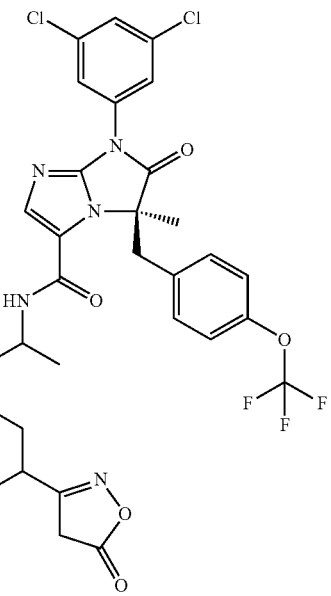

To a solution of 3-[(R)-1-((S)-2-{[(R)-7-(3,5-dichlorophenyl)-5-methyl-6-oxo-5-(4-trifluoromethoxy-benzyl)-6,7-dihydro-5H-imidazo[1,2-a]imidazole-3-carbonyl]-amino}-propionyl)-piperidin-3-yl]-3-oxo-propionic acid ethyl ester (70 mg, 0.09 mmol) in 1 mL THF was added NaOH (60 mg in 0.5 mL H₂O) at 0° C. and stirred for 10 min. The above solution was added dropwise to a pre-cooled solution of hydroxylamine-HCl (20 mg, 0.28 mmol) in THF (1 mL) at 0° C. The pH value of the reaction mixture was adjusted from 7~8 to 10~11. After 30 min, the reaction mixture was poured into concentrated HCl (0.5 mL) at 0° C. and stirred overnight. The crude mixture was purified using reverse phase HPLC to afford the title compounds: (3R)-1-(3,5-dichlorophenyl)-N-{2-[(3R)-3-(3-hydroxyisoxazol-5-yl)piperidin-1-yl]-1-methyl-2-oxoethyl}-3-methyl-2-oxo-3-[4-(trifluoromethoxy)benzyl]-2,3-dihydro-1H-imidazo[1,2-a]imidazole-5-carboxamide m/z 721.0 [M+1]⁺, and (3R)-1-(3,5-dichlorophenyl)-3-methyl-N-{1-methyl-2-oxo-2-[(3R)-3-(5-oxo-4,5-dihydroisoxazol-3-yl)piperidin-1-yl]ethyl}-2-oxo-3-[4-(trifluoromethoxy)benzyl]-2,3-dihydro-1H-imidazo[1,2-a]imidazole-5-carboxamide, m/z 721.0 [M+1]⁺.

Example 8

(3R)—N-{(1S)-2-[(3R)-3-Carbamoylpiperidin-1-yl]-1-methyl-2-oxoethyl}-3-(4-cyanobenzyl)-1-(3,5-dichlorophenyl)-3-methyl-2-oxo-2,3-dihydro-4H-imidazo[1,2-a]imidazole-5-carboxamide

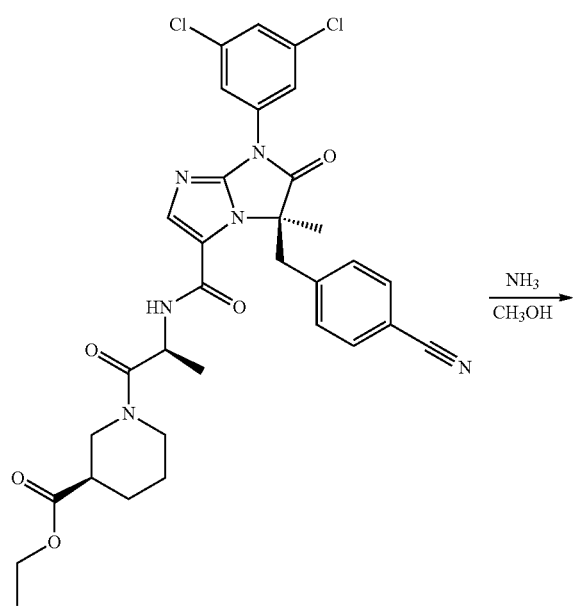

NH₃ / CH₃OH →

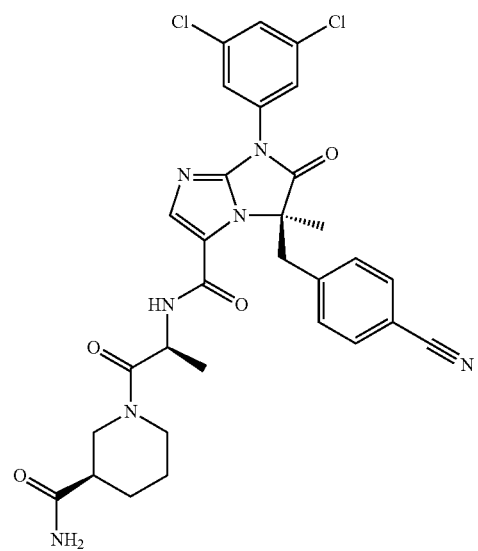

(R)-1-((S)-2-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-propionyl)-piperidine-3-carboxylic acid ethyl ester was dissolved in 7N NH₃ in MeOH (5 mL) and heated to 70° C. for 48 h. The volatiles were removed in vacuo and the crude residue was purified by reverse phase HPLC to afford 0.049 g of the title compound as a white foam, m/z 622.3 [M+1]⁺.

The following compounds were prepared by procedures analogous to those described above:

Compound 83, m/z 622.4 [M+1]⁺
Compound 159, m/z 622.0 [M+1]⁺
Compound 92, m/z 622.2 [M+1]⁺
Compound 104, m/z 622.1 [M+1]⁺
Compound 121, m/z 622.2 [M+1]⁺

Example 9

(1R,3R)-3-((S)-2-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-propionylamino)-cyclopentanecarboxylic acid

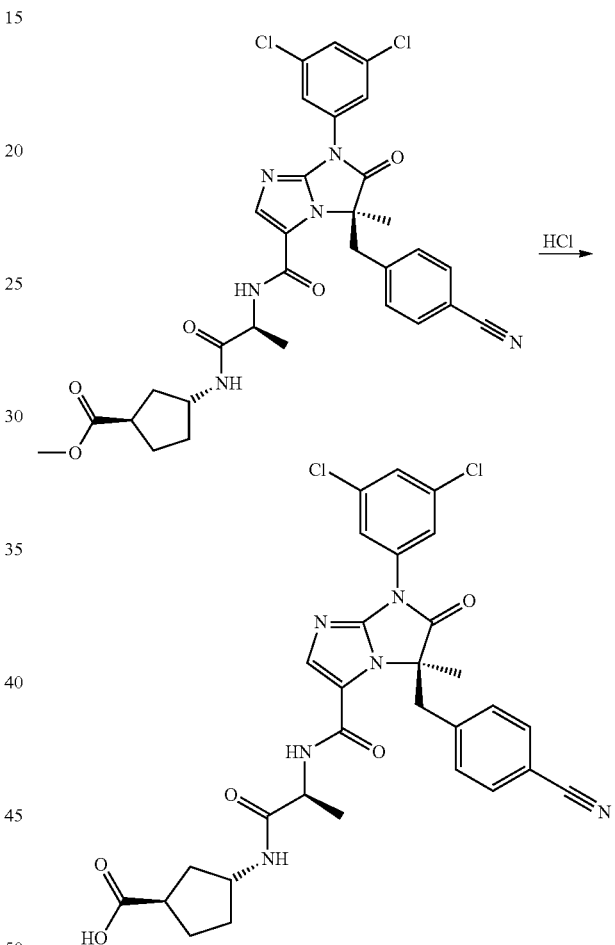

To (1R,3R)-3-((S)-2-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-propionylamino)-cyclopentanecarboxylic acid methyl ester (35.1 mg, 0.055 mmol) were added 1N HCl in 1,4-dioxane (1 mL, 1 mmol) and 1N HCl (0.5 mL, 0.5 mmol). The reaction tube was sealed and the reaction solution was stirred at 100° C. for 1 h. The reaction solution was then cooled to room temperature, filtered, and was purified by reverse phase HPLC to afford 21 mg of the title compound as a white solid, m/z 623.1 [M+1]⁺.

The following compounds were prepared using a procedure analogous to that described above:
Compound 265, m/z 623.1 [M+1]⁺
Compound 270, m/z 623.5 [M+1]⁺
Compound 177, m/z 623.1 [M+1]⁺
Compound 278, m/z 623.0 [M+1]⁺

Example 10

(R)-5-(4-Cyano-benzyl)-7-(3,5-dichloro-phenyl)-5-methyl-6-oxo-6,7-dihydro-5H-imidazo[1,2-a]imidazole-3-carboxylic acid ((S)-1-benzylcarbamoyl-ethyl)-amide

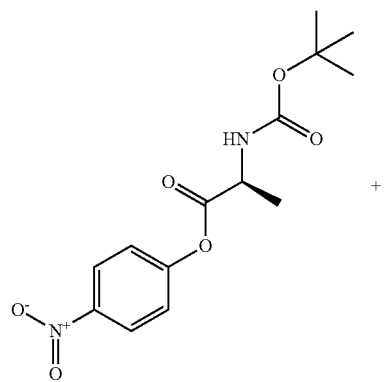

+

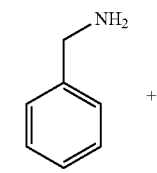

+

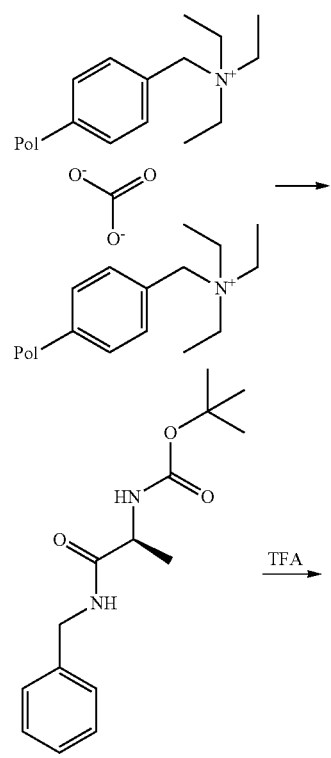

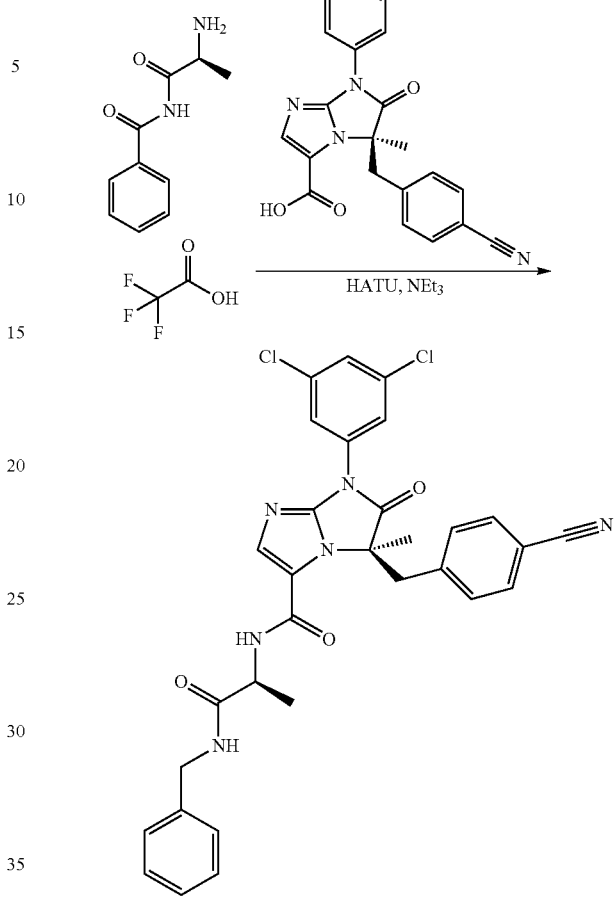

To a solution of (S)-2-tert-butoxycarbonylamino-propionic acid 4-nitro-phenyl ester (200 mg, 0.645 mmol) and MP-carbonate (664 mg, 1.93 mmol, Biotage, Part #:800268) in CH$_2$Cl$_2$ (1.5 mL) was added benzylamine (70 mg, 0.645 mmol). The reaction mixture was stirred for 1 h. The reaction mixture was then filtered and concentrated in vacuo to afford ((S)-1-benzylcarbamoyl-ethyl)-carbamic acid tert-butyl ester, m/z 279.4 [M+1]$^+$.

To a solution of ((S)-1-benzylcarbamoyl-ethyl)-carbamic acid tert-butyl ester (180 mg, 0.645 mmol) in dichloromethane (1.0 mL) was added trifluoroacetic acid (0.500 mL, 6.73 mmol). The reaction mixture was stirred for 4 h. The reaction mixture was then concentrated in vacuo to afford (S)-1-benzylcarbamoyl-ethyl-ammonium trifluoro-acetate, m/z 179.2 [M+1]$^+$.

To a solution of (R)-5-(4-cyano-benzyl)-7-(3,5-dichloro-phenyl)-5-methyl-6-oxo-6,7-dihydro-5H-imidazo[1,2-a] imidazole-3-carboxylic acid (100 mg, 0.227 mmol) and [dimethylamino-(1,2,3-triazolo[4,5-b]pyridin-3-yloxy)-methylene]-dimethyl-ammonium hexafluoro phosphate (95 mg, 0.249 mmol) were added the (S)-1-benzylcarbamoyl-ethyl-ammonium trifluoro-acetate (94 mg, 0.322 mmol) in THF (1 mL) and triethylamine (126 µL, 0.906 mmol). The reaction mixture was stirred for 4 h. The reaction mixture was concentrated in vacuo. The resulting residue was purified by reverse phase HPLC to afford 121 mg of the trifluoroacetic acid salt of the title compound as a white solid, m/z 601.5 [M+1]$^+$.

The following compounds were prepared using procedures similar to those described above using either (R)-5-(4-Cyanobenzyl)-7-(3,5-dichloro-phenyl)-5-methyl-6-oxo-6,7-dihydro-5H-imidazo[1,2-a]imidazole-3-carboxylic acid or (R)-7-(3,5-Dichloro-phenyl)-5-methyl-6-oxo-5-(4-trifluoromethoxy-benzyl)-6,7-dihydro-5H-imidazo[1,2-a]imidazole-3-carboxylic acid as a starting material:

Compound 124, m/z 615.5 [M+1]⁺

Compound 147, m/z 615.5 [M+1]⁺

Compound 262, m/z 629.5 [M+1]⁺

Compound 247, m/z 616.5 [M+1]⁺

Compound 248, m/z 616.5 [M+1]⁺

Compound 249, m/z 605.4 [M+1]⁺

Compound 284, m/z 621.4 [M+1]⁺

Compound 32, m/z 628.7 [M+1]⁺

Compound 46, m/z 671.8 [M+1]⁺

Compound 47, m/z 730.8 [M+1]⁺

Compound 346, m/z 644.08 [M+2]⁺ Compound 354, m/z 662.57 [M+1]⁺

Compound 422, m/z 782.8 [M+1]⁺ Compound 423, m/z 739.8 [M+1]⁺

Example 11

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid [(S)-1-(1-pyridin-2-yl-cyclopropylcarbamoyl)-ethyl]-amide

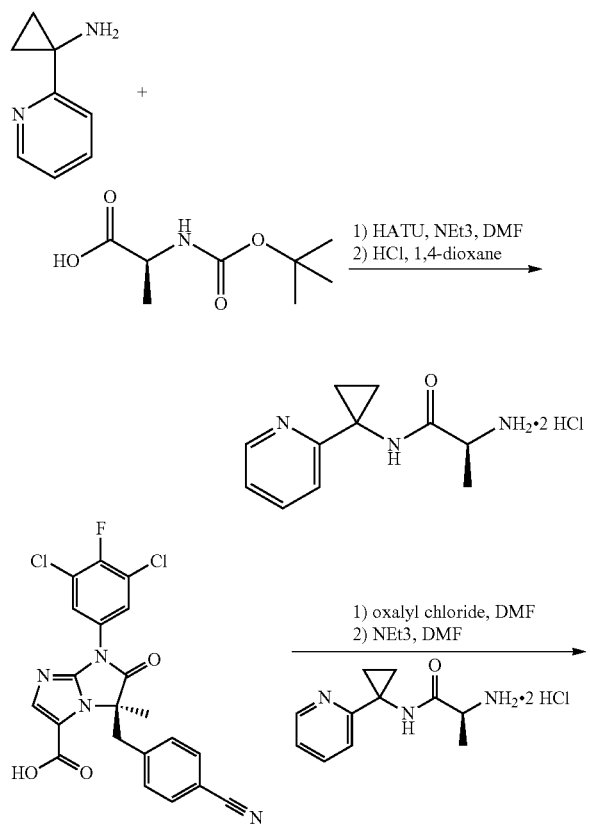

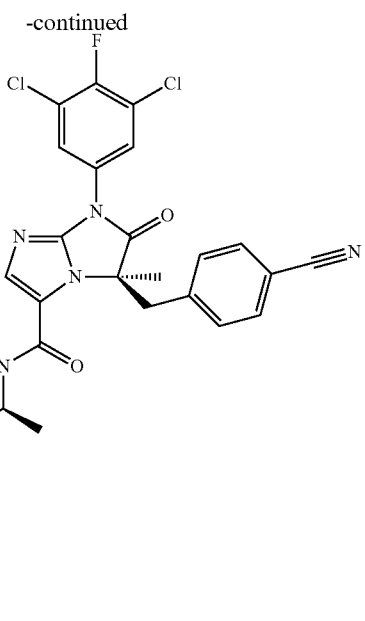

To a solution of Boc-Ala (100 mg, 0.53 mmol), HATU (261 mg, 0.69 mmol) and triethylamine (0.15 mL, 1.1 mmol) in DMF (2 mL) was added a solution of 1-pyridin-2-yl-cyclopropylamine (80 mg, 0.60 mmol) in DMF (1 mL). The mixture was stirred for 1.5 h then diluted with EtOAc (30 mL), washed with water (3×30 mL), brine (1×25 mL), dried with MgSO₄, filtered, and concentrated to afford a crude solid. The crude material was purified by flash chromatography on silica gel, eluting with Hex/EtOAc (50/50 to 75/25) to afford [(S)-1-(1-pyridin-2-yl-cyclopropylcarbamoyl)-ethyl]-carbamic acid tert-butyl ester (120 mg, 74%) as a white solid.

A solution of [(S)-1-(1-pyridin-2-yl-cyclopropylcarbamoyl)-ethyl]-carbamic acid tert-butyl ester (120 mg, 0.39 mmol) in CH₂Cl₂ (5 mL) was added 4M HCl in dioxane (0.98 mL, 3.9 mmol). The solution stirred for 4 hours then was concentrated in vacuo to afford crude (S)-2-amino-N-(1-pyridin-2-yl-cyclopropyl)-propionamide dihydrochloride (100 mg, 0.36 mmol).

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid (300 mg, 0.65 mmol) was dissolved in CH₂Cl₂ (4 mL). To this solution was added oxalyl chloride (0.11 mL, 1.3 mmol) followed by DMF (0.05 mL). The reaction was allowed to stir for 2 h. The volatiles were removed in vacuo to yield the crude acid chloride (300 mg).

The crude acid chloride (100 mg, 0.21 mmol) was dissolved in anhydrous THF (2 mL). To this solution was added a solution of (S)-2-amino-N-(1-pyridin-2-yl-cyclopropyl)-propionamide dihydrochloride (70 mg, 0.25 mmol) dissolved in DMF (0.5 mL). Triethylamine (0.11 mL, 0.63 mmol) was then added. The reaction was allowed to stir for 2 hours. The volatiles were removed in vacuo and the resultant residue was diluted with EtOAc (20 ml) and poured into saturated aqueous NaCl:10% NaHCO₃ (1:1) (30 ml). The aqueous phase was separated and further extracted with EtOAc (2×20 mL). The organic layers were combined, dried (Na₂SO₄), decanted and concentrated. The crude residue was purified by flash chromatography on silica gel, eluting with 1-5% MeOH in CH₂Cl₂, to furnish 130 mg (96%) of (R)-5-(4-cyano-benzyl)-7-(3,5-dichloro-4-fluoro-phenyl)-5-methyl-6-oxo-6,7dihydro-5H-imidazo[1,2-a]imidazole-3-carboxylic acid [(S)-1-

(1-pyridin-2-yl-cyclopropyl carbamoyl)-ethyl]-amide as a pale yellow solid, m/z 646.6 [M+1]$^+$.

The following compounds were prepared using procedures similar to those described above:
Compound 300, m/z 646.4 [M+1]$^+$.
Compound 329, m/z 690.43 [M+1]$^+$ Compound 351, m/z 659.64 [M+1]$^+$ Compound 385, m/z 676.8 [M+1]$^+$ Compound 383, m/z 618.9 [M+1]$^+$ Compound 394, m/z 711.6 [M+1]$^+$
Compound 352, m/z 647.3 [M+1]$^+$ Example 12

(3R)-3-(4-Cyanobenzyl)-1-(3,5-dichlorophenyl)-3-methyl-2-oxo-N-(1-{[2-(2H-tetrazol-5-yl)ethyl]carbamoyl}cyclopropyl)-2,3-dihydro-1H-imidazo[1,2-a]imidazole-5-carboxamide

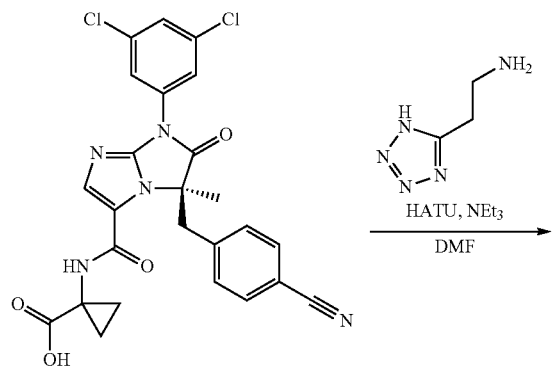

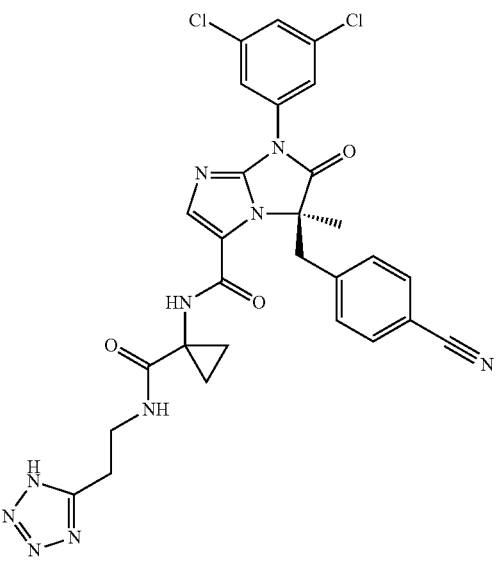

1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid (50 mg, 0.09 mmol) and HATU (57 mg, 0.15 mmol), were combined with a heterogeneous solution of 2-(1H-tetrazol-5-yl)-ethylamine formiate (45 mg, 0.26 mmol) in anhydrous DMF (1 mL) and cooled to 0° C. Et$_3$N (0.043 mL, 0.3 mmol) was added to the reaction. After 18 h the reaction slowly warmed to room temperature. The crude reaction solution was filtered and purified via reverse HPLC to yield 45 mg of the title compound as a white solid, m/z 619.5 [M+1]$^+$).

The following compounds were prepared using procedures similar to those described above using either 1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid, 1-{[(R)-5-(4-cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropanecarboxylic acid, or 1-{[(R)-7-(3,5-dichloro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarboxylic acid as a starting material:

Compound 41, m/z=644.64 [M+2]$^+$
Compound 48, m/z=661.66 [M+2]$^+$
Compound 301, m/z=532.63 [M+2]$^+$
Compound 49, m/z=690.69 [M+2]$^+$
Compound 62, m/z=649.65 [M+2]$^+$
Compound 305, m/z=690.69 [M+2]$^+$
Compound 306, m/z=645.65 [M+2]$^+$
Compound 307, m/z=663.67 [M+2]$^+$
Compound 308, m/z=648.65 [M+2]$^+$
Compound 324, m/z=708.7 [M+1]$^+$ Compound 328, m/z 660.55 [M+1]$^+$
Compound 330, m/z 632.52 [M+1]$^+$
Compound 331, m/z 697.36 [M+1]$^+$
Compound 332, m/z 681.34 [M+1]$^+$. This compound was obtained by separation (via HPLC) from its diastereomer resulting from the coupling of rac-1-(1H-Pyrrolo[2,3-b]pyridin-6-yl)-propylamine with 1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid.
Compound 333, m/z 697.39 [M+1]$^+$
Compound 348, m/z 641.8 [M+1]$^+$
Compound 347, m/z 642.8 [M+1]$^+$ Compound 349, m/z 641.73 [M+1]$^+$
Compound 350, m/z 641.61 [M+1]$^+$
Compound 353, m/z 659.62 [M+1]$^+$
Compound 355, m/z 655.68 [M+1]$^+$
Compound 356, m/z 656.70 [M+1]$^+$
[1-(6-{1-[(1-{[(R)-5-(4-Cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropanecarbonyl)-amino]-cyclopropyl}-pyridazin-3-yl)-1-methyl-ethyl]-carbamic acid benzyl ester, m/z 850.88 [M+1]$^+$
Compound 411, m/z 641.66 [M+1]$^+$ Compound 389, m/z 669.9 [M+1]$^+$
Compound 409, m/z 728.4 [M+1]$^+$
Compound 50, m/z 631.6 [M+1]$^+$

Example 13

(R)-1-(1-{[(R)-7-(3,5-Dichloro-phenyl)-5-methyl-6-oxo-5-(4-trifluoro-methoxy-benzyl)-6,7-dihydro-5H-imidazo[1,2-a]imidazole-3-carbonyl]-amino}-cyclopropanecarbonyl)-pyrrolidine-3-carboxylic acid

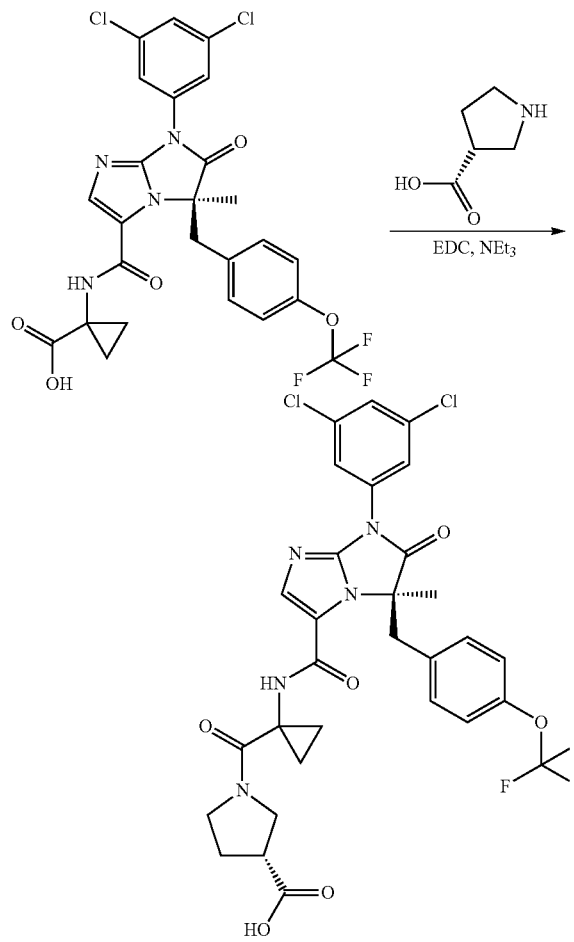

To a solution of 1-{[(R)-7-(3,5-dichloro-phenyl)-5-methyl-6-oxo-5-(4-trifluoromethoxy-benzyl)-6,7-dihydro-5H-imidazo[1,2-a]imidazole-3-carbonyl]-amino}-cyclopropane-carboxylic acid (0.10 g, 0.17 mmol) in DMF (1 mL) was added EDC (0.059 g, 0.26 mmol) and the mixture allowed to stir for 10 min. In a separate reaction vessel, pyrrolidine 3-carboxylic acid (0.039 g, 0.34 mmol) was dissolve in DMF (1 mL) and to this was added Et$_3$N (0.049 mL, 0.34 mmol). The amine solution was then slowly added to the acid mixture and the reaction allowed to stir at room temperature for 12 h. The crude reaction mixture was purified by reverse-phase HPLC to give 54 mg of the title compound as a white solid, m/z 680.5 [M+]$^+$.

The following compounds were prepared using procedures similar to those described above using either 1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid, 1-{[(R)-5-(4-cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropanecarboxylic acid, or 1-{[(R)-7-(3,5-dichloro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarboxylic acid (1-{[(R)-7-(3,5-dichloro-phenyl)-5-methyl-6-oxo-5-(4-1,2,4-triazol-1-yl-benzyl)-6,7-dihydro-5H-imidazo[1,2-a]imidazole-3-carbonyl]-amino}-cyclopropanecarboxylic acid, 1-{[(R)-7-(3,5-Dichloro-phenyl)-5-methyl-6-oxo-5-(4-1,2,3-triazol-1-yl-benzyl)-6,7-dihydro-5H-imidazo[1,2-a]imidazole-3-carbonyl]-amino}-cyclopropanecarboxylic acid, 1-{[(R)-7-(3,5-Dichloro-phenyl)-5-methyl-6-oxo-5-(4-1,2,3-triazol-2-yl-benzyl)-6,7-dihydro-5H-imidazo[1,2-a]imidazole-3-carbonyl]-amino}-cyclopropanecarboxylic acid, 1-{[(R)-5-(4-chloro-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid as a starting material:

Compound 81, m/z 621.4 [M+1]$^+$
Compound 232, m/z 621.4 [M+1]$^+$
Compound 91, m/z 614.5 [M+1]$^+$
Compound 176, m/z 621.5 [M+1]$^+$
Compound 196, m/z 634.5 [M+1]$^+$
Compound 200, m/z 634.5 [M+1]$^+$
Compound 133, m/z 608.5 [M+1]$^+$
Compound 164, m/z 620.4 [M+1]$^+$
Compound 192, m/z 620.5 [M+1]$^+$
Compound 79, m/z 676.9 [M+1]$^+$
Compound 8, m/z 645.5 [M+1]$^+$
Compound 76, m/z 645.5 [M+1]$^+$
Compound 173, m/z 659.6 [M+1]$^+$
Compound 225, m/z 658.9 [M+1]$^+$
Compound 18, m/z 760.2 [M+1]$^+$
Compound 6, m/z 599.5 [M+1]$^+$
Compound 12, m/z 634.6 [M+1]$^+$
Compound 14, m/z 634.6 [M+1]$^+$
Compound 17, m/z 613.5 [M+1]$^+$
Compound 160, m/z 592.8 [M+1]$^+$
Compound 162, m/z 663.6 [M+1]$^+$
Compound 174, m/z 593.0 [M+1]$^+$
Compound 185, m/z 656.6 [M+1]$^+$
Compound 189, m/z 648.6 [M+1]$^+$
Compound 201, m/z 648.5 [M+1]$^+$
Compound 143, m/z 647.9 [M+1]$^+$
Compound 234, m/z 621.6 [M+1]$^+$
Compound 241, m/z 620.6 [M+1]$^+$
Compound 9, m/z 661.5 [M+1]$^+$
Compound 152, m/z 633.5 [M+1]$^+$
Compound 15, m/z 718.6 [M+1]$^+$
Compound 22, m/z 659.6 [M+1]$^+$
Compound 74, m/z 602.5 [M+1]$^+$
Compound 94, m/z 594.5 [M+1]$^+$
Compound 108, m/z 608.5 [M+1]$^+$
Compound 72, m/z 606.5 [M+1]$^+$
Compound 3, m/z 628.5 [M+1]$^+$
Compound 220, m/z 660.5 [M+1]$^+$
Compound 268, m/z 632.5 [M+1]$^+$
Compound 267, m/z 646.6 [M+1]$^+$
Compound 126, m/z 646.5 [M+1]$^+$
Compound 154, m/z 632.5 [M+1]$^+$
Compound 137, m/z 707.6 [M+1]$^+$
Compound 101, m/z 646.5 [M+1]$^+$
Compound 272, m/z 647.5 [M+1]$^+$
Compound 151, m/z 663.5 [M+1]$^+$
Compound 31, m/z 640.6 [M+1]$^+$
Compound 254, m/z 642.5 [M+1]$^+$
Compound 255, m/z 682.5 [M+1]$^+$
Compound 109, m/z 649.21 [M+1]$^+$ Compound 89, m/z 649.01 [M+1]+
Compound 98, m/z 649.01 [M+1]+
Compound 156, m/z 649.15 [M+1]+
Compound 125, m/z 620.4 [M+1]+
Compound 123, m/z, 605 [M+1]+
Compound 80, m/z 659.1 [M+1]+
Compound 77, m/z 735.9 [M+1]+
Compound 19, m/z 704.6 [M+1]+
Compound 171, m/z 718.6 [M+1]+
Compound 199, m/z 718.2 [M+1]+
Compound 10, m/z 693.4 [M+1]+
Compound 11, m/z 653.5 [M+1]+
Compound 16, m/z 693.1 [M+1]+
Compound 20, m/z 673.4 [M+1]+
Compound 84, m/z 653.5 [M+1]+
Compound 187, m/z 722.7 [M+1]+
Compound 194, m/z 707.5 [M+1]+
Compound 207, m/z 707.1 [M+1]+
Compound 211, m/z 715.5 [M+1]+
Compound 214, m/z 706.8 [M+1]+
Compound 221, m/z 679.6 [M+1]+
Compound 231, m/z 679.6 [M+1]+
Compound 4, m/z 720.6 [M+1]+
Compound 5, m/z 704.2 [M+1]+
Compound 23, m/z 661.5 [M+1]+
Compound 253, m/z 673.5 [M+1]+
Compound 68, m/z 699.5 [M+1]+
Compound 69, m/z 665.5 [M+1]+
Compound 30, m/z 687.5 [M+1]+
Compound 58, m/z 689.7 [M+1]+
Compound 33, m/z 670.7 [M+1]+
Compound 34, m/z 670.7 [M+1]+
Compound 59, m/z 688.7 [M+1]+
Compound 36, m/z 647.7 [M+1]+
Compound 56, m/z 659.0 [M+1]+
Compound 64, m/z 663.7 [M+1]+
Compound 37, m/z 646.00 [M+1]+
Compound 38, m/z 717.06 [M+1]+
Compound 57, m/z 673.1 [M+1]+
Compound 40, m/z 683.4 [M+1]+
Compound 39, m/z 742.8 [M+1]+
Compound 41, m/z 644 [M+1]+
Compound 48, m/z 661 [M+1]+
Compound 50, m/z 631.1 [M+1]+
Compound 42, m/z 631 [M+1]+
Compound 256, m/z 622.7 [M+1]+
Compound 257, m/z 640.7 [M+1]+
Compound 288, m/z=686.53 [M+1]+
Compound 289, m/z=687.69 [M+1]+
Compound 290, m/z=681.64 [M+1]+
Compound 321, m/z=732.8 [M+1]+
Compound 322, m/z=689.7 [M+1]+
Compound 323, m/z=730.7 [M+1]+ Compound 325, m/z=683.7 [M+1]+
Compound 326, m/z=684.5 [M+1]+
Compound 327, m/z=700.6 [M+1]+
Compound 365, m/z 671.7 [M+1]+
Compound 366, m/z 675.8 [M+1]+
Compound 367, m/z 645.7 [M+1]+
Compound 368, m/z 673.8 [M+1]+
Compound 369, m/z 713.6 [M+1]+
Compound 370, m/z 659.8 [M+1]+
Compound 371, m/z 689.8 [M+1]+
Compound 372, m/z 674.8 [M+1]+ Compound 374, m/z 682.7 [M+1]+
Compound 375, m/z 649.6 [M+1]+
Compound 376, m/z 682.7 [M+1]+

Compound 377, m/z 682.5 [M+1]+
Compound 379, m/z 784.7 [M+1]+
Compound 384, m/z 688.8 [M+1]+
Compound 386, m/z 654.7 [M+1]+ Compound 387, m/z 720.5 [M+1]+
Compound 393, m/z 653.2 [M]+
Compound 396, m/z 777.8 [M+1]+

Example 14

(3R)-3-(4-Bromobenzyl) —N-{(1R)-2-[(3R)-3-cyanopiperidin-1-yl]-1-methyl-2-oxoethyl}-1-(3,5-dichlorophenyl)-3-methyl-2-oxo-2,3-dihydro-1H-imidazo[1,2-a]imidazole-5-carboxamide and (3R)-3-(4-bromobenzyl) —N-{(1S)-2-[(3R)-3-cyanopiperidin-1-yl]-1-methyl-2-oxoethyl}-1-(3,5-dichlorophenyl)-3-methyl-2-oxo-2,3-dihydro-1H-imidazo[1,2-a]imidazole-5-carboxamide

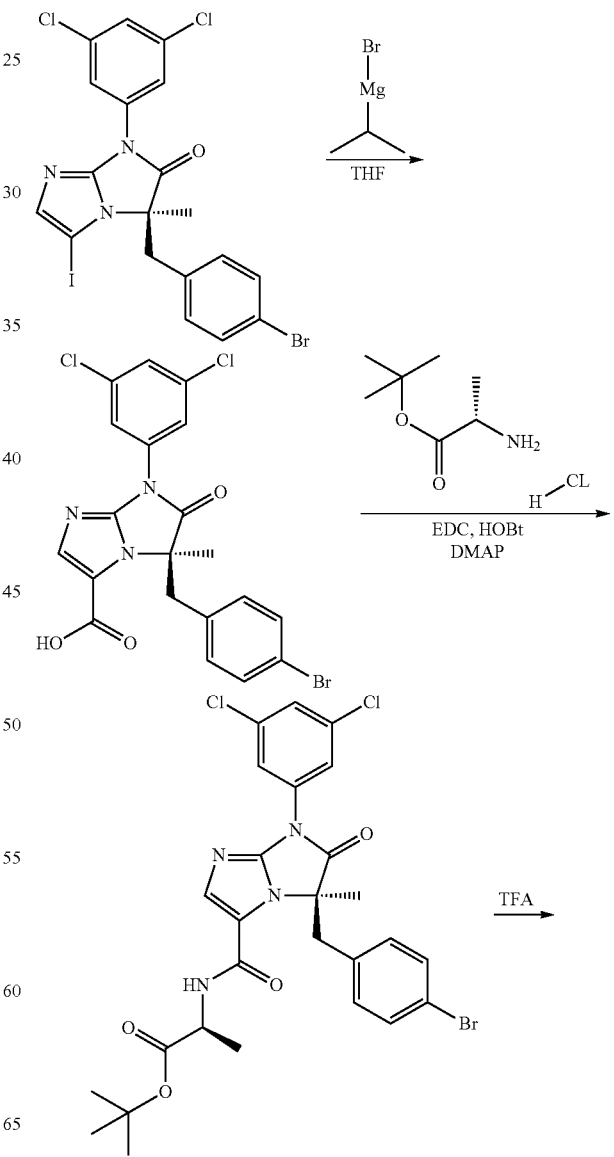

-continued

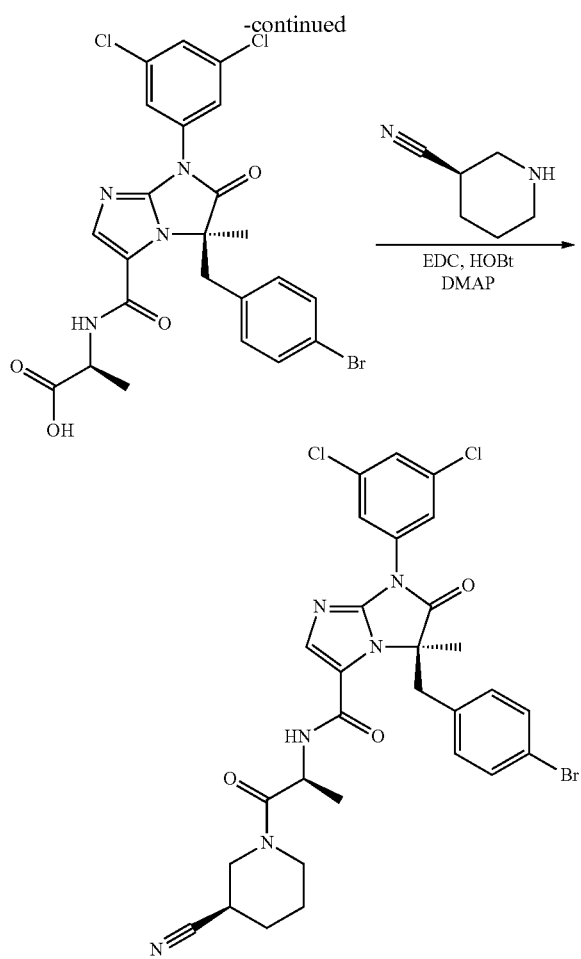

A solution of (R)-3-(4-bromo-benzyl)-1-(3,5-dichloro-phenyl)-5-iodo-3-methyl-1H-imidazo[1,2-a]imidazol-2-one (4.5 g, 7.8 mmol) in THF (50 mL) was cooled to −40° C. To this was slowly added isopropyl magnesium bromide (1M in THF, 15.6 mL, 15.6 mmol) over 30 min. The reaction mixture was stirred at −40° C. for 1 h and then CO$_2$ gas passed through the solution for 1 h. The reaction mixture was concentrated under reduced pressure and diluted with water. The mixture was acidified with 1N HCl and extracted with CH$_2$Cl$_2$ (3×100 mL). The combined extracts were washed with water, brine and dried with MgSO$_4$. The mixture was filtered and concentrated in vacuo. The residue was dissolved in toluene (40 mL) and hexane was added (100 mL). The resulting precipitate was filtered and washed with hexane to afford 2.6 g of (R)-5-(4-bromo-benzyl)-7-(3,5-dichloro-phenyl)-5-methyl-6-oxo-6,7-dihydro-5H-imidazo[1,2-a]imidazole-3-carboxylic acid as a purple solid, m/z 495.5 [M+]$^+$.

To a solution of (R)-5-(4-bromo-benzyl)-7-(3,5-dichloro-phenyl)-5-methyl-6-oxo-6,7-dihydro-5H-imidazo[1,2-a]imidazole-3-carboxylic acid (2.5 g, 5.0 mmol) in DMF (5 mL) was added (S)-2-amino-propionic acid tert-butyl ester hydrochloride (0.92 g, 5.0 mmol), HOBt (0.68 g, 5.0 mmol), EDC (0.97 g, 5.0 mmol) and DMAP (0.061 g, 0.50 mmol). The reaction mixture was heated at 80° C. for 12 h. The mixture was allowed to cool to room temperature and diluted with water (100 mL). The mixture was extracted with EtOAc (3×100 mL) and the combined organic layers were washed with water, brine and dried with MgSO$_4$. The mixture was filtered and concentrated in vacuo to give 2.5 g of (S)-2-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-propionic acid tert-butyl ester as a yellow solid, m/z 623.5 [M+1]$^+$.

To a solution of (S)-2-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-propionic acid tert-butyl ester (3.0 g, 4.8 mmol) in CH$_2$Cl$_2$ (20 mL) was added TFA (1 mL). The reaction was allowed to stir for 30 minutes and then the solvent removed in vacuo to afford 2.2 g of (S)-2-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-propionic acid as a white solid, m/z 442.2 [M+]$^+$.

To a solution of (S)-2-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-propionic acid (2.7 g, 4.8 mmol) in DMF (5 mL) and Et$_3$N (2 mL) was added (R)-piperidine-3-carbonitrile trifluoroacetic acid (1.1 g, 4.8 mmol), HOBt (0.64 g, 4.8 mmol), EDC (0.91 g, 4.8 mmol) and DMAP (0.010 g, 0.082 mmol). The reaction was heated at 80° C. for 5 h. The mixture was cooled to room temperature and diluted with water (100 mL). The mixture was extracted with EtOAc (3×100 mL) and the combined extracts were washed with water, brine (2×100 mL) and dried with MgSO$_4$. The mixture was filtered, concentrated in vacuo and purified by flash chromatography on silica gel. The resulting residue (200 mg) was dissolved in MeOH and purified by reverse phase HPLC to give 12 mg of (3R)-3-(4-bromobenzyl)—N-{(1R)-2-[(3R)-3-cyanopiperidin-1-yl]-1-methyl-2-oxoethyl}-1-(3,5-dichlorophenyl)-3-methyl-2-oxo-2,3-dihydro-1H-imidazo[1,2-a]imidazole-5-carboxamide (eluted first), m/z 659.3 [M+1]$^+$ and 15 mg of (3R)-3-(4-bromobenzyl)-N-{(1S)-2-[(3R)-3-cyanopiperidin-1-yl]-1-methyl-2-oxoethyl}-1-(3,5-dichlorophenyl)-3-methyl-2-oxo-2,3-dihydro-1H-imidazo[1,2-a]imidazole-5-carboxamide m/z 659.3 [M+1]$^+$.

The following compounds were prepared using procedures similar to those described above:

Compound 373, m/z 683.5 [M+1]$^+$

Example 15

(3R)-3-(4-bromobenzyl)-1-(3,5-dichlorophenyl)-3-methyl-N-{(1S)-1-methyl-2-oxo-2-[(3R)-3-(1H-tetrazol-5-yl)piperidin-1-yl]ethyl}-2-oxo-2,3-dihydro-1H-imidazo[1,2-a]imidazole-5-carboxamide

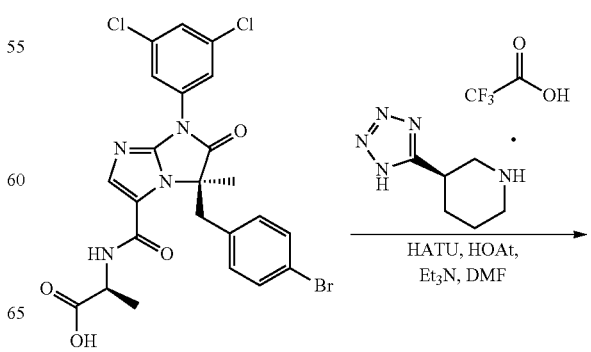

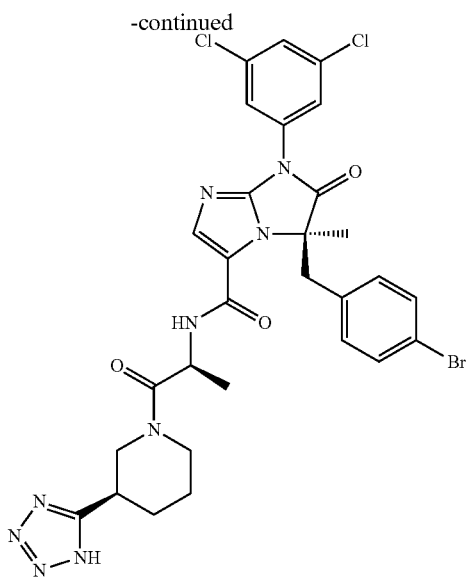

To a cold (0° C.) solution of (S)-2-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-propionic acid (0.050 g, 0.088 mmol) in DMF (1 mL) was added (R)-3-(1H-tetrazol-5-yl)-piperidine trifluoro-acetic acid salt (0.047 g, 0.18 mmol), HATU (0.040 g, 0.11 mmol) and Et$_3$N (0.026 mL, 0.18 mmol). The reaction was allowed to stir for 10 minutes and HOAt (0.024 g, 0.18 mmol) was added and the mixture allowed to warm to room temperature overnight. The crude reaction mixture was purified by reverse-phase HPLC to give 10 mg of the title compound as a white solid, m/z 701.4 [M]$^+$.

Example 16

(3R)-1-(3,5-dichlorophenyl)-3-[(4'-fluorobiphenyl-4-yl)methyl]-3-methyl-N-{(1S)-1-methyl-2-oxo-2-[(3R)-3-(1H-tetrazol-5-yl)piperidin-1-yl]ethyl}-2-oxo-2,3-dihydro-1H-imidazo[1,2-a]imidazole-5-carboxamide

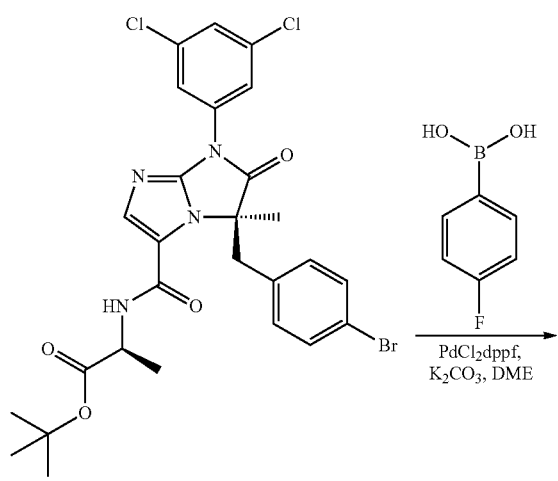

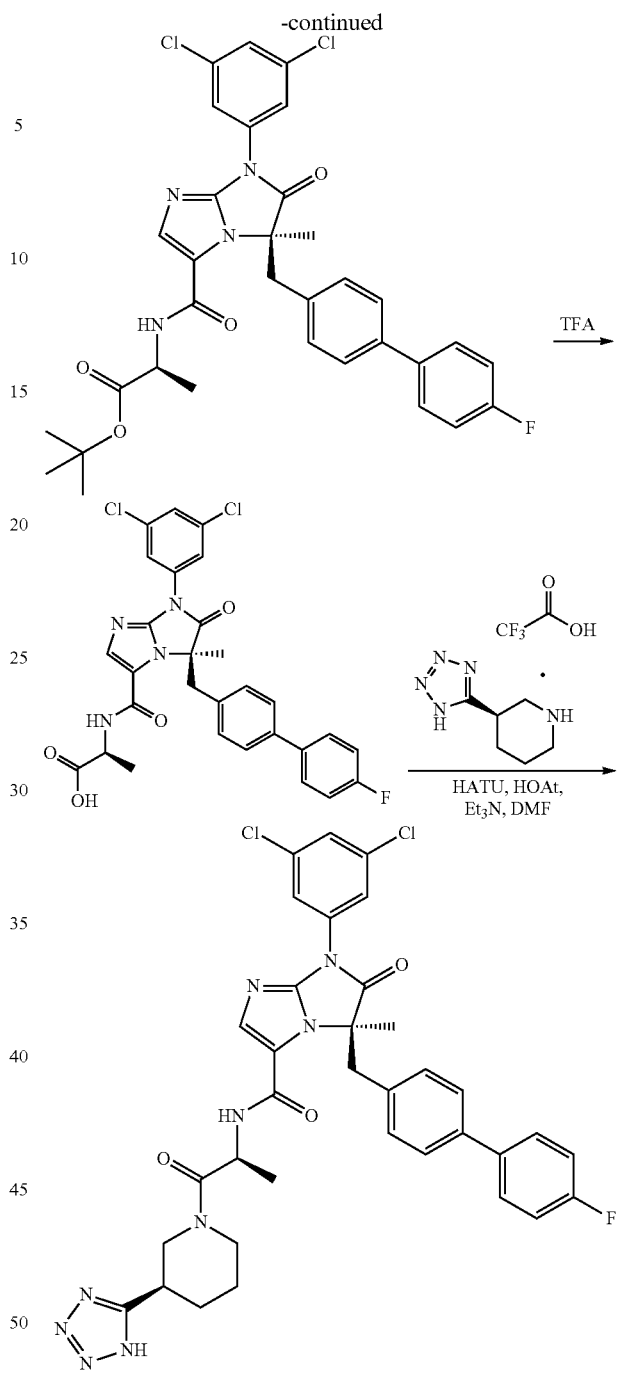

A solution of (S)-2-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-propionic acid tert-butyl ester (0.20 g, 0.32 mmol), 4-fluorophenyl boronic acid (0.059 g, 0.43 mmol) and K$_2$CO$_3$ (0.15 g, 1.1 mmol) in DME (5 mL) was degassed under N$_2$ for 10 minutes. To this was added PdCl$_2$(dppf) (5 mg) and the mixture heated at 80° C. for 12 h. The resulting black mixture was cooled to room temperature, diluted with saturated NH$_4$Cl and extracted with EtOAc (3×50 mL). The combined organic extracts were washed with water, brine, dried with MgSO$_4$ and concentrated. The residue was purified by silica gel chromatography to afford 150 mg of (S)-2-{[(R)-7-(3,5-dichloro-phenyl)-5-(4'-fluoro-biphenyl-4-ylmethyl)-5-methyl-6-oxo-6,7-dihydro-5H-imidazo[1,2-a]imidazole-3-carbonyl]-amino}-propionic acid tert-butyl ester as a white solid, m/z 637.5 [M+]+.

To a solution of (S)-2-{[(R)-7-(3,5-dichloro-phenyl)-5-(4'-fluoro-biphenyl-4-ylmethyl)-5-methyl-6-oxo-6,7-dihydro-5H-imidazo[1,2-a]imidazole-3-carbonyl]-amino}-propionic acid tert-butyl ester (0.15 g, 0.24 mmol) in CH$_2$Cl$_2$ (10 mL) was added TFA (4 mL) and the mixture stirred at room temperature for 12 h. The mixture was diluted with water (50 mL) and extracted with EtOAc (3×50 mL). The combined organic extracts were washed with water, brine and dried with MgSO$_4$. The mixture was filtered and concentrated to give 120 mg of (S)-2-{[(R)-7-(3,5-dichloro-phenyl)-5-(4'-fluoro-biphenyl-4-ylmethyl)-5-methyl-6-oxo-6,7-dihydro-5H-imidazo[1,2-a]imidazole-3-carbonyl]-amino}-propionic acid as a white solid, m/z 581.3 [M]+.

To a cold (0° C.) solution of (S)-2-{[(R)-7-(3,5-dichloro-phenyl)-5-(4'-fluoro-biphenyl-4-ylmethyl)-5-methyl-6-oxo-6,7-dihydro-5H-imidazo[1,2-a]imidazole-3-carbonyl]-amino}-propionic acid (0.12 g, 0.21 mmol) in DMF (1 mL) was added (R)-3-(1H-tetrazol-5-yl)-piperidine trifluoro-acetic acid salt (0.055 g, 0.21 mmol), HATU (0.093 mg, 0.25 mmol) and Et$_3$N (0.059 mL, 0.41 mmol). The reaction was allowed to stir for 10 min and then HOAt (0.056 g, 0.41 mmol) was added. The mixture was allowed to warm to room temperature overnight. The crude reaction mixture was purified by reverse phase HPLC to give 35 mg of the title compound as a white solid, m/z 716.6 [M]+.

The following compound was prepared using similar procedures as described above:

Compound 86, m/z 698.2 [M+]+

Example 17

(3R)—N-{(1S)-4-Amino-1-[(3-carbamoylpiperidin-1-yl)carbonyl]-4-oxobutyl}-3-(4-cyanobenzyl)-1-(3,5-dichlorophenyl)-3-methyl-2-oxo-2,3-dihydro-1H-imidazo[1,2-a]imidazole-5-carboxamide

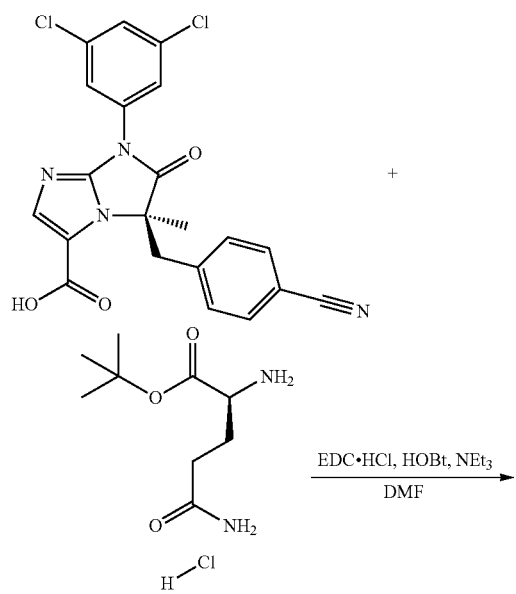

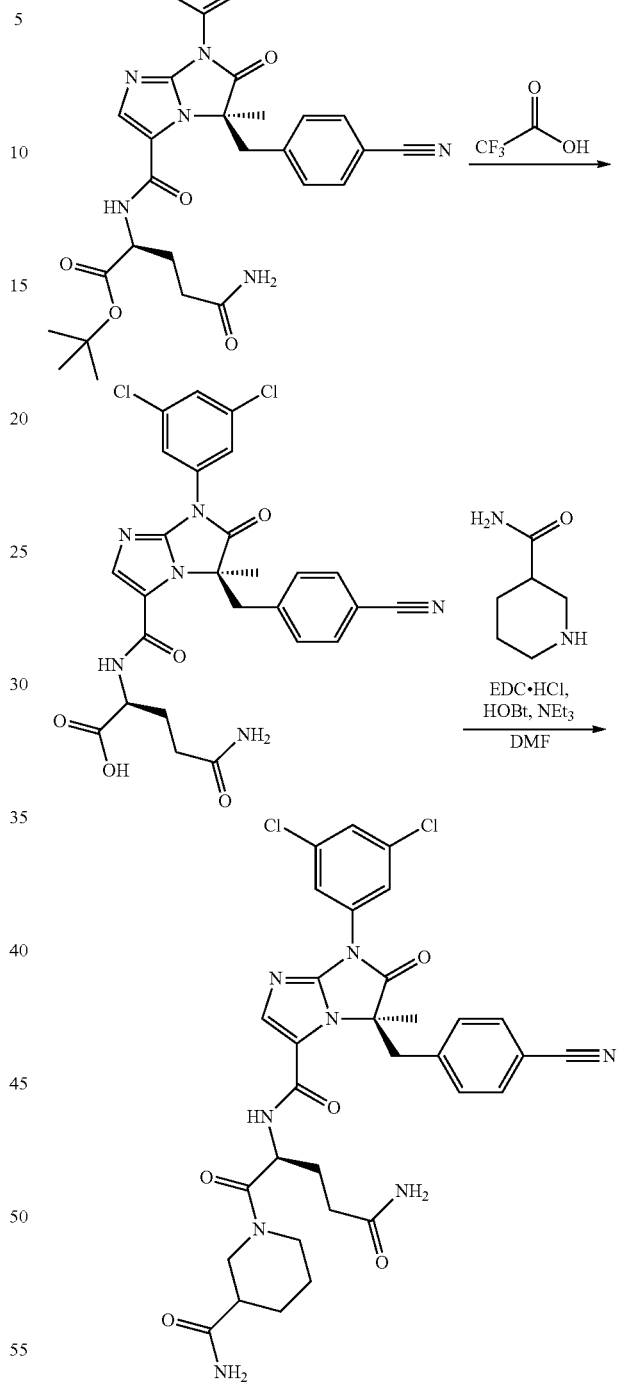

To a solution of (R)-5-(4-cyano-benzyl)-7-(3,5-dichloro-phenyl)-5-methyl-6-oxo-6,7-dihydro-5H-imidazo[1,2-a]imidazole-3-carboxylic acid (1.0 g, 2.3 mmol) in DMF (25 mL) were added (3-dimethylamino-propyl)-ethyl-carbodiimide hydrochloride (652 mg, 3.4 mmol), benzotriazol-1-ol (459 mg, 3.4 mmol) and triethylamine (1.2 mL, 10.9 mmol). The reaction mixture was stirred at room temperature for 20 min, and (S)-2-amino-4-carbamoyl-butyric acid tert-butyl ester hydrochloride (811 mg, 3.4 mmol) was added.

The reaction mixture was stirred at room temperature for 64 h then diluted with water and filtered through a glass frit. The solution was then extracted with dichloromethane (×3). The combined organic layers were then washed with water (×3). The organic phase was dried over anhydrous Na₂SO, decanted and concentrated in vacuo. The resulting residue was purified by flash chromatography on silica gel (40 to 100% ethyl acetate in hexanes) to afford 999 mg of (S)-4-carbamoyl-2-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-butyric acid tert-butyl ester as a white solid, m/z 625.5 [M+1]⁺.

To a solution of (S)-4-carbamoyl-2-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-butyric acid tert-butyl ester (970 mg, 1.5 mmol) in CH₂Cl₂ (10 mL) was added trifluoroacetic acid (5.0 mL, 28 mmol). The reaction mixture was stirred at room temperature for 4 h. The reaction mixture was then concentrated in vacuo to afford 882 mg of (S)-4-carbamoyl-2-{[(R)-5-(4-cyano-benzyl)-7-[3,5-dichloro-phenyl)-5-methyl-6-oxo-6,7-dihydro-5H-imidazo[1,2-a]imidazole-3-carbonyl]-amino}-butyric acid as a white solid, m/z 569.4 [M+1]⁺.

To a solution of (S)-4-carbamoyl-2-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-butyric acid (50 mg, 0.088 mmol) in DMF (1 mL) was added (3-dimethylamino-propyl)-ethyl-carbodiimide hydrochloride (25 mg, 0.132 mmol), benzotriazol-1-ol (18 mg, 0.132 mmol) and triethylamine (47 μL, 0.395 mmol). The reaction mixture was stirred at room temperature for 20 min then piperidine-3-carboxylic acid amide (17 mg, 0.132 mmol) was added. The reaction mixture was stirred at room temperature for 64 h. The reaction mixture was then diluted with water and filtered through a glass frit. The solution was then extracted with CH₂Cl₂ (×3). The combined organic layers were then washed with water (×3). The organic phase was dried over anhydrous Na₂SO₄ and concentrated in vacuo. The resulting residue was purified via reverse phase HPLC to afford 60 mg of the title compound as a white solid, m/z 679.6 [M+1]⁺.

The following compound was prepared using similar procedures as described above:
Compound 71, m/z 659.5 [M+1]⁺

Example 18

(3R)-1-(3,5-Dichlorophenyl)-3-methyl-2-oxo-N-{2-oxo-2-[(3R)-3-(2H-tetrazol-5-yl)pyrrolidin-1-yl]ethyl}-3-[4-(trifluoromethoxy)benzyl]-2,3-dihydro-1H-imidazo[1,2-a]imidazole-5-carboxamide

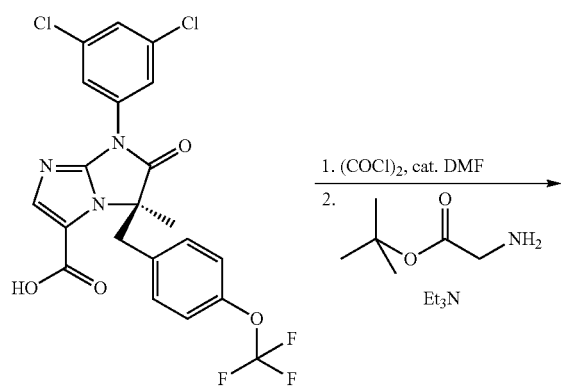

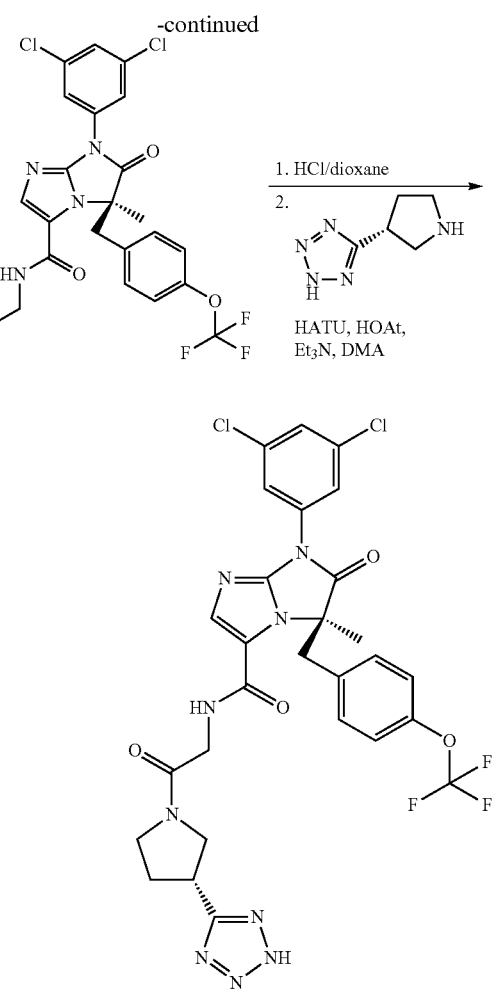

To a solution of (R)-7-(3,5-dichloro-phenyl)-5-methyl-6-oxo-5-(4-trifluoromethoxy-benzyl)-6,7-dihydro-5H-imidazo[1,2-a]imidazole-3-carboxylic acid (0.500 g, 1.0 mmol) in CH₂Cl₂ (15 mL) was added oxalyl chloride (0.194 mL, 2.2 mmol), followed by slow addition of DMF (0.05 mL). The reaction was stirred for 90 min. The volatiles were removed in vacuo, and the residue dissolved in THF (15 mL). To this cloudy solution was added diisopropylethylamine (0.88 mL, 5.0 mmol) followed by glycine tert-butyl ester (0.30 mL, 2.2 mmol). The reaction was stirred for another 14 h. The volatiles were removed in vacuo at 40° C. The reaction mixture was diluted with ethyl acetate and washed with 1 N aqueous HCl (×2), 10% aqueous Na₂CO₃ (×2) and brine (×2). The organic phase was dried over anhydrous Na₂SO₄ and concentrated in vacuo to afford {[(R)-7-(3,5-dichloro-phenyl)-5-methyl-6-oxo-5-(4-trifluoromethoxy-benzyl)-6,7-dihydro-5H-imidazo[1,2-a]imidazole-3-carbonyl]-amino}-acetic acid tert-butyl ester (0.483 g) as a colorless foam.

{[(R)-7-(3,5-Dichloro-phenyl)-5-methyl-6-oxo-5-(4-trifluoromethoxy-benzyl)-6,7-dihydro-5H-imidazo[1,2-a]imidazole-3-carbonyl]-amino}-acetic acid tert-butyl ester (0.061 g, 0.1 mmol) was dissolved in CH₂Cl₂ (0.5 mL) and 4N HCl/dioxane (1 mL) added. The solution was agitated on an orbital shaker for 14 h and then concentrated in vacuo. The resulting residue was dissolved in DMA (2 mL), and (R)-5-pyrrolidin-3-yl-2H-tetrazole (0.21 g, 0.15 mmol), HOAt (0.041 g, 0.3 mmol), triethylamine (0.09 mL, 0.6 mmol) and HATU (0.057 g, 0.15 mmol) were added. The reaction mixture was agitated for 14 h and then concentrated in vacuo. The residue was dissolved in DMSO (1 mL) and water (0.1 mL)

and purified via reverse phase HPLC purification to afford 0.045 g of (3R)-1-(3,5-dichlorophenyl)-3-methyl-2-oxo-N-{2-oxo-2-[(3R)-3-(2H-tetrazol-5-yl)pyrrolidin-1-yl]ethyl}-3-[4-(trifluoromethoxy)benzyl]-2,3-dihydro-1H-imidazo[1,2-a]imidazole-5-carboxamide as a white solid, m/z 680.1 [M+1]$^+$ The following compounds were prepared using similar procedures as described above:
Compound 274, m/z 621.1 [M+1]$^+$
Compound 175, m/z 649.1 [M+1]$^+$
Compound 161, m/z 706.3 [M+1]$^+$
Compound 236, m/z 635.0 [M+1]$^+$
Compound 209, m/z 694.0 [M+1]$^+$
Compound 280, m/z 621.1 [M+1]$^+$
Compound 223, m/z 680.0 [M+1]$^+$
Compound 186, m/z 708.1 [M+1]$^+$
Compound 242, m/z 635.1 [M+1]$^+$
Compound 210, m/z 694.0 [M+1]$^+$
Compound 264, m/z 595.0 [M+1]$^+$
Compound 134, m/z 654.0 [M+1]$^+$
Compound 153, m/z 623.1 [M+1]$^+$
Compound 116, m/z 682.0 [M+1]$^+$
Compound 144, m/z 609.1 [M+1]$^+$
Compound 112, m/z 668.0 [M+1]$^+$
Compound 271, m/z 609.1 [M+1]$^+$
Compound 155, m/z 668.0 [M+1]$^+$
Compound 158, m/z 637.1 [M+1]$^+$
Compound 128, m/z 696.1 [M+1]$^+$
Compound 287, m/z 623.1 [M+1]$^+$
Compound 119, m/z 682.0 [M+1]$^+$
Compound 183, m/z 635.1 [M+1]$^+$
Compound 163, m/z 694.1 [M+1]$^+$
Compound 237, m/z 663.0 [M+1]$^+$
Compound 202, m/z 722.1 [M+1]$^+$
Compound 279, m/z 635.1 [M+1]$^+$
Compound 238, m/z 694.1 [M+1]$^+$
Compound 275, m/z 663.0 [M+1]$^+$
Compound 224, m/z 722.1 [M+1]$^+$ Example 19

4-Acetyl-1-{[1-({[(3R)-3-(4-cyanobenzyl)-1-(3,5-dichlorophenyl)-3-methyl-2-oxo-2,3-dihydro-1H-imidazo[1,2-a]imidazol-5-yl]carbonyl}amino)-cyclopropyl]carbonyl}piperazine-2-carboxylic acid

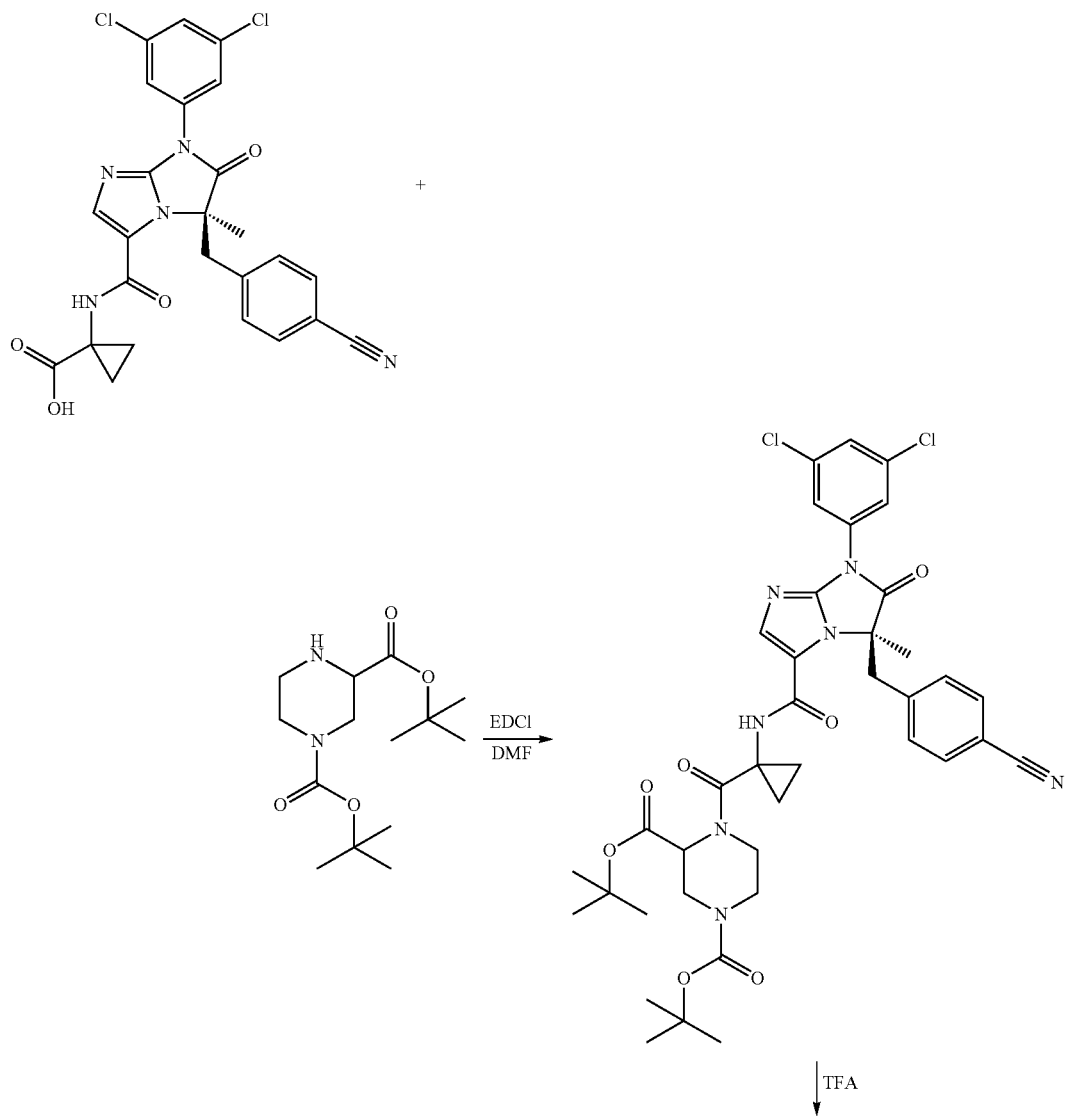

309

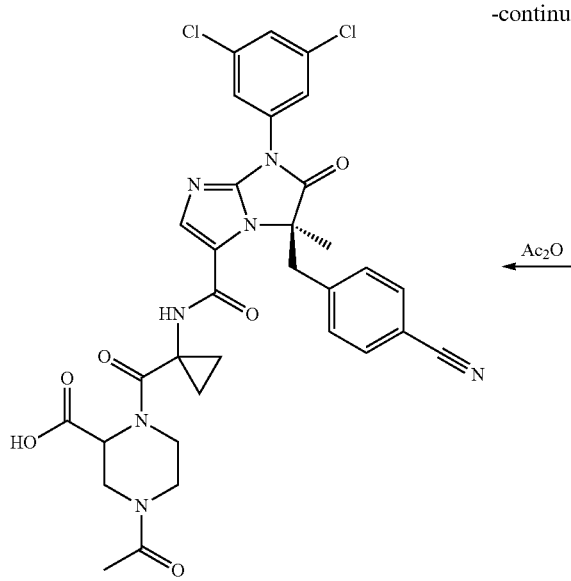

⟵ Ac₂O

310

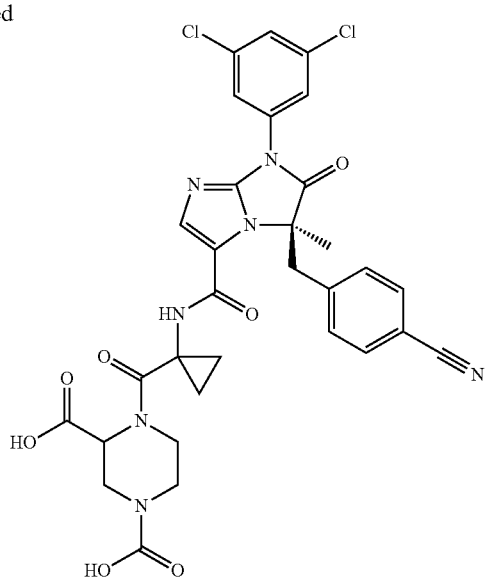

-continued

1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid (100 mg, 0.19 mmol), piperazine-1,3-dicarboxylic acid di-tert-butyl ester (109 mg, 0.38 mmol) and EDC (46 mg, 0.24 mmol) were dissolved in DMF (1 mL) and triethylamine (0.07 mL, 0.38 mmol) was added. After 20 h, the reaction was diluted with CH₂Cl₂ and water. The layers were separated and the aqueous layer was extracted with CH₂Cl₂ (2×). The combined organic layers were washed with water (2×), dried over MgSO₄, filtered and concentrated in vacuo to yield a colorless oil. Purification by flash chromatography on silica gel (0-15% MeOH in CH₂Cl₂) yielded 51 mg of a tan solid as 4-(1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-piperazine-1,3-dicarboxylic acid di-tert-butyl ester (approximately 75% pure) which was used without further purification.

4-(1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-piperazine-1,3-dicarboxylic acid di-tert-butyl ester (256 mg, 0.32 mmol) was dissolved in CH₂Cl₂ (2 mL) and TFA (2 mL) was added dropwise. After 16 h, the reaction was concentrated in vacuo. The crude orange oil was dissolved in DMSO (1.5 mL), purified via reverse phase HPLC to afford 64 mg of 1-(1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclo-propanecarbonyl)-piperazine-2-carboxylic acid trifluoroacetic acid salt as a white solid.

1-(1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-piperazine-2-carboxylic acid trifluoroacetic acid salt (40 mg, 0.05 mmol) was dissolved in pyridine (1 mL), and acetic anhydride (0.01 mL, 0.11 mmol) was added dropwise. After 30 min, the reaction was partitioned between CH₂Cl₂ and water, and the aqueous layer was acidified with 1M HCl to pH 2. The layers were separated and the aqueous layer was extracted with CH₂Cl₂ (2×) and CHCl₃ (1×). The combined organic layers were dried over MgSO₄, filtered and concentrated to yield 35 mg of a white solid. The crude product was dissolved in DMSO (1.3 mL) and purified via reverse phase HPLC to yield 23 mg of the title compound, m/z 678.5 [M+1]⁺.

Example 20

1-Acetyl-4-{[1-({[(3R)-3-(4-cyanobenzyl)-1-(3,5-dichlorophenyl)-3-methyl-2-oxo-2,3-dihydro-1H-imidazo[1,2-a]imidazol-5-yl]carbonyl}amino)-cyclopropyl]carbonyl}piperazine-2-carboxylic acid

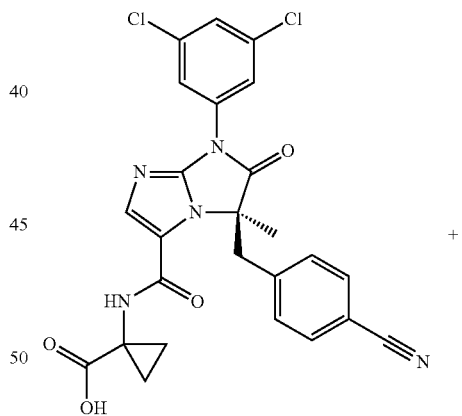

+

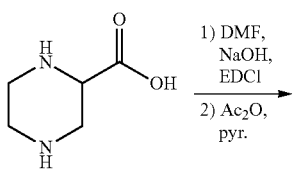

1) DMF, NaOH, EDCI
2) Ac₂O, pyr.

311
-continued

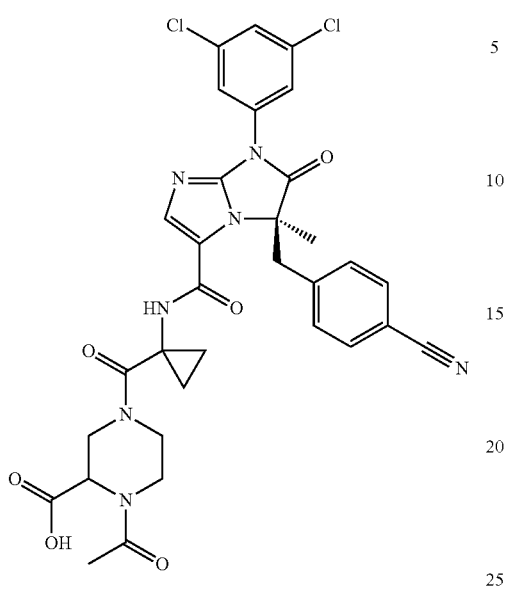

1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid (200 mg, 0.38 mmol) and EDC (81 mg, 0.42 mmol) were combined and dissolved in DMF (1 mL) and stirred for 15 min. In another vial, piperazine-2-carboxylic acid dihydrochloride (132 mg, 0.65 mmol) was neutralized with 4M NaOH solution (0.65 mL, 2.6 mmol). The aqueous solution of the amine was added dropwise to the DMF solution of carboxylic acid and EDC. After 2 h, the heterogeneous reaction was acidified with 1M HCl (10 drops). The crude solution was purified via reverse phase HPLC to yield 110 mg of 4-(1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-piperazine-2-carboxylic acid trifluoroacetic acid salt as a colorless oil.

4-(1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-piperazine-2-carboxylic acid trifluoroacetic acid salt (60 mg, 0.08 mmol) was dissolved in pyridine (1 mL) and acetic anhydride (0.015 mL, 0.16 mmol) was added dropwise. After 30 min, the reaction was partitioned between $CH_2Cl_2$ and water and the aqueous layer was acidified with 1M HCl to pH2. The layers were separated and the aqueous layer was extracted with $CH_2Cl_2$ (2×) and $CHCl_3$ (1×). The combined organic layers were dried over $MgSO_4$, filtered and concentrated to yield 50 mg of a white solid. The crude product was dissolved in DMSO (1.3 mL) and purified via reverse phase HPLC to yield 21 mg of the title compound as a colorless oil which slowly solidifies, m/z 678.6 [M+1]$^+$.

312

Example 21

(1S,3R)-3-({[1-({[(3R)-3-(4-Cyanobenzyl)-1-(3,5-dichlorophenyl)-3-methyl-2-oxo-2,3-dihydro-1H-imidazo[1,2-a]imidazol-5-yl]carbonyl}amino)-cyclopropyl]carbonyl}amino)cyclopentanecarboxylic acid (4)

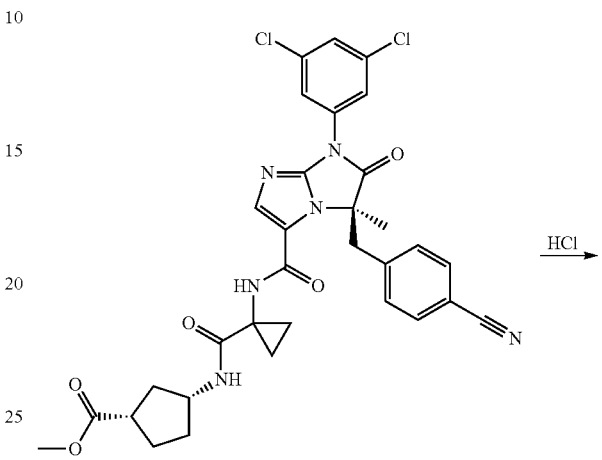

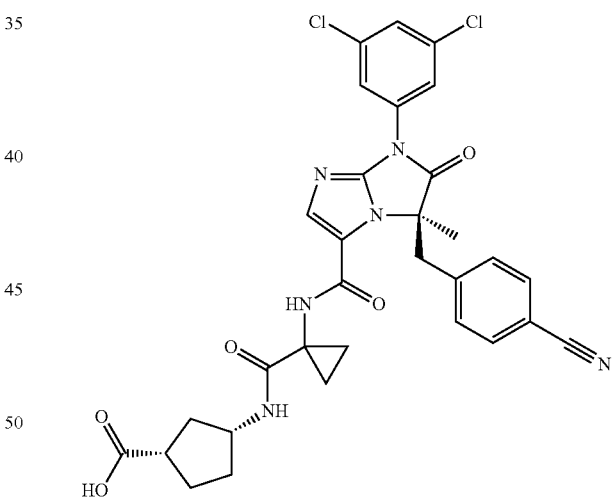

1N HCl in 1,4-dioxane (1 mL, 1 mmol) and 1N HCl (aq.) (0.5 mL, 0.5 mmol) were added to methyl (1S,3R)-3-({[1-({[(3R)-3-(4-cyanobenzyl)-1-(3,5-dichlorophenyl)-3-methyl-2-oxo-2,3-dihydro-1H-imidazo[1,2-a]imidazol-5-yl]carbonyl}amino)cyclopropyl]-carbonyl}amino)cyclopentanecarboxylate (35 mg, 0.054 mmol). The reaction tube was sealed and the reaction solution was stirred at 100° C. for 1 h. The reaction solution was then cooled to room temperature, filtered and purified via reverse phase HPLC. The title compound (23.1 mg) was isolated as a white solid, m/z 635.1 [M+1]$^+$.

The following compounds were prepared using similar procedures as described above:

Compound 260, m/z 635.2 [M+1]+ Compound 273, m/z 635.0 [M+1]+.

Example 22

(3R)—N-(1-{[(1R,3S)-3-carbamoylcyclopentyl]carbamoyl}cyclopropyl)-3-(4-cyanobenzyl)-1-(3,5-dichlorophenyl)-3-methyl-2-oxo-2,3-dihydro-1H-imidazo-[1,2-a]imidazole-5-carboxamide Compound 96, m/z 634.2 [M+1]+ Compound 73, m/z 634.2 [M+1]+ Compound 142, m/z 634.2 [M+1]+.

Example 23

(3R)-1-(3,5-Dichlorophenyl)-N-(1-{[(3R)-3-(3-hydroxy-1H-pyrazol-5-yl)pyrrolidin-1-yl]carbonyl}cyclopropyl)-3-methyl-2-oxo-3-[4-(trifluoromethoxy)-benzyl]-2,3-dihydro-1H-imidazo[1,2-a]imidazole-5-carboxamide

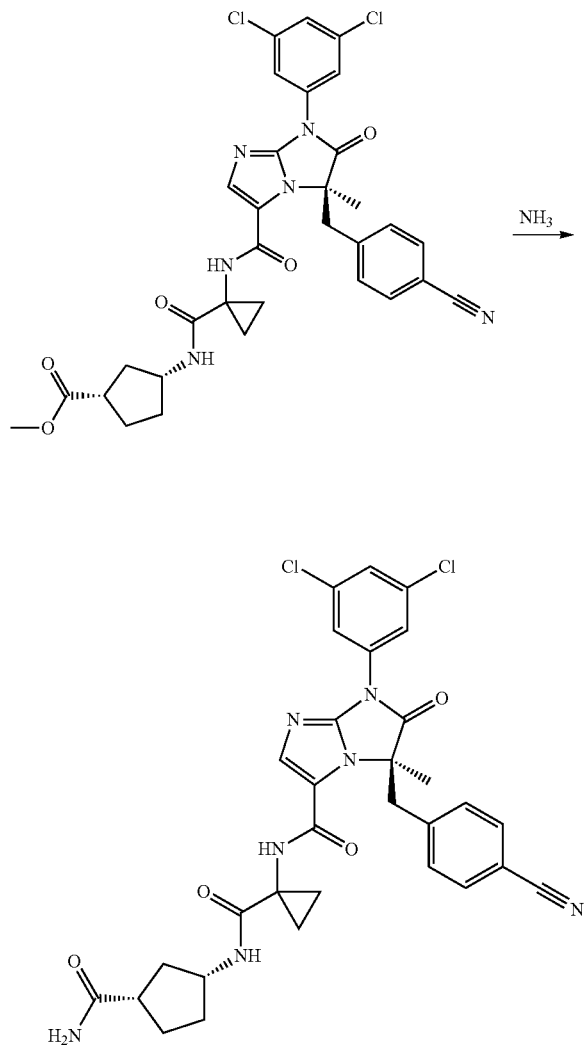

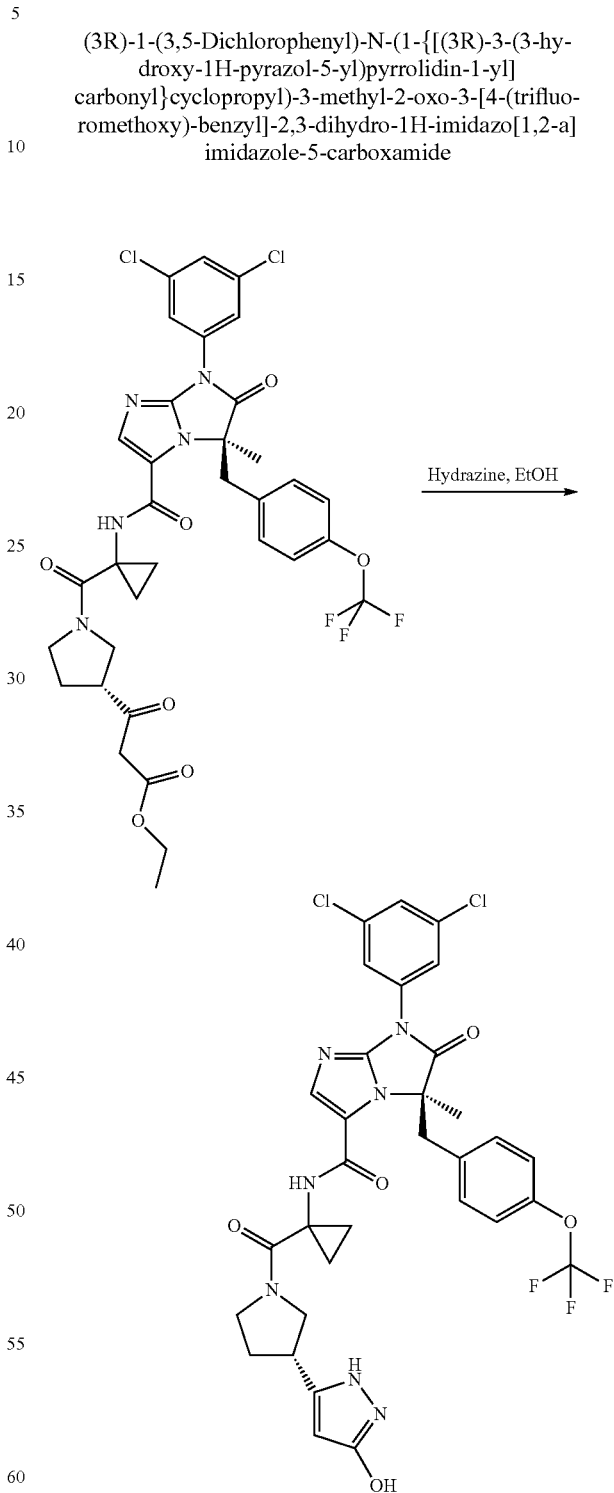

To methyl (1S,3R)-3-({[1-({[(3R)-3-(4-cyanobenzyl)-1-(3,5-dichlorophenyl)-3-methyl-2-oxo-2,3-dihydro-1H-imidazo[1,2-a]imidazol-5-yl]carbonyl}amino)cyclopropyl]carbonyl}amino)cyclopentanecarboxylate (109.2 mg, 0.168 mmol) was added ammonia (7N in methanol, 4 mL, 28 mmol) and the reaction tube was sealed. The reaction solution was stirred at 80° C. for 65 h. The reaction solution was then cooled to room temperature and concentrated in vacuo. The resultant residue was purified via reverse phase HPLC to afford 58.6 mg of the title compound as a white solid, m/z 634.2 [M+1]+.

The following compounds were prepared using similar procedures as described above:

To a solution of 3-[(R)-1-(1-{[(R)-7-(3,5-dichloro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarbonyl)-pyrrolidin-3-yl]-3-oxo-propionic acid ethyl ester (35 mg, 0.05 mmol) in ethanol (2 mL) was added hydrazine (7.0 μL, 0.23 mmol). The reaction mixture was stirred at room temperature for 1.5 h. The solvent was evaporated in vacuo, and the residue was purified via reverse phase HPLC to afford the title compound (20 mg, 60%) as a white solid, m/z 718.1 [M+1]+.

Example 24

(R)-5-(4-Cyanobenzyl)-7-(3,5-dichlorophenyl)-5-methyl-6-oxo-6,7-dihydro-5H-imidazo[1,2-a]imidazole-3-carboxylic acid [1-acetyl-4-(1-pyridin-2-yl-cyclopropylcarbamoyl)-piperidin-4-yl]-amide

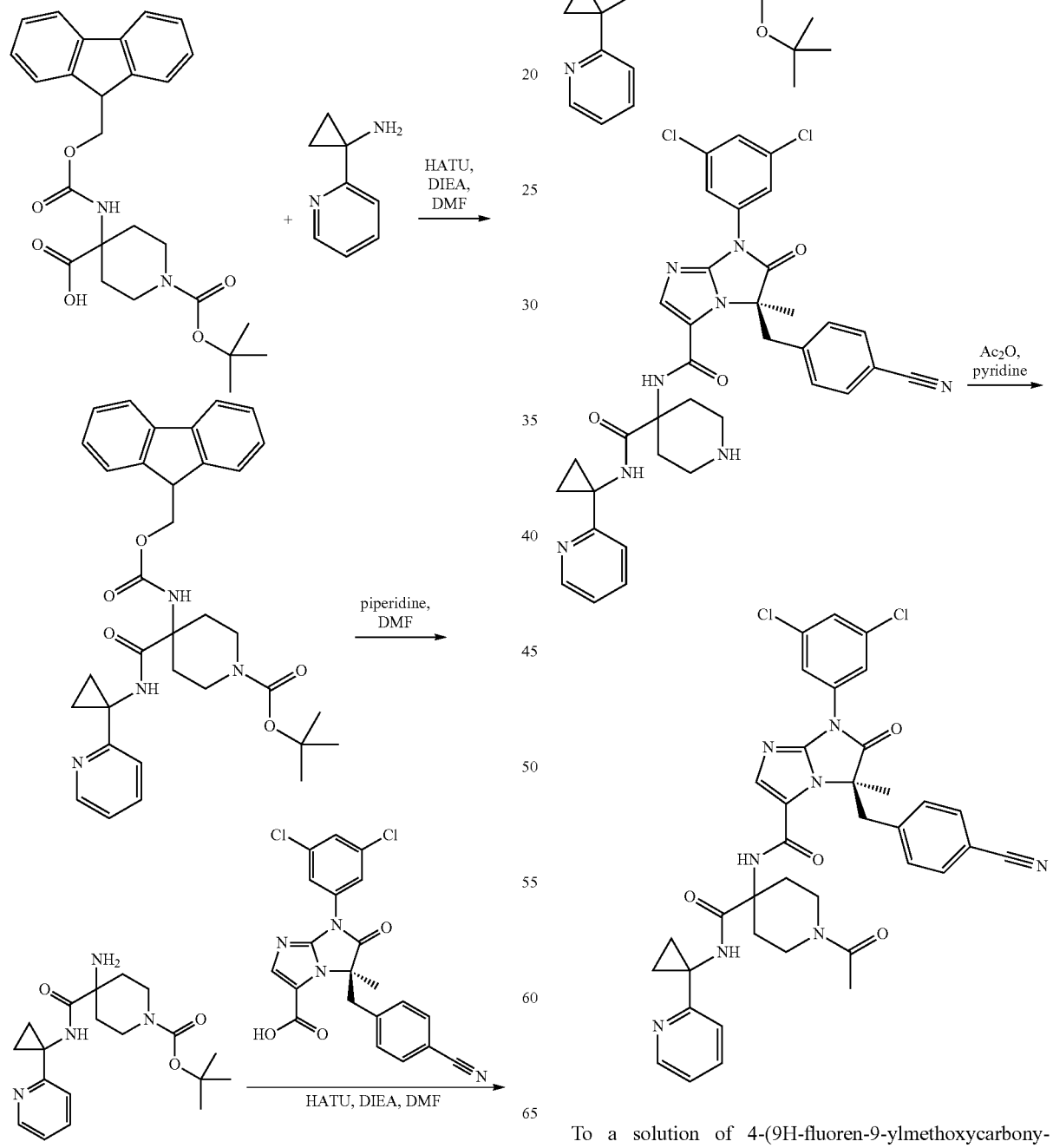

To a solution of 4-(9H-fluoren-9-ylmethoxycarbonylamino)-piperidine-1,4-dicarboxylic acid mono-tert-butyl ester (100 mg, 0.21 mmol) and 1-pyridin-2-yl-cyclopropylamine (35 mg, 0.26 mmol) in DMF (0.5 mL) was added HATU (98 mg, 0.26 mmol) followed by diisopropylethylamine (0.5 mL). The reaction mixture was stirred at room temperature for 3 h. The crude reaction mixture was used in the next step.

To the solution of crude 4-(9H-fluoren-9-ylmethoxycarbonylamino)-4-(1-pyridin-2-yl-cyclopropylcarbamoyl)-piperidine-1-carboxylic acid tert-butyl ester in DMF (0.5 mL) was added piperidine (0.2 mL). The mixture was stirred at room temperature. After 1 h, the solution was diluted with EtOAc (20 mL) and washed with water (4×20 mL). The organic phase was dried over anhydrous $Na_2SO_4$ and concentrated in vacuo. The resulting residue was purified via flash chromatography on silica gel (10% MeOH in $CH_2Cl_2$ containing 0.1% $NH_4OH$) to afford 74 mg of 4-amino-4-(1-pyridin-2-yl-cyclopropylcarbamoyl)-piperidine-1-carboxylic acid tert-butyl ester as a white solid.

To a mixture of (R)-5-(4-cyano-benzyl)-7-(3,5-dichlorophenyl)-5-methyl-6-oxo-6,7-dihydro-5H-imidazo[1,2-a]imidazole-3-carboxylic acid (80 mg, 0.18 mmol) and 4-amino-4-(1-pyridin-2-yl-cyclopropylcarbamoyl)-piperidine-1-carboxylic acid tert-butyl ester (74 mg, 0.20 mmol) in DMF (1 mL) was added HATU (76 mg, 0.19 mmol) and diisopropylethylamine (47 mg, 0.36 mmol). The reaction was stirred at room temperature for 7 h. After addition of water (10 mL) the mixture was extracted with EtOAc (2×15 mL). The organic layer was washed with brine and dried over $Na_2SO_4$. The solvent was removed in vacuo and the remaining residue was purified via reverse phase HPLC to afford 4-{[(R)-5-(4-cyanobenzyl)-7-(3,5-dichlorophenyl)-5-methyl-6-oxo-6,7-dihydro-5H-imidazo[1,2-a]imidazole-3-carbonyl]-amino}-4-(1-pyridin-2-yl-cyclopropyl-carbamoyl)-piperidine-1-carboxylic acid tert-butyl ester as a white solid (140 mg), m/z 784.9 $[M+1]^+$.

To a solution of 4-{[(R)-5-(4-cyanobenzyl)-7-(3,5-dichlorophenyl)-5-methyl-6-oxo-6,7-dihydro-5H-imidazo[1,2-a]imidazole-3-carbonyl]-amino}-4-(1-pyridin-2-yl-cyclopropyl-carbamoyl)-piperidine-1-carboxylic acid tert-butyl ester (140 mg, 0.18 mmol) in $CH_2Cl_2$ (0.5 mL) was added TFA (0.5 mL) and stirred at room temperature for 1 h. The solvent was removed in vacuo to afford (R)-5-(4-cyanobenzyl)-7-(3,5-dichlorophenyl)-5-methyl-6-oxo-6,7-dihydro-5H-imidazo[1,2-a]imidazole-3-carboxylic acid [4-(1-pyridin-2-yl-cyclopropylcarbamoyl)-piperidin-4-yl]-amide as a white solid (120 mg), m/z 683.8 $[M+1]^+$.

To a solution of (R)-5-(4-cyanobenzyl)-7-(3,5-dichlorophenyl)-5-methyl-6-oxo-6,7-dihydro-5H-imidazo[1,2-a]imidazole-3-carboxylic acid [4-(1-pyridin-2-yl-cyclopropylcarbamoyl)-piperidin-4-yl]-amide (20 mg, 0.03 mmol) in pyridine (0.5 mL) was added acetic anhydride (0.5 mL). The reaction mixture was stirred at room temperature for 1 h. The solvent was removed in vacuo and the remaining residue was dissolved in water and extracted with $CH_2Cl_2$ (3×10 mL). The organic layer was washed with brine and dried over $Na_2SO_4$. After removal of the solvent in vacuo, the title compound was obtained as a white solid (21 mg), m/z 725.5 $[M+1]^+$.

The following compounds were prepared using procedures similar to those described above using (R)-5-(4-cyano-benzyl)-7-(3,5-dichloro-4-fluoro-phenyl)-5-methyl-6-oxo-6,7-dihydro-5H-imidazo[1,2-a]imidazole-3-carboxylic acid, (R)-7-(3,5-dichloro-4-fluoro-phenyl)-5-methyl-6-oxo-5-(4-trifluoromethoxy-benzyl)-6,7-dihydro-5H-imidazo[1,2-a]imidazole-3-carboxylic acid or (R)-7-(3,5-dichloro-phenyl)-5-methyl-6-oxo-5-(4-trifluoromethoxy-benzyl)-6,7-dihydro-5H-imidazo[1,2-a]imidazole-3-carboxylic acid as a starting material:

Compound 310, m/z=744.3 $[M+1]^+$ Compound 314, m/z=770.4 $[M+1]^+$
Compound 317, m/z=726.5 $[M+1]^+$ Compound 316, m/z=740.7 $[M+1]^+$ Compound 318, m/z=754.5 $[M+1]^+$
Compound 335, m/z 711.9 $[M+1]^+$
Compound 303, m/z 819.9 $[M+1]^+$
Compound 445, m/z 643.5 $[M+1]^+$
Compound 446, m/z 726.6 $[M+1]^+$
Compound 447, m/z 708.6 $[M+1]^+$
Compound 448, m/z 662.4 $[M+1]^+$
Compound 450, m/z 760.4 $[M+1]^+$
Compound 451, m/z 704.7 $[M+1]^+$
Compound 302, m/z 657.4 $[M+1]^+$
[(S)-3-{[(R)-5-(4-Cyano-benzyl)-7-(3,5-dichloro-4-fluorophenyl)-5-methyl-6-oxo-6,7-dihydro-5H-imidazo[1,2-a]imidazole-3-carbonyl]-amino}-3-(1-pyrimidin-2-yl-cyclopropylcarbamoyl)-propyl]-carbamic acid tert-butyl ester, m/z 776.5 $[M+1]^+$ Example 25

(R)-5-(4-Cyano-benzyl)-7-(3,5-dichloro-phenyl)-5-methyl-6-oxo-6,7-dihydro-5H-imidazo[1,2-a]imidazole-3-carboxylic acid [3-(1-pyridin-2-yl-cyclo-propylcarbamoyl)-oxetan-3-yl]-amide

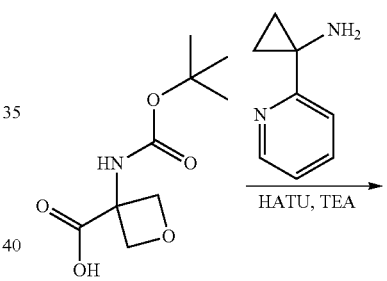

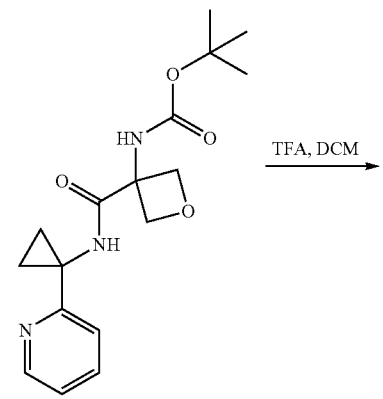

-continued

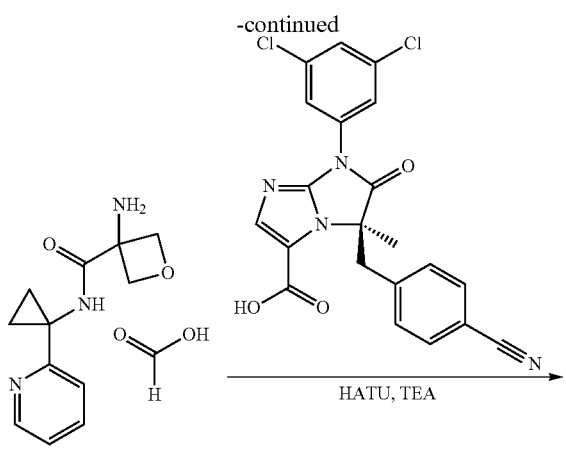

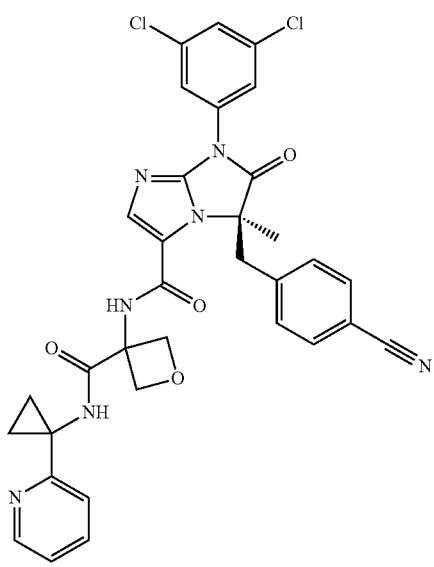

3-Benzylamino-oxetane-3-carboxylic acid (200 mg, 0.97 mmol), prepared from oxetan-3-one (Wuitschik, G. W. et al. Angew. Chem. Int. Ed. 2006, 7736-7739) according to the procedure of Kozikowski and Fauq (Kozikowski, A. P.; Fauq, A. H. Synlett 1991, 783-784), was suspended in MeOH (10 mL). Palladium hydroxide (20% on carbon, 50 wt % water, 100 mg) was added, and the mixture stirred under 1 atm of hydrogen for 30 h. The resulting suspension was heated to 60° C. for 5 min and filtered through a 0.45 μm PTFE syringe filter. To this solution was added Boc$_2$O (421 mg, 1.93 mmol) and triethylamine (274 μL, 1.93 mmol), and the reaction stirred at room temperature for 48 h. The solvent was removed in vacuo and the resulting oil was purified by reverse phase HPLC to give 3-tert-butoxycarbonylamino-oxetane-3-carboxylic acid as a white solid (82 mg, 39%) after lyophilization, m/z 218.5 [M+1]$^+$.

A solution of 3-tert-butoxycarbonylamino-oxetane-3-carboxylic acid (82 mg, 0.38 mmol), 1-pyridin-2-yl-cyclopropylamine (56 mg, 0.42 mmol), HATU (215 mg, 0.57 mmol), and triethylamine (77 μL, 0.57 mmol) in DMF (0.5 mL) was stirred at room temperature for 29 h. Water (0.2 mL) and MeOH (1 mL) were added, and the resulting clear solution was purified directly by reverse phase HPLC to give [3-(1-pyridin-2-yl-cyclopropylcarbamoyl)-oxetan-3-yl]-carbamic acid tert-butyl ester as a tan solid (132 mg, >100%) after lyophilization, m/z 334.8 [M+1]$^+$, that was carried on without further purification.

To a solution of [3-(1-pyridin-2-yl-cyclopropylcarbamoyl)-oxetan-3-yl]-carbamic acid tert-butyl ester (100 mg, 0.30 mmol) in CH$_2$Cl$_2$ (2 mL) was added TFA (1 mL). The solution was stirred at room temperature for 17 h and then concentrated in vacuo. The residue was purified by reverse phase HPLC to give 3-amino-oxetane-3-carboxylic acid (1-pyridin-2-yl-cyclopropyl)-amide formate as a white powder (72 mg, 86%) after lyophilization, m/z 234 (free base) [M+1]$^+$.

A solution of (R)-5-(4-cyano-benzyl)-7-(3,5-dichloro-phenyl)-5-methyl-6-oxo-6,7-dihydro-5H-imidazo[1,2-a]imidazole-3-carboxylic acid (66 mg, 0.15 mmol) and HATU (71 mg, 0.19 mmol) in DMF (0.5 mL) was stirred at room temperature for 2 h. To this solution was added triethylamine (27 μL, 0.19 mmol) and 3-carboxylic acid (1-pyridin-2-yl-cyclopropyl)-amide formate (35 mg, 0.13 mmol). The reaction mixture was stirred at 50° C. for 15 h, then purified via reverse phase HPLC to give (R)-5-(4-cyano-benzyl)-7-(3,5-dichloro-phenyl)-5-methyl-6-oxo-6,7-dihydro-5H-imidazo[1,2-a]imidazole-3-carboxylic acid [3-(1-pyridin-2-yl-cyclopropylcarbamoyl)-oxetan-3-yl]-amide as a white powder (32 mg, 39%) after lyophilization, m/z 656.7 [M+1]$^+$.

The following compounds were prepared using procedures similar to those described above using either (R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid, (R)-5-(4-Cyano-benzyl)-7-(3,5-dichloro-phenyl)-5-methyl-6-oxo-6,7-dihydro-5H-imidazo[1,2-a]imidazole-3-carboxylic acid, (R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carboxylic acid or (R)-7-(3,5-Dichloro-phenyl)-5-methyl-6-oxo-5-(4-trifluoromethoxy-benzyl)-6,7-dihydro-5H-imidazo[1,2-a]imidazole-3-carboxylic acid, as a starting material:

Compound 309, m/z=751.1 [M+1]$^+$

Compound 311, m/z=704.4 [M+1]$^+$

Compound 312, m/z=727.5 [M+1]$^+$ Compound 313, m/z=727.4 [M+1]$^+$

Compound 319, m/z=726.6 [M+1]$^+$

Compound 378, m/z 676.7 [M+1]$^+$

Compound 410, m/z 682.46 [M+1]$^+$

Example 26

(R)-5-(4-Cyano-benzyl)-7-(3,5-dichloro-phenyl)-5-methyl-6-oxo-6,7-dihydro-5H-imidazo[1,2-a]imidazole-3-carboxylic acid [(R)-1-carbamoylmethyl-2-(3,3-difluoro-azetidin-1-yl)-2-oxo-ethyl]-amide

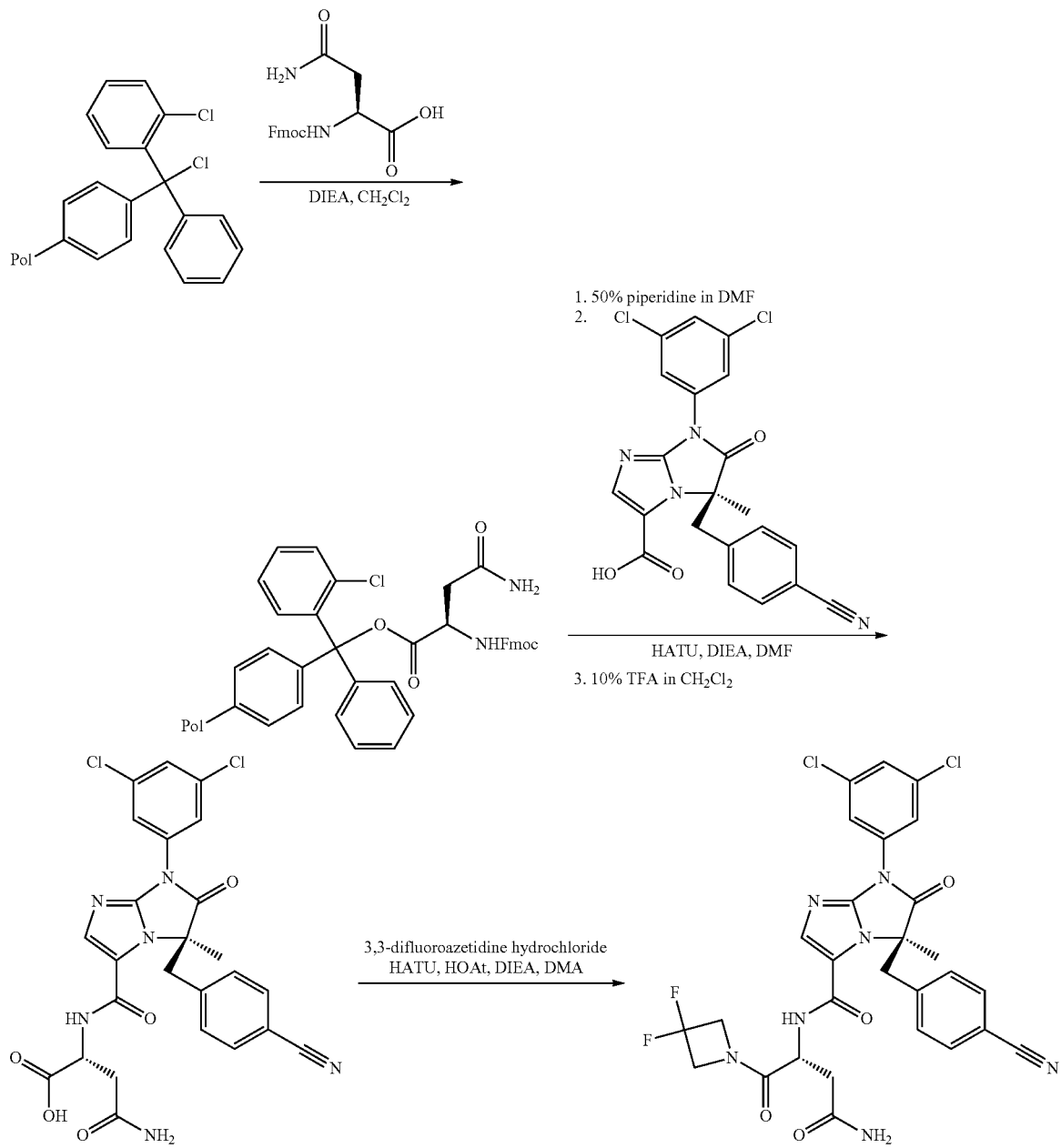

2-Chlorotrityl resin (0.536 g, 0.75 mmol/g) was placed in a dry glass fritted shaker flask. To the resin was added CH₂Cl₂ (10 mL), diisopropylethylamine (0.522 mL) and Fmoc-L-asparagine (0.265 g, 0.75 mmol) and the reaction was agitated on an orbital shaker for 14 h. The reaction solution was drained and the resin washed with CH₂Cl₂/MeOH/DIEA (17:2:1; 3×10 mL), CH₂Cl₂ (3×10 mL), DMF (3×10 mL), and CH₂Cl₂ (3×10 mL). The resin was swelled with DMF (2 mL) and the solvent drained. A solution of 50% piperidine in DMF (10 mL) was added to the resin and the reaction was agitated on an orbital shaker for 90 min. The reaction solution was drained and the resin washed with DMF (2×10 mL), CH₂Cl₂ (2×10 mL), DMF (2×10 mL), CH₂Cl₂ (2×10 mL), and DMA (1×2 mL). (R)-5-(4-Cyano-benzyl)-7-(3,5-dichloro-phenyl)-5-methyl-6-oxo-6,7-dihydro-5H-imidazo[1,2-a]imidazole-3-carboxylic acid (0.132 g, 0.30 mmol) and HATU (0.285 g, 0.75 mmol) were dissolved in DMA (2 mL), and the resulting solution added to the resin. Diisopropylethylamine (0.130 mL, 0.75 mmol) was added and the reaction agitated on an orbital shaker for 48 h. The reaction solution was drained and washed as described above. The resin was treated with 10% TFA in CH$_2$Cl$_2$ and agitated on an orbital shaker for 90 min. The reaction solution was collected and the resin washed with CH$_2$Cl$_2$ (4×3 mL). The filtrates were combined with the supernatant and the volatiles removed in vacuo at 40° C. The residue was dissolved in CH$_2$Cl$_2$ (5 mL) and washed with water (2×5 mL) and brine (5 mL). The organic layer was dried over anhydrous Na$_2$SO$_4$, the solution decanted, and the solvent removed in vacuo to afford 0.122 g (73%) of (R)-2-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-succinamic acid as an orange foam.

A solution of the resulting intermediate (S)-2-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-succinamic acid (0.039 g, 0.070 mmol) in DMA (0.5 mL) was added to a solution of 3,3-difluoroazetidine hydrochloride (0.014 g, 0.135 mmol) in DMA (0.5 mL). A solution of HOAt (0.015 g, 0.110 mmol) in DMA (0.5 mL) was added to the reaction mixture, followed by HATU (0.04 g, 0.105 mmol) in 0.5 mL DMA. The reaction mixture was agitated on an orbital shaker for 3 h. Diisopropylethylamine (0.036 mL, 0.207 mmol) was added and the resulting solution was agitated on an orbital shaker for 14 h. The volatiles were removed in vacuo at 40° C. and the crude product was dissolved in DMSO (1 mL) and water (0.1 mL) and purified via reverse phase HPLC to afford 0.020 g (45%) of (R)-5-(4-cyano-benzyl)-7-(3,5-dichloro-phenyl)-5-methyl-6-oxo-6,7-dihydro-5H-imidazo[1,2-a]imidazole-3-carboxylic acid [(S)-1-carbamoylmethyl-2-(3,3-difluoro-azetidin-1-yl)-2-oxo-ethyl]-amide as a white solid, m/z 632.3 [M+1]$^+$.

The following compounds were prepared using similar procedures as described above:
Compound 24, m/z 646.27 [M+1]$^+$
Compound 25, m/z 660.34 [M+1]$^+$
Compound 26, m/z 734.31 [M+1]$^+$
Compound 27 m/z 687.34 [M+1]$^+$
Compound 28, m/z 722.32 [M+1]$^+$
Compound 29, m/z 660.35 [M+1]$^+$
Compound 360, m/z 672.73 [M+1]$^+$
Compound 361, m/z 697.74 [M+1]$^+$
Compound 362, m/z 686.8 [M+1]$^+$
Compound 363 m/z 684.82 [M+1]$^+$ Compound 54, m/z 670.8 [M+1]$^+$ (R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(5-cyclopropyl-4H-1,2,4-triazol-3-yl)-cyclopropylcarbamoyl]-cyclopropyl}-amide (BI00659245, Kd=? nM, WB=12×)

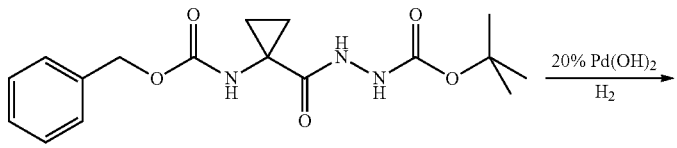

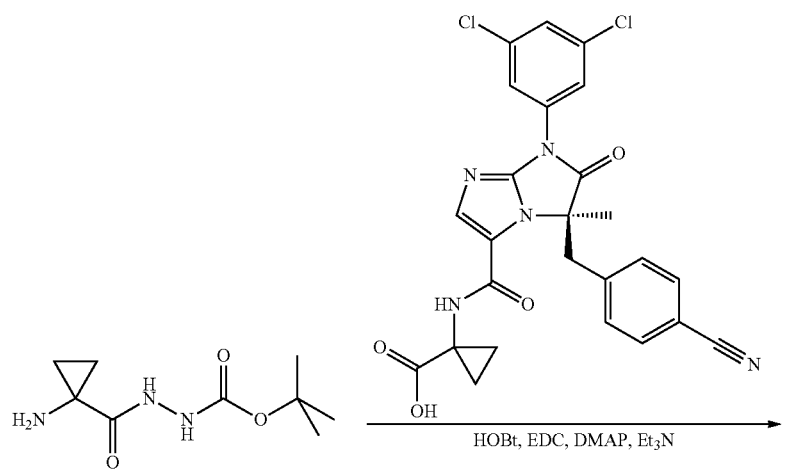

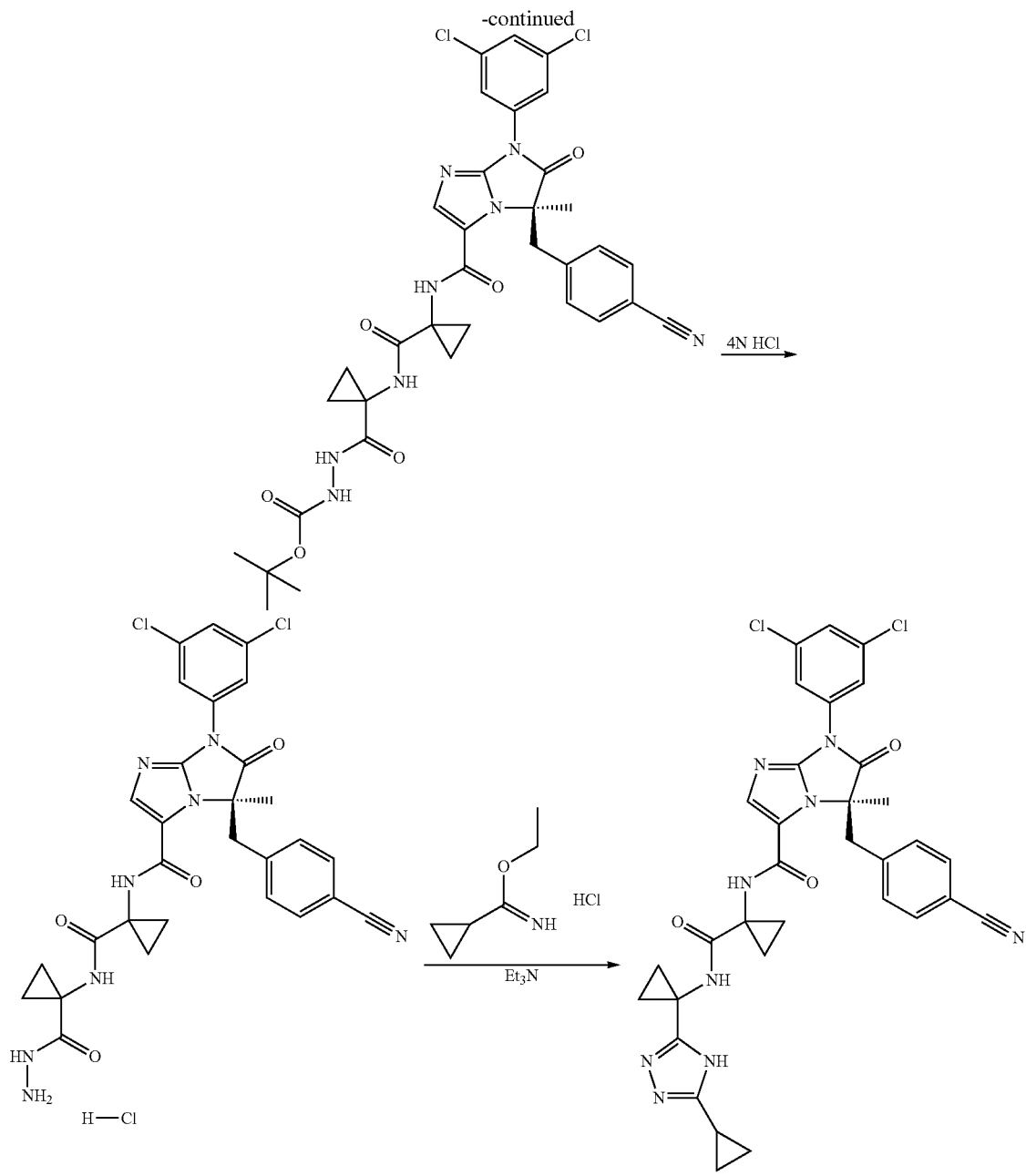

N'-(1-Benzyloxythiocabonylamino-cyclopropyl)-hydrazinecarboxylic acid tert-butyl ester (2.0 g, 5.72 mmol) was dissolved in MeOH (20 mL) and to this was suspended 20% Pd(OH)$_2$ (0.1 g). The reaction flask was sealed with a septum and purged with H$_2$. After 3 days under H$_2$ atmosphere, the mixture was filtered through a plug of diatomaceous earth and concentrated in vacuo to give N'-(1-amino-cyclopropanecarbonyl)-hydrazinecarboxylic acid tert-butyl ester (1.21 g, 98%) as a clear, colorless oil, m/z 215.5 [M+1]$^+$.

To a solution of 1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid (0.25 g, 0.48 mmol) in DMF (2 mL) was added HOAt (0.065 g, 0.48 mmol), EDC (0.092 g, 0.48 mmol), DMAP (0.005 g, 0.041 mmol), Et$_3$N (0.066 mL, 0.48 mmol). The reaction allowed to stir for 10 min at room temperature. To this mixture was added N'-(1-amino-cyclopropanecarbonyl)-hydrazinecarboxylic acid tert-butyl ester (0.10 g, 0.48 mmol) and the reaction was heated at 70° C. for 15 h. The mixture was cooled to room temperature, diluted with water and extracted with EtOAc (3×50 mL). The combined extracts were washed with saturated NaHCO$_3$, 2N HCl, brine and dried with MgSO$_4$. The mixture was filtered and concentrated in vacuo to give N'-{1-[(1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-amino]-cyclopropanecarbonyl}-hydrazinecarboxylic acid tert-butyl ester (0.33 g, 96%) as a yellow solid, m/z 721.9 [M+1]$^+$.

N'-{1-[(1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-amino]- cyclopropanecarbonyl}-hydrazinecarboxylic acid tert-butyl ester (0.30 g, 0.42 mmol) was dissolved in 4 N HCl in dioxane (3 mL) and allowed to stir at room temperature for 40 min. The resulting white suspension was diluted with $Et_2O$ and the precipitate was collected by filtration. The solid was washed twice with $Et_2O$ to give (R)-5-(4-cyano-benzyl)-7-(3,5-dichloro-phenyl)-5-methyl-6-oxo-6,7-dihydro-5H-imidazo-[1,2-a]imidazole-3-carboxylic acid [1-(1-hydrazinocarbonyl-cyclopropylcarbamoyl)-cyclopropyl]-amide hydrochloride (0.15 g, 52%) as a white powder, m/z 621.7 $[M+1]^+$.

Cyclopropanecarbonitrile (0.56 mL, 7.5 mmol) was dissolved in EtOH freshly saturated with HCl (20 mL) and the reaction allowed to stir at room temperature for 12 h. The solvent was removed under reduced pressure to give cyclopropanecarboximidic acid ethyl ester hydrochloride (0.55 g) as a white solid.

To a solution of (R)-5-(4-cyano-benzyl)-7-(3,5-dichloro-phenyl)-5-methyl-6-oxo-6,7-dihydro-5H-imidazo[1,2-a]imidazole-3-carboxylic acid [1-(1-hydrazinocarbonyl-cyclopropylcarbamoyl)-cyclopropyl]-amide hydrochloride (0.080 g, 0.12 mmol) and cyclopropanecarboximidic acid ethyl ester hydrochloride (0.018 g, 0.12 mmol) in DMF (1 mL) was added $Et_3N$ (0.051 mL, 0.37 mmol). The reaction was heated in a microwave at 140° C. for 45 min and then at 180° C. for 1.5 h. The mixture was cooled to room temperature and purified via reverse-phase HPLC to give (R)-5-(4-cyano-benzyl)-7-(3,5-dichloro-phenyl)-5-methyl-6-oxo-6,7-dihydro-5H-imidazo[1,2-a]imidazole-3-carboxylic acid {1-[1-(5-cyclopropyl-4H-1,2,4-triazol-3-yl)-cyclopropylcarbamoyl]-cyclopropyl}-amide (0.022 g, 28%) as a white solid, m/z 670.8 $[M+1]^+$.

Example 28

(R)-5-(4-Cyano-benzyl)-7-(3,5-dichloro-phenyl)-5-methyl-6-oxo-6,7-dihydro-5H-imidazo[1,2-a]imidazole-3-carboxylic acid [1-(1-thiazol-2-yl-cyclo-propylcarbamoyl)-cyclopropyl]-amide

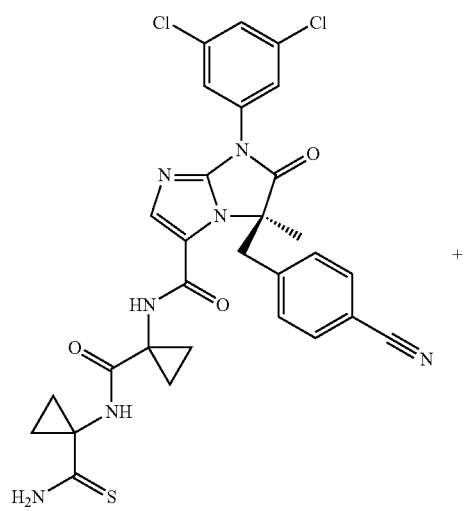

+

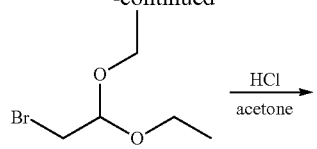

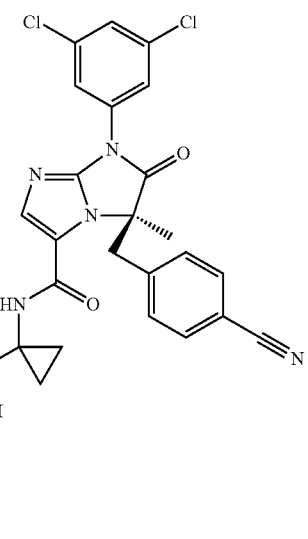

To a solution of (R)-5-(4-cyano-benzyl)-7-(3,5-dichloro-phenyl)-5-methyl-6-oxo-6,7-dihydro-5H-imidazo[1,2-a]imidazole-3-carboxylic acid [1-(1-thiocarbamoyl-cyclo-propylcarbamoyl)-cyclopropyl]-amide (92 mg, 0.15 mmol) in 1.5 mL of acetone was added bromoacetaldehyde diethyl acetal (0.089 mL, 0.59 mmol) and HCl in dioxane (4 M, 0.002 mL, 0.01 mmol). The reaction mixture was heated at reflux for 15 h, and then cooled to room temperature and concentrated in vacuo. The residue was dissolved in 25 mL of ethyl acetate and washed with 10 mL of saturated $NaHCO_3$ solution. The organic phase was washed with water and brine (10 mL each), dried over $Na_2SO_4$, filtered, and concentrated in vacuo to yield a pale brown oil. The crude product was purified by flash chromatography on silica gel (1-5% MeOH in $CH_2Cl_2$), to furnish 30 mg (31%) of the title compound as a pale brown foam, m/z 646.7 $[M+1]^+$.

The following compound was prepared using similar procedures as described above:

Compound 60, m/z 664.7 $[M+1]^+$

Example 29

(R)-7-(3,5-Dichloro-phenyl)-5-methyl-6-oxo-5-(4-trifluoromethoxy-benzyl)-6,7-dihydro-5H-imidazo[1,2-a]imidazole-3-carboxylic acid {1-[1-(6-amino-pyridin-2-yl)-cyclopropylcarbamoyl]-cyclopropyl}-amide

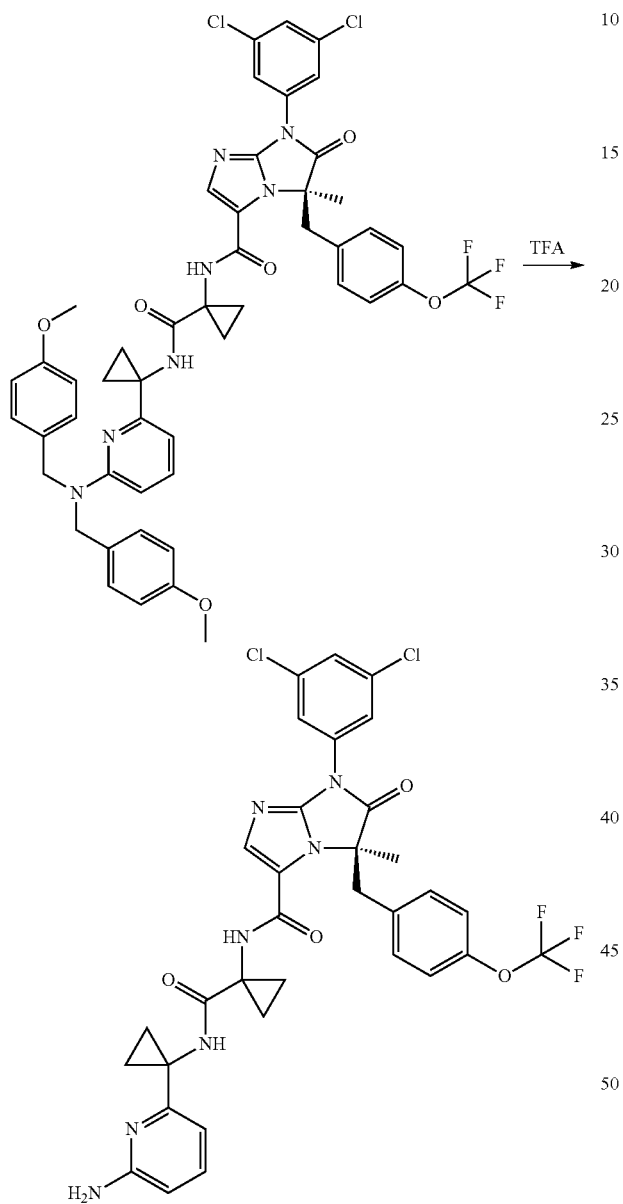

A solution of (R)-7-(3,5-dichloro-phenyl)-5-methyl-6-oxo-5-(4-trifluoromethoxy-benzyl)-6,7-dihydro-5H-imidazo[1,2-a]imidazole-3-carboxylic acid [1-(1-{6-[bis-(4-methoxy-benzyl)-amino]-pyridin-2-yl}-cyclopropylcarbamoyl)-cyclopropyl]-amide (80 mg, 0.084 mmol) in trifluoroacetic acid (2 mL) was stirred at room temperature for 4 h. The solvent was removed under a stream of $N_2$ and the residue was partitioned between EtOAc (4 mL) and saturated aqueous $NaHCO_3$ (4 mL). The layers were separated and the aqueous layer was further extracted with EtOAc (2×4 mL). The combined organics were evaporated in vacuo, and the residue was purified via reverse phase HPLC. The purified material was then passed through a basic amino group functionalized solid phase extraction cartridge to give 31 mg (51%) of the title compound as a white solid, m/z 715.0 $[M+2]^+$.

The following compounds were prepared using similar procedures as described above:
Compound 53, m/z 656.1 $[M+2]^+$

Example 30

(R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(4-aminomethyl-pyridin-2-yl)-cyclopropylcarbamoyl]-cyclopropyl}-amide

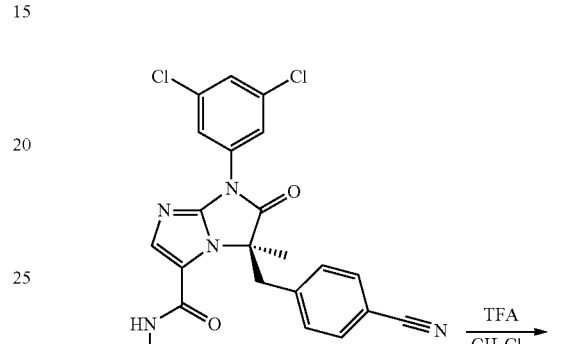

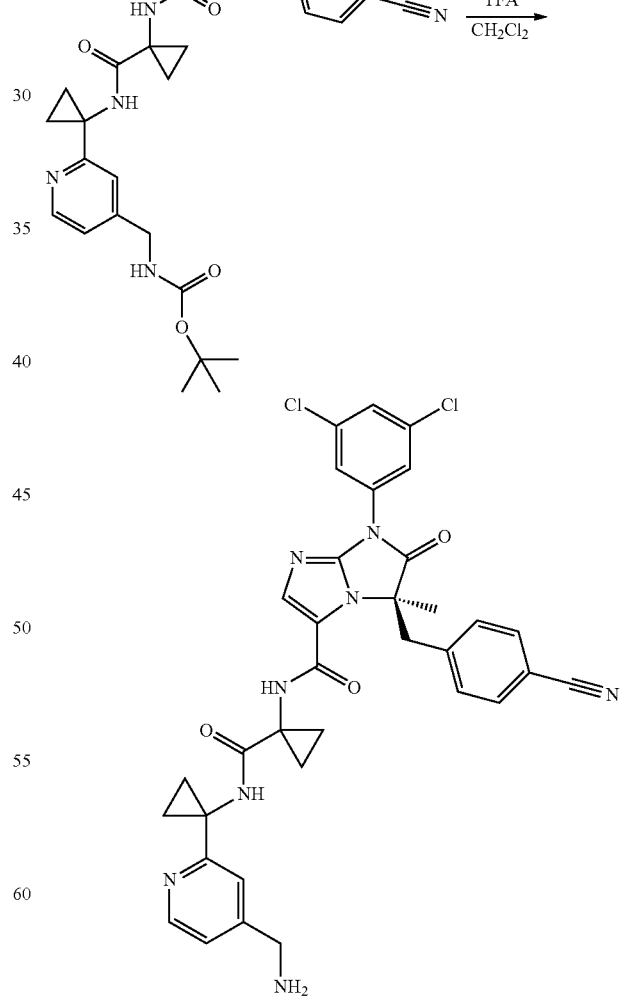

To a solution of (2-{1-[(1-{[(R)-5-(4-cyano-benzyl)-7-(3,5-dichloro-phenyl)-5-methyl-6-oxo-6,7-dihydro-5H-imidazo imidazole-3-carbonyl]-amino}-cyclopropane-carbonyl)-amino]-cyclopropyl}-pyridin-4-ylmethyl)-carbamic acid tert-butyl ester (45 mg, 0.22 mmol) in CH$_2$Cl$_2$ (5 mL) was added TFA (1 mL). The reaction mixture was stirred at room temperature for 16 h. Water (10 mL) was added and the resulting solution extracted with 5% MeOH/CH$_2$Cl$_2$ (3×20 mL). The organics were combined, dried and concentrated in vacuo. The residue was purified via reverse phase HPLC to afford (R)-5-(4-cyano-benzyl)-7-(3,5-dichloro-phenyl)-5-methyl-6-oxo-6,7-dihydro-5H-imidazo[1,2-a]imidazole-3-carboxylic acid {1-[1-(4-aminomethyl-pyridin-2-yl)-cyclopropyl-carbamoyl]-cyclopropyl}-amide as a solid, m/z 669.5 [M]$^+$.

The following compounds were prepared using similar procedures as described above:

Compound 43, m/z 728.5 [M]$^+$ Compound 63, m/z 687.7 [M+1]$^+$ (2-{1-[(1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-amino]-cyclopropyl}-pyridin-4-ylmethyl)-carbamic acid tert-butyl ester, m/z 769.6 [M]$^+$, (2-{1-[(1-{[(R)-5-(4-cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropanecarbonyl)-amino]-cyclopropyl}-pyridin-4-ylmethyl)-carbamic acid tert-butyl ester, and (2-{1-[(1-{[(R)-7-(3,5-dichloro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarbonyl)-amino]-cyclopropyl}-pyridin-4-ylmethyl)-carbamic acid tert-butyl ester were prepared using similar procedures as in Example 12.

Example 31

(R)-5-(4-Cyano-benzyl)-7-(3,5-dichloro-phenyl)-5-methyl-6-oxo-6,7-dihydro-5H-imidazo[1,2-a]imidazole-3-carboxylic acid [(S)-1-(1-pyrimidin-2-yl-cyclopropylcarbamoyl)-ethyl]-amide

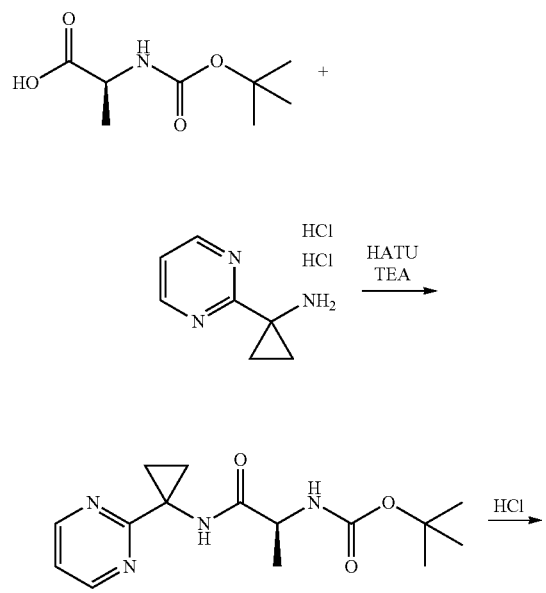

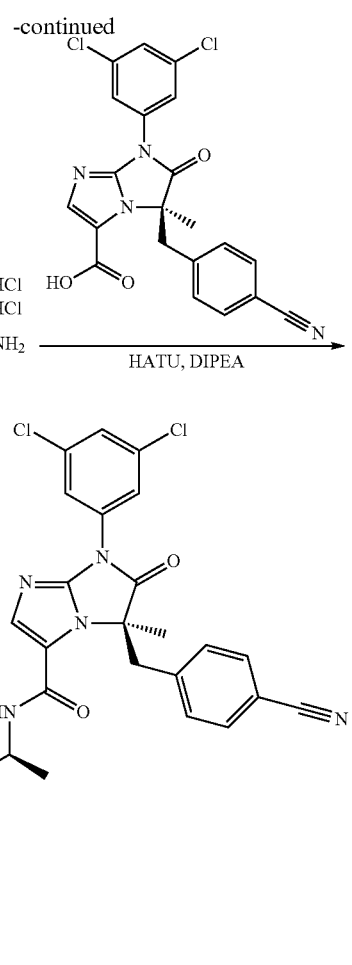

To a suspension of the (S)-2-tert-Butoxycarbonylamino-propionic acid (43 mg, 0.23 mmol), HATU (99 mg, 0.26 mmol), and 1-Pyrimidin-2-yl-cyclopropylamine dihydrochloride (45 mg, 0.22 mmol) in CH$_2$Cl$_2$ (1.5 mL) was added triethylamine (0.12 mL, 0.87 mmol). The reaction was stirred at room temperature for 22 h, diluted with CH$_2$Cl$_2$ (7 mL) and then washed with saturated aqueous NaHCO$_3$ (2×6 mL) and brine (1×6 mL). The organic phase was dried with MgSO$_4$ and concentrated to afford 54 mg of [(S)-1-(1-Pyrimidin-2-yl-cyclopropylcarbamoyl)-ethyl]-carbamic acid tert-butyl ester as white solid, m/z 307.56 [M+1]$^+$.

[(S)-1-(1-Pyrimidin-2-yl-cyclopropylcarbamoyl)-ethyl]-carbamic acid tert-butyl ester (54 mg, 0.18 mmol) was dissolved in CH$_2$Cl$_2$ (1 mL). HCl solution (4M in 1,4-dioxane, 1.5 mL, 6.0 mmol) was added via in one portion via syringe and the reaction was allowed to stir for 1.5 h. Solvents were removed in vacuo yielding (S)-2-Amino-N-(1-pyrimidin-2-yl-cyclopropyl)-propionamide as a white powder, m/z 207.41 [M+1]$^+$.

To a solution of (R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid (85 mg, 0.19 mmol) and (S)-2-Amino-N-(1-pyrimidin-2-yl-cyclopropyl)-propionamide (49 mg, 0.18 mmol) in THF (1.0 mL) and DMF (0.7 mL), was added HATU (80 mg, 0.21 mmol) followed by DIPEA (0.15 mL, 0.88 mmol). The reaction was stirred at room temperature for 20 h. The THF was removed under a stream of N$_2$ and the reaction mixture was purified by reverse phase HPLC. The purified material was then passed through a basic amino group functionalized solid phase extraction cartridge to give 80 mg of the title compound as a solid, m/z 647.34 [M+1]$^+$.

The following compounds were prepared using similar procedures as described above:

Compound 441, m/z 768.7 [M+1]$^+$
Compound 419, m/z 727.8 [M+1]$^+$
Compound 420, m/z 713.9 [M+1]$^+$
Compound 439, m/z 698.8 [M+1]$^+$ Compound 440, m/z 697.7 [M+1]$^+$
Compound 442, m/z 697.8 [M+1]$^+$
Compound 443, m/z 768.8 [M+1]$^+$
Compound 291, m/z 699.6 [M+1]$^+$
Compound 292, m/z 698.6 [M+1]$^+$
Compound 293, m/z 710.6 [M+1]$^+$
Compound 294, m/z 709.7 [M+1]$^+$
Compound 295, m/z 708.7 [M+1]$^+$
Compound 296, m/z 709.7 [M+1]$^+$ Compound 297, m/z 709.7 [M+1]$^+$ Compound 298, m/z 745.6 [M+1]$^+$ Compound 388, m/z 709.6 [M+1]$^+$ Compound 397, m/z 709.7 [M+1]$^+$
Compound 402, m/z 739.6 [M+1]$^+$ Compound 403, m/z 663.3 [M+1]$^+$
Compound 404, m/z 677.6 [M+1]$^+$ Example 32

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid {1-[1-(1-oxy-pyridazin-3-yl)-cyclopropylcarbamoyl]-cyclopropyl}-amide

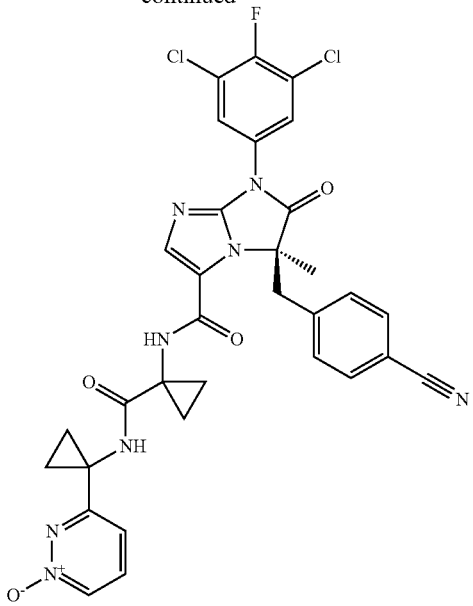

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid [1-(1-pyridazin-3-yl-cyclopropylcarbamoyl)-cyclopropyl]-amide (10 mg, 0.015 mmol) was dissolved in CH$_2$Cl$_2$ at 0° C. in an ice bath. mCPBA (7 mg, 0.03 mmol) was added as a solid in one portion. After 40 min the solvent was removed under a stream of N$_2$ and the resulting solid purified by reversed phase HPLC (30→95% MeCN/H$_2$O+0.1% TFA) to give 7 mg of the title compound as an off-white powder, m/z 675.64 [M+1]$^+$.

Example 33

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid (1-{1-[6-(1-amino-1-methyl-ethyl)-pyridazin-3-yl]-cyclopropylcarbamoyl}-cyclopropyl)-amide trifluoroacetate

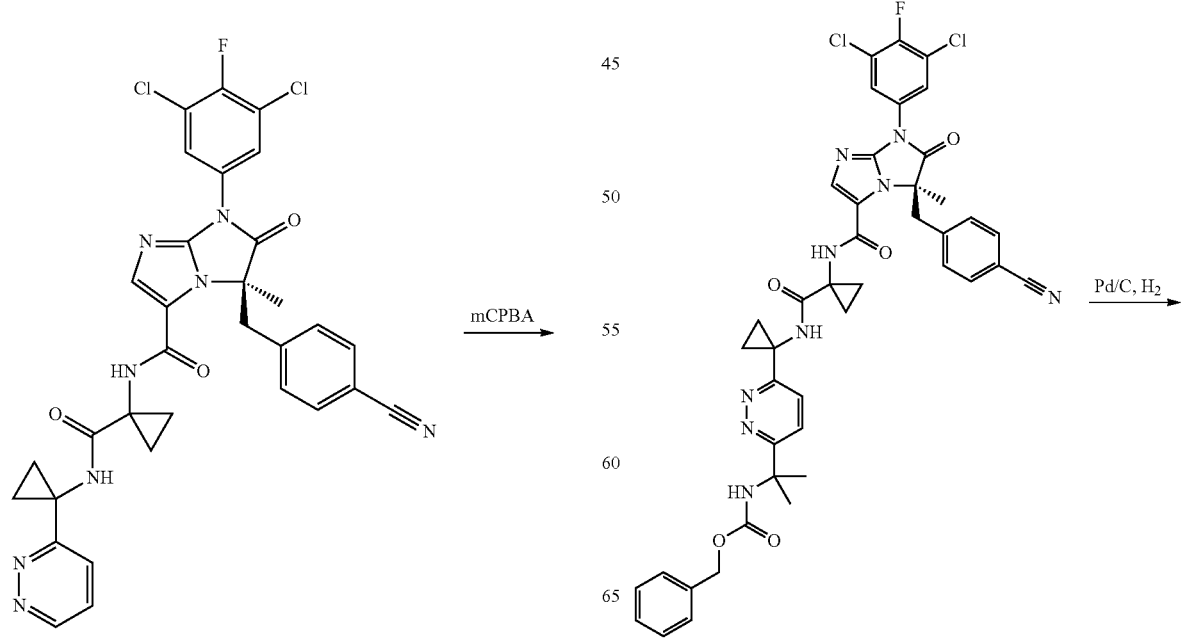

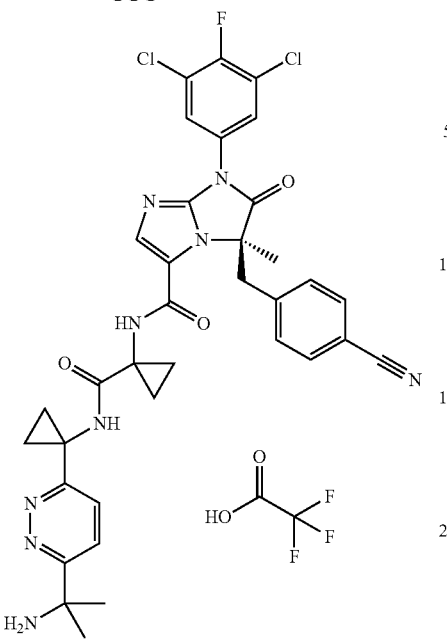

[1-(6-{1-[(1-{[(R)-5-(4-Cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropanecarbonyl)-amino]-cyclopropyl}-pyridazin-3-yl)-1-methyl-ethyl]-carbamic acid benzyl ester (64 mg, 0.075 mmol) was dissolved in a mixture of MeOH (0.32 mL) and $CH_2Cl_2$ (3.2 mL). Pd/C (10 wt %, 3 mg, 0.002 mmol) was added and a $H_2$ balloon was affixed to the reaction flask. The reaction was evacuated and flushed with $H_2$ three times and then stirred under $H_2$ (1 atm) for 6 h. The suspension was filtered through a plug of diatomaceous earth and concentrated to give a pale yellow oily residue. The residue was purified by reversed phase HPLC (30→60% $MeCN/H_2O$+0.1% TFA) to provide, after lyophilization, 10 mg of the title compound as white powder, m/z 716.72 $[M+1]^+$.

Example 34

1-{[(R)-7-(3,5-dichloro-phenyl)-5-(4-iodo-benzyl)-5-methyl-6-oxo-6,7-dihydro-5H-imidazo[1,2-a]imidazole-3-carbonyl]-amino}-cyclopropanecarboxylic acid allyl ester

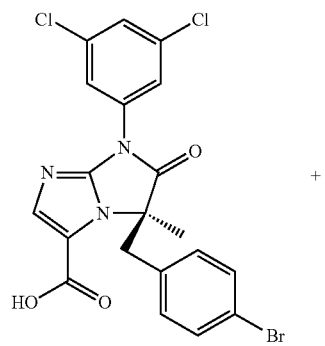

+

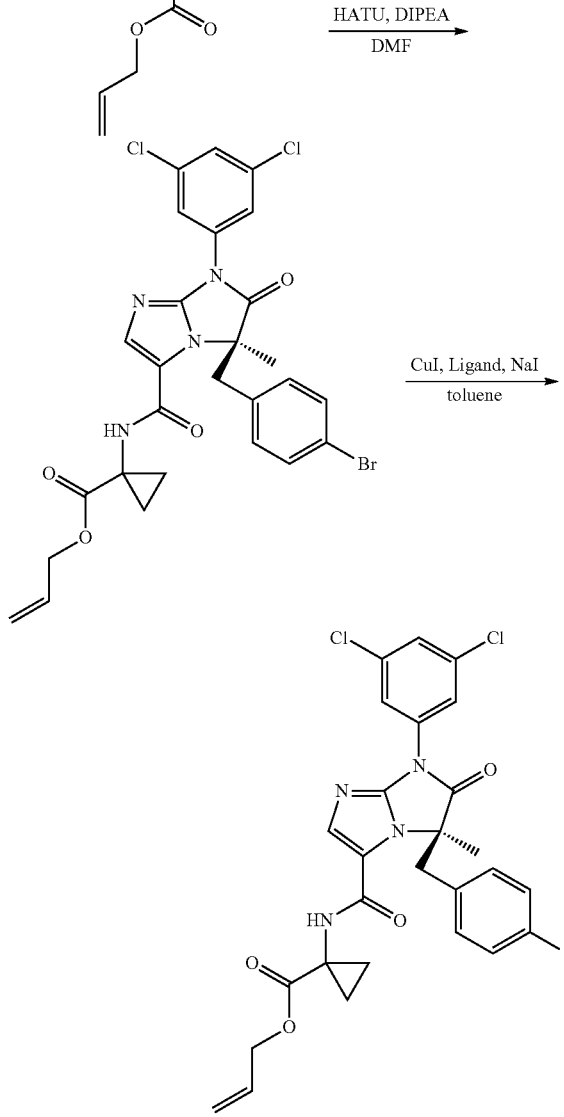

To a suspension of (R)-5-(4-bromo-benzyl)-7-(3,5-dichloro-phenyl)-5-methyl-6-oxo-6,7-dihydro-5H-imidazo[1,2-a]imidazole-3-carboxylic acid (1.00 g, 2.02 mmol) and 1-amino-cyclopropanecarboxylic acid allyl ester hydrochloride (430 mg, 2.42 mmol) in 6 mL of DMF at room temperature was added diisopropylethylamine (1.05 mL, 6.06 mmol), and the reaction mixture (became mostly clear) was stirred for 10 min. HATU (845 mg, 2.22 mmol) was then added, and the clear yellow reaction mixture was stirred at room temperature for 21 h. The reaction mixture was partitioned between 150 mL of ethyl acetate and 50 mL of 1 M HCl. The organic phase was washed with satd. $NaHCO_3$ solution, water (2×), and brine, dried over $Na_2SO_4$, filtered, and concentrated. The residue was purified by flash chromatography on silica gel (50 g, 10-30% EtOAc in hexanes), to furnish 1.16 g of 1-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid allyl ester (93%) as a colorless foam.

An 8-mL vial was charged with the 1-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid allyl ester (350 mg, 0.566 mmol), sodium iodide (170 mg, 1.13 mmol), CuI (16 mg, 0.08 mmol), (1R,2R)—N,N'-dimethyl-cyclohexane-1,2-diamine
(24 mg, 0.17 mmol), and 0.5 mL of toluene, and the vial was purged with N₂. The reaction mixture was heated at reflux for 18 h. The reaction mixture was filtered through a plug of silica gel topped with Celite, washing with ethyl acetate, and then concentrated to a dark green oil. The residue was dissolved in CH₂Cl₂ and filtered through a small plug of silica gel, washing with CH₂Cl₂. The clear orange filtrates were concentrated to a pale orange/yellow foam. The crude was purified by flash chromatography on silica gel (20 g, 15-40% EtOAc/hexanes) to provide 271 mg (72%) of 1-{[(R)-7-(3,5-dichloro-phenyl)-5-(4-iodo-benzyl)-5-methyl-6-oxo-6,7-dihydro-5H-imidazo[1,2-a]imidazole-3-carbonyl]-amino}-cyclopropanecarboxylic acid allyl ester as a colorless foam.

Example 35

1-{[(R)-7-(3,5-dichloro-phenyl)-5-methyl-6-oxo-5-(4-1,2,4-triazol-1-yl-benzyl)-6,7-dihydro-5H-imidazo[1,2-a]imidazole-3-carbonyl]-amino}-cyclopropane-carboxylic acid

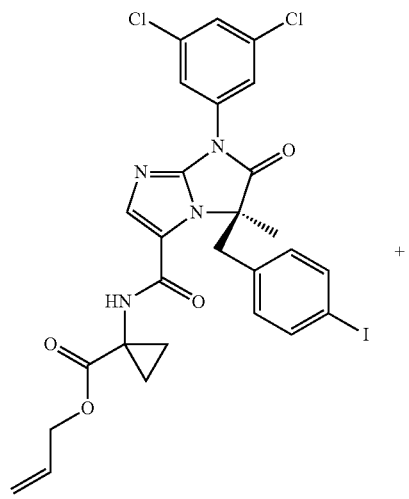

+

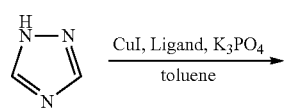

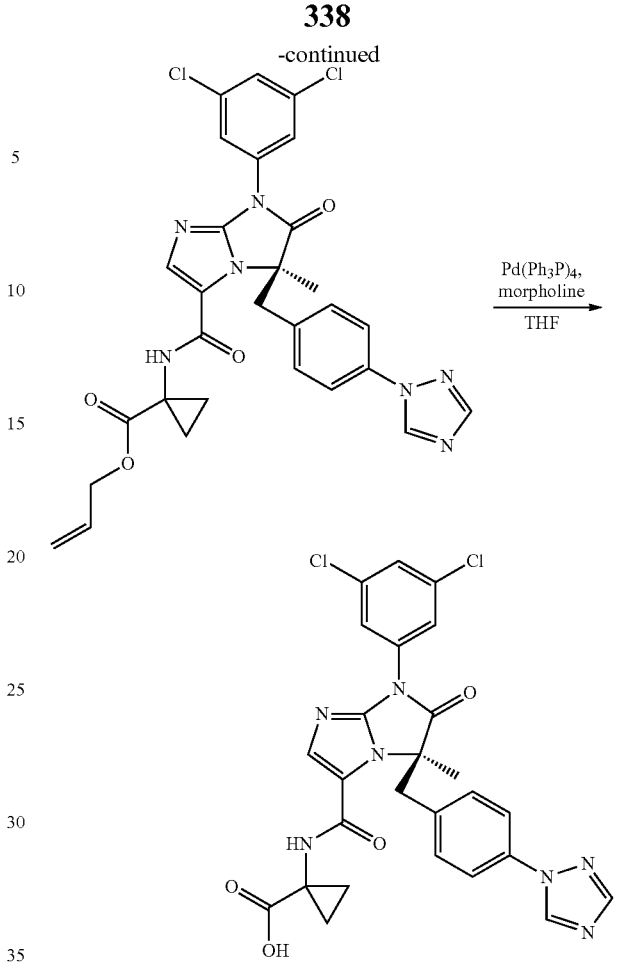

An 8-mL vial was charged with 1-{[(R)-7-(3,5-dichloro-phenyl)-5-(4-iodo-benzyl)-5-methyl-6-oxo-6,7-dihydro-5H-imidazo[1,2-a]imidazole-3-carbonyl]-amino}-cyclopropanecarboxylic acid allyl ester (251 mg, 0.377 mmol), 1,2,4-triazole (39 mg, 0.57 mmol), and (1R,2R)—N,N'-dimethyl-cyclohexane-1,2-diamine (16 mg, 0.11 mmol), K₃PO₄ (160 mg, 0.76 mmol), and 0.5 mL of DMF. The vial was purged with N₂ and sealed with a screw cap. The green reaction mixture was heated at reflux for 20 h. The reaction mixture was cooled to room temperature, diluted with 3 mL of EtOAc, and filtered through a small plug of Celite, washing with 20 mL of ethyl acetate. The filtrates were washed with 3×10 mL of water and 10 mL of brine, dried over Na₂SO₄, filtered, and concentrated. The crude was purified by flash chromatography on silica gel (20 g, 0-3% MeOH/CH₂Cl₂) to provide 109 mg (48%) of 1-{[(R)-7-(3,5-dichloro-phenyl)-5-methyl-6-oxo-5-(4-1,2,4-triazol-1-yl-benzyl)-6,7-dihydro-5H-imidazo[1,2-a]imidazole-3-carbonyl]-amino}-cyclopropanecarboxylic acid allyl ester as a pale orange foam.

To a solution of 1-{[(R)-7-(3,5-dichloro-phenyl)-5-methyl-6-oxo-5-(4-1,2,4-triazol-1-yl-benzyl)-6,7-dihydro-5H-imidazo[1,2-a]imidazole-3-carbonyl]-amino}-cyclopropanecarboxylic acid allyl ester (109 mg, 0.18 mmol) and morpholine (0.157 mL, 1.80 mmol) in 1 mL of THF was added Pd(Ph₃P)₄ (10 mg, 0.009 mmol). The reaction mixture was stirred at room temperature for 3 h. The reaction mixture was then diluted with 30 mL of EtOAc and washed with 10 mL each of 10% HCl solution, water, and brine, dried over Na₂SO₄, filtered, and concentrated to afford 114 mg of 1-{[(R)-7-(3,5-dichloro-phenyl)-5-methyl-6-oxo-5-(4-1,2,4- triazol-1-yl-benzyl)-6,7-dihydro-5H-imidazo[1,2-a]imidazole-3-carbonyl]-amino}-cyclopropanecarboxylic acid as an orange oily solid that was carried to the next step without further purification.

The following compounds were prepared using similar procedures as described above:

1-{[(R)-7-(3,5-Dichloro-phenyl)-5-methyl-6-oxo-5-(4-1,2,3-triazol-1-yl-benzyl)-6,7-dihydro-5H-imidazo[1,2-a]imidazole-3-carbonyl]-amino}-cyclopropanecarboxylic acid 1-{[(R)-7-(3,5-Dichloro-phenyl)-5-methyl-6-oxo-5-(4-1,2,3-triazol-2-yl-benzyl)-6,7-dihydro-5H-imidazo[1,2-a]imidazole-3-carbonyl]-amino}-cyclopropanecarboxylic acid Example 36

1-{[(R)-5-(4-Chloro-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid

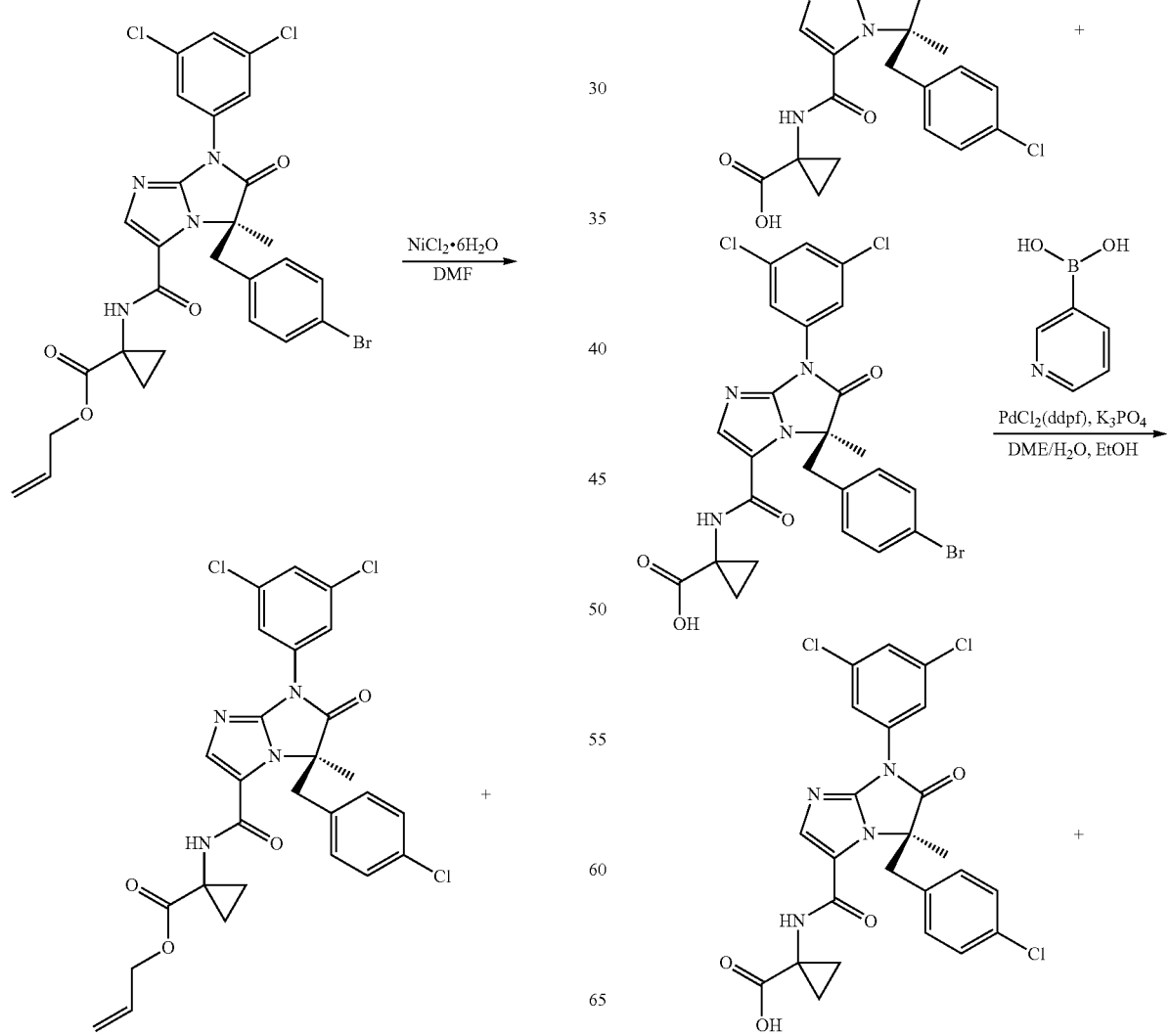

-continued

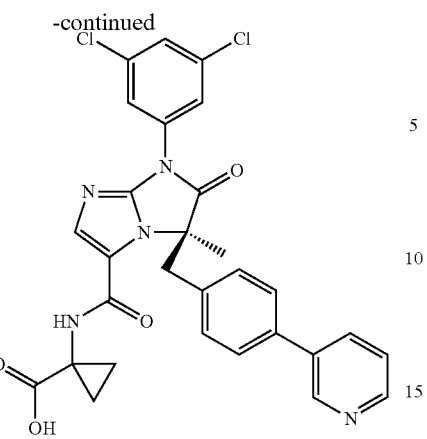

A microwave vial was charged with 1-{[(R)-5-(4-bromo-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid allyl ester (400 mg, 0.647 mmol), NiCl$_2$.6H$_2$O (231 mg, 1.22 mmol), and 1.5 mL of DMF. The vial was sealed and heated in the microwave at 170° C. for 40 min, and then for 1 h. The crude reaction mixture was diluted with 30 mL of EtOAc and 15 mL of water (the solids were not soluble). The aqueous phase was extracted with 10 mL of EtOAc. The combined organics were washed with 5% NaCl solution (2×15 mL) and brine, dried over Na$_2$SO$_4$, filtered, and concentrated to afford 299 mg of a cloudy green oil, isolated as a ~1:1 mixture of product to starting material.

To a solution of the crude allyl esters (299 mg, ~0.25 mmol) and morpholine (0.436 mL, 5.0 mmol) in 3 mL of THF was added Pd(Ph$_3$P)$_4$ (29 mg, 0.0259 mmol). The reaction mixture was stirred at room temperature for 2 h. The reaction mixture was then diluted with 30 mL of EtOAc and washed with 10 mL each of 10% HCl solution, water, and brine, dried over Na$_2$SO$_4$, filtered, and concentrated. The crude product was isolated as a ~1:1 mixture of chloro to bromo acids and was carried to the next step without further purification.

The crude bromide/chloride acid mixture (~0.25 mmol) was concentrated in a microwave vial. To this mixture was added 3-pyridyl boronic acid (45 mg, 0.37 mmol), PdCl$_2$(dppf) (20 mg, 0.024 mmol), 4 mL of DME/H$_2$O/EtOH (7/3/2), and aqueous K$_3$PO$_4$ solution (0.730 mL, 1 M, 0.73 mmol). The vial was sealed and heated in the microwave at 100° C. for 15 min, followed by heating at 130° C. for an additional 30 min. The reaction mixture was then filtered through a plug of silica gel, washing with 10 mL of MeOH, and concentrated. The residue was diluted with 30 mL of EtOAc and washed with 10 mL each of 10% HCl solution, water, and brine, dried over Na$_2$SO$_4$, filtered, and concentrated. The crude oil was dissolved in DMSO/CH$_3$CN/H$_2$O (1:2:1, 1.2 mL) and purified by reverse-phase HPLC (40-95% CH$_3$CN/H$_2$O, 0.1% TFA). Concentration of the product fractions by Genevac afforded 52 mg (~40%) of 1-{[(R)-5-(4-chloro-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid.

Example 37

Phosphoric acid mono-[(S)-2-{[(R)-5-(4-cyano-benzyl)-7-(3,5-dichloro-4-fluoro-phenyl)-5-methyl-6-oxo-6,7-dihydro-5H-imidazo[1,2-a]imidazole-3-carbonyl]-amino}-2-(1-methyl-1-pyridin-2-yl-propylcarbamoyl)-ethyl]ester

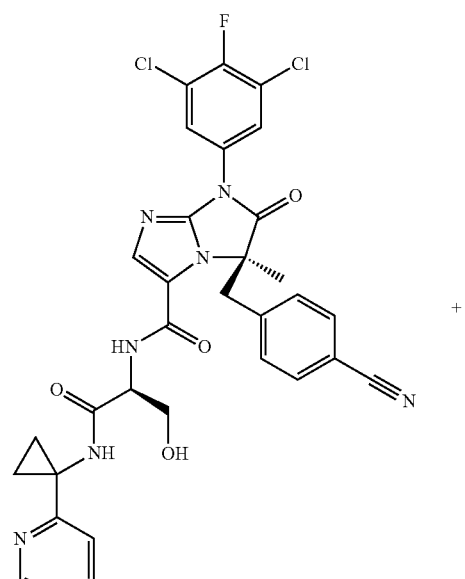

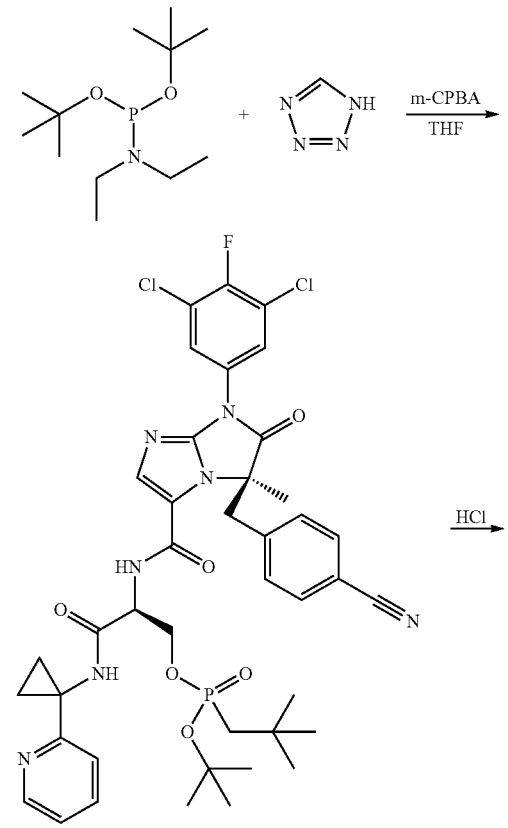

343
-continued

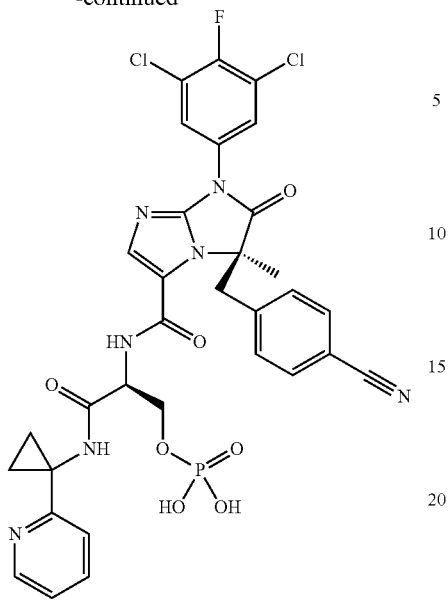

To a solution of (R)-5-(4-cyano-benzyl)-7-(3,5-dichloro-4-fluoro-phenyl)-5-methyl-6-oxo-6,7-dihydro-5H-imidazo[1,2-a]imidazole-3-carboxylic acid [(S)-2-hydroxy-1-(1-pyridin-2-yl-cyclopropylcarbamoyl)-ethyl]-amide (99 mg, 0.15 mmol) and di-tert-butyl-N,N-diethylphosphoramidite (0.107 mL, 0.359 mmol) in 1 mL of THF at 0° C. was added 1H-tetrazole (21 mg, 0.30 mmol). The reaction mixture was warmed to room temperature and stirred for 3 h. The reaction mixture was cooled to 0° C., and a solution of m-CPBA (60 mg, 0.27 mmol) in 1 mL of dichloromethane was then added rapidly dropwise. The reaction mixture was warmed to room temperature and stirred for 3 h. The reaction mixture was quenched with 4 mL of 10% NaHSO$_3$ solution and stirred for 10 min, then extracted with 40 mL of EtOAc. The organic phase was washed with 10 mL each of satd. NaHCO$_3$ solution, water, and brine, dried over Na$_2$SO$_4$, filtered, and concentrated to furnish a clear oil. The crude was purified by flash chromatography on silica gel (10 g, 1-6% MeOH/CH$_2$Cl$_2$) to afford product 101158-038-a. The isolated product was contaminated with unreacted phosphoramidite and was repurified by reverse-phase HPLC (50-100% CH$_3$CN/H$_2$O, 0.1% TFA) to give phosphoric acid di-tert-butyl ester (S)-2-{[(R)-5-(4-cyano-benzyl)-7-(3,5-dichloro-4-fluoro-phenyl)-5-methyl-6-oxo-6,7-dihydro-5H-imidazo[1,2-a]imidazole-3-carbonyl]-amino}-2-(1-methyl-1-pyridin-2-yl-propylcarbamoyl)-ethyl ester as a colorless oil.

A solution of the phosphate ester (~0.15 mmol) in 1 mL of CH$_2$Cl$_2$ was treated with HCl in dioxane (0.100 mL, 4 M, 0.400 mmol). A few drops of MeOH were added to aid solubility. The reaction mixture was stirred at room temperature for 24 h. Ether (4 mL) was added, and a white precipitate formed. The reaction mixture was filtered, washing with 10 mL of ether, to provide 67 mg of a pale yellow solid. The product was purified by reverse-phase HPLC (40% CH$_3$CN/H$_2$O, 0.1% TFA) to give 33 mg (26%, two steps) of the title compound as a white solid, isolated as the TFA salt, m/z 742.9 [M+1]$^+$.

Example 38

(S)-4-{[(R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carbonyl]-amino}-4-(1-methyl-1-pyridin-2-yl-propylcarbamoyl)-butyric acid

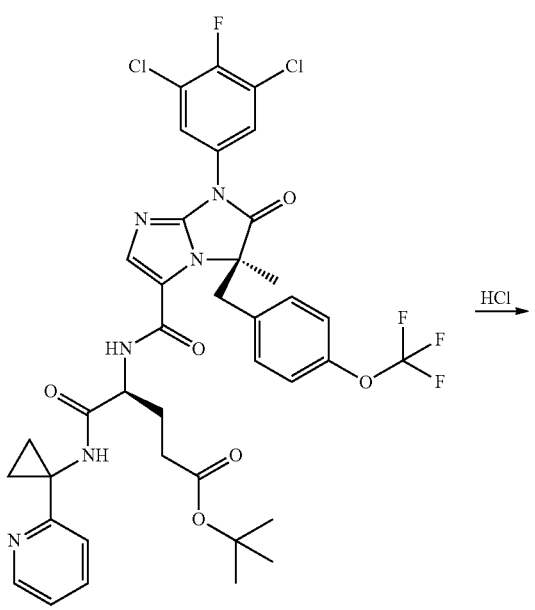

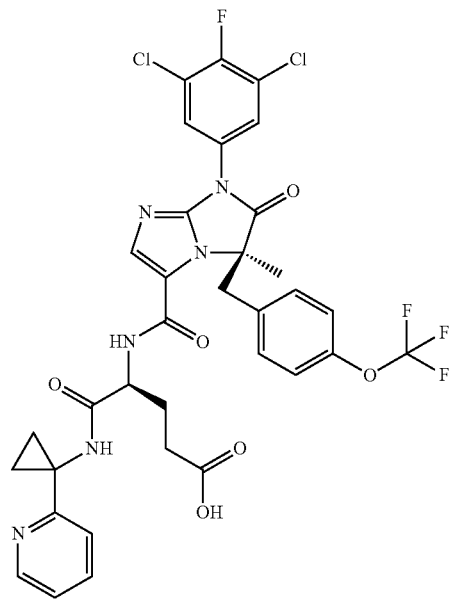

To a solution of (S)-4-{[(R)-7-(3,5-dichloro-4-fluoro-phenyl)-5-methyl-6-oxo-5-(4-trifluoromethoxy-benzyl)-6,7-dihydro-5H-imidazo[1,2-a]imidazole-3-carbonyl]-amino}-4-(1-methyl-1-pyridin-2-yl-propylcarbamoyl)-butyric acid tert-butyl ester (116 mg, 0.142 mmol) in 2 mL of CH₂Cl₂ was added HCl in dioxane (0.177 mL, 0.708 mmol). The reaction mixture was stirred at room temperature for 6 h. An additional portion of HCl in dioxane (0.177 mL, 0.708 mmol) was added, and the reaction mixture was stirred for 4 h and then concentrated to a colorless oil. The residue was purified by reverse-phase HPLC (20-90% CH₃CN/H₂O, 0.1% TFA) to give 45 mg (42%) of the title compound, isolated as the TFA salt, m/z 763.8 [M+1]⁺.

The following compound was prepared using similar procedures as described above:

Compound 451, m/z 704.7 [M+1]⁺

Example 39

(R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(4-methanesulfonylamino-pyridin-2-yl)-cyclopropylcarbamoyl]-cyclopropyl}-amide,

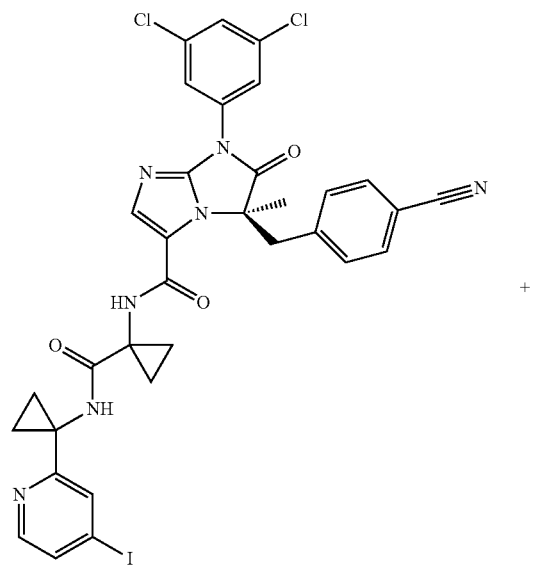

+

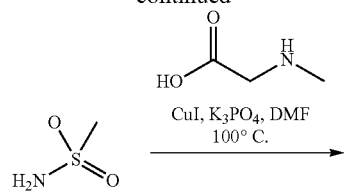

-continued

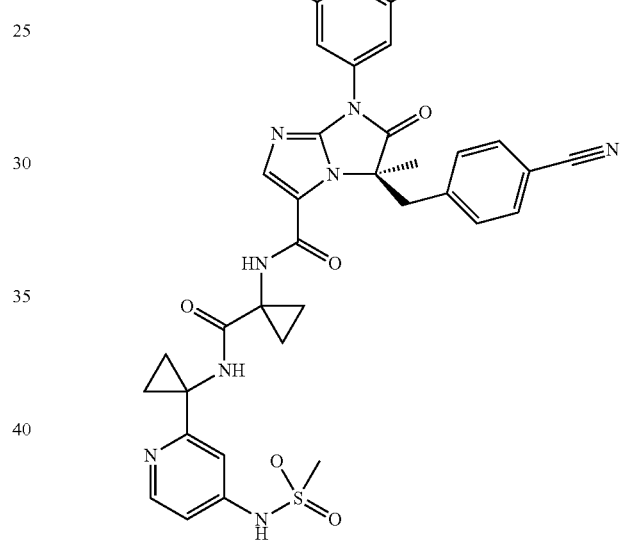

(R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(4-iodo-pyridin-2-yl)-cyclopropylcarbamoyl]-cyclopropyl}-amide (50 mg, 0.065 mmol), methanesulfonamide (7.4 mg, 0.078 mmol), sarcosine (1.2 mg, 0.13 mmol), copper (I) iodide 0.76 mg, 0.004 mmol) and potassium phosphate (33.9 mg, 0.126 mmol) were combined in a Biotage microwave tube and flushed with Ar. The reaction was diluted with DMF and sealed.

The reaction was heated in a Biotage microwave at 100° C. for 1.5 h. The reaction was diluted with EtOAc and water. The layers were separated and the aqueous layer was extracted with EtOAc. The combined organic layers were washed with water and brine, dried over MgSO₄, filtered and concentrated to yield 36 mg of a colorless oil. The oil was dissolve in DMSO (1.0 mL) and purified via reverse phase HPLC and yielded 13 mg of the title compound as a white solid, m/z 733.6 [M+1]⁺.

Example 40

(R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(4-cyano-pyridin-2-yl)-cyclopropylcarbamoyl]-cyclopropyl}-amide

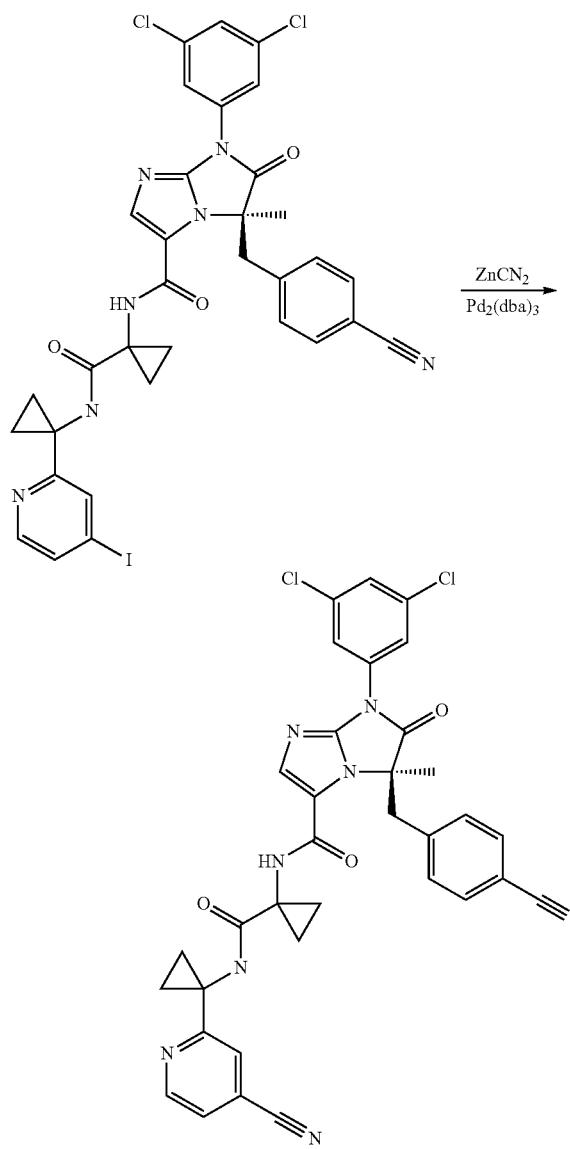

A solution of (R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(4-iodo-pyridin-2-yl)-cyclopropylcarbamoyl]-cyclopropyl}-amide (0.1 g, 0.13 mmol) in DMF (5 mL) was degassed with a stream of N₂ for 1 h. ZnCN₂ (0.015 g, 0.13 mmol) was added followed by Pd₂dba₃ (0.0012 g, 0.013 mmol) and dppf (0.0072 g, 0.13 mmol). The reaction was heated at 120° C. for 2 h. The mixture was cooled to room temperature and the solvent removed under reduced pressure. The residue was partitioned between EtOAc (400 mL) and water (300 mL). The organics were washed with brine and dried over Na₂SO₄. The mixture was filtered, concentrated and purified by reverse phase HPLC to give (R)-5-(4-cyano-benzyl)-7-(3,5-dichloro-phenyl)-5-methyl-6-oxo-6,7-dihydro-5H-imidazo[1,2-a]imidazole-3-carboxylic acid {1-[1-(4-cyano-pyridin-2-yl)-cyclopropylcarbamoyl]-cyclopropyl}-amide (0.051 g, 0.077 mmol) as a brown solid, m/z 665.7 [M+1]⁺.

Example 41

(R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(4-azetidin-1-ylmethyl-pyridin-2-yl)-cyclopropylcarbamoyl]-cyclopropyl}-amide

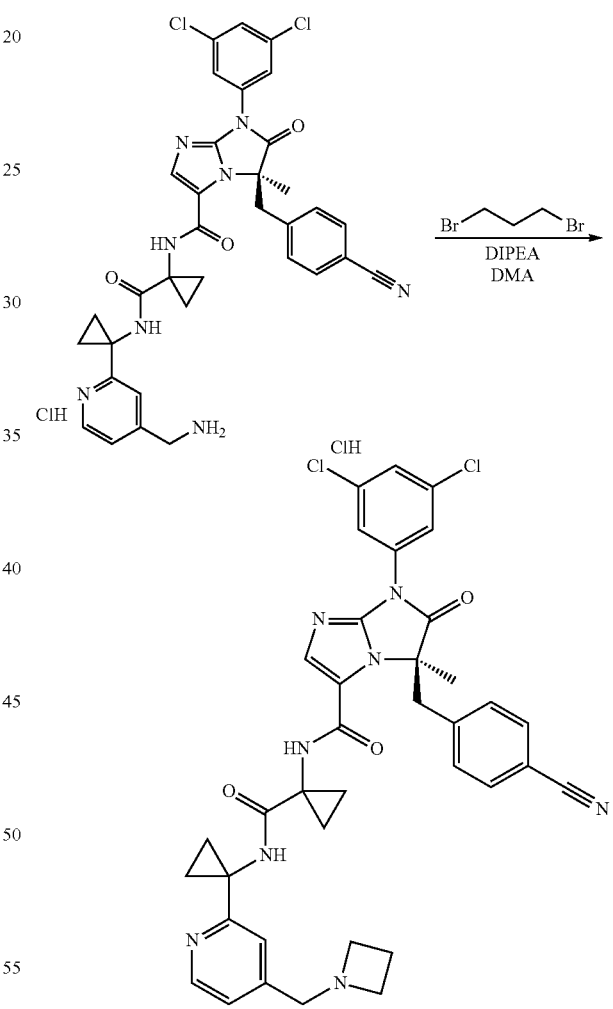

To the solution of (R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(4-aminomethyl-pyridin-2-yl)-cyclopropylcarbamoyl]-cyclopropyl}-amide dihydrochloric acid salt (60 mg, 0.081 mmol) in dry DMA (5 mL) was added DIPEA (0.071 mL, 0.405 mmol) followed by 1,3-dibromopropane (0.0415 mL, 0.405 mmol). The reaction mixture was heated in the microwave at 100° C. for 2×10 min. Diluted with EtOAc (50 mL). Washed with saturated NaHCO₃ (2×25 mL). Layers were separated. The organic layer was dried, filtered, and concentrated. The resultant crude product was purified by prep-TLC using 5% MeOH/DCM as the eluent. The prep TLC plate looked messy, presumably due to the significant existence of DMA. The product fraction was collected and redissolved in EtOAc (50 mL), washed with water (3×15 mL), dried, filtered, and concentrated. The crude product was purified by prep-TLC using 5% MeOH/DCM as the eluent to afford 7.5 mg of the title compound as a light yellow solid, m/z 709.8 [M+1]$^+$.

The following compound was prepared using similar procedures as described above:
Compound 425, m/z 725.7 [M+1]$^+$.

Example 42

(R)-5-(4-Cyano-benzyl)-7-(3,5-dichloro-phenyl)-5-methyl-6-oxo-6,7-dihydro-5H-imidazo[1,2-a]imidazole-3-carboxylic acid (1-{1-[4-(acetylamino-methyl)-pyridin-2-yl]-cyclopropylcarbamoyl}-cyclopropyl)-amide

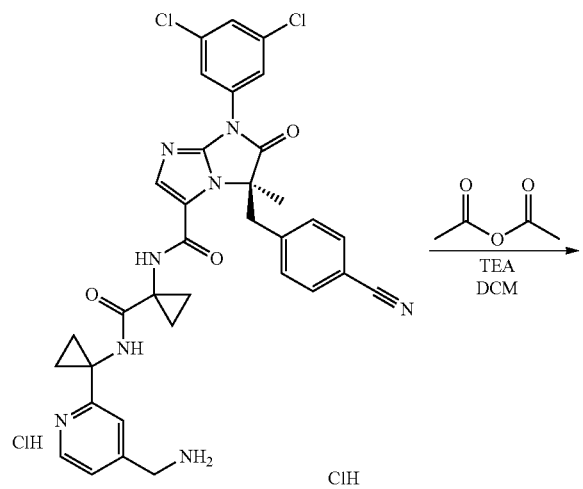

(R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(4-aminomethyl-pyridin-2-yl)-cyclopropylcarbamoyl]-cyclopropyl}-amide dihydrochloric acid salt (40 mg, 0.0539 mmol) was suspended in DCM (1 mL). TEA (0.038 mL, 0.269 mmol) was then added and the reaction mixture became homogeneous. Acetic anhydride (0.00624 mL, 0.0646 mmol) was then added. Stirred for 5 min. Solvent was evaporated. The resultant crude product was purified by reverse phase HPLC using 30-100% ACN/water as the gradient. Solvent was evaporated. The product was redissolved in 10% MeOH/DCM and filtered through a basic (NH$_2$) cartridge. Solvent was evaporated to afford 24 mg of the title compound as a white solid, m/z 711.7 [M+1]$^+$.

The following compounds were prepared using similar procedures as described above:

Compound 431, m/z 711.7 [M+1]$^+$.
Compound 427, m/z 747.6 [M+1]$^+$.
Compound 433, m/z 747.6 [M+1]$^+$. Compound 436, m/z 773.6 [M+1]$^+$.
Compound 437, m/z 765.7 [M+1]$^+$. Compound 438, m/z 791.7 [M+1]$^+$. Compound 432, m/z 712.7 [M+1]$^+$. Compound 428, m/z 712.7 [M+1]$^+$.

Example 43

(R)-5-(4-Cyano-benzyl)-7-(3,5-dichloro-phenyl)-5-methyl-6-oxo-6,7-dihydro-5H-imidazo[1,2-a]imidazole-3-carboxylic acid [1-(1-{4-[(cyclopropanecarbonyl-amino)-methyl]-pyridin-2-yl}-cyclopropylcarbamoyl)-cyclopropyl]-amide

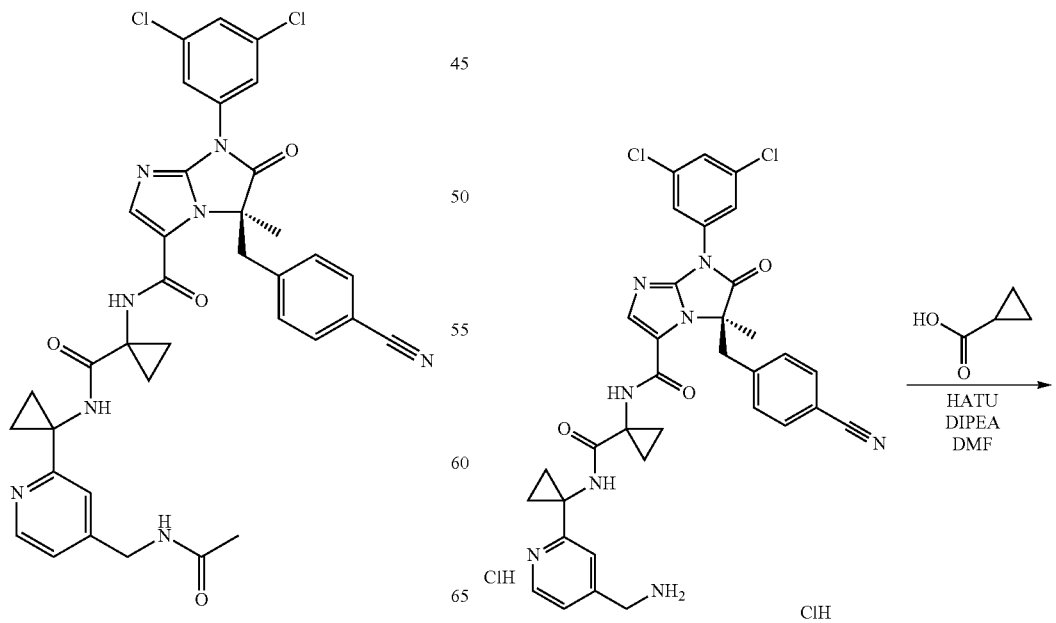

351
-continued

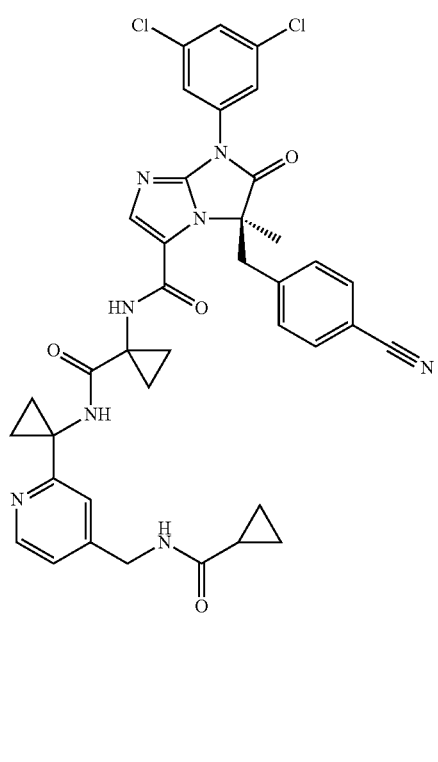

Cyclopropanecarboxylic acid (0.00903 mL, 0.108 mmol) and HATU (25.605 mg, 0.0673 mmol) were dissolved in dry DMF (1 mL). Stirred for 5 min. To this solution was added (R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(4-aminomethyl-pyridin-2-yl)-cyclopropylcarbamoyl]-cyclopropyl}-amide dihydrochloric acid salt (40 mg, 0.0539 mmol) followed by DIPEA (0.038 mL, 0.215 mmol). Stirred at room temperature for 30 min. Diluted with ACN (1 mL) and water (1 mL) and filtered. The crude product was purified by reverse phase HPLC using 20-95% ACN/water as the gradient. Solvent was evaporated. The resultant product was redissolved in 10% MeOH/DCM and filtered through a basic (NH$_2$) cartridge. Solvent was evaporated to afford 28.1 mg of the title compound as a white solid, m/z 737.7 [M+1]$^+$.

The following compounds were prepared using similar procedures as described above:

Compound 430, m/z 753.7 [M+1]$^+$.
Compound 434, m/z 737.6 [M+1]$^+$.
Compound 435, m/z 753.7 [M+1]$^+$.

352

Example 44

(R)-5-(4-Cyano-benzyl)-7-(3,5-dichloro-phenyl)-5-methyl-6-oxo-6,7-dihydro-5H-imidazo[1,2-a]imidazole-3-carboxylic acid [1-(1-{4-[(cyclopropanecarbonyl-amino)-methyl]-pyridin-2-yl}-cyclopropylcarbamoyl)-cyclopropyl]-amide

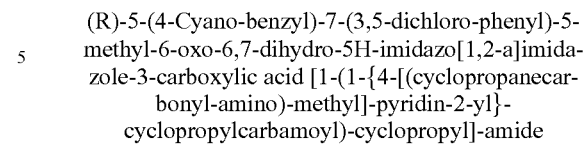

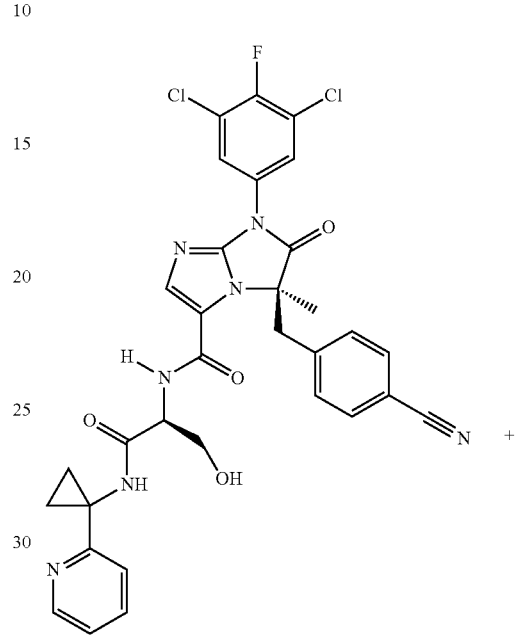

+

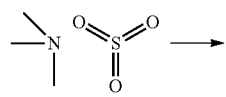

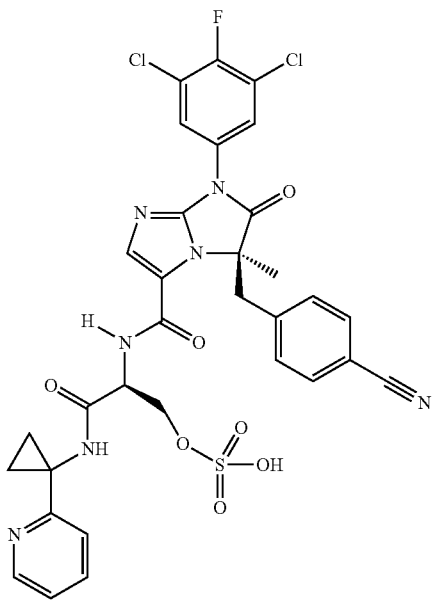

To a solution of (R)-5-(4-cyano-benzyl)-7-(3,5-dichloro-4-fluoro-phenyl)-5-methyl-6-oxo-6,7-dihydro-5H-imidazo[1,2-a]imidazole-3-carboxylic acid [(S)-2-hydroxy-1-(1-pyridin-2-yl-cyclopropylcarbamoyl)-ethyl]-amide (4.6 mg, 0.007 mmol) in DMF (0.2 mL) was added sulfur trioxide trimethylamine complex (3.06 mg, 0.021 mmol). The reaction mixture was stirred at 50° C. for 16 h. The reaction was poured into ice water (20 mL) and extracted with EtOAc (3×5 mL). The organic layer was washed with brine and dried over Na2SO4. After removal of the solvent in vacuo the remaining residue was purified on silica gel using 10% MeOH in DCM as an eluent to afford the title compound as a white solid (5 mg), m/z 742.4 [M+1]$^+$.

Example 45

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid [(S)-3-dimethylamino-1-(1-pyrimidin-2-yl-cyclopropylcarbamoyl)-propyl]-amide

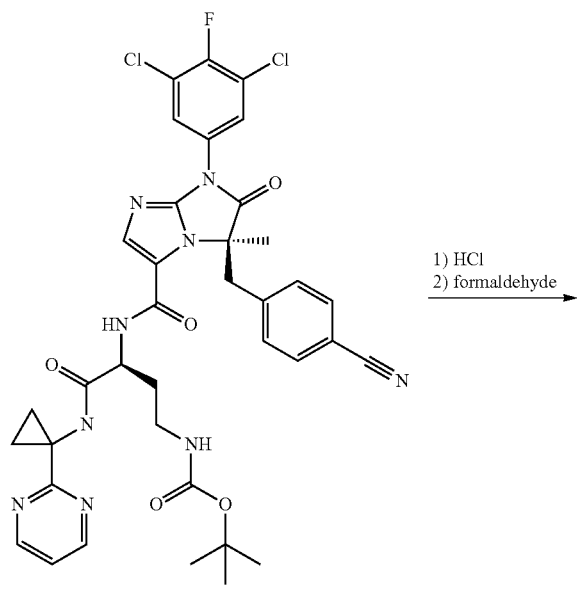

1) HCl
2) formaldehyde

-continued

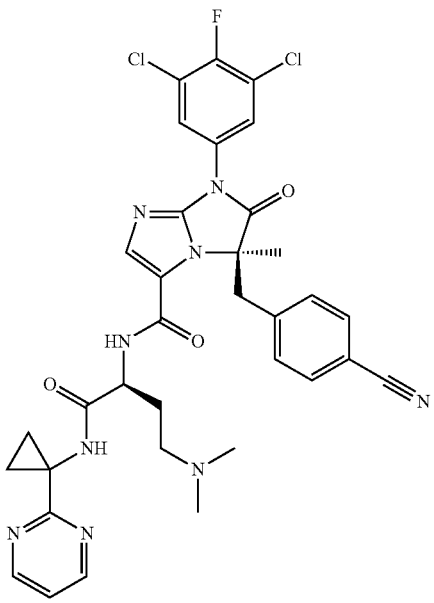

[(S)-3-{[(R)-5-(4-Cyano-benzyl)-7-(3,5-dichloro-4-fluoro-phenyl)-5-methyl-6-oxo-6,7-dihydro-5H-imidazo[1,2-a]imidazole-3-carbonyl]-amino}-3-(1-pyrimidin-2-yl-cyclopropylcarbamoyl)-propyl]-carbamic acid tert-butyl ester (109 mg, 0.14 mmol) was suspended in 1 mL of CH$_2$Cl$_2$ and 3 mL of 4 M HCl in dioxane was added. The mixture was stirred for 2.5 h. The mixture was concentrated under a flow of N$_2$ to provide a white powder, some of which was blown out of the flask.

The residue was dissolved in 3 mL of 1% HOAc in EtOH and the NaOAc (24 mg, 0.29 mmol) was added, followed by the formaldehyde (0.1 mL, 37% solution) and finally the NaCNBH$_3$ (36 mg, 0.57 mmol). The mixture was stirred for 2.5 h. The mixture was poured into NaHCO$_3$ and extracted with EtOAc. The extract was washed with water and brine, then dried over Na$_2$SO$_4$, was filtered and concentrated. The residue was purified by reverse phase HPLC. The pure fractions were diluted in NaHCO$_3$ and extracted with EtOAc. The extract was washed brine, then dried over Na$_2$SO$_4$, was filtered and concentrated or provide 31 mg of the title compound as a colorless glass, m/z 704.5 [M+1]$^+$.

The following compounds were prepared using similar procedures as described above:

Compound 334, m/z 685.9 [M+1]$^+$

Example 46

(R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(4-aminomethyl-pyridin-2-yl)-cyclopropylcarbamoyl]-cyclopropyl}-amide

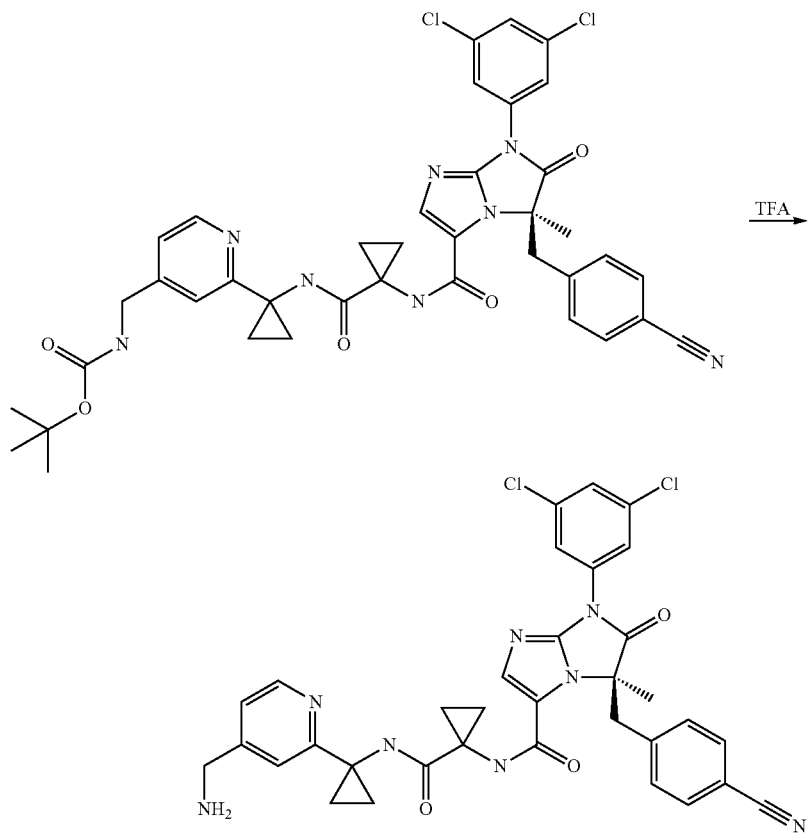

(2-{1-[(1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-amino]-cyclopropyl}-pyridin-4-ylmethyl)-carbamic acid tert-butyl ester (45 mg, 0.06 mmol) was placed in RBF with CH2Cl2 and TFA was added. The reaction was diluted with 10 mL 10% MeOH/CH2Cl2 and washed with water (2×5 mL). The organic layer was separated, dried (MgSO$_4$), and concentrated. Reverse Phase HPLC purification (30-100% CH3CN/H2O as gradient) yielded 66 mg of the title compound as a bis-TFA salt, m/z=669.5 [M+1]$^+$.

The following compounds were synthesized from either (R)-5-(4-cyano-benzyl)-7-(3,5-dichloro-phenyl)-5-methyl-6-oxo-6,7-dihydro-5H-imidazo[1,2-a]imidazole-3-carboxylic acid {1-[1-(4-iodo-pyridin-2-yl)-cyclopropylcarbamoyl]-cyclopropyl}-amide, (R)-5-(4-cyano-benzyl)-7-(3,5-dichloro-phenyl)-5-methyl-6-oxo-6,7-dihydro-5H-imidazo[1,2-a]imidazole-3-carboxylic acid {1-[1-(5-iodo-pyridin-2-yl)-cyclopropylcarbamoyl]-cyclopropyl}-amide, (R)-5-(4-cyano-benzyl)-7-(3,5-dichloro-4-fluoro-phenyl)-5-methyl-6-oxo-6,7-dihydro-5H-imidazo[1,2-a]imidazole-3-carboxylic acid {1-[1-(5-iodo-pyridin-2-yl)-cyclopropylcarbamoyl]-cyclopropyl}-amide or (R)-7-(3,5-dichloro-4-fluoro-phenyl)-5-methyl-6-oxo-5-(4-trifluoromethoxy-benzyl)-6,7-dihydro-5H-imidazo[1,2-a]imidazole-3-carboxylic acid {1-[1-(5-iodo-pyridin-2-yl)-cyclopropylcarbamoyl]-cyclopropyl}-amide in a similar manner as was described for (R)-5-(4-cyano-benzyl)-7-(3,5-dichloro-4-fluoro-phenyl)-5-methyl-6-oxo-6,7-dihydro-5H-imidazo[1,2-a]imidazole-3-carboxylic acid:

Compound 415, m/z 684.6 [M+1]$^+$ Compound 416, m/z 684.7 [M+1]$^+$ Compound 417, m/z 702.9 [M+1]$^+$ Compound 418, m/z 761.9 [M+1]$^+$ Description of Biological Properties The biological properties of representative compounds of the formula I were investigated by way of the experimental protocol described below.

Assay to Determine Inhibition of LFA-1 Binding to ICAM-1

Purpose of Assay:

This assay protocol is designed to study the direct antagonism, by a test compound, of the interaction of ICAM-1 with the Leukointegrin CD18/CD11a (LFA-1).

Description of Assay Protocol:

LFA-1 is immunopurified using the TS2/4 antibody from a 20 g pellet of human JY or SKW3 cells, utilizing a protocol previously described (Dustin, M. J.; et al., *J. Immunol.* 1992, 148, 2654-2660). The LFA-1 is purified from SKW3 lysates by immunoaffinity chromatography on TS2/4 LFA-1 mAb Sepharose and eluted at pH 11.5 in the presence of 2 mM MgCl$_2$ and 1% octylglucoside. After collection and neutralization of fractions from the TS2/4 column, samples are pooled and precleared with Protein G agarose.

A soluble form of ICAM-1 is constructed, expressed, purified and characterized as previously described (Marlin, S.; et al., Nature, 1990, 344, 70-72 and see Arruda, A.; et al., *Antimicrob. Agents Chemother.* 1992, 36, 1186-1192). Briefly, isoleucine 454 which is located at the putative boundary between domain 5 of the ectodomain and the transmembrane domain, is changed to a stop codon using standard oligonucleotide-directed mutagenesis. This construction yields a molecule identical with the first 453 amino acids of membrane bound ICAM-1. An expression vector is created with a hamster dihydrofolate reductase gene, a neomycin-resistance marker, and the coding region of the sICAM-1 construct described above, along with the promoter, splice signals, and polyadenylation signal of the SV40 early region. The recombinant plasmid is transfected into CHO DUX cells using standard calcium phosphate methods. Cells are passaged in selective media (G418) and colonies secreting sICAM-1 are amplified using methotrexate. sICAM-1 is purified from serum-free media using traditional non-affinity chromatographic techniques, including ion exchange and size exclusion chromatography.

LFA-1 binding to ICAM-1 is monitored by first incubating sICAM-1 at 40 μg/mL in Dulbecco's phosphate buffered saline with calcium and magnesium, additional 2 mM MgCl$_2$ and 0.1 mM PMSF (Diluting Buffer) in a 96-well plate for 30 min at room temperature. Plates are then blocked by the addition of 2% (w/v) bovine serum albumin in Diluting Buffer for 37° C. for 1 h. Blocking solution is removed from wells, and test compounds are diluted and then added followed by the addition of approximately 25 ng of immunoaffinity purified LFA-1. The LFA-1 is incubated in the presence of test compound and ICAM-1 at 37° C. for 1 h. Wells are washed 3 times with Diluting Buffer. The bound LFA-1 is detected by the addition of a polyclonal antibody directed against a peptide corresponding to the CD18 cytoplasmic tail in a 1:100 dilution with Diluting Buffer and 1% BSA and allowed to incubate for 45 min at 37° C. Wells are washed 3 times with Diluting Buffer and the bound polyclonal antibody is detected by the addition of a 1:4000 dilution of horse radish peroxidase conjugated to goat immunoglobulin directed against rabbit immunoglobulin. This reagent is allowed to incubate for 20 min at 37° C., wells are washed as above and the substrate for the horse radish peroxidase is added to each well to develop a quantitative colorimetric signal proportional to the amount of LFA-1 bound to sICAM-1. Soluble ICAM-1 (60 μg/mL) is used as a positive control for inhibition of the LFA-1/ICAM-1 interaction. The lack of the addition of LFA-1 to the binding assay is used as a background control for all samples. A dose-response curve is obtained for all test compounds.

Representative compounds made in the above examples were tested in this assay and each found to have a $K_d$<1 μM. Data from this assay for certain representative compounds are given below:

| Compound number | LFA/ICAM1 Kd (nM) |
|---|---|
| 107 | 28 |
| 129 | 45 |
| 2 | 8.9 |
| 72 | 8.4 |
| 114 | 32 |
| 215 | 39 |
| 259 | 120 |
| 13 | 2.4 |
| 55 | 10 |
| 9 | 4.6 |
| 60 | 13 |
| 286 | 100 |
| 12 | 5.4 |
| 201 | 34 |
| 185 | 24 |
| 187 | 22 |
| 143 | 71 |
| 160 | 5.9 |
| 37 | 6.6 |
| 38 | 8.2 |
| 62 | 7 |
| 109 | 28 |
| 105 | 24 |
| 270 | 420 |

Assay to Determine Inhibition of Interleukin-2 Production in Whole Blood
Purpose of Assay:

The SEB human whole blood interleukin 2 (SEB-HWB-IL2) assay measures the ability of test compounds to inhibit the elaboration of IL-2 by human whole blood, mediated through the interaction of ICAM-1 with the Leukointegrin CD18/CD11a (LFA-1), following stimulation with staphylococcal enterotoxin B (SEB) ex vivo.
Description of Assay Protocol:

Test compound (15 uL, diluted in human serum to 11× final assay concentration) is added to 96-well polypropylene plates, followed by the addition of 140 uL of freshly drawn heparinized human whole blood. After 30 minutes at 37 C, 10 uL of SEB is added for a final assay concentration of 300 ng/mL and the plates are placed on an orbital shaker for 30 seconds to ensure mixing, and then incubated for 18-24 hours at 37 C. After incubation, 100 uL of PBS-EDTA is added, the plates centrifuged to pellet cells, and the diluted plasma removed for IL-2 quantitation by standard ECL, DELFIA, or ELISA methods. Compound IC50 values are determined by nonlinear curve fitting of the data from 11-point concentration-effect curves.

The majority of the compounds made in the above examples were tested in this assay and found to have an IC$_{50}$<10 μM and preferred compounds have an IC$_{50}$<1 μM.
Description of Therapeutic Use The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g., as competitive inhibitors of intercellular ligand/receptor binding reactions involving CAMs and Leukointegrins. To be more specific, the compounds of the invention may be used to treat certain inflammatory conditions, including conditions resulting from a response of the specific immune system in a mammal (e.g., asthma, psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus) and conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction, acute glomerulonephritis, vasculitis, reactive arthritis, dermatosis with acute inflammatory components, stroke, thermal injury, hemodialysis, leukapheresis, necrotizing enterocolitis and granulocyte transfusion associated syndrome). Preferably, the compounds of the invention can be used to treat psoriasis and multiple sclerosis.

Thus, another aspect of the invention is directed to a compound of formula I for use as a medicament and, in a particular aspect, for use as a medicament for the treatment of inflammation or an inflammatory condition. In another particular aspect, the invention is directed to a compound of formula I for use as a medicament for the treatment of any of the diseases or conditions listed in the previous paragraph. In another aspect, the invention is directed to the use of a compound of formula I for the manufacture of a medicament for the treatment of any of the diseases or conditions listed in the previous paragraph.

Thus, another aspect of the invention is the provision of a method for the treatment or prophylaxis of the above-described conditions through the administration of therapeutic or prophylactic amounts of one or more compounds of the formula I.

In accordance with the method provided by the invention, the novel compounds of formula I may be administered for either a prophylactic or therapeutic purpose either alone or with other immunosuppressive or antiinflammatory agents. When provided prophylactically, the immunosuppressive compound(s) are provided in advance of any inflammatory response or symptom (for example, prior to, at, or shortly after the time of a relapse in multiple sclerosis). The prophylactic administration of a compound of the formula I serves to prevent or attenuate any subsequent inflammatory response (such as, for example, a relapse in multiple sclerosis). The therapeutic administration of a compound of the formula I serves to attenuate any actual inflammation (such as, for example, a relapse in multiple sclerosis). Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day, preferably in the range of 1 mg to 100 mg per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered topically or by suppository.

The invention claimed is:
1. A compound of formula I:

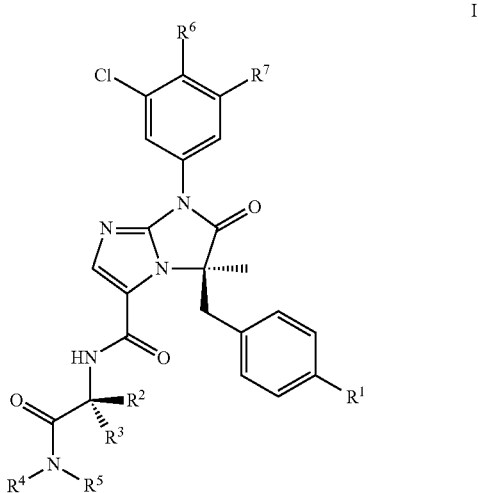

wherein:
R$^1$ is selected from —CN, —OCF$_3$, halogen, heteroaryl, optionally substituted with halogen or C$_{1-3}$alkyl optionally substituted with halogen and phenyl, optionally substituted with halogen;

$R^2$ is selected from:
- (A) H,
- (B) $C_{1-3}$alkyl optionally substituted with one or two groups selected from:
  - a) $C_{3-6}$cycloalkyl,
  - b) —$OR^9$,
  - c) —$NR^9R^{10}$,
  - d) —$SOR^9$,
  - e) —$SO_2R^9$,
  - f) —$C(O)NH_2$,
  - g) heteroaryl optionally substituted with $C_{1-2}$alkyl,
  - h) heterocyclyl,
  - i) phenyl,
  - j) —$CO_2R^9$,
  - k) —$OPO(OH)_2$, and
  - l) —$OSO_2(OH)$;
- (C) $C_{3-6}$cycloalkyl,
- (D) heteroaryl, and
- (E) phenyl, optionally substituted with halogen, —$OR^9$, —CN or —$CF_3$;

$R^3$ is H or $C_{1-3}$alkyl; or $R^2$ and $R^3$, together with the carbon they are bonded to, form a saturated hydrocarbon ring of 3 to 7 carbon atoms and wherein one carbon atom in said hydrocarbon ring may be optionally replaced by —O—, —S—, —S(O)—, —$SO_2$—, —$NC(O)R^9$— or —$NR^9$—;

$R^4$ is selected from:
- (A) $C_{1-5}$alkyl substituted with one or two groups selected from:
  - a) —$CF_3$,
  - b) —$C(O)OR^9$,
  - c) —$C(O)NR^9R^{10}$,
  - d) —$C(S)NR^9R^{10}$,
  - e) —$NR^9R^{10}$,
  - f) —$N(R^9)C(O)R^{10}$,
  - g) —$C(O)NH(CH_2)_2$—O—$(CH_2)_2OH$,
  - h) —$OR^9$,
  - i) phenyl optionally substituted with halogen, —$NR^9R^{10}$, —$OR^9$, $C_{3-5}$cycloalkyl or $C_{1-5}$alkyl, wherein said $C_{1-5}$alkyl is optionally substituted with —F, —$NR^9R^{10}$ or —$OR^9$,
  - j) heteroaryl optionally substituted with halogen, —$NR^9R^{10}$, —$OR^9$, $C_{3-5}$cycloalkyl or $C_{1-5}$alkyl, wherein said $C_{1-5}$alkyl is optionally substituted with —F, —$NR^9R^{10}$ or —$OR^9$,
  - k) —$SO_2NR^9R^{10}$,
  - l) —$SO_2R^9$, and
  - m) —$SO_2$Het, wherein Het is selected from heterocyclyl and heteroaryl;
- (B) $C_{3-6}$cycloalkyl substituted with one or two groups selected from:
  - a) —$C(O)OR^9$,
  - b) —$C(O)NR^9R^{10}$,
  - c) —$C(S)NR^9R^{10}$,
  - d) —$OR^9$,
  - e) phenyl optionally substituted with halogen, —$NR^9R^{10}$, —$OR^9$, $C_{3-5}$cycloalkyl or $C_{1-5}$alkyl, wherein said $C_{1-5}$alkyl is optionally substituted with —F, —$CF_3$, —$NR^9R^{10}$ or —$OR^9$, and
  - f) heteroaryl optionally substituted with:
    1) —$NR^9R^{10}$,
    2) —$NHC(O)R^9$,
    3) —$NHSO_2R^9$,
    4) —$OR^9$,
    5) —$C_{1-2}$alkyl$NR^9R^{10}$,
    6) —$C_{1-2}$alkyl$NR^{10}(CO)NR^9R^{10}$,
    7) —$C_{1-2}$alkyl$NR^{10}(CO)R^9$,
    8) —$C_{1-2}$alkyl$OR^9$,
    9) —$C_{1-2}$alkyl$NHSO_2R^9$,
    10) —$CO_2R^9$,
    11) —$COCH_3$,
    12) halogen,
    13) —$SO_2R^9$,
    14) —$C_{3-5}$cycloalkyl,
    15) -cyano and
    16) $C_{1-5}$alkyl, wherein said $C_{1-5}$alkyl is optionally substituted with halogen, —$CF_3$, —$NR^9R^{10}$ or —$OR^9$;
- (C) heteroaryl optionally substituted with one to two groups selected from:
  - a) —$R^9$ optionally substituted with halogen or —OH,
  - b) —$CF_3$,
  - c) —$OR^9$,
  - d) —$NR^9R^{10}$,
  - e) halogen,
  - f) —$C(O)NR^9R^{10}$,
  - g) —$C(O)NH(CH_2)_2OH$,
  - h) —$C_{1-3}$alkyl$NR^9R^{10}$; and
- (D) —$C_{0-5}$alkylheterocyclyl wherein the heterocycle is optionally substituted with —$C(O)CH_3$, oxo, or —$C_{1-3}C(S)NH_2$, $R^5$ is selected from H, $C_{1-3}$alkyl, —$(CH_2)_2OH$ and —$(CH_2)_2OCH_3$; or $R^4$ and $R^5$ constitute a saturated hydrocarbon bridge of 3 to 6 carbon atoms which together with the N they are bonded to, form a heterocyclic ring, and wherein:
- a) one or two carbon atoms in said heterocyclic ring are mono or disubstituted with $R^8$ and
- b) one carbon atom in said heterocyclic ring is optionally replaced by —O—, —S—, —S(O)—, —$SO_2$— or —$NC(O)CH_3$—;

$R^6$ is H or halogen;

$R^7$ is halogen or —$CF_3$;

$R^8$ is selected from $C_{1-3}$alkyl, halogen, —OH, —$CH_2OH$, —$C(O)R^9$, —$SO_2R^9$, —$C(O)CH_2CO_2R^9$, —$NR^9R^{10}$, —$C(O)NR^9R^{10}$, —CN, —$C(O)OR^9$, —$N(R^9)C(O)R^{10}$, heterocyclyl and heteroaryl, wherein said heterocyclyl and heteroaryl are optionally substituted with $C_{1-4}$alkyl, —OH or —$CF_3$;

$R^9$ is H or $C_{1-5}$alkyl or $C_{3-4}$cycloalkyl, which $C_{1-5}$alkyl is optionally substituted with —OH;

$R^{10}$ is —H or —$CH_3$; or $R^9$ and $R^{10}$ constitute a saturated hydrocarbon bridge of 3 to 6 carbon atoms which together with the N they are bonded to, form a heterocyclic ring, wherein one carbon atom in said heterocyclic ring may be optionally monosubstituted with —OH or wherein one carbon atom in said heterocyclic ring may be optionally replaced by —O—, —S—, —SO—, —$SO_2$—, —NH—, —$NCH_3$—, or —$NC(O)CH_3$—;

or a pharmaceutically acceptable salt thereof.

2. A compound according to claim 1 wherein:

$R^1$ is selected from —CN, —$OCF_3$, —$CF_3$, —Cl, —Br and phenyl, pyrimidinyl and triazolyl, wherein said phenyl ring is optionally substituted with —F;

$R^2$ is selected from:
- (A) H, and
- (B) $C_{1-2}$alkyl optionally substituted with one or two groups selected from:
  - a) —$OR^9$,
  - b) —$S(O)R^9$,
  - c) —$SO_2R^9$,
  - d) —$C(O)NH_2$,
  - e) —$CO_2R^9$, f) —OPO(OH)$_2$,
g) —OSO$_2$(OH),
h) triazolyl,
i) imidazolyl optionally substituted with C$_{1-2}$alkyl, and
j) —NR$^9$R$^{10}$;

R$^3$ is H or —CH$_3$; or

R$^2$ and R$^3$, together with the carbon they are bonded to, form a saturated hydrocarbon ring of 3 to 6 carbon atoms and wherein one carbon atom in said hydrocarbon ring may be optionally replaced by —O—, —SO$_2$—, —NC(O)R$^9$— or —NR$^9$—;

R$^4$ is selected from:

(A) C$_{1-5}$alkyl substituted with one or two groups selected from:
  a) —CF$_3$,
  b) —C(O)OR$^9$,
  c) —C(O)NR$^9$R$^{10}$,
  d) —C(S)NH$_2$,
  e) —NR$^9$R$^{10}$,
  f) —N(R$^9$)C(O)R$^{10}$,
  g) —C(O)NH(CH$_2$)$_2$—O—(CH$_2$)$_2$OH,
  h) —OR$^9$,
  i) phenyl, and
  j) heteroaryl, optionally substituted with —OH;

(B) C$_{3-5}$cycloalkyl substituted with one group selected from:
  a) —C(O)OR$^9$,
  b) —C(O)NR$^9$R$^{10}$,
  c) —C(S)NR$^9$R$^{10}$, and
  d) heteroaryl optionally substituted with:
    1) —NR$^9$R$^{10}$,
    2) —NHC(O)R$^9$,
    3) —NHSO$_2$R$^9$,
    4) —OR$^9$,
    5) —C$_{1-2}$alkylNR$^9$R$^{10}$,
    6) —C$_{1-2}$alkylNR$^{10}$(CO)NR$^9$R$^{10}$,
    7) —C$_{1-2}$alkylNR$^{10}$(CO)R$^9$,
    8) —C$_{1-2}$alkylOR$^9$,
    9) —C$_{1-2}$alkylNHSO$_2$R$^9$,
    10) —CO$_2$R$^9$,
    11) —COCH$_3$,
    12) halogen,
    13) —SO$_2$R$^9$,
    14) —C$_{1-2}$alkyl optionally substituted with halogen,
    15) -cyano and
    16) —C$_{3-5}$cycloalkyl;

(C) heteroaryl optionally substituted with one to two groups selected from:
  a) —R$^9$ optionally substituted with halogen or —OH,
  b) —C(O)NR$^9$R$^{10}$,
  c) —C(O)NH(CH$_2$)$_2$OH,
  d) —NR$^9$R$^{10}$,
  e) —C$_{1-3}$alkylNR$^9$R$^{10}$, and
  f) halogen; and (D) —C$_{0-5}$alkylheterocyclyl wherein the heterocycle is optionally substituted with —C(O)CH$_3$, oxo, or —C$_{1-3}$C(S)NH$_2$;

R$^5$ is selected from H, and C$_{1-3}$alkyl; or

R$^4$ and R$^5$ constitute a saturated hydrocarbon bridge of 3 to 5 carbon atoms which together with the N they are bonded to, form a heterocyclic ring, and wherein:
a) one or two carbon atoms in said heterocyclic ring are mono or disubstituted with R$^8$, and
b) one carbon atom in said heterocyclic ring may be optionally replaced by —NC(O)CH$_3$—;

R$^6$ is H, —F or —Cl;

R$^7$ is —Cl;

R$^8$ is selected from —CH$_3$, —F, —OH, —CH$_2$OH, —SO$_2$CH$_3$, —N(CH$_3$)$_2$, —C(O)NR$^9$R$^{10}$, —C(O)CH$_2$CO$_2$Et, —CN, —C(O)OR$^9$, —N(R$^9$)C(O)R$^{10}$, heterocyclyl and heteroaryl, wherein said heteroaryl is optionally substituted with C$_{1-4}$alkyl or —OH;

R$^9$ is H, C$_{1-5}$alkyl or C$_{3-4}$cycloalkyl, which C$_{1-5}$alkyl is optionally substituted with —OH; and R$^{10}$ is H or —CH$_3$; or R$^9$ and R$^{10}$ constitute a saturated hydrocarbon bridge of 3 to 6 carbon atoms which together with the N they are bonded to, form a heterocyclic ring, wherein one carbon atom in said heterocyclic ring may be optionally monosubstituted with —OH or wherein one carbon atom in said heterocyclic ring may be optionally replaced by —O—, —NCH$_3$— or —NC(O)CH$_3$—;

or a pharmaceutically acceptable salt thereof.

3. A compound according to claim 1 wherein:

R$^1$ is selected from —CN, —OCF$_3$, —CF$_3$, —Cl, —Br, phenyl, pyrimidinyl and triazolyl wherein said phenyl ring is optionally substituted with —F;

R$^2$ is selected from:
(A) H, and
(B) C$_{1-2}$alkyl optionally substituted with one or two groups selected from:
  a) —OH,
  b) —OCH$_3$,
  c) —S(O)R$^9$,
  d) —SO$_2$R$^9$,
  e) —C(O)NH$_2$,
  f) —CO$_2$R$^9$,
  g) —OPO(OH)$_2$,
  h) —OSO$_2$(OH),
  h) triazolyl,
  i) imidazolyl optionally substituted with C$_{1-2}$alkyl, and
  j) —NR$^9$R$^{10}$;

R$^3$ is H or —CH$_3$; or

R$^2$ and R$^3$, together with the carbon they are bonded to, form a saturated hydrocarbon ring of 3 to 6 carbon atoms and wherein one carbon atom in said hydrocarbon ring may be optionally replaced by —O—, —SO$_2$—, —NC(O)R$^9$— or —NR$^9$—;

R$^4$ is selected from:

(A) C$_{1-3}$alkyl substituted with one or two groups selected from:
  a) —CF$_3$,
  b) —C(O)OR$^9$,
  c) —C(O)NH$_2$,
  d) —C(S)NH$_2$,
  e) —NHC(O)CH$_3$,
  f) —OR$^9$,
  g) phenyl, and
  h) heteroaryl optionally substituted with —OH, (B) C$_{3-5}$cycloalkyl substituted with one group selected from:
  a) —CO$_2$CH$_3$,
  b) —CONH$_2$,
  c) —CSNH$_2$, and
  d) heteroaryl optionally substituted with:
    1) —NR$^9$R$^{10}$,
    2) —NHC(O)R$^9$,
    3) —NHSO$_2$R$^9$,
    4) —OR$^9$,
    5) —C$_{1-2}$alkylNR$^9$R$^{10}$,
    6) —C$_{1-2}$alkylNR$^{10}$(CO)NR$^9$R$^{10}$,
    7) —C$_{1-2}$alkylNR$^{10}$(CO)R$^9$,
    8) —C$_{1-2}$alkylOR$^9$, 9) —C$_{1-2}$alkylNHSO$_2$R$^9$,
10) —CO$_2$R$^9$,
11) —COCH$_3$,
12) halogen,
13) —SO$_2$R$^9$,
14) —C$_{1-2}$alkyl optionally substituted with halogen,
15) -cyano and
16) —C$_{3-5}$cycloalkyl;
(C) heteroaryl optionally substituted with one to two groups selected from:
   a) —R$^9$ optionally substituted with —F or —OH,
   b) —C(O)NR$^9$R$^{10}$,
   c) —C(O)NH(CH$_2$)$_2$OH,
   d) —NR$^9$R$^{10}$,
   e) —C$_{1-3}$alkylNR$^9$R$^{10}$, and
   f) halogen; and
(D) —C$_{0-3}$alkylheterocyclyl wherein the heterocycle is optionally substituted with —C(O)CH$_3$ or oxo;
R$^5$ is selected from H, and —CH$_3$; or
R$^4$ and R$^5$ constitute a saturated hydrocarbon bridge of 3 to 5 carbon atoms which together with the N they are bonded to, form a heterocyclic ring, and wherein:
   a) one or two carbon atoms in said heterocyclic ring are mono or disubstituted with R$^8$ and
   b) one carbon atom in said heterocyclic ring is optionally replaced by —NC(O)CH$_3$—;
R$^6$ is H —F or —Cl;
R$^7$ is —Cl;
R$^8$ is selected from —CH$_3$, —F, —OH, —CH$_2$OH, —SO$_2$CH$_3$, —N(CH$_3$)$_2$, —C(O)NH$_2$, —C(O)N(CH$_3$)$_2$, —CN, —C(O)OR$^9$, —N(R$^9$)C(O)CH$_3$, heterocyclyl and heteroaryl, wherein said heteroaryl is optionally substituted with C$_{1-4}$alkyl or —OH;
R$^9$ is H, C$_{1-4}$alkyl or C$_{3-4}$cycloalkyl, which C$_{1-4}$alkyl is optionally substituted with —OH; and
R$^{10}$ is H or —CH$_3$; or
R$^9$ and R$^{10}$ constitute a saturated hydrocarbon bridge of 3 to 6 carbon atoms which together with the N they are bonded to, form a heterocyclic ring, wherein one carbon atom in said heterocyclic ring may be optionally monosubstituted with —OH or wherein one carbon atom in said heterocyclic ring may be optionally replaced by —O— or —NCH$_3$—;
or a pharmaceutically acceptable salt thereof.

4. A compound according to claim 1 wherein:
R$^1$ is selected from —CN, —OCF$_3$, —CF$_3$, —Cl, phenyl, pyrimidinyl and triazolyl;
R$^2$ is selected from:
(A) C$_{1-2}$alkyl optionally substituted with one or two groups selected from:
   a) —OH,
   b) —OCH$_3$,
   c) —S(O)R$^9$,
   d) —SO$_2$R$^9$,
   e) —C(O)NH$_2$,
   f) —CO$_2$R$^9$,
   g) —OPO(OH)$_2$,
   h) —OSO$_2$(OH),
   i) triazolyl,
   j) imidazolyl optionally substituted with C$_{1-2}$alkyl, and
   k) —NR$^9$R$^{10}$;
R$^3$ is H; or
R$^2$ and R$^3$, together with the carbon they are bonded to, form a saturated hydrocarbon ring of 3 to 6 carbon atoms and wherein one carbon atom in said hydrocarbon ring may be optionally replaced by —O—, —SO$_2$— or —NC(O)R$^9$—;
R$^4$ is selected from:
(A) C$_{2-3}$alkyl substituted with pyridinyl, thiazolyl, or pyrrolopyridinyl, and
(B) C$_{3-5}$cycloalkyl substituted with one group selected from:
   a) —C(O)NH$_2$,
   b) pyridinyl optionally substituted with:
      1) —NR$^9$R$^{10}$,
      2) —NHC(O)R$^9$,
      3) —NHSO$_2$R$^9$,
      4) —OR$^9$,
      5) —C$_{1-2}$alkylNR$^9$R$^{10}$,
      6) —C$_{1-2}$alkylNR$^{10}$(CO)NR$^9$R$^{10}$,
      7) —C$_{1-2}$alkylNR$^{10}$(CO)R$^9$,
      8) —C$_{1-2}$alkylOR$^9$,
      9) —C$_{1-2}$alkylNHSO$_2$R$^9$,
      10) —CO$_2$R$^9$,
      11) —COCH$_3$,
      12) halogen,
      13) —SO$_2$R$^9$,
      14) —C$_{1-2}$alkyl optionally substituted with halogen, and
      15) -cyano;
   c) oxadiazolyl optionally substituted with, —NR$^9$R$^{10}$, or R$^9$ wherein R$^9$ is optionally substituted with —F or —OH,
   d) imidazolyl optionally substituted with R$^9$ or —CF$_3$,
   e) triazolyl optionally substituted with R$^9$,
   f) oxazolyl optionally substituted with R$^9$ or —CONH$_2$,
   g) thiazolyl optionally substituted with R$^9$,
   h) thiadiazolyl,
   i) pyrimidinyl optionally substituted with —NR$^9$R$^{10}$,
   j) pyridopyrimidinyl,
   k) pyrazinyl optionally substituted with C$_{1-2}$alkyl,
   l) pyridazinyl optionally substituted with C$_{1-3}$alkylNR$^9$R$^{10}$,
   m) naphthyridinyl,
   n) quinazolinyl optionally substituted with halogen,
   o) pyrrolopyridin-6-yl,
   p) quinolinyl,
   q) triazinyl mono- or disubstituted with —NH$_2$,
   r) oxazolopyridinyl,
   s) benzooxazolyl,
   t) tetrazolyl, and
   u) isoxazolyl;
R$^5$ is H; or
R$^4$ and R$^5$ constitute a saturated hydrocarbon bridge of 3 to 5 carbon atoms which together with the N they are bonded to, form a heterocyclic ring, and wherein one carbon atom in said heterocyclic ring is mono or disubstituted with R$^8$;
R$^6$ is H or —F;
R$^7$ is —Cl;
R$^8$ is selected from —F, —OH, —CH$_2$OH, —NHC(O)CH$_3$, —C(O)NH$_2$, —CN, —CO$_2$Et, —CO$_2$H, 3-hydroxy-1H-pyrazol-5-yl, 5-oxo-4,5-dihydro-1,2,4-oxadiazol-3-yl, 5-oxo-4,5-dihydro-1,2,4-thiadiazol-3-yl and tetrazolyl, wherein said tetrazolyl is optionally substituted with C$_{1-4}$alkyl;

$R^9$ is H, $C_{1-4}$alkyl or $C_{3-4}$cycloalkyl and
$R^{10}$ is H or —$CH_3$; or
$R^9$ and $R^{10}$ constitute a saturated hydrocarbon bridge of 3 to 6 carbon atoms which together with the N they are bonded to, form a heterocyclic ring, wherein one carbon atom in said heterocyclic ring is optionally monosubstituted with —OH or wherein one carbon atom in said heterocyclic ring may be optionally replaced by —O—;
or a pharmaceutically acceptable salt thereof.

5. A compound according to claim 1 wherein:
$R^1$ is selected from —CN and —$OCF_3$, —$CF_3$, pyrimidin-5-yl or triazolyl;
$R^2$ is selected from:
(A) $C_{1-2}$alkyl optionally substituted with one or two groups selected from:
  a) —OH,
  b) —$OCH_3$,
  c) —$SO_2R^9$,
  d) —$C(O)NH_2$,
  e) —$CO_2R^9$, and
  f) —$OPO(OH)_2$,
  g) —$OSO_2(OH)$, and
  h) heteroaryl selected from triazol-2-yl or imidazol-4-yl which imidazol-4-yl is optionally substituted with $C_{1-2}$alkyl;
$R^3$ is H; or
$R^2$ and $R^3$, together with the carbon they are bonded to, form a saturated hydrocarbon ring of 3 to 6 carbon atoms and wherein one carbon atom in said hydrocarbon ring is optionally replaced by —O—, —$SO_2$—, or —NC(O)$R^9$—;
$R^4$ is selected from:
(A) $C_2$alkyl substituted with pyridin-2-yl, and
(B) Cyclopropyl substituted with one group selected from:
  a) —$C(O)NH_2$,
  b) pyridin-2-yl optionally substituted with:
    1) —$NR^9R^{10}$,
    2) —$NHC(O)R^9$,
    3) —$OR^9$,
    4) —$C_{1-2}$alkyl$NR^9R^{10}$,
    5) —$C_{1-2}$alkyl$NR^{10}(CO)NR^9R^{10}$,
    6) —$C_{1-2}$alkyl$NR^{10}(CO)R^9$,
    7) —$C_{1-2}$alkyl$OR^9$,
    8) —$CO_2R^9$,
    9) —$COCH_3$,
    10) halogen,
    11) —$C_{1-2}$alkyl$NHSO_2R^9$,
    12) —$SO_2R^9$,
    13) —$C_{1-2}$alkyl;
  c) 1,2,4-oxadiazolyl substituted with $R^9$, —$CHF_2$, $C_{1-2}$alkylOH or —$NR^9R^{10}$,
  d) imidazolyl optionally substituted with $R^9$ or —$CF_3$,
  e) 1,2,4-triazol-3-yl, optionally substituted with $R^9$,
  f) oxazolyl optionally substituted with $R^9$ or —$CONH_2$,
  g) thiazol-2-yl optionally substituted with $R^9$,
  h) thiazol-4-yl optionally substituted with —$CH_3$,
  i) 1,3,4-thiadiazol-2-yl,
  j) pyrimidinyl optionally substituted with —$NH_2$,
  k) pyrido[2,3-d]pyrimidin-2-yl,
  l) pyrazin-2-yl optionally substituted with $C_{1-2}$alkyl,
  m) pyridazin-3-yl,
  n) naphthyridin-2-yl,
  o) quinazolin-2-yl optionally substituted with halogen,
  p) 1H-pyrrolo[2,3-β]pyridin-6-yl,
  q) quinolin-2-yl,
  r) oxazolopyridin-2-yl, and
  s) benzooxazol-2-yl;

$R^5$ is H; or
$R^4$ and $R^5$ constitute a saturated hydrocarbon bridge of 3 to 5 carbon atoms which together with the N they are bonded to, form a heterocyclic ring, and wherein one carbon atom in said heterocyclic ring is mono or disubstituted with $R^8$;
$R^6$ is H or F;
$R^7$ is Cl;
$R^8$ is selected from —F, —OH, —$NHC(O)CH_3$, —$C(O)NH_2$, —CN, —$CO_2H$, 5-oxo-4,5-dihydro-1,2,4-oxadiazol-3-yl, and tetrazolyl, wherein tetrazolyl is optionally substituted with $C_{1-4}$alkyl;
$R^9$ is H, $C_{1-4}$-alkyl or $C_{3-4}$-cycloalkyl and
$R^{10}$ is H or —$CH_3$; or
$R^9$ and $R^{10}$ constitute a saturated hydrocarbon bridge of 3 to 6 carbon atoms which together with the N they are bonded to, form a heterocyclic ring, wherein one carbon atom in said heterocyclic ring is optionally monosubstituted with —OH or wherein one carbon atom in said heterocyclic ring may be optionally replaced by —O—;
or a pharmaceutically acceptable salt thereof.

6. A compound according to claim 1 wherein:
$R^1$ is selected from —CN and —$OCF_3$ or pyrimidin-5-yl;
$R^2$ is selected from:
(A) $C_{1-2}$alkyl optionally substituted with one group selected from:
  a) —OH,
  b) —$CO_2H$,
  c) —$CONH_2$,
  d) —$OPO(OH)_2$ and
  e) —$OSO_2(OH)$;
$R^3$ is H; or
$R^2$ and $R^3$, together with the carbon they are bonded to, form a cyclopropyl or cyclohexyl ring wherein one carbon atom in said cyclohexyl ring is replaced with —NC(O)$R^9$— or —$SO_2$—;
$R^4$ is cyclopropyl substituted with one group selected from:
(A) pyridin-2-yl optionally substituted with:
  a) —$NHC(O)R^9$,
  b) —$CH_2NH_2$,
  b) —$CH_2NHC(O)R^9$,
  c) —$CH_2NHSO_2R^9$,
  d) —$CO_2H$,
  e) —$NR^9R^{10}$, or
  f) —$OR^9$;
(B) pyridazin-3-yl,
I pyrimidin-2-yl,
(D) naphthyridin-2-yl,
(E) quinazolin-2-yl optionally substituted with chlorine,
(F) 1H-pyrrolo[2,3-β]pyridin-6-yl,
(G) 2-isopropyl-oxazol-4-yl,
(H) 1-isopropyl-1H-imidazol-4-yl, or
(I) thiazol-2-yl;
$R^5$ is H;
$R^6$ is H or F;
$R^7$ is Cl;
$R^9$ is H, —$CH_3$ or cyclopropyl;
$R^{10}$ is H or —$CH_3$;
or a pharmaceutically acceptable salt thereof.

7. A compound according to claim 1, which is provided in the table below:
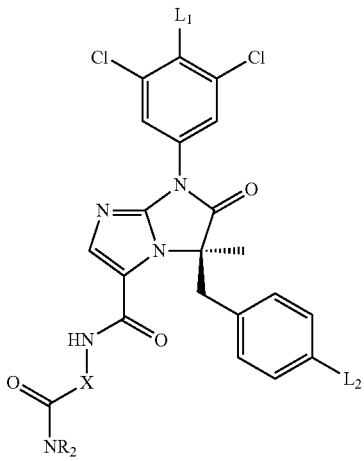
| Cpd # | NR₂ | X | L₁ | L₂ |
|---|---|---|---|---|
| 57 | 1-(5-aminopyridin-2-yl)cyclopropyl-NH– | cyclopropyl | F | CN |
| 56 | 1-(pyridin-2-yl)cyclopropyl-NH– | cyclopropyl | F | CN |
| 59 | 1-(6-methoxypyridin-2-yl)cyclopropyl-NH– | cyclopropyl | F | CN |
| 60 | 1-(thiazol-2-yl)cyclopropyl-NH– | cyclopropyl | F | CN |

-continued
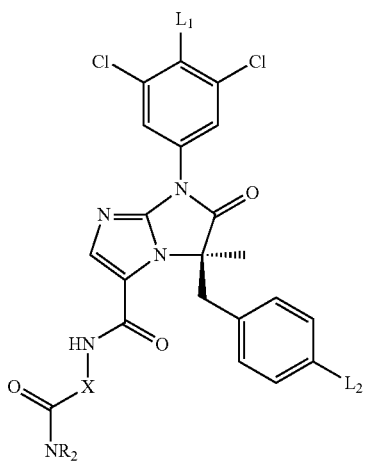
| Cpd # | NR₂ | X | L₁ | L₂ |
|---|---|---|---|---|
| 58 | 1-(4-methoxypyridin-2-yl)cyclopropyl-NH- | cyclopropyl | F | CN |
| 55 | 1-(pyridin-2-yl)cyclopropyl-NH- | CH(CH₃) | F | CN |
| 4 | (3R)-3-(5-oxo-4,5-dihydro-1,2,4-oxadiazol-3-yl)pyrrolidin-1-yl | cyclopropyl | H | OCF3 |
| 38 | 1-(3-morpholino-1,2,4-oxadiazol-5-yl)cyclopropyl-NH- | cyclopropyl | H | CN |

-continued
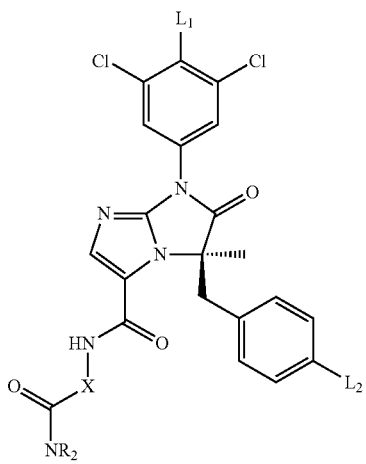
| Cpd # | NR₂ | X | L₁ | L₂ |
|---|---|---|---|---|
| 5 | (S)-3-(tetrazol-5-yl)pyrrolidin-1-yl | cyclopropyl | H | OCF3 |
| 1 | 3-(tetrazol-5-yl)-1-methylpiperidinyl | CH(CH₃) | H | CN |
| 48 | 1-(2-methylthiazol-4-yl)cyclopropylamino | cyclopropyl | H | CN |
| 6 | 3,3-difluoroazetidin-1-yl | cyclopropyl | H | CN |
| 31 | 1-(pyridin-2-yl)cyclopropylamino | cyclopropyl | H | CN |

-continued
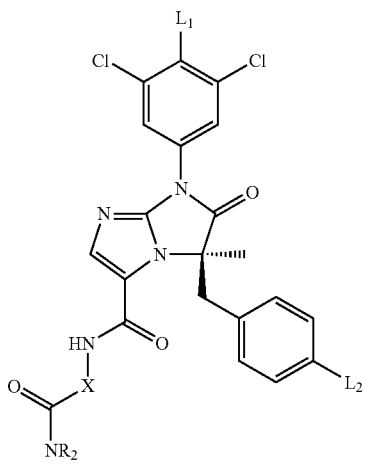
| Cpd # | NR2 | X | L1 | L2 |
|---|---|---|---|---|
| 43 | 1-(pyridin-2-yl, 4-aminomethyl)cyclopropyl-NH- | cyclopropyl | H | OCF3 |
| 7 | 3-(2H-tetrazol-5-yl)piperidin-1-yl | CH(CH3)- | H | OCF3 |
| 8 | (R)-3-(2H-tetrazol-5-yl)pyrrolidin-1-yl | cyclopropyl | H | CN |
| 9 | 3-(1,2,4-oxadiazolidin-5-on-3-yl)pyrrolidin-1-yl | cyclopropyl | H | CN |
| 10 | (R)-3-acetamidopyrrolidin-1-yl | cyclopropyl | H | OCF3 |

-continued
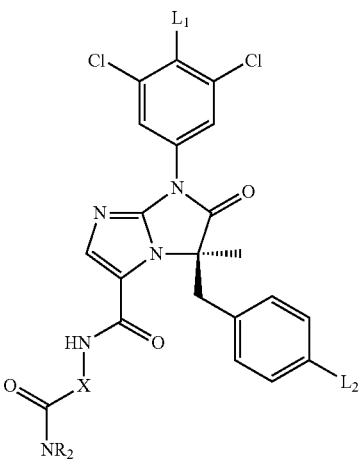
| Cpd # | NR₂ | X | L₁ | L₂ |
|---|---|---|---|---|
| 41 | 1-(1-methylimidazol-4-yl)cyclopropyl-NH- | cyclopropyl | H | CN |
| 45 | 1-(4-(aminomethyl)pyridin-2-yl)cyclopropyl-NH- | cyclopropyl | H | CN |
| 11 | (3S)-3-hydroxypyrrolidin-1-yl | cyclopropyl | H | OCF3 |
| 12 | (3S)-3-acetamidopyrrolidin-1-yl | cyclopropyl | H | CN |
| 34 | 1-(6-methoxypyridin-2-yl)cyclopropyl-NH- | cyclopropyl | H | CN |

-continued
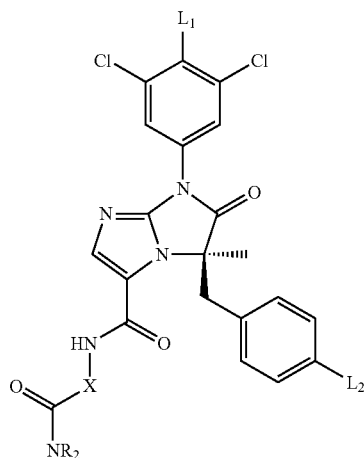
| Cpd # | NR₂ | X | L₁ | L₂ |
|---|---|---|---|---|
| 62 | 1-(4H-1,2,4-triazol-3-yl)cyclopropyl-NH- | 1-substituted cyclopropyl | F | CN |
| 66 | (1S)-1-(pyridin-2-yl)ethyl-NH- | sec-butyl | H | OCF3 |
| 68 | 1-(pyridin-2-yl)cyclopropyl-NH- | 1-substituted cyclopropyl | H | OCF3 |
| 13 | (3S)-3-carbamoylpiperidin-1-yl | sec-butyl | H | CN |
| 39 | 1-(5-(dimethylamino)pyridin-2-yl)cyclopropyl-NH- | 1-substituted cyclopropyl | H | OCF3 |

-continued
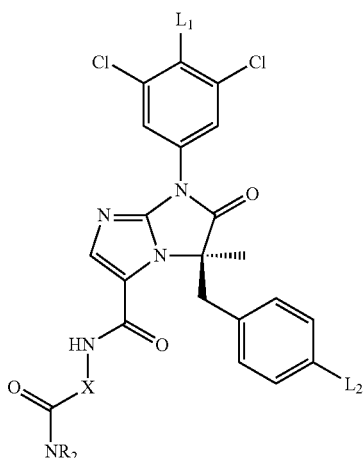
| Cpd # | NR₂ | X | L₁ | L₂ |
|---|---|---|---|---|
| 53 | 1-(6-aminopyridin-2-yl)cyclopropyl-NH- | 1-substituted cyclopropyl | H | CN |
| 14 | (3R)-3-acetamidopyrrolidin-1-yl | 1-substituted cyclopropyl | H | CN |
| 33 | 1-(4-methoxypyridin-2-yl)cyclopropyl-NH- | 1-substituted cyclopropyl | H | CN |
| 65 | 3,3-difluoroazetidin-1-yl | 1-substituted cyclopropyl | H | OCF3 |
| 50 | 1-(oxazol-4-yl)cyclopropyl-NH- | 1-substituted cyclopropyl | H | CN |

-continued
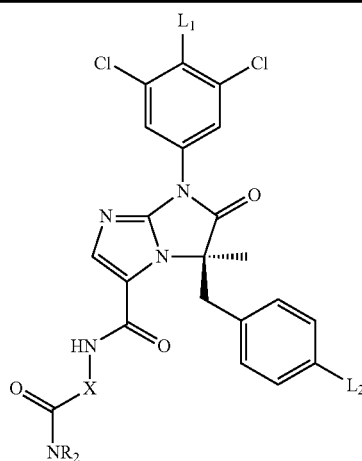
| Cpd # | NR₂ | X | L₁ | L₂ |
|---|---|---|---|---|
| 3 | (S)-1-(pyridin-2-yl)ethyl-NH– | cyclopropyl | H | CN |
| 30 | (S)-1-(pyridin-2-yl)ethyl-NH– | cyclopropyl | H | OCF3 |
| 35 | 1-(thiazol-2-yl)cyclopropyl-NH– | cyclopropyl | H | CN |
| 40 | 1-(5-(dimethylamino)pyridin-2-yl)cyclopropyl-NH– | cyclopropyl | H | CN |
| 15 | (R)-3-(2-methyl-2H-tetrazol-5-yl)pyrrolidin-1-yl | cyclopropyl | H | OCF3 |

-continued
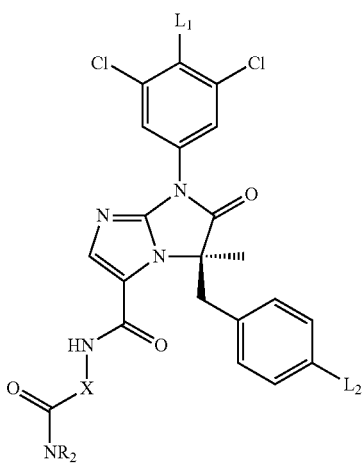
| Cpd # | NR₂ | X | L₁ | L₂ |
|---|---|---|---|---|
| 16 | (S)-3-acetamidopyrrolidin-1-yl | 1,1-cyclopropylene | H | OCF3 |
| 27 | 1-(pyridin-2-yl)cyclopropylamino | CH(CH₂CH₂C(O)NH₂)– | H | CN |
| 29 | 1-(pyridin-2-yl)cyclopropylamino | CH(CH₂OMe)– | H | CN |
| 52 | 1-(6-aminopyridin-2-yl)cyclopropylamino | 1,1-cyclopropylene | H | OCF3 |
| 61 | 1-(1,3,4-thiadiazol-2-yl)cyclopropylamino | 1,1-cyclopropylene | F | CN |

-continued
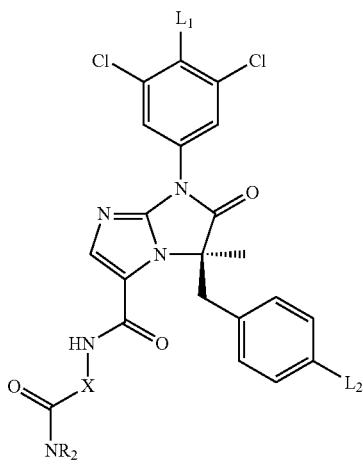
| Cpd # | NR₂ | X | L₁ | L₂ |
|---|---|---|---|---|
| 17 | 3,3-difluoropyrrolidin-1-yl | cyclopropyl | H | CN |
| 2 | (1-(pyridin-2-yl)ethyl)amino | sec-butyl | H | CN |
| 18 | (3R)-3-(2-tert-butyl-2H-tetrazol-5-yl)pyrrolidin-1-yl | cyclopropyl | H | OCF3 |
| 19 | (3R)-3-(2H-tetrazol-5-yl)pyrrolidin-1-yl | cyclopropyl | H | OCF3 |
| 24 | (1-(pyridin-2-yl)cyclopropyl)amino | 1-hydroxymethyl-ethyl | H | CN |

-continued
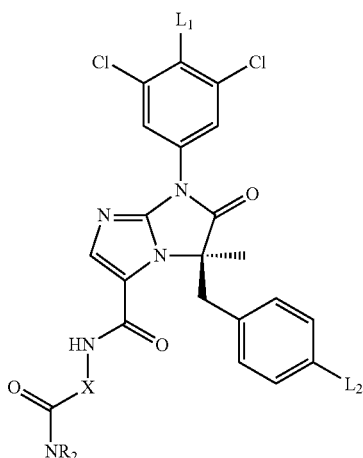
| Cpd # | NR₂ | X | L₁ | L₂ |
|---|---|---|---|---|
| 44 | 1-(pyridin-2-yl)cyclopropylamino | 4-acetylpiperidin-4-yl | H | CN |
| 67 | 1-(pyridin-2-yl)cyclopropylamino | sec-butyl | H | OCF3 |
| 20 | 3,3-difluoropyrrolidin-1-yl | 1-cyclopropyl | H | OCF3 |
| 28 | 1-(pyridin-2-yl)cyclopropylamino | 1-methyl-3-(methylsulfonyl)propyl | H | CN |
| 42 | 1-(4H-1,2,4-triazol-3-yl)cyclopropylamino | 1-cyclopropyl | H | CN |

-continued
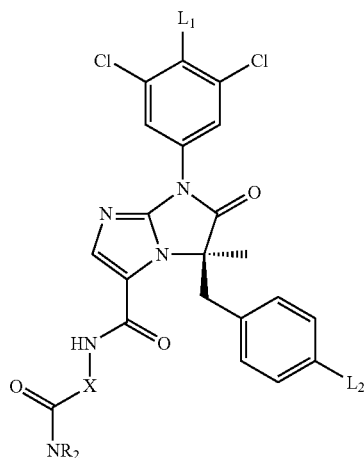
| Cpd # | NR₂ | X | L₁ | L₂ |
|---|---|---|---|---|
| 25 | cyclopropyl-NH with 2-pyridyl | CH(CH₃)CH(OH)- | H | CN |
| 46 | cyclopropyl-NH with 5-(dimethylamino)pyridin-2-yl | CH(CH₃)- | H | CN |
| 21 | piperidin-3-carboxamide, N-linked | CH(CH₃)- | H | CN |
| 26 | cyclopropyl-NH with 2-pyridyl | 1,1-dioxo-thian-4-yl (spiro) | H | CN |
| 32 | cyclopropyl-NH with 2-pyridyl | CH(CH₃)- | H | CN |

-continued
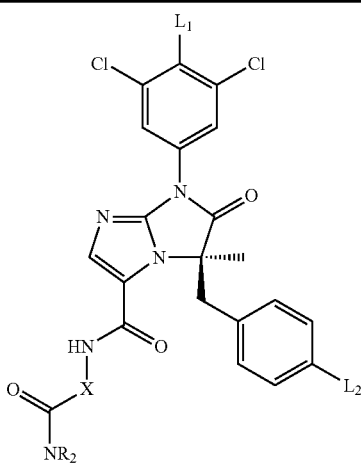
| Cpd # | NR₂ | X | L₁ | L₂ |
|---|---|---|---|---|
| 54 | 1-(5-cyclopropyl-4H-1,2,4-triazol-3-yl)cyclopropyl-NH- | cyclopropyl | H | CN |
| 22 | (3R)-3-(2-methyltetrazol-5-yl)pyrrolidin-1-yl | cyclopropyl | H | CN |
| 37 | 1-(3-methyl-1,2,4-oxadiazol-5-yl)cyclopropyl-NH- | cyclopropyl | H | CN |
| 49 | 1-(4H-1,2,4-triazol-3-yl)cyclopropyl-NH- | cyclopropyl | H | OCF3 |
| 69 | 1-carbamoylcyclopropyl-NH- | cyclopropyl | H | OCF3 |

-continued
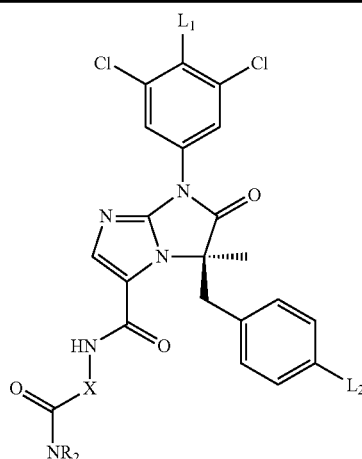
| Cpd # | NR₂ | X | L₁ | L₂ |
|---|---|---|---|---|
| 70 | pyrrolidine-N, 3-COOH | cyclopropyl | H | OCF3 |
| 64 | 1-(3-methyl-1,2,4-oxadiazol-5-yl)cyclopropyl-NH | cyclopropyl | F | CN |
| 47 | 1-(5-(dimethylamino)pyridin-2-yl)cyclopropyl-NH | CH(CH₃) | H | OCF3 |
| 23 | pyrrolidine-N, 3-CN | cyclopropyl | H | OCF3 |
| 36 | 1-(1,3,4-thiadiazol-2-yl)cyclopropyl-NH | cyclopropyl | H | CN |

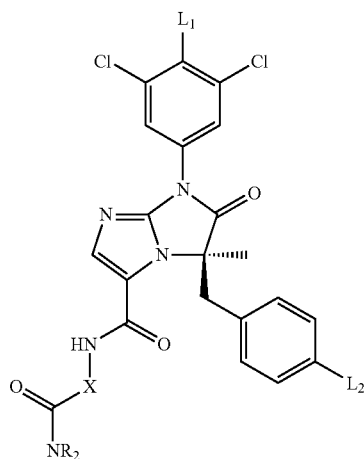
| Cpd # | NR₂ | X | L₁ | L₂ |
|---|---|---|---|---|
| 51 | cyclopropyl-NH-(2-pyridyl) | oxetanyl | H | CN |
| 320 | cyclopropyl-NH-(pyridyl with NHC(O)cyclopropyl) | cyclopropyl | F | CN |
| 394 | cyclopropyl-NH-(2-pyridyl) | cyclopropyl | F | pyrimidin-5-yl |
| 294 | cyclopropyl-NH-(1,8-naphthyridin-2-yl) | cyclopropyl | F | CN |

-continued
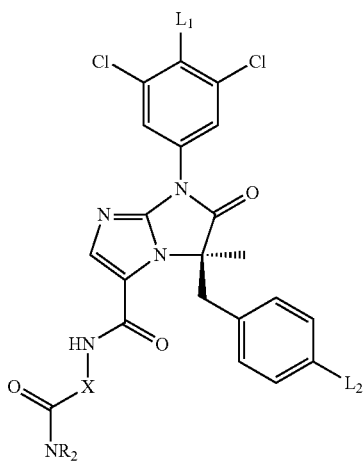
| Cpd # | NR₂ | X | L₁ | L₂ |
|---|---|---|---|---|
| 296 | (1-(1,7-naphthyridin-2-yl)cyclopropyl)amino | cyclopropylidene | F | CN |
| 451 | (1-(pyridin-2-yl)cyclopropyl)amino | CH(CH₂CH₂COOH) | F | CN |
| 333 | N-methyl-(1-(1H-pyrrolo[2,3-b]pyridin-6-yl)cyclopropyl)amino | cyclopropylidene | F | CN |
| 353 | (1-(pyridazin-3-yl)cyclopropyl)amino | cyclopropylidene | F | CN |

-continued
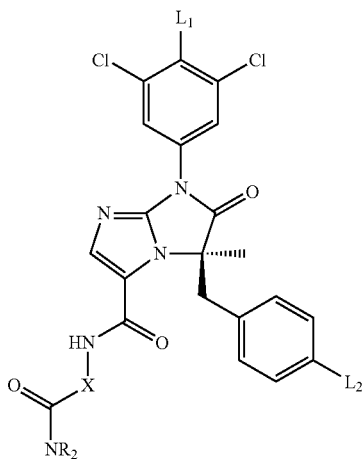
| Cpd # | NR₂ | X | L₁ | L₂ |
|---|---|---|---|---|
| 437 | cyclopropyl-NH-[6-(pyridin-2-yl)]-5-CH₂-NH-S(O)₂-CH₃ | cyclopropyl | F | CN |
| 436 | cyclopropyl-NH-[6-(pyridin-2-yl)]-5-CH₂-NH-S(O)₂-cyclopropyl | cyclopropyl | H | CN |
| 359 | cyclopropyl-NH-[6-(pyridin-2-yl)]-5-C(O)OH | cyclopropyl | H | CN |

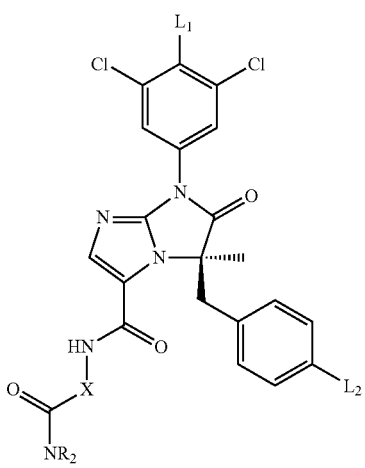

-continued
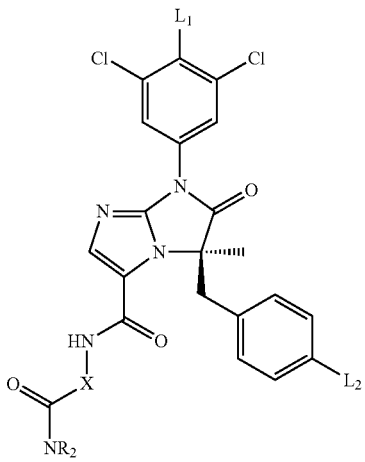
| Cpd # | NR₂ | X | L₁ | L₂ |
|---|---|---|---|---|
| 427 | cyclopropyl-NH linked to pyridine with CH₂-NH-S(O)₂-CH₃ substituent | cyclopropyl | H | CN |
| 297 | cyclopropyl-NH linked to quinazoline | cyclopropyl | F | CN |
| 311 | cyclopropyl-NH linked to pyrimidine | CH(CH₂CH₂C(O)NH₂)— | F | CN |
| 378 | cyclopropyl-NH linked to pyridine | CH(CH(OH)CH₃)— | F | CN |

-continued
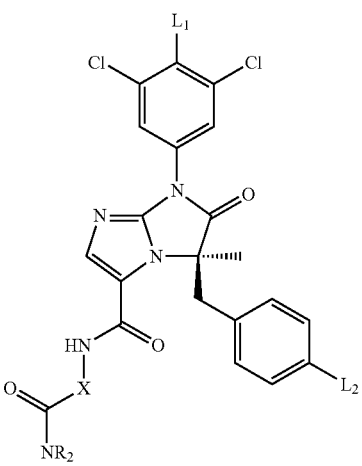
| Cpd # | NR₂ | X | L₁ | L₂ |
|---|---|---|---|---|
| 342 | cyclopropyl-NH linked to 2-isopropyl-oxazol-4-yl | cyclopropyl | F | CN |
| 416 | cyclopropyl-NH linked to 6-(5-carboxy)pyridin-2-yl | cyclopropyl | H | CN |
| 305 | cyclopropyl-NH linked to 1-isopropyl-imidazol-4-yl | cyclopropyl | F | CN |
| 343 | cyclopropyl-NH linked to 5-(aminomethyl)pyridin-2-yl | cyclopropyl | F | CN |

-continued
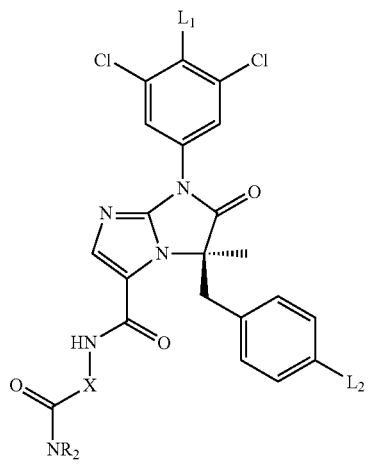
| Cpd # | NR₂ | X | L₁ | L₂ |
|---|---|---|---|---|
| 298 | 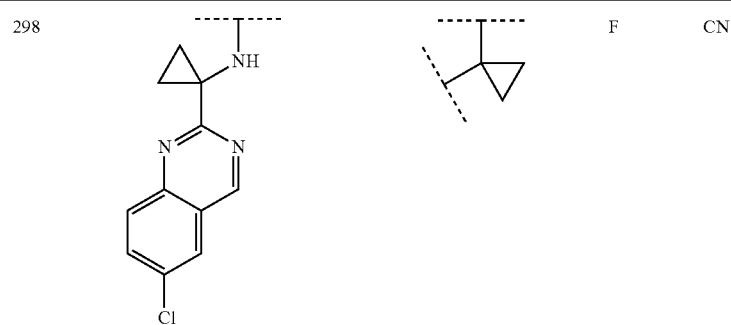 | | F | CN |
| 426 | 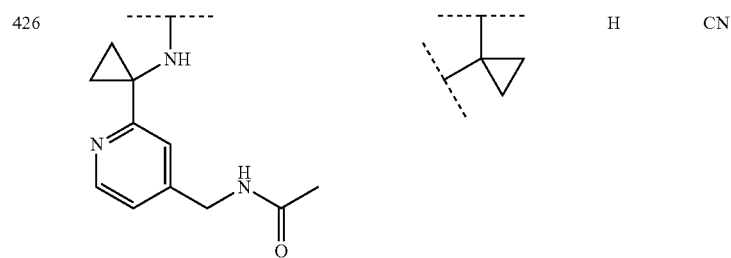 | | H | CN |
| 380 | 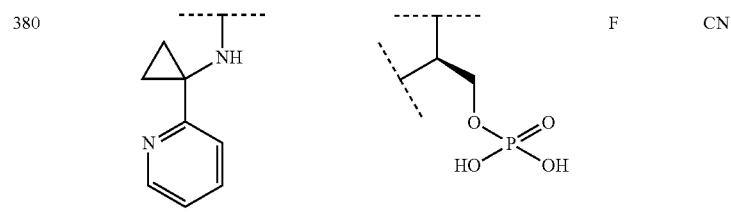 | | F | CN |

-continued
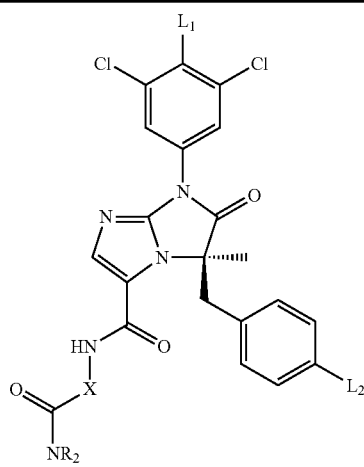
| Cpd # | NR₂ | X | L₁ | L₂ |
|---|---|---|---|---|
| 438 | cyclopropyl-NH attached to pyridine with CH₂NH-SO₂-cyclopropyl | CH(cyclopropyl) | F | CN |
| 309 | cyclopropyl-NH attached to pyrimidine | 1,1-dioxo-tetrahydrothiopyran | F | CN |
| 432 | cyclopropyl-NH attached to pyridine with CH₂NH-C(O)NH₂ | cyclopropylmethyl | H | CN |
| 381 | cyclopropyl-NH attached to pyridine | CH(CH₂CH₂COOH) | F | OCF3 |

-continued
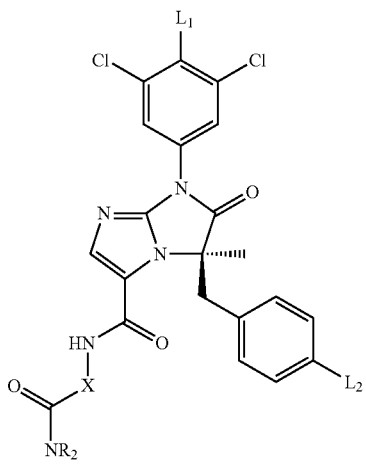
| Cpd # | NR₂ | X | L₁ | L₂ |
|---|---|---|---|---|
| 293 | 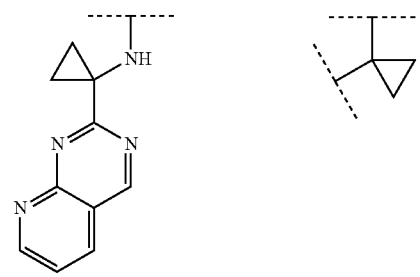 | | F | CN |
| 413 | | | H | CN |
| 351 | 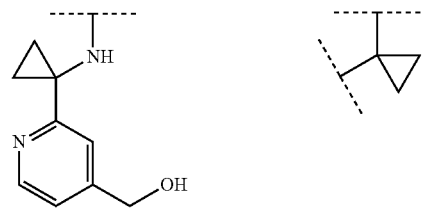 | | F | CN |
| 428 | 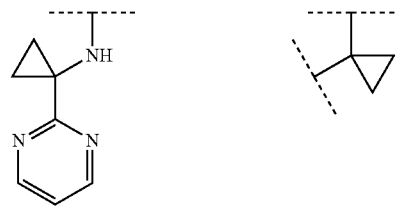 | | H | CN |
|  | 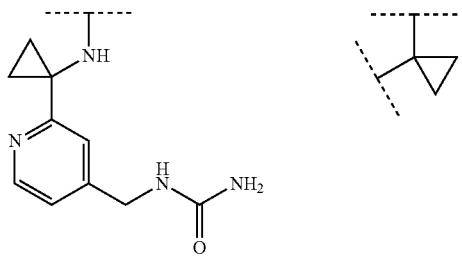 | | | |

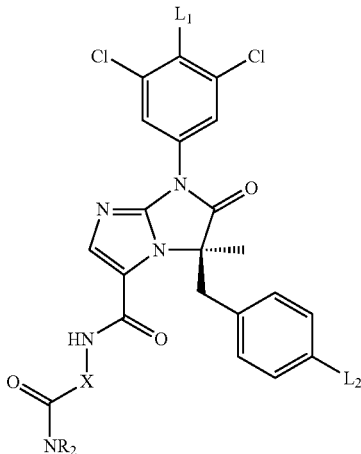
| Cpd # | NR₂ | X | L₁ | L₂ |
|---|---|---|---|---|
| 410 | 1-(5-acetylpyridin-2-yl)cyclopropyl-NH– | cyclopropyl | H | CN |
| 48 | 1-(2-methylthiazol-4-yl)cyclopropyl-NH– | cyclopropyl | H | CN |
| 340 | 1-(5-(hydroxymethyl)pyridin-2-yl)cyclopropyl-NH– | cyclopropyl | H | CN |
| 310 | 1-(pyrimidin-2-yl)cyclopropyl-NH– | 1-acetylpiperidin-4-yl (spiro) | F | CN |

-continued
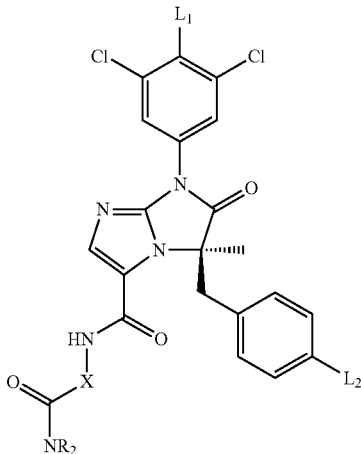
| Cpd # | NR₂ | X | L₁ | L₂ |
|---|---|---|---|---|
| 405 | 1-(pyrimidin-2-yl)cyclopropyl-NH- | -CH(CH(OH)CH₃)- | F | CN |
| 415 | 1-(4-carboxypyridin-2-yl)cyclopropyl-NH- | 1,1-cyclopropyl | H | CN |
| 355 | 1-(5-methylpyrazin-2-yl)cyclopropyl-NH- | 1,1-cyclopropyl | H | CN |
| 368 | 1-(5-isopropyl-1,2,4-oxadiazol-3-yl)cyclopropyl-NH- | 1,1-cyclopropyl | H | CN |

-continued
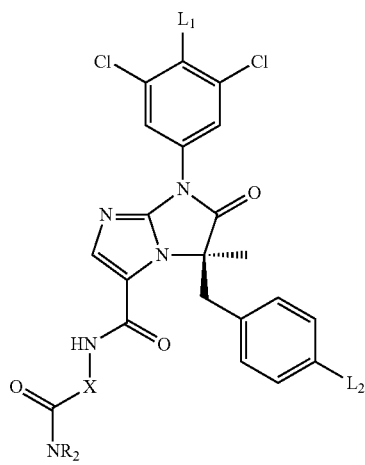
| Cpd # | NR₂ | X | L₁ | L₂ |
| --- | --- | --- | --- | --- |
| 43 | cyclopropyl-NH linked to pyridine with CH₂NH₂ | cyclopropyl | H | OCF3 |
| 384 | cyclopropyl-NH linked to triazole with cyclopropyl | cyclopropyl | F | CN |
| 425 | cyclopropyl-NH linked to pyridine with CH₂-azetidine-OH | cyclopropyl | H | CN |
| 387 | cyclopropyl-NH linked to 6-bromopyridine | cyclopropyl | H | CN |

-continued
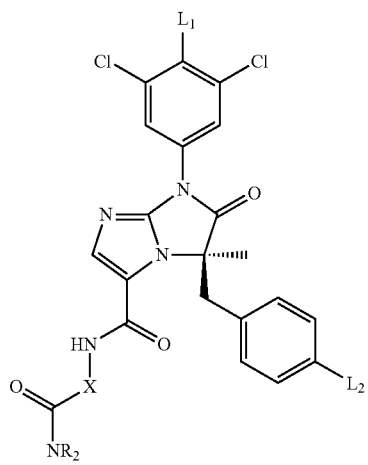
| Cpd # | NR₂ | X | L₁ | L₂ |
|---|---|---|---|---|
| 331 | 1-(5-(trifluoromethyl)-1H-imidazol-2-yl)cyclopropyl-NH- | 1,1-cyclopropyl | H | CN |
| 429 | 1-(4-((cyclopropanecarboxamido)methyl)pyridin-2-yl)cyclopropyl-NH- | 1,1-cyclopropyl | H | CN |
| 387 | 1-(6-bromopyridin-2-yl)cyclopropyl-NH- | 1,1-cyclopropyl | H | CN |
| 322 | 1-(5-cyclopropyl-1,2,4-oxadiazol-3-yl)cyclopropyl-NH- | 1,1-cyclopropyl | F | CN |

-continued
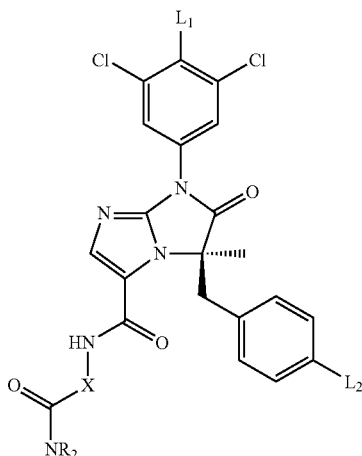
| Cpd # | NR₂ | X | L₁ | L₂ |
|---|---|---|---|---|
| 289 | 1-(3-tert-butyl-1,2,4-oxadiazol-5-yl)cyclopropyl-NH- | cyclopropyl | H | CN |
| 41 | 1-(1-methyl-1H-imidazol-4-yl)cyclopropyl-NH- | cyclopropyl | H | CN |
| 62 | 1-(1H-1,2,4-triazol-3-yl)cyclopropyl-NH- | cyclopropyl | F | CN |
| 321 | 1-(3-isopropyl-1,2,4-oxadiazol-5-yl)cyclopropyl-NH- | cyclopropyl | H | OCF3 |

-continued
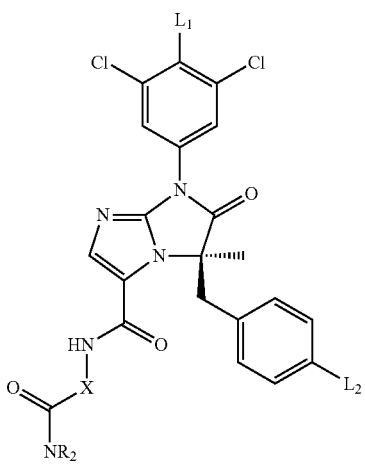
| Cpd # | NR₂ | X | L₁ | L₂ |
|---|---|---|---|---|
| 424 | cyclopropyl-NH attached to pyridine (2-position); pyridine 4-position has CH₂-azetidinyl | cyclopropyl | H | CN |
| 402 | cyclopropyl-NH attached to pyrimidin-2-yl | CH(CH(-)CH₂CH₂S(=O)(=O)CH₃) | F | CN |
| 338 | cyclopropyl-NH attached to oxazol-4-yl; oxazole 2-position has cyclopropyl | cyclopropyl | H | CN |
| 357 | cyclopropyl-NH attached to pyridazin-3-yl N-oxide | cyclopropyl | F | CN |

-continued
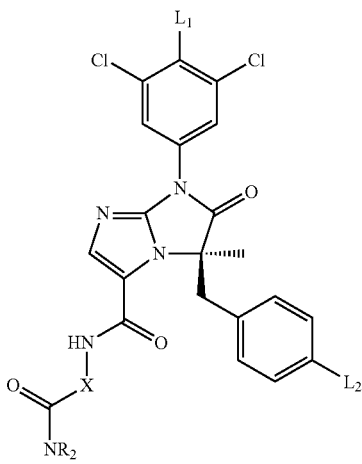
| Cpd # | NR₂ | X | L₁ | L₂ |
|---|---|---|---|---|
| 295 | 1-(quinolin-2-yl)cyclopropyl-NH– | cyclopropyl | F | CN |
| 376 | 1-(pyridin-2-yl)cyclopropyl-NH– | cyclopropyl | H | 1,2,3-triazol-1-ylmethyl |
| 39 | 1-(5-(dimethylamino)pyridin-2-yl)cyclopropyl-NH– | cyclopropyl | H | OCF3 |
| 403 | 1-(pyrimidin-2-yl)cyclopropyl-NH– | CH(CH₂OH)– | F | CN |

-continued
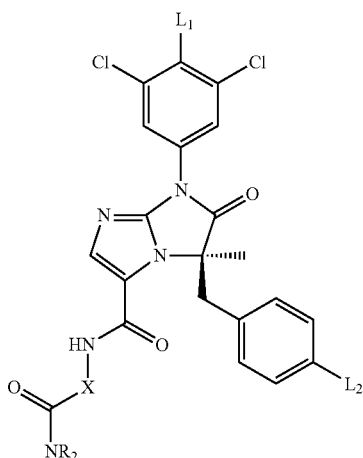
| Cpd # | NR2 | X | L1 | L2 |
|---|---|---|---|---|
| 288 | 1-(3-cyclobutyl-1,2,4-oxadiazol-5-yl)cyclopropylamino | cyclopropyl | H | CN |
| 423 | 1-(3-(morpholinomethyl)pyridin-2-yl)cyclopropylamino | cyclopropyl | H | CN |
| 409 | 1-(pyrimidin-2-yl)cyclopropylamino | CH(CH2-2H-1,2,3-triazol-2-yl) | F | CN |
| 327 | 1-(pyrimidin-2-yl)cyclopropylamino | cyclopropyl | H | OCF3 |

-continued
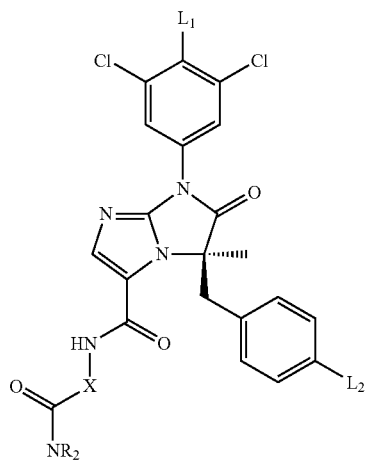
| Cpd # | NR₂ | X | L₁ | L₂ |
|---|---|---|---|---|
| 379 | cyclopropyl-NH attached to 2-(5-iodo)pyridyl | cyclopropyl | F | CN |
| 336 | cyclopropyl-NH attached to 2-(5-aminomethyl)pyridyl | cyclopropyl | H | CN |
| 290 | cyclopropyl-NH attached to 5-(3-difluoromethyl-1,2,4-oxadiazolyl) | cyclopropyl | H | CN |
| 50 | cyclopropyl-NH attached to 4-oxazolyl | cyclopropyl | H | CN |

-continued
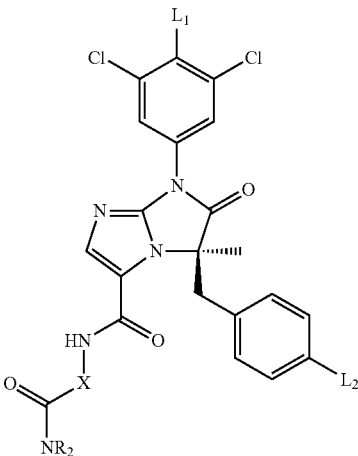
| Cpd # | NR<sub>2</sub> | X | L<sub>1</sub> | L<sub>2</sub> |
|---|---|---|---|---|
| 389 | 1-(3-cyclopropyl-1,2,4-oxadiazol-5-yl)cyclopropylamino | cyclopropylidene | H | CN |
| 404 | 1-(pyrimidin-2-yl)cyclopropylamino | (methoxymethyl)methylene | F | CN |
| 365 | 1-(5-cyclopropyl-1,2,4-oxadiazol-3-yl)cyclopropylamino | cyclopropylidene | H | CN |
| 448 | 1-(pyridin-2-yl)cyclopropylamino | (hydroxymethyl)methylene | F | CN |

-continued
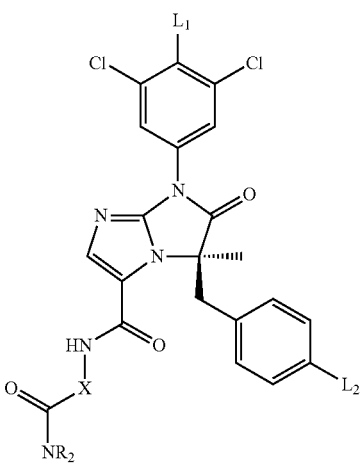
| Cpd # | NR₂ | X | L₁ | L₂ |
|---|---|---|---|---|
| 411 | cyclopropyl-NH-pyrimidin-4-yl | cyclopropyl | H | CN |
| 431 | cyclopropyl-NH- attached to pyridine with CH₂NHC(O)CH₃ | cyclopropyl | H | CN |
| 307 | cyclopropyl-NH- attached to 5-methyl-4H-1,2,4-triazol-3-yl | cyclopropyl | F | CN |
| 40 | cyclopropyl-NH- attached to 5-(dimethylamino)pyridin-2-yl | cyclopropyl | H | CN |

-continued
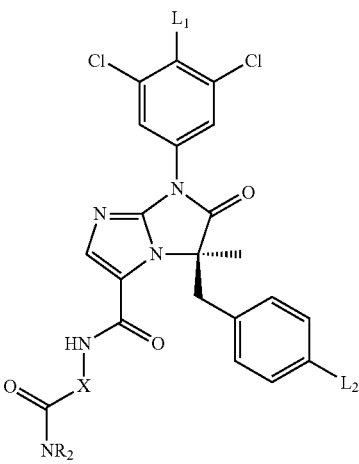
| Cpd # | NR₂ | X | L₁ | L₂ |
|---|---|---|---|---|
| 422 | cyclopropyl-NH attached to pyridine with pyrrolidinylmethyl | cyclopropyl | H | OCF3 |
| 430 | cyclopropyl-NH attached to pyridine with CH₂NHC(O)C(CH₃)₃ | cyclopropyl | H | CN |
| 323 | cyclopropyl-NH attached to 1,2,4-oxadiazole with cyclopropyl | cyclopropyl | H | OCF3 |
| 349 | cyclopropyl-NH attached to pyrazine | cyclopropyl | H | CN |

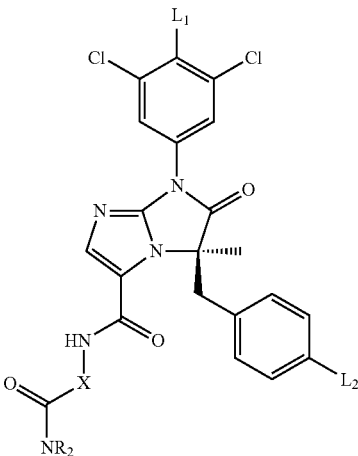
| Cpd # | NR₂ | X | L₁ | L₂ |
|---|---|---|---|---|
| 293 | cyclopropyl-NH- substituted with pyrido[2,3-d]pyrimidin-2-yl | cyclopropyl | F | CN |
| 414 | cyclopropyl-NH- substituted with 5-bromopyridin-2-yl | cyclopropyl | F | CN |
| 341 | cyclopropyl-NH- substituted with 2-isopropyloxazol-4-yl | cyclopropyl | H | CN |
| 52 | cyclopropyl-NH- substituted with 6-aminopyridin-2-yl | cyclopropyl | H | OCF3 |

-continued
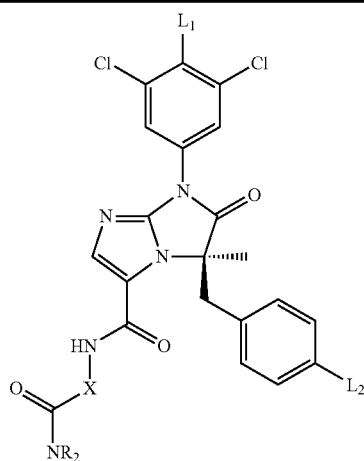
| Cpd # | NR₂ | X | L₁ | L₂ |
|---|---|---|---|---|
| 374 | 1-(pyridin-2-yl)cyclopropylamino | spiro[2.2]pentyl | H | 1H-1,2,4-triazol-1-ylmethyl |
| 61 | 1-(1,3,4-thiadiazol-2-yl)cyclopropylamino | spiro[2.2]pentyl | F | CN |
| 407 | 1-(3-cyclopropyl-1,2,4-oxadiazol-5-yl)cyclopropylamino | spiro[2.2]pentyl | F | CN |
| 306 | 1-(5-methyl-4H-1,2,4-triazol-3-yl)cyclopropylamino | spiro[2.2]pentyl | H | CN |
| 335 | 1-(pyridin-2-yl)cyclopropylamino | 2-acetyl-2-azaspiro[4.4]... | H | CN |

-continued
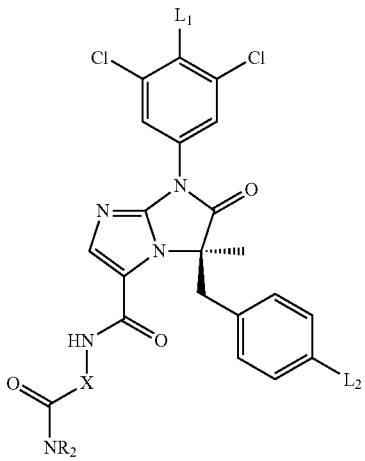
| Cpd # | NR₂ | X | L₁ | L₂ |
|---|---|---|---|---|
| 292 | 2-(benzoxazol-2-yl)cyclopropylamino | cyclopropyl | F | CN |
| 291 | 2-(oxazolo[5,4-b]pyridin-2-yl)cyclopropylamino | cyclopropyl | F | CN |
| 313 | 1-(pyrimidin-2-yl)cyclopropylamino | CH(1-methylimidazol-5-ylmethyl) | F | CN |
| 308 | 1-(1H-imidazol-4-yl)cyclopropylamino | cyclopropyl | F | CN |

-continued
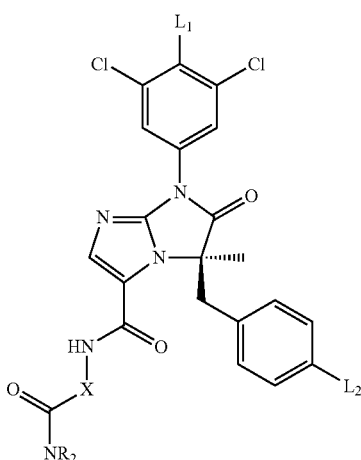
| Cpd # | NR₂ | X | L₁ | L₂ |
|---|---|---|---|---|
| 64 | 1-(3-methyl-1,2,4-oxadiazol-5-yl)cyclopropyl-NH- | cyclopropyl | F | CN |
| 408 | 1-(3-cyclopropyl-1,2,4-oxadiazol-5-yl)cyclopropyl-NH- | CH(CH₃)- | H | OCF3 |
| 44 | 1-(pyridin-2-yl)cyclopropyl-NH- | 1-acetyl-4-piperidinyl | H | CN |
| 370 | 1-(3-ethyl-1,2,4-oxadiazol-5-yl)cyclopropyl-NH- | cyclopropyl | H | CN |

-continued
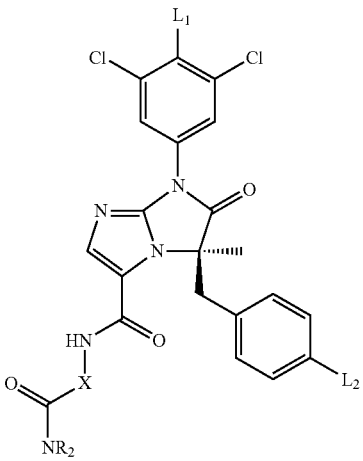
| Cpd # | NR₂ | X | L₁ | L₂ |
|---|---|---|---|---|
| 372 | 1-(3-(dimethylamino)-1,2,4-oxadiazol-5-yl)cyclopropyl-NH- | cyclopropyl | H | CN |
| 385 | 1-(5-cyclopropyl-4H-1,2,4-triazol-3-yl)cyclopropyl-NH- | CH(CH₃) | F | CN |
| 386 | 1-(6-methylpyridin-2-yl)cyclopropyl-NH- | cyclopropyl | H | CN |
| 400 | 1-(4-carbamoyloxazol-2-yl)cyclopropyl-NH- | cyclopropyl | H | CN |

-continued
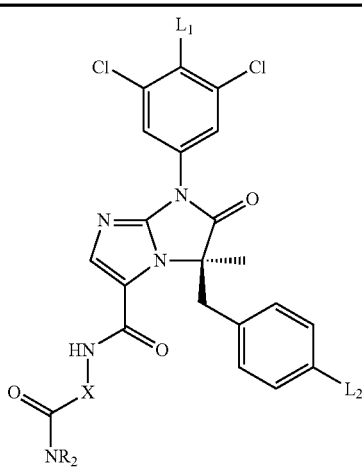
| Cpd # | NR₂ | X | L₁ | L₂ |
|---|---|---|---|---|
| 354 | 1-(6-chloropyridin-2-yl)cyclopropyl-NH- | -CH(CH₃)- | H | CN |
| 396 | 1-(5-(methylsulfonyl)pyridin-2-yl)cyclopropyl-NH- | 1,1-cyclopropyl | H | OCF3 |
| 325 | 1-(pyridin-2-yl)cyclopropyl-NH- | 1,1-cyclopropyl | H | CF₃ |
| 348 | 1-(pyrimidin-2-yl)cyclopropyl-NH- | 1,1-cyclopropyl | H | CN |
| 356 | 1-(4-aminopyrimidin-2-yl)cyclopropyl-NH- | 1,1-cyclopropyl | H | CN |

-continued
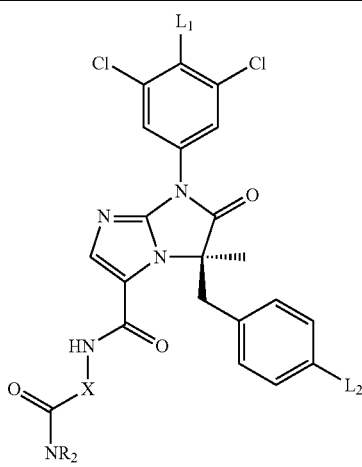
| Cpd # | NR₂ | X | L₁ | L₂ |
|---|---|---|---|---|
| 312 | cyclopropyl-NH, pyrimidin-2-yl | CH(–)CH₂-(1-methylimidazol-4-yl) | F | CN |
| 434 | cyclopropyl-NH, 6-(pyridin-2-yl) with 5-CH₂NHC(O)-cyclopropyl | cyclopropyl (spiro) | H | CN |
| 49 | cyclopropyl-NH, (1H-1,2,4-triazol-3-yl) | cyclopropyl (spiro) | H | OCF₃ |
| 54 | cyclopropyl-NH, (5-cyclopropyl-1H-1,2,4-triazol-3-yl) | cyclopropyl (spiro) | H | CN |

-continued
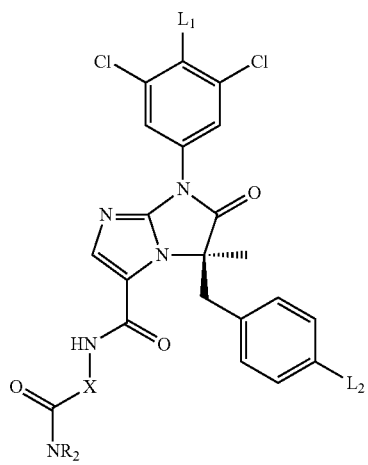
| Cpd # | NR₂ | X | L₁ | L₂ |
|---|---|---|---|---|
| 367 | 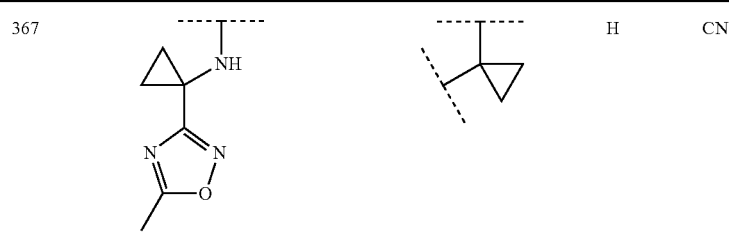 | | H | CN |
| 434 | 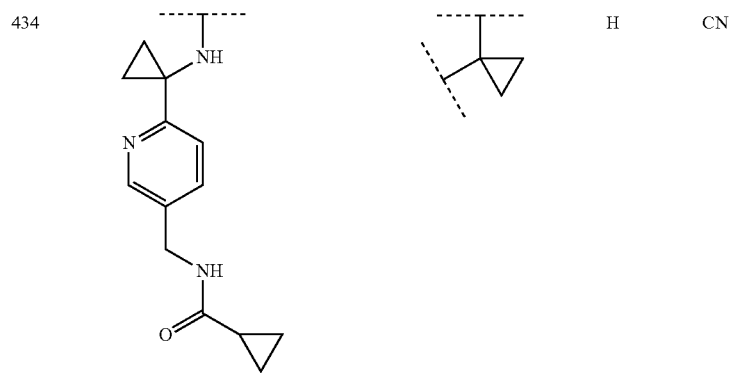 | | H | CN |
| 324 | 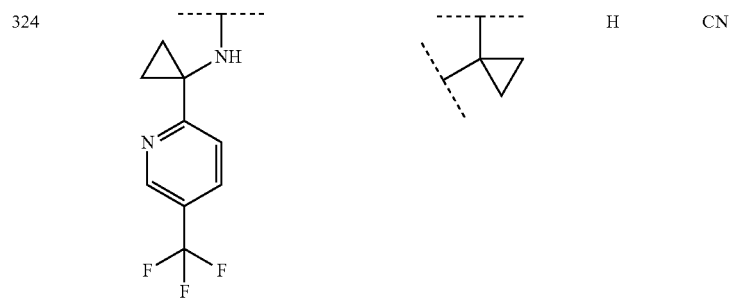 | | H | CN |

-continued
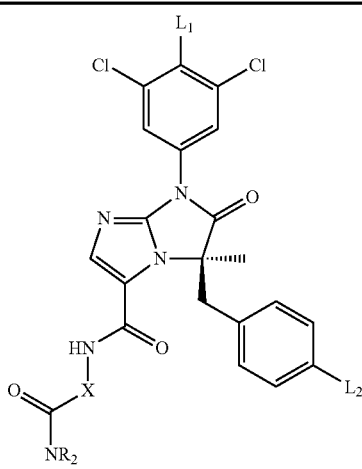
| Cpd # | NR₂ | X | L₁ | L₂ |
|---|---|---|---|---|
| 24 | 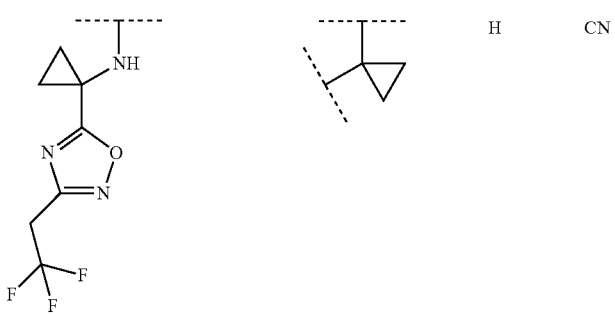 | | H | CN |
| and, | | | | |
| 369 | | | H | CN |
or is a pharmaceutically acceptable salt of any of the foregoing compounds.

8. A compound according to claim 1, which is provided in the table below:
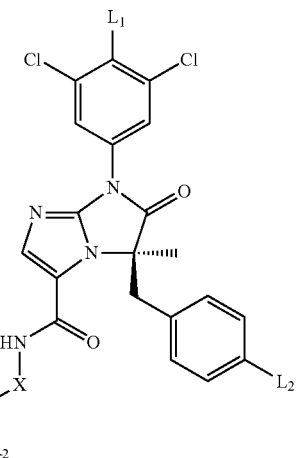
| Cpd # | NR₂ | X | L₁ | L₂ |
|---|---|---|---|---|
| 57 | 1-(5-aminopyridin-2-yl)cyclopropyl-NH— | cyclopropyl | F | CN |
| 56 | 1-(pyridin-2-yl)cyclopropyl-NH— | cyclopropyl | F | CN |
| 59 | 1-(6-methoxypyridin-2-yl)cyclopropyl-NH— | cyclopropyl | F | CN |
| 60 | 1-(thiazol-2-yl)cyclopropyl-NH— | cyclopropyl | F | CN |

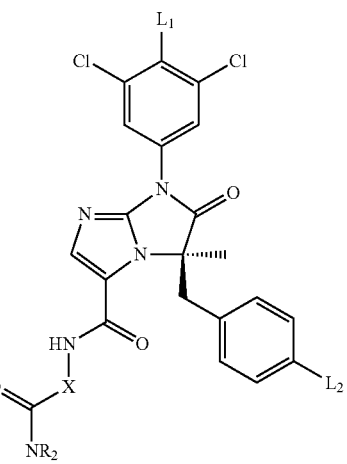

-continued
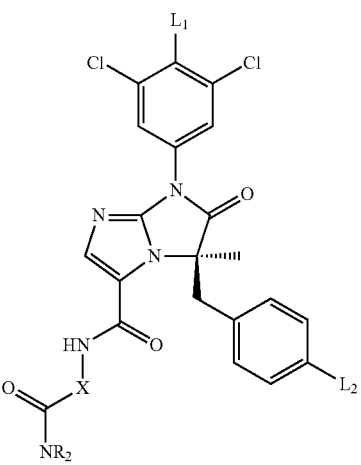
| Cpd # | NR₂ | X | L₁ | L₂ |
|---|---|---|---|---|
| 294 | 1-(1,8-naphthyridin-2-yl)cyclopropyl-NH– | cyclopropyl | F | CN |
| 296 | 1-(2,7-naphthyridin-3-yl)cyclopropyl-NH– | cyclopropyl | F | CN |
| 451 | 1-(pyridin-2-yl)cyclopropyl-NH– | CH(CH₂CH₂COOH)– | F | CN |
| 333 | 1-(7-azaindol-6-yl)cyclopropyl-N(CH₃)– | cyclopropyl | F | CN |

-continued
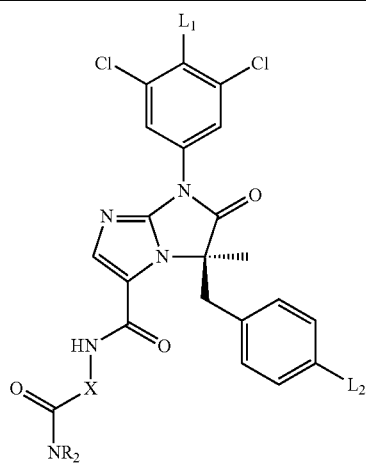
| Cpd # | NR2 | X | L₁ | L₂ |
|---|---|---|---|---|
| 353 | 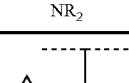 | 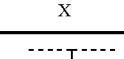 | F | CN |
| 437 | 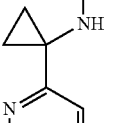 | 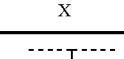 | F | CN |
| 436 | 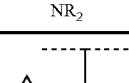 | 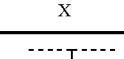 | H | CN |

-continued
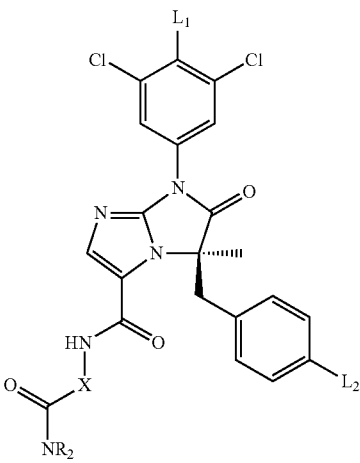
| Cpd # | NR2 | X | L1 | L2 |
|---|---|---|---|---|
| 417 | 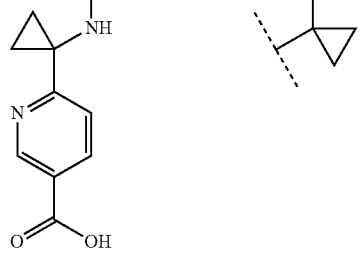 | | F | CN |
| 350 | | | H | CN |
| 314 | 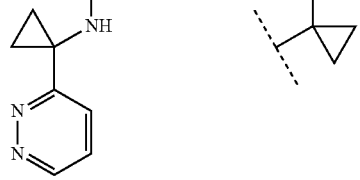 | 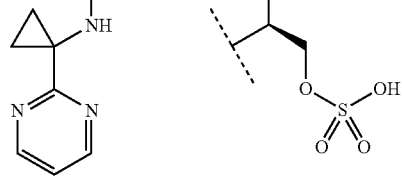 | F | CN |
| 449 | | 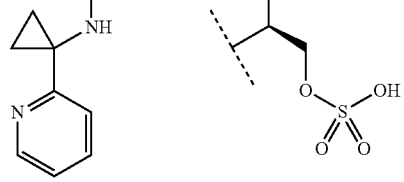 | F | CN |

-continued
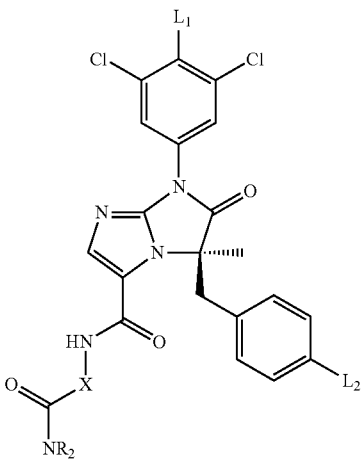
| Cpd # | NR₂ | X | L₁ | L₂ |
|---|---|---|---|---|
| 433 | cyclopropyl-NH attached to pyridine (N at 1), with CH₂-NH-S(O)₂-CH₃ substituent | cyclopropyl | H | CN |
| 427 | cyclopropyl-NH attached to pyridine (N at 1), with CH₂-NH-S(O)₂-CH₃ substituent | cyclopropyl | H | CN |
| 297 | cyclopropyl-NH attached to quinazolin-2-yl | cyclopropyl | F | CN |
| 311 | cyclopropyl-NH attached to pyrimidin-2-yl | CH(CH₃)CH₂CH₂C(O)NH₂ | F | CN |

-continued
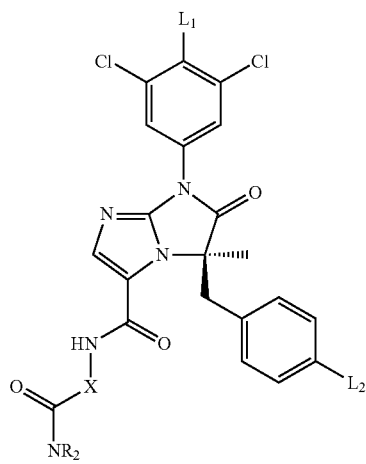
| Cpd # | NR₂ | X | L₁ | L₂ |
|---|---|---|---|---|
| 378 | cyclopropyl-NH with 2-pyridyl | CH(OH)CH(CH₃) | F | CN |
| 342 | cyclopropyl-NH with 2-isopropyl-oxazol-4-yl | cyclopropyl | F | CN |
| 416 | cyclopropyl-NH with 6-(5-carboxy)pyridyl | cyclopropyl | H | CN |
| 305 | cyclopropyl-NH with 1-isopropyl-imidazol-4-yl | cyclopropyl | F | CN |

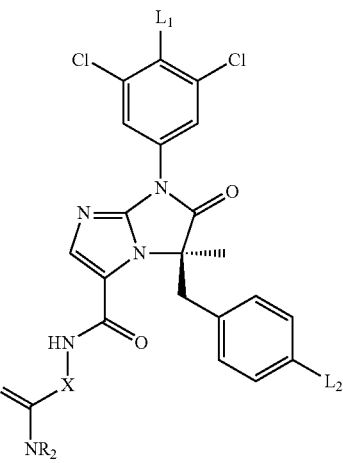
| Cpd # | NR2 | X | L1 | L2 |
|---|---|---|---|---|
| 343 | 1-(5-(aminomethyl)pyridin-2-yl)cyclopropyl-NH- | cyclopropyl-1,1-diyl | F | CN |
| 298 | 1-(6-chloroquinazolin-2-yl)cyclopropyl-NH- | cyclopropyl-1,1-diyl | F | CN |
| 426 | 1-(4-(acetamidomethyl)pyridin-2-yl)cyclopropyl-NH- | cyclopropyl-1,1-diyl | H | CN |
| 380 | 1-(pyridin-2-yl)cyclopropyl-NH- | -CH(CH2OP(O)(OH)2)- | F | CN |

-continued
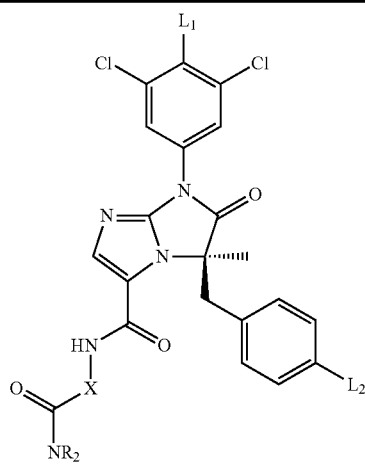
| Cpd # | NR₂ | X | L₁ | L₂ |
|---|---|---|---|---|
| 438 | 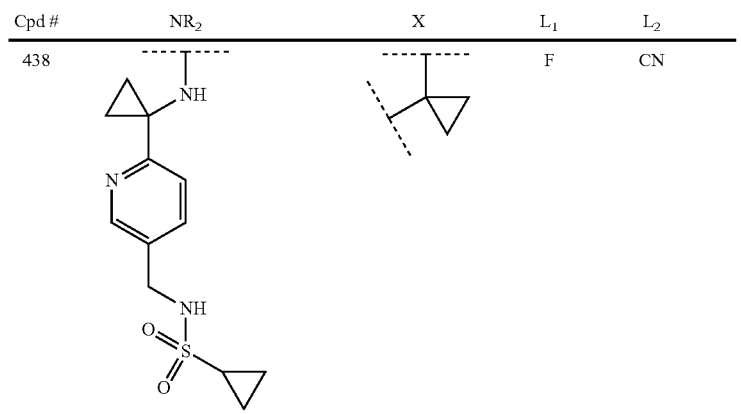 | | F | CN |
| 309 | 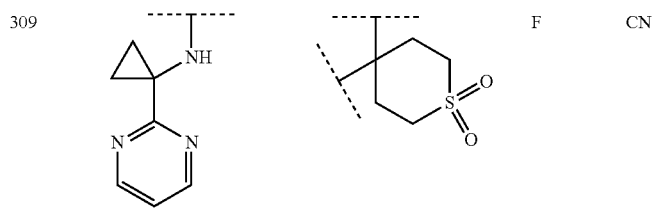 | | F | CN |
| and, | | | | |
| 432 | 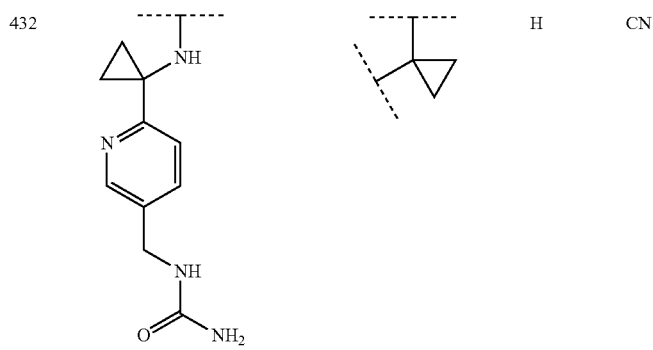 | | H | CN |
or is a pharmaceutically acceptable salt of any of the foregoing compounds.

9. A pharmaceutical composition comprising a compound in accordance with claim 1 and at least one pharmaceutically acceptable carrier or adjuvant.

10. A method for treating adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction, acute glomerulonephritis, vasculitis, reactive arthritis, dermatosis with acute inflammatory components, stroke, thermal injury, hemodialysis, leukapheresis, necrotizing enterocolitis or granulocyte transfusion associated syndrome, psoriasis, organ/tissue transplant rejection, graft vs, host reaction, Raynaud's syndrome, autoimmune thyroiditis, dermatitis, multiple sclerosis, rheumatoid arthritis, insulin-dependent diabetes mellitus, uveitis, inflammatory bowel disease, Crohn's disease, ulcerative colitis or systemic lupus erythematosus or asthma in a patient which comprises administering to said patient a therapeutically effective amount of a compound in accordance with claim 1, or a pharmaceutically acceptable salt thereof.

11. The compound 57 according to claim 8, or a pharmaceutically acceptable salt thereof.

12. The compound 56 according to claim 8, or a pharmaceutically acceptable salt thereof.

13. The compound 59 according to claim 8, or a pharmaceutically acceptable salt thereof.

14. The compound 60 according to claim 8, or a pharmaceutically acceptable salt thereof.

15. The compound 58 according to claim 8, or a pharmaceutically acceptable salt thereof.

16. The compound 55 according to claim 8, or a pharmaceutically acceptable salt thereof.

17. The compound 320 according to claim 8, or a pharmaceutically acceptable salt thereof.

18. The compound 394 according to claim 8, or a pharmaceutically acceptable salt thereof.

19. The compound 294 according to claim 8, or a pharmaceutically acceptable salt thereof.

20. The compound 296 according to claim 8, or a pharmaceutically acceptable salt thereof.

21. The compound 451 according to claim 8, or a pharmaceutically acceptable salt thereof.

22. The compound 333 according to claim 8, or a pharmaceutically acceptable salt thereof.

23. The compound 353 according to claim 8, or a pharmaceutically acceptable salt thereof.

24. The compound 437 according to claim 8, or a pharmaceutically acceptable salt thereof.

25. The compound 436 according to claim 8, or a pharmaceutically acceptable salt thereof.

26. The compound 417 according to claim 8, or a pharmaceutically acceptable salt thereof.

27. The compound 350 according to claim 8, or a pharmaceutically acceptable salt thereof.

28. The compound 314 according to claim 8, or a pharmaceutically acceptable salt thereof.

29. The compound 449 according to claim 8, or a pharmaceutically acceptable salt thereof.

30. The compound 433 according to claim 8, or a pharmaceutically acceptable salt thereof.

31. The compound 427 according to claim 8, or a pharmaceutically acceptable salt thereof.

32. The compound 297 according to claim 8, or a pharmaceutically acceptable salt thereof.

33. The compound 311 according to claim 8, or a pharmaceutically acceptable salt thereof.

34. The compound 378 according to claim 8, or a pharmaceutically acceptable salt thereof.

35. The compound 342 according to claim 8, or a pharmaceutically acceptable salt thereof.

36. The compound 416 according to claim 8, or a pharmaceutically acceptable salt thereof.

37. The compound 305 according to claim 8, or a pharmaceutically acceptable salt thereof.

38. The compound 343 according to claim 8, or a pharmaceutically acceptable salt thereof.

39. The compound 298 according to claim 8, or a pharmaceutically acceptable salt thereof.

40. The compound 426 according to claim 8, or a pharmaceutically acceptable salt thereof.

41. The compound 380 according to claim 8, or a pharmaceutically acceptable salt thereof.

42. The compound 438 according to claim 8, or a pharmaceutically acceptable salt thereof.

43. The compound 309 according to claim 8, or a pharmaceutically acceptable salt thereof.

44. The compound 432 according to claim 8, or a pharmaceutically acceptable salt thereof.

45. A method according to claim 10, where the condition to be treated is multiple sclerosis.

46. A method according to claim 10, where the condition to be treated is psoriasis.

47. A method according to claim 10, where the condition to be treated is organ/tissue transplant rejection.

48. A method according to claim 10, where the condition to be treated is graft vs, host reaction.

49. A method according to claim 10, where the condition to be treated is systemic lupus erythematosus.

* * * * *

UNITED STATES PATENT AND TRADEMARK OFFICE
CERTIFICATE OF CORRECTION

| | | |
|---|---|---|
| PATENT NO. | : 8,552,205 B2 | Page 1 of 1 |
| APPLICATION NO. | : 12/745439 | |
| DATED | : October 8, 2013 | |
| INVENTOR(S) | : Barbosa, Jr. et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 272 days.

Signed and Sealed this
Twenty-fifth Day of August, 2015

Michelle K. Lee
*Director of the United States Patent and Trademark Office*